United States Patent
Matsumura et al.

(10) Patent No.: US 12,312,473 B2
(45) Date of Patent: May 27, 2025

(54) COMPOSITION, FILM, NEAR-INFRARED CUT FILTER, PATTERN FORMING METHOD, LAMINATE, SOLID-STATE IMAGING ELEMENT, INFRARED SENSOR, IMAGE DISPLAY DEVICE, CAMERA MODULE, AND COMPOUND

(71) Applicant: FUJIFILM Corporation, Tokyo (JP)

(72) Inventors: Tokihiko Matsumura, Shizuoka (JP); Suguru Samejima, Shizuoka (JP); Ryoji Orita, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 579 days.

(21) Appl. No.: 17/672,687

(22) Filed: Feb. 16, 2022

(65) Prior Publication Data
US 2022/0251391 A1 Aug. 11, 2022

Related U.S. Application Data

(63) Continuation of application No. PCT/JP2020/028114, filed on Jul. 20, 2020.

(30) Foreign Application Priority Data

Aug. 29, 2019 (JP) .................................. 2019-157412
Mar. 17, 2020 (JP) .................................. 2020-047017

(51) Int. Cl.
*C09B 67/20* (2006.01)
*C07D 519/00* (2006.01)
(Continued)

(52) U.S. Cl.
CPC .......... *C09B 57/004* (2013.01); *C07D 519/00* (2013.01); *C09B 67/006* (2013.01);
(Continued)

(58) Field of Classification Search
CPC ... C09B 57/004; C09B 67/006; C07D 519/00; G03F 7/0007
See application file for complete search history.

(56) References Cited

U.S. PATENT DOCUMENTS

| 7,060,843 B1 | 6/2006 | Otani et al. |
| 2004/0009368 A1 | 1/2004 | Otani et al. |

(Continued)

FOREIGN PATENT DOCUMENTS

| CN | 104094435 | 10/2014 |
| CN | 107407754 | 11/2017 |

(Continued)

OTHER PUBLICATIONS

Georg M. Fischer et al., "Selective NIR chromophores: Bis(Pyrrolopyrrole) Cyanines", Angewandte Chemie International Edition, Feb. 7, 2011, pp. 1406-1409.

(Continued)

*Primary Examiner* — Peter L Vajda
(74) *Attorney, Agent, or Firm* — JCIPRNET

(57) ABSTRACT

Provided are a composition including a coloring agent having a structure represented by Formula (1), an organic solvent, and a curable compound, in which a solubility of the coloring agent having a structure represented by Formula (1) in propylene glycol methyl ether acetate at 25° C. is 100 mg/L or less; a compound having a structure represented by Formula (4-1); a film formed of the composition; a near-infrared cut filter; a pattern forming method; a laminate; a solid-state imaging element; an infrared sensor; an image display device; a camera module; and a novel compound.

$$(Dye)_n\text{-}L^1 \qquad (1)$$

In Formula (1), $L^1$ represents an n-valent linking group, n represents an integer of 2 to 10, where in a case where n is 2, $L^1$ may be a single bond, and Dye's each independently (Continued)

represent a coloring agent structure having a maximal absorption wavelength in a wavelength range of 650 nm to 2,000 nm.

17 Claims, 1 Drawing Sheet

(51) Int. Cl.
  *C09B 57/00* (2006.01)
  *G02B 5/22* (2006.01)
  *G02B 5/28* (2006.01)
  *G03F 7/00* (2006.01)
(52) U.S. Cl.
  CPC .............. *G02B 5/223* (2013.01); *G02B 5/285* (2013.01); *G03F 7/0007* (2013.01)

(56) References Cited

U.S. PATENT DOCUMENTS

| | | | |
|---|---|---|---|
| 2009/0140220 | A1 | 6/2009 | Lee et al. |
| 2014/0217329 | A1 | 8/2014 | Hayoz et al. |
| 2018/0118865 | A1* | 5/2018 | Arayama ................ G03F 7/027 |
| 2019/0196073 | A1 | 6/2019 | Samejima et al. |

FOREIGN PATENT DOCUMENTS

| | | |
|---|---|---|
| CN | 107922751 | 4/2018 |
| CN | 109642972 | 4/2019 |
| EP | 3059288 | 8/2016 |
| JP | 2001139940 | 5/2001 |
| JP | 2006310538 | 11/2006 |
| JP | 2014071416 | 4/2014 |
| JP | 2014533303 | 12/2014 |
| KR | 20030073256 | 9/2003 |
| KR | 20190027931 | 3/2019 |
| TW | 200933297 | 8/2009 |
| TW | 201700631 | 1/2017 |
| TW | 201702643 | 1/2017 |
| TW | 201839085 | 11/2018 |
| WO | 2016158461 | 10/2016 |
| WO | 2016194527 | 12/2016 |
| WO | 2018043185 | 3/2018 |

OTHER PUBLICATIONS

"Search Report of Europe Counterpart Application", issued on Sep. 2, 2022, p. 1-p. 10.

"International Search Report (Form PCT/ISA/210) of PCT/JP2020/028114," mailed on Oct. 20, 2020, with English translation thereof, pp. 1-7.

"Written Opinion of the International Searching Authority (Form PCT/ISA/237)" of PCT/JP2020/028114, mailed on Oct. 20, 2020, with English translation thereof, pp. 1-8.

"Office Action of Europe Counterpart Application", issued on May 2, 2023, p. 1-p. 4.

"Office Action of China Counterpart Application", issued on Jan. 1, 2024, with English translation thereof, pp. 1-13.

"Notice of Reasons for Refusal of Japan Counterpart Application", issued on Nov. 15, 2022, with English translation thereof, p. 1-p. 5.

"Office Action of Korea Counterpart Application", issued on Feb. 15, 2024, with English translation thereof, p. 1-p. 16.

"Second Notice of Examination Opinion of China Counterpart Application", issued on Aug. 21, 2024, with partial English translation thereof, pp. 1-11.

"Notice of Examination Opinion of Taiwan Counterpart Application", issued on Nov. 27, 2024, with English translation thereof, pp. 1-13.

* cited by examiner

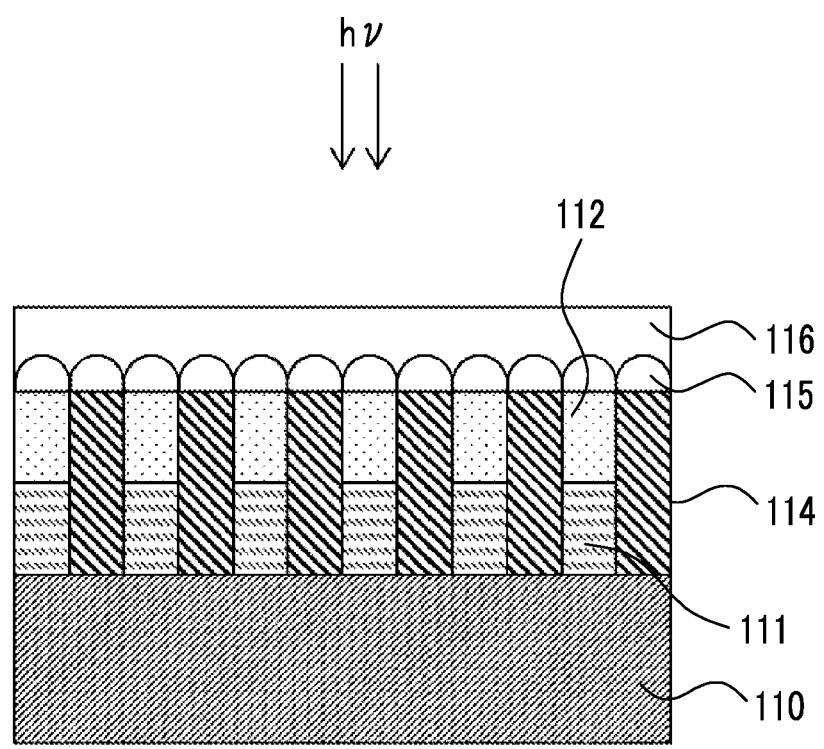

COMPOSITION, FILM, NEAR-INFRARED CUT FILTER, PATTERN FORMING METHOD, LAMINATE, SOLID-STATE IMAGING ELEMENT, INFRARED SENSOR, IMAGE DISPLAY DEVICE, CAMERA MODULE, AND COMPOUND

CROSS-REFERENCE TO RELATED APPLICATIONS

This application is a continuation application of International Application No. PCT/JP2020/028114, filed Jul. 20, 2020, the disclosure of which is incorporated herein by reference in its entirety. Further, this application claims priority from Japanese Patent Application No. 2019-157412, filed Aug. 29, 2019, and Japanese Patent Application No. 2020-047017, filed Mar. 17, 2020, the disclosures of which are incorporated herein by reference in their entirety.

BACKGROUND OF THE INVENTION

1. Field of the Invention

The present disclosure relates to a composition, a film, a near-infrared cut filter, a pattern forming method, a laminate, a solid-state imaging element, an infrared sensor, an image display device, a camera module, and a compound.

2. Description of the Related Art

Members such as a color filter are manufactured by a photolithographic method with a photosensitive coloring composition formed by containing a polyfunctional monomer, a photopolymerization initiator, an alkali-soluble resin, and other components in a pigment dispersion composition such as a curable composition in which an organic pigment or an inorganic pigment is dispersed.

As the above-described pigment, it has been known to use a squarylium compound having a dihydroperimidine skeleton.

In addition, examples of a pigment and dye in the related art include those disclosed in WO2018/043185A and WO2016/194527A.

WO2018/043185A discloses a composition including a near-infrared absorbing compound having a maximal absorption wavelength in a range of 650 to 1000 nm, an organic solvent, and a resin, in which the near-infrared absorbing compound is at least one selected from a pyrrolopyrrole compound, a rylene compound, an oxonol compound, a squarylium compound, a croconium compound, a zinc phthalocyanine compound, a cobalt phthalocyanine compound, a vanadium phthalocyanine compound, a copper phthalocyanine compound, a magnesium phthalocyanine compound, a naphthalocyanine compound, a pyrylium compound, an azrenium compound, an indigo compound, or a pyrromethene compound, and a solubility of the near-infrared absorbing compound in propylene glycol methyl ether acetate at 25° C. is 0.01 to 30 mg/L.

WO2016/194527A discloses a near-infrared absorbing coloring agent multimer having a maximal absorption wavelength in a range of 700 to 1200 nm.

SUMMARY OF THE INVENTION

An object to be achieved by one embodiment of the present disclosure is to provide a composition in which a cured film to be obtained has excellent spectral characteristics.

An object to be achieved by another embodiment of the present disclosure is to provide a film formed of the composition, a near-infrared cut filter, a pattern forming method, a laminate, a solid-state imaging element, an infrared sensor, an image display device, and a camera module.

An object to be achieved by still another embodiment of the present disclosure is to provide a novel compound.

The present disclosure includes the following aspects.

<1> A composition comprising:
a coloring agent having a structure represented by Formula (1);
an organic solvent; and
a curable compound,
in which a solubility of the coloring agent having a structure represented by Formula (1) in propylene glycol methyl ether acetate at 25° C. is 100 mg/L or less, $$(Dye)_n\text{-}L^1 \qquad (1)$$

in Formula (1), $L^1$ represents an n-valent linking group, n represents an integer of 2 to 10, where in a case where n is 2, $L^1$ may be a single bond, and Dye's each independently represent a coloring agent structure having a maximal absorption wavelength in a wavelength range of 650 nm to 2,000 nm.

<2> The composition according to <1>,
in which the coloring agent having a structure represented by Formula (1) is at least one compound selected from the group consisting of a pyrrolopyrrole compound, a rylene compound, an oxonol compound, a squarylium compound, a croconium compound, a vanadium phthalocyanine compound, a naphthalocyanine compound, an indigo compound, and a pyrromethene compound.

<3> The composition according to <1> or <2>,
in which the coloring agent having a structure represented by Formula (1) is at least one compound selected from the group consisting of a pyrrolopyrrole compound, a squarylium compound, a croconium compound, and a pyrromethene compound.

<4> The composition according to any one of <1> to <3>,
in which $L^1$ in Formula (1) is a divalent to 10-valent linking group having at least two or more ring structures selected from the group consisting of an aliphatic ring, an aromatic ring, and a heterocyclic ring.

<5> The composition according to any one of <1> to <4>,
in which a molecular weight of the coloring agent having a structure represented by Formula (1) is less than 4,000.

<6> The composition according to any one of <1> to <5>,
in which a total number of carbon atoms included in $L^1$ in Formula (1) is 1 to 18.

<7> The composition according to any one of <1> to <6>,
in which a volume average particle diameter of the coloring agent having a structure represented by Formula (1) is 1 nm to 500 nm.

<8> The composition according to any one of <1> to <7>,
in which n in Formula (1) is 2.

<9> The composition according to any one of <1> to <8>,
in which, in Formula (1), n is 2 and $L^1$ is a group represented by Formula (2) or Formula (3), $$\text{*---}X^1\text{-}A^1\text{-}X^2\text{---*} \qquad \text{Formula (2)}$$

in Formula (2), $X^1$ and $X^2$ each independently represent a single bond, —O—, —S—, —$NR^{1A}$—, —CO—, —COO—, —OCOO—, —$SO_2NR^{1A}$—, —$CONR^{1A}$—, —$OCONR^{1A}$—, or —$NR^{1A}CONR^{1A}$—, $R^{1A}$ represents a hydrogen atom, an alkyl group, or an aryl group, $A^1$ represents a single bond, an aliphatic ring structure, an aromatic ring structure, or a heterocyclic ring structure, and * represents a connection position with Dye, where in a case where $A^1$ is a single bond, both $X^1$ and $X^2$ are not single bonds, $$*-X^3-A^2-L^2-A^3-X^4-* \quad \text{Formula (3)}$$

in Formula (3), $X^3$ and $X^4$ each independently represent a single bond, —O—, —S—, —$NR^{2A}$—, —CO—, —COO—, —OCOO—, —$SO_2NR^{2A}$—, —$CONR^{2A}$—, —$OCONR^{2A}$—, or —$NR^{2A}CONR^{2A}$—, $R^{2A}$ represents a hydrogen atom or an alkyl group, $L^2$ represents a single bond, —O—, —S—, $NR^{2B}$—, —CO—, —COO—, —OCOO—, —$SO_2NR^{2B}$—, —$CONR^{2B}$—, —$OCONR^{2B}$—, —$NR^{2B}CONR^{2B}$—, an alkylene group having 1 to 6 carbon atoms, an alkenyl group, an alkynyl group, an aromatic ring structure, or a group of a combination of these groups, $R^{2B}$ represents a hydrogen atom or an alkyl group, and $A^2$ and $A^3$ each independently represent an aliphatic ring structure, an aromatic ring structure, or a heterocyclic ring structure.

<10> The composition according to any one of <1> to <9>, further comprising:

a pigment derivative.

<11> The composition according to any one of <1> to <10>, in which the curable compound includes a polymerizable compound, and the composition further includes a photopolymerization initiator.

<12> The composition according to any one of <1> to <11>, further comprising:

an alkali-soluble resin.

<13> A film which consists of the composition according to any one of <1> to <12> or is obtained by curing the composition.

<14> A near-infrared cut filter comprising:

the film according to <13>.

<15> The near-infrared cut filter according to <14>, further comprising:

a glass substrate.

<16> A pattern forming method, comprising:

a step of forming a composition layer on a support using the composition according to any one of <1> to <12>; and a step of forming a pattern on the composition layer by a photolithography method or a dry etching method.

<17> A laminate comprising:

the film according to <13>; and a color filter including a chromatic colorant.

<18> A solid-state imaging element comprising:

the film according to <13>.

<19> An image display device comprising:

the film according to <13>.

<20> A camera module comprising:

the film according to <13>.

<21> An infrared sensor comprising:

the film according to <13>.

<22> A pyrrolopyrrole compound represented by Formula (4-1),

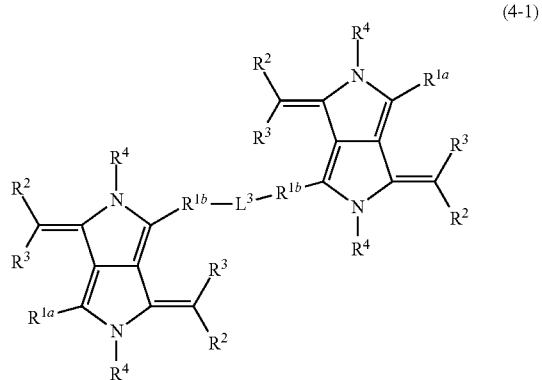

In Formula (4-1), $R^{1a}$ and $R^{1b}$ each independently represent an aryl group or a heteroaryl group, $R^2$ and $R^3$ each independently represent a hydrogen atom or a substituent, $R^2$ and $R^3$ may be bonded to each other to form a ring, $R^4$'s each independently represent a hydrogen atom, an alkyl group, an aryl group, a heteroaryl group, —$BR^{4A}R^{4B}$, or a metal atom, $R^4$ may be covalently or coordinately bonded to at least one selected from the group consisting of $R^{1a}$, $R^{1b}$, and $R^3$, $R^{4A}$ and $R^{4B}$ each independently represent a hydrogen atom or a substituent, and $L^3$ represents a group represented by Formula (2) or Formula (3), $$*-X^1-A^1-X^2-* \quad \text{Formula (2)}$$

in Formula (2), $X^1$ and $X^2$ each independently represent a single bond, —O—, —S—, —$NR^{1A}$—, —CO—, —COO—, —OCOO—, —$SO_2NR^{1A}$—, —$CONR^{1A}$—, —$OCONR^{1A}$—, or —$NR^{1A}CONR^{1A}$—, $R^{1A}$ represents a hydrogen atom, an alkyl group, or an aryl group, A represents a single bond, an aliphatic ring structure, an aromatic ring structure, or a heterocyclic ring structure, and * represents a connection position with Dye, where in a case where A is a single bond, both $X^1$ and $X^2$ are not single bonds, $$*X^3-A^2-L^2-A^3-X^4* \quad \text{Formula (3)}$$

in Formula (3), $X^3$ and $X^4$ each independently represent a single bond, —O—, —S—, —$NR^{2A}$—, —CO—, —COO—, —OCOO—, —$SO_2NR^{2A}$—, —$CONR^{1A}$—, —$OCONR^{2A}$—, or —$NR^{2A}CONR^{2A}$—, $R^{2A}$ represents a hydrogen atom or an alkyl group, $L^2$ represents a single bond, —O—, —S—, $NR^{2B}$—, —CO—, —COO—, —OCOO—, —$SO_2NR^{2B}$—, —$CONR^{2B}$—, —$OCONR^{2B}$—, —$NR^{2B}CONR^{2B}$—, an alkylene group having 1 to 6 carbon atoms, an alkenyl group, an alkynyl group, an aromatic ring structure, or a group of a combination of these groups, $R^{2B}$ represents a hydrogen atom or an alkyl group, and $A^2$ and $A^3$ each independently represent an aliphatic ring structure, an aromatic ring structure, or a heterocyclic ring structure.

According to one embodiment of the present disclosure, a composition in which a cured film to be obtained has excellent spectral characteristics is provided.

In addition, according to another embodiment of the present disclosure, a film formed of the composition, a near-infrared cut filter, a pattern forming method, a laminate, a solid-state imaging element, an infrared sensor, an image display device, and a camera module are provided.

According to still another embodiment of the present disclosure, a novel compound is provided.

BRIEF DESCRIPTION OF THE DRAWINGS

FIG. 1 is a schematic diagram indicating an embodiment of an infrared sensor according to the present disclosure.

DESCRIPTION OF THE PREFERRED EMBODIMENTS

Hereinafter, the contents of the present disclosure will be described in detail.

In the present disclosure, a "total solid content" refers to a total mass of components obtained by removing a solvent from the whole composition of the composition. In addition, a "solid content" is a component obtained by removing a solvent as described above, and for example, the component may be solid or may be liquid at 25° C.

Regarding a term of a group (atomic group) of the present disclosure, a term with no description of "substituted" and "unsubstituted" includes both a group not including a substituent and a group including a substituent. For example, an "alkyl group" includes not only an alkyl group having no substituent (unsubstituted alkyl group), but also an alkyl group having a substituent (substituted alkyl group).

In the present disclosure, unless specified otherwise, "exposure" denotes not only exposure using light but also drawing using a corpuscular beam such as an electron beam or an ion beam. In addition, generally, examples of light used for the exposure include actinic rays or radiation such as a bright line spectrum of a mercury lamp, far ultraviolet rays typified by an excimer laser, extreme ultraviolet rays (EUV light), X-rays, or electron beams.

In the present disclosure, the numerical ranges shown using "to" means ranges including the numerical values described before and after "to" as the minimum value and the maximum value.

In a numerical range described in a stepwise manner in the present disclosure, an upper limit value or a lower limit value described in a certain numerical range may be replaced with an upper limit value or a lower limit value in another numerical range described in a stepwise manner. In addition, in a numerical range described in the present disclosure, an upper limit value or a lower limit value described in a certain numerical range may be replaced with a value described in Examples.

In the present disclosure, "(meth)acrylate" denotes either or both of acrylate and methacrylate, "(meth)acryl" denotes either or both of acryl and methacryl, and "(meth)acryloyl" denotes either or both of acryloyl and methacryloyl.

In the present disclosure, in a chemical formula, Me represents a methyl group, Et represents an ethyl group, Pr represents a propyl group, Bu represents a butyl group, Ac represents an acetyl group, Bn represents a benzyl group, and Ph represents a phenyl group.

In the present disclosure, the term "step" is not only an independent step, but also includes a step which is not clearly distinguished from other steps in a case where an intended action of the step is obtained.

In the present disclosure, "mass %" is identical to "weight %" and "part by mass" is identical to "part by weight".

Furthermore, in the present disclosure, a combination of two or more preferred aspects is a more preferred aspect.

Unless otherwise specified, a transmittance in the present disclosure is a transmittance at 25° C.

In the present disclosure, a weight-average molecular weight and a number-average molecular weight are defined as values in terms of polystyrene measured by gel permeation chromatography (GPC).

(Composition)

A composition according to an embodiment of the present disclosure includes a coloring agent having a structure represented by Formula (1), an organic solvent, and a curable compound, in which a solubility of the coloring agent having a structure represented by Formula (1) in propylene glycol methyl ether acetate at 25° C. is 100 mg/L or less.

$(Dye)_n\text{-}L^1$                  (1)

In Formula (1), $L^1$ represents an n-valent linking group, n represents an integer of 2 to 10, where in a case where n is 2, $L^1$ may be a single bond, and Dye's each independently represent a coloring agent structure having a maximal absorption wavelength in a wavelength range of 650 nm to 2,000 nm.

By using the composition according to the embodiment of the present disclosure, a cured film having excellent spectral characteristics can be obtained.

For example, in a cured film including the pigment disclosed in WO2018/043185A or the coloring agent multimer disclosed in WO2016/194527A, which are coloring agents in the related art, the spectral characteristics may not be sufficient.

As a result of intensive studies, the present inventors have found that, by using the composition including the coloring agent represented by Formula (1), an organic solvent, and a curable compound, in which the solubility of the coloring agent in propylene glycol methyl ether acetate at 25° C. is 100 mg/L or less, a cured film having spectral characteristics is obtained.

Although the reason why the above-described effect is obtained is unclear, the coloring agent having a structure represented by Formula (1), included in the composition according to the embodiment of the present disclosure, is more likely to associate with each other than the pigment disclosed in WO2018/043185A or the coloring agent multimer disclosed in WO2016/194527A, or the association state is adjusted, so that an amorphous component is reduced. As a result, it is presumed that a width of the maximal absorption wavelength is narrowed, and spectral characteristics of the obtained film are excellent.

In addition, since the coloring agent having a structure represented by Formula (1), included in the composition according to the embodiment of the present disclosure, has the specific linking structure, it is presumed that rigidity of molecules is improved, and since the solubility of the coloring agent having a structure represented by Formula (1) in propylene glycol methyl ether acetate is 100 mg/L or less, it is presumed that stability of the molecule itself to light and heat is improved, and heat resistance and light resistance are also excellent.

Hereinafter, details of each component included in the composition according to the embodiment of the present disclosure will be described.

<Coloring Agent Having Structure Represented by Formula (1)>

The composition according to the embodiment of the present disclosure includes the above-described coloring agent having a structure represented by Formula (1).

The solubility of the coloring agent having a structure represented by Formula (1) (hereinafter, also referred to as a "specific coloring agent") in propylene glycol methyl ether acetate (hereinafter, also referred to as "PGMEA") at 25° C. is 100 mg/L or less.

The above-described coloring agent having a structure represented by Formula (1) can be suitably used as an infrared absorbing coloring agent.

In addition, the above-described coloring agent having a structure represented by Formula (1) is preferably a pigment. In the present disclosure, a pigment means a coloring agent which is not dissolved in a solvent. In addition, a dye means a coloring agent which is dissolved in a solvent.

In the present disclosure, the solubility of the coloring agent having a structure represented by Formula (1) (that is, the specific coloring agent) is measured and obtained by the following method.

Under atmospheric pressure, approximately 100 mg (precisely weighed value is X mg) of the coloring agent having a structure represented by Formula (1) is added to 1 L of propylene glycol methyl ether acetate at 25° C., and the mixture is stirred for 30 minutes, allowed to stand for 5 minutes, and filtered. Thereafter, the filtrate is dried under reduced pressure at 80° C. for 2 hours and precisely weighed (precisely weighed value is Y mg), and the solubility of the specific coloring agent dissolved in propylene glycol methyl ether acetate is calculated from the following expression.

PGMEA solubility (mg/L) of specific coloring agent=X—Y

From the viewpoint of spectral characteristics, heat resistance, and light resistance, the solubility of the coloring agent having a structure represented by Formula (1) in PGMEA at 25° C. is preferably 0.01 mg/L to 100 mg/L, more preferably 0.01 mg/L to 50 mg/L, still more preferably 0.01 mg/L to 10 mg/L, and particularly preferably 0.01 mg/L to 10 mg/L.

Examples of a method for lowering the solubility of the coloring agent having a structure represented by Formula (1) in PGMEA include the following.

(1): improving leveling of the structure represented by Formula (1). Specific examples thereof include introducing at least one ring structure selected from the group consisting of an aliphatic ring, an aromatic ring, and a heterocyclic ring into $L^1$.

(2): introducing a urea structure, a triazine structure, or a structure having a hydrogen bonding group such as a hydroxy group into the structure represented by Formula (1).

From the viewpoint of lowering the solubility of the coloring agent having a structure represented by Formula (1) in PGMEA, $L^1$ is preferably a linking group having at least one ring structure selected from the group consisting of an aliphatic ring, an aromatic ring, and a heterocyclic ring, more preferably a linking group having at least one of an aliphatic ring, an aromatic ring, or a heterocyclic ring, and still more preferably a linking group having at least two of an aliphatic ring, an aromatic ring, or a heterocyclic ring.

The aliphatic ring, aromatic ring, and heterocyclic ring may have a substituent. Examples of the substituent include an alkyl group, a halogen atom, an alkenyl group, an aryl group, a monovalent heterocyclic group, a nitro group, and a cyano group. Among these, an alkyl group or a halogen atom is preferable, an alkyl group is more preferable, and an alkyl group having 1 to 4 carbon atoms is still more preferable.

From the viewpoint of spectral characteristics, heat resistance, and light resistance, it is preferable that the aliphatic ring, aromatic ring, and heterocyclic ring are unsubstituted or have an alkyl group or a halogen atom as the substituent, it is more preferable to be unsubstituted or have an alkyl group as the substituent, it is still more preferable to be unsubstituted or have an alkyl group having 1 to 4 carbon atoms as the substituent, and it is particularly preferable to be unsubstituted.

In the above-described coloring agent having a structure represented by Formula (1), L represents an n-valent linking group. From the viewpoint of spectral characteristics, heat resistance, and light resistance, $L^1$ is preferably a divalent to octavalent linking group, more preferably a divalent to hexavalent linking group, still more preferably a divalent to tetravalent linking group, and particularly preferably a divalent or trivalent linking group.

The valence of n in $L^1$ is synonymous with n in Formula (1) described later.

In the above-described coloring agent having a structure represented by Formula (1), n represents an integer of 2 to 10. From the viewpoint of spectral characteristics, heat resistance, and light resistance, n is preferably an integer of 2 to 8, more preferably an integer of 2 to 6, still more preferably an integer of 2 to 4, particularly preferably 2 or 3, and most preferably 2.

In the above-described coloring agent having a structure represented by Formula (1), in a case where n is 2, $L^1$ may be a single bond.

From the viewpoint of spectral characteristics, heat resistance, and light resistance, $L^1$ in Formula (1) is preferably a divalent to 10-valent linking group (preferably a divalent to octavalent linking group, more preferably a divalent to hexavalent linking group, still more preferably a divalent to tetravalent linking group, and particularly preferably a divalent or trivalent linking group) having two or more of at least one ring structure selected from the group consisting of an aliphatic ring, an aromatic ring, and a heterocyclic ring, more preferably a divalent to 10-valent linking group (preferably a divalent to octavalent linking group, more preferably a divalent to hexavalent linking group, still more preferably a divalent to tetravalent linking group, and particularly preferably a divalent or trivalent linking group) having two or more of at least one ring structure selected from the group consisting of an aliphatic ring and an aromatic ring, and still more preferably a divalent to 10-valent linking group (preferably a divalent to octavalent linking group, more preferably a divalent to hexavalent linking group, still more preferably a divalent to tetravalent linking group, and particularly preferably a divalent or trivalent linking group) having two or more aromatic rings.

From the viewpoint of spectral characteristics, heat resistance, and light resistance, the total number of carbon atoms (also referred to as "carbon atom number") included in $L^1$ of Formula (1) is preferably 24 or less, more preferably 1 to 18, and still more preferably 9 to 18.

In Formula (1), from the viewpoint of spectral characteristics, heat resistance, and light resistance, it is preferable that n is 2 and $L^1$ is a group represented by Formula (2) or Formula (3).

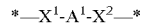  Formula (2)

In Formula (2), $X^1$ and $X^2$ each independently represent a single bond, —O—, —S—, —NR$^{1A}$—, —CO—, —COO—, —OCOO—, —SO$_2$NR$^{1A}$—, —CONR$^{1A}$—, —OCONR$^{1A}$—, or —NR$^{1A}$CONR$^{1A}$—, R$^{1A}$ represents a hydrogen atom, an alkyl group, or an aryl group, A represents a single bond, an aliphatic ring structure, an aromatic ring structure, or a heterocyclic ring structure, and * represents a connection position with Dye, where in a case where A is a single bond, both $X^1$ and $X^2$ are not single bonds.

In Formula (2), in a case where $X^1$ and $X^2$ each independently represent —$NR^{1A}$—, —$SO_2NR^{1A}$—, —$CONR^{1A}$—, —$OCONR^{1A}$—, or —$NR^{1A}CONR^{1A}$—, $R^{1A}$ is preferably a hydrogen atom, an alkyl group having 1 to 4 carbon atoms, or an aromatic hydrocarbon group having 6 to 30 carbon atoms, more preferably a hydrogen atom, a methyl group, a phenyl group, or a naphthyl group, and still more preferably a hydrogen atom or a phenyl group.

In Formula (2), from the viewpoint of spectral characteristics, heat resistance, and light resistance, $X^1$ and $X^2$ are each independently preferably a single bond, —O—, —$NR^{1A}$—, —COO—, —OCOO—, —$CONR^{1A}$—, —$OCONR^{1A}$—, or —$NR^{1A}CONR^{1A}$—, more preferably a single bond, —$NR^{1A}$—, —COO—, or —OCOO—, and still more preferably a single bond or —COO—.

In Formula (2), $A^1$ represents a single bond, an aliphatic ring structure, an aromatic ring structure, or a heterocyclic ring structure.

The aliphatic ring in the aliphatic ring structure may be a monocyclic ring or a fused aliphatic ring in which two or more aliphatic rings are condensed, but a monocyclic ring is preferable.

The number of ring members in the aliphatic ring is not particularly limited, but is preferably 5 to 8, more preferably 5 or 6, and particularly preferably 6.

Examples of the aliphatic ring include a cyclopentane ring and a cyclohexane ring.

The heterocyclic ring in the heterocyclic ring structure may be a monocyclic ring or a fused heterocyclic ring in which two or more heterocyclic rings or a heterocyclic ring and an aromatic ring are condensed, but a monocyclic ring is preferable.

The number of ring members in the heterocyclic ring is not particularly limited, but is preferably 5 to 8 and more preferably 5 or 6.

It is preferable that the heterocyclic ring is a heterocyclic ring having at least one heteroatom selected from the group consisting of a nitrogen atom, an oxygen atom, or a sulfur atom, it is more preferable that the heterocyclic ring has at least one heteroatom selected from the group consisting of a nitrogen atom and a sulfur atom, it is still more preferable that the heterocyclic ring includes a nitrogen atom or a sulfur atom, and it is particularly preferable that the heterocyclic ring includes a nitrogen atom.

Examples of the heterocyclic ring include a pyridine ring, a pyrimidine ring, a thiophene ring, a furan ring, and a pyrrole ring.

The aromatic ring in the aromatic ring structure may be a monocyclic ring or a fused aromatic ring in which two or more aromatic rings are condensed, but a monocyclic ring is preferable.

As the aromatic ring, an aromatic hydrocarbon ring is preferable, a monocyclic aromatic hydrocarbon ring is more preferable, and a benzene ring is still more preferable.

In Formula (2), from the viewpoint of spectral characteristics, heat resistance, and light resistance, $A^1$ is preferably a single bond or an aromatic ring structure, and more preferably a benzene ring structure.

In Formula (2), from the viewpoint of spectral characteristics, heat resistance, and light resistance, it is preferable that $X^1$ and $X^2$ are each independently a single bond, —O—, —$NR^{1A}$, —COO—, —OCOO—, —$CONR^{1A}$—, —$OCONR^{1A}$—, or —$NR^{1A}CONR^{1A}$— and $A^1$ is a single bond or an aromatic ring structure, it is more preferable that $X^1$ and $X^2$ are each independently a single bond, —$NR^{1A}$—, —COO—, or —OCOO— and $A^1$ is a single bond or a monocyclic aromatic ring structure, and it is still more preferable that $X^1$ and $X^2$ are each independently a single bond or —COO— and $A^1$ is a single bond or a benzene ring structure.

$$*—X^3-A^2-L^2-A^3-X^4—* \quad \text{Formula (3)}$$

In Formula (3), $X^3$ and $X^4$ each independently represent a single bond, —O—, —S—, —$NR^{2A}$—, —CO—, —COO—, —OCOO—, —$SO_2NR^{2A}$—, —$CONR^{2A}$—, —$OCONR^{2A}$—, or —$NR^{2A}CONR^{2A}$—, $R^{2A}$ represents a hydrogen atom or an alkyl group, $L^2$ represents a single bond, —O—, —S—, $NR^{2B}$—, —CO—, —COO—, —OCOO—, —$SO_2NR^{2B}$—, —$CONR^{2B}$—, —$OCONR^{2B}$—, —$NR^{2B}CONR^{2B}$—, an alkylene group having 1 to 6 carbon atoms, an alkenyl group, an alkynyl group, an aromatic ring structure, or a group of a combination of these groups, $R^{2B}$ represents a hydrogen atom or an alkyl group, and $A^2$ and $A^3$ each independently represent an aliphatic ring structure, an aromatic ring structure, or a heterocyclic ring structure.

The aliphatic ring structure, aromatic ring structure, and heterocyclic ring structure in $A^2$ and $A^3$ of Formula (3) are synonymous with the aliphatic ring structure, aromatic ring structure, and heterocyclic ring structure in $A^1$ of Formula (2).

In Formula (3), in a case where $X^3$ and $X^4$ each independently represent —$NR^{1A}$—, —$SO_2R^{2A}$—, —$CONR^{2A}$—, —$OCONR^{2A}$—, or —$NR^{2A}CONR^{2A}$—, $R^{2A}$ is preferably a hydrogen atom or an alkyl group having 1 to 4 carbon atoms, more preferably a hydrogen atom or a methyl group, and still more preferably a hydrogen atom.

In Formula (3), in a case where $L^2$'s each independently represent —$NR^{2B}$—, —$SO_2R^{2B}$—, —$CONR^{2B}$—, —$OCONR^{2B}$—, or —$NR^{2B}CONR^{2B}$—, $R^{2B}$ is preferably a hydrogen atom or an alkyl group having 1 to 4 carbon atoms, more preferably a hydrogen atom or a methyl group, and still more preferably a hydrogen atom.

In Formula (3), from the viewpoint of spectral characteristics, heat resistance, and light resistance, $X^3$ and $X^4$ are each independently preferably a single bond, —O—, —$NR^{2A}$—, —COO—, or —$CONR^{2A}$—, more preferably a single bond, —O—, —$NR^{2A}$—, or —COO—, and still more preferably a single bond or —COO—.

In Formula (3), from the viewpoint of spectral characteristics, heat resistance, and light resistance, $L^2$ is preferably a single bond, —O—, —S—, or —CO—, more preferably a single bond, —O—, or —S—, and still more preferably a single bond.

In Formula (3), from the viewpoint of spectral characteristics, heat resistance, and light resistance, $A^2$ and $A^3$ are each independently preferably a single bond or an aromatic ring structure, more preferably a monocyclic aromatic ring structure, and still more preferably a benzene ring structure.

In Formula (3), from the viewpoint of spectral characteristics, heat resistance, and light resistance, it is preferable that $X^3$ and $X^4$ are each independently a single bond, —O—, —$NR^{2A}$—, —COO—, or —$CONR^{2A}$—, $L^2$ is a single bond, —O—, —S—, or —CO—, and $A^2$ and $A^3$ are each independently a single bond or an aromatic ring structure, it is more preferable that $X^3$ and $X^4$ are each independently a single bond, —O—, —$NR^{2A}$—, or —COO—, $L^2$ is a single bond, —O—, or —S—, and $A^2$ and $A^3$ are each independently a monocyclic aromatic ring structure, and it is still more preferable that $X^3$ and $X^4$ are each independently a single bond or —COO—, $L^2$ is a single bond, and $A^2$ and $A^3$ are each independently a benzene ring structure.

Dye in the above-described coloring agent having a structure represented by Formula (1) represents a coloring agent structure having a maximal absorption wavelength in a wavelength range of 650 nm to 2,000 nm (hereinafter, also referred to as a "coloring agent structure Dye").

In Dye of the present disclosure, the "coloring agent structure having a maximal absorption wavelength in a wavelength range of 650 nm to 2,000 nm" means that, in the absorption spectrum of a compound having a coloring agent structure represented by Dye in a solution, the compound has a wavelength showing the maximum absorbance in the wavelength range of 650 nm to 2,000 nm.

A measurement solvent used for measuring the absorption spectrum of the compound having the coloring agent structure represented by Dye in a solvent may be a solvent in which the compound having the coloring agent structure represented by Dye is dissolved, and from the viewpoint of solubility, preferred examples thereof include chloroform, dimethylformamide, tetrahydrofuran, and methylene chloride. For example, in a case of a compound which is dissolved in chloroform, chloroform is used as the measurement solvent. In a case where the compound is not dissolved in chloroform, methylene chloride is used. In addition, in a case where the compound is not dissolved in either chloroform and methylene chloride, dimethylformamide is used. In addition, in a case where the compound is not dissolved in chloroform, methylene chloride, and dimethylformamide, tetrahydrofuran is used.

The coloring agent structure Dye has the maximal absorption wavelength in a wavelength range of preferably 700 nm to 1,200 nm, more preferably 750 nm to 1,200 nm, and still more preferably 750 nm to 1,000 nm.

As the coloring agent structure Dye having a maximal absorption wavelength within the above-described wavelength range, it is preferable to have a coloring agent structure derived from at least one coloring agent selected from the group consisting of a pyrrolopyrrole coloring agent, a polymethine coloring agent, a diimmonium coloring agent, a phthalocyanine coloring agent, a naphthalocyanine coloring agent, a rylene coloring agent, a dithiol complex coloring agent, a triarylmethane coloring agent, a pyrromethene coloring agent, an azomethine coloring agent, an anthraquinone coloring agent, and a dibenzofuranone coloring agent.

Depending on a type of atomic group to which a coloring agent is bonded, the polymethine coloring agent may include a cyanine coloring agent, a merocyanine coloring agent, a squarylium coloring agent, a croconium coloring agent, an oxonol coloring agent, or the like. Among these, as the polymethine coloring agent, a cyanine coloring agent, a squarylium coloring agent, or an oxonol coloring agent is preferable, and a cyanine coloring agent or a squarylium coloring agent is more preferable.

As the coloring agent structure Dye, it is preferable to have a coloring agent structure derived from at least one coloring agent selected from the group consisting of a pyrrolopyrrole coloring agent, a cyanine coloring agent, a squarylium coloring agent, a diimmonium coloring agent, a phthalocyanine coloring agent, a naphthalocyanine coloring agent, and an oxonol coloring agent, and it is more preferable to have a structure derived from a squarylium coloring agent or a pyrrolopyrrole coloring agent.

—Pyrrolopyrrole Coloring Agent Structure—

As the structure derived from a pyrrolopyrrole coloring agent (pyrrolopyrrole coloring agent structure), a structure represented by Formula (PP) is preferable.

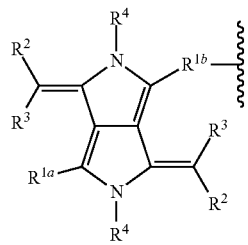

(PP)

In Formula (PP), $R^{1a}$ and $R^{1b}$ each independently represent an alkyl group, an aryl group, or a heteroaryl group, $R^2$ and $R^3$ each independently represent a hydrogen atom or a substituent, $R^2$ and $R^3$ may be bonded to each other to form a ring, $R^4$'s each independently represent a hydrogen atom, an alkyl group, an aryl group, a heteroaryl group, $-BR^{4A}R^{4B}$, or a metal atom, $R^4$ may be covalently or coordinately bonded to at least one selected from $R^{1a}$, $R^{1b}$, or $R^3$, $R^{4A}$ and $R^{4B}$ each independently represent a substituent, and a wavy line represents a linking portion with $L^1$ in Formula (1).

With regard to details of Formula (PP), reference can be made to the description in paragraph Nos. 0017 to 0047 of JP2009-263614A, paragraph Nos. 0011 to 0036 of JP2011-68731A, and paragraph Nos. 0010 to 0024 of WO2015/166873A, the contents of which are incorporated herein by reference.

In Formula (PP), $R^{1a}$ and $R^{1b}$ are each independently preferably an aryl group or a heteroaryl group, and more preferably an aryl group. In addition, the alkyl group, aryl group, and heteroaryl group represented by $R^{1a}$ and $R^{1b}$ may have a substituent or may be unsubstituted. Examples of the substituent include a substituent T described later.

In Formula (PP), $R^2$ and $R^3$ each independently represent a hydrogen atom or a substituent. Examples of the substituent include the substituent T described later. At least one of $R^2$ or $R^3$ is preferably an electron withdrawing group, more preferably a cyano group, a carboxy group, an acyl group, an alkoxycarbonyl group, an aryloxycarbonyl group, a carbamoyl group, an alkylcarbonyl group, an arylcarbonyl group, an alkylsulfonyl group, or an arylsulfonyl group, and still more preferably a cyano group.

In Formula (PP), it is preferable that $R^2$ represents an electron withdrawing group (preferably, a cyano group) and $R^3$ represents a heteroaryl group. It is preferable that the heteroaryl group is a 5-membered ring or a 6-membered ring. In addition, the heteroaryl group is preferably a monocyclic ring or a fused ring, more preferably a monocyclic ring or a fused ring composed of 2 to 8 rings, and still more preferably a monocyclic ring or a fused ring composed of 2 to 4 rings. The number of heteroatoms constituting the heteroaryl group is preferably 1 to 3 and more preferably 1 or 2. Examples of the heteroatom include a nitrogen atom, an oxygen atom, and a sulfur atom. It is preferable that the heteroaryl group has one or more nitrogen atoms. Two $R^2$'s in Formula (PP) may be the same or different from each other. In addition, two $R^3$'s in Formula (PP) may be the same or different from each other.

In Formula (PP), $R^4$ is preferably a hydrogen atom, an alkyl group, an aryl group, a heteroaryl group, or a group represented by $-BR^{4A}R^{4B}$, more preferably a hydrogen atom, an alkyl group, an aryl group, or a group represented by $-BR^{4A}R^{4B}$, and still more preferably a group represented by $-BR^{4A}R^{4B}$. As the substituent represented by $R^{4A}$ and $R^{4B}$, a halogen atom, an alkyl group, an alkoxy group, an aryl group, or a heteroaryl group is preferable, an alkyl group, an aryl group, or a heteroaryl group is more preferable, and an aryl group is particularly preferable. These groups may further have a substituent. Two $R^4$'s in Formula (PP) may be the same or different from each other. $R^{4A}$ and $R^{4B}$ may be bonded to each other to form a ring.

In a case where the coloring agent structure Dye in Formula (1) is a pyrrolopyrrole coloring agent structure and n is 2, the coloring agent represented by Formula (1) is preferably a structure represented by Formula (4-1).

A compound having the structure represented by Formula (4-1), that is, a compound according to the embodiment of the present disclosure is a novel compound.

The compound according to the embodiment of the present disclosure can be suitably used as a coloring agent or an infrared absorbing coloring agent, and can be more suitably used as an infrared absorbing coloring agent.

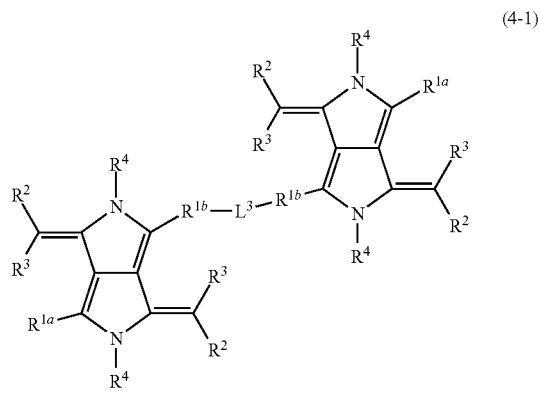

(4-1)

In Formula (4-1), $R^{1a}$ and $R^{1b}$ each independently represent an aryl group or a heteroaryl group, $R^2$ and $R^3$ each independently represent a hydrogen atom or a substituent, $R^2$ and $R^3$ may be bonded to each other to form a ring, $R^4$'s each independently represent a hydrogen atom, an alkyl group, an aryl group, a heteroaryl group, $-BR^{4A}R^{4B}$, or a metal atom, $R^4$ may be covalently or coordinately bonded to at least one selected from the group consisting of $R^{1a}$, $R^{1b}$, and $R^3$, $R^{4A}$ and $R^{4B}$ each independently represent a hydrogen atom or a substituent, and $L^3$ represents a group represented by Formula (2) or Formula (3).

$R^{1a}$, $R^{1b}$, $R^2$, $R^3$, and $R^4$ in Formula (4-1) have the same meaning as $R^{1a}$, $R^{1b}$, $R^2$, $R^3$, and $R^4$ in Formula (PP), respectively, and the preferred aspects thereof are also the same.

\*—$X^1$-$A^1$-$X^2$—\*      Formula (2)

In Formula (2), $X^1$ and $X^2$ each independently represent a single bond, $-O-$, $-S-$, $-NR^{1A}-$, $-CO-$, $-COO-$, $-OCOO-$, $-SO_2NR^{1A}-$, $-CONR^{1A}-$, $-OCONR^{1A}-$ or $-NR^{1A}CONR^{1A}-$, $R^{1A}$ represents a hydrogen atom, an alkyl group, or an aryl group, $A^1$ represents a single bond, an aliphatic ring structure, an aromatic ring structure, or a heterocyclic ring structure, and \* represents a connection position with Dye, where in a case where A is a single bond, both $X^1$ and $X^2$ are not single bonds.

$X^1$, $X^2$, $R^{1A}$, and $A^1$ in Formula (4-1) have the same meaning as $X^1$, $X^2$, $R^{1A}$, and $A^1$ in Formula (2) described above, respectively, and the preferred aspects thereof are also the same.

\*-$X^3$-$A^2$-$L^2$-$A^3$-$X^4$—\*      Formula (3)

In Formula (3), $X^3$ and $X^4$ each independently represent a single bond, $-O-$, $-S-$, $-NR^{2A}-$, $-CO-$, $-COO-$, $-OCOO-$, $-SO_2NR^{2A}-$, $-CONR^{2A}-$, $-OCONR^{2A}-$, or $-NR^{2A}CONR^{2A}-$, $R^{2A}$ represents a hydrogen atom or an alkyl group, $L^2$ represents a single bond, $-O-$, $-S-$, $NR^{2B}-$, $-CO-$, $-COO-$, $-OCOO-$, $-SO_2NR^{2B}-$, $-CONR^{2B}-$, $-OCONR^{2B}-$, $-NR^{2B}CONR^{2B}-$, an alkylene group having 1 to 6 carbon atoms, an alkenyl group, an alkynyl group, an aromatic ring structure, or a group of a combination of these groups, $R^{2B}$ represents a hydrogen atom or an alkyl group, and $A^2$ and $A^3$ each independently represent an aliphatic ring structure, an aromatic ring structure, or a heterocyclic ring structure.

$X^3$, $X^4$, $R^{2A}$, $R^{2B}$, $L^2$, $A^2$, and $A^3$ in Formula (4-1) have the same meaning as $X^3$, $X^4$, $R^{2A}$, $R^{2B}$, $L^2$, $A^2$, and $A^3$ in Formula (2) described above, respectively, and the preferred aspects thereof are also the same.

The coloring agent represented by Formula (1) is preferably a structure represented by Formula (4-2).

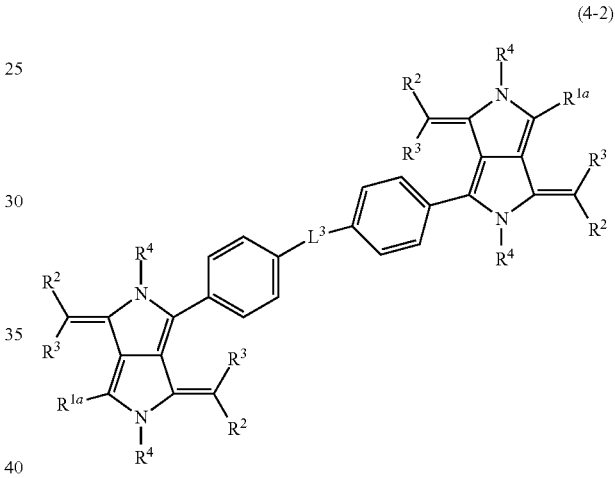

(4-2)

In Formula (4-2), $R^{1a}$ represents an aryl group or a heteroaryl group, $R^2$ and $R^3$ each independently represent a hydrogen atom or a substituent, $R^2$ and $R^3$ may be bonded to each other to form a ring, $R^4$'s each independently represent a hydrogen atom, an alkyl group, an aryl group, a heteroaryl group, $-BR^{4A}R^{4B}$ or a metal atom, $R^4$ may be covalently or coordinately bonded to at least one selected from the group consisting of $R^{1a}$, $R^{1b}$ and $R^3$, $R^{4A}$ and $R^{4B}$ each independently represent a hydrogen atom or a substituent, and $L^3$ represents a group represented by Formula (2) or Formula (3).

$R^{1a}$, $R^2$, $R^3$, and $R^4$ in Formula (4-2) have the same meaning as $R^{1a}$, $R^2$, $R^3$, and $R^4$ in Formula (PP), respectively, and the preferred aspects thereof are also the same.

$L^3$ in Formula (4-2) has the same meaning as $L^3$ in Formula (4-1), and the preferred aspect thereof is also the same.

Examples of the pyrrolopyrrole compound include compounds described in paragraph Nos. 0016 to 0058 of JP2009-263614A and compounds described in paragraph Nos. 0037 to 0052 of JP2011-68731A, the contents of which are incorporated herein by reference.

—Squarylium Coloring Agent Structure—

As the squarylium coloring agent structure, a structure derived from a compound represented by Formula (SQ) is preferable.

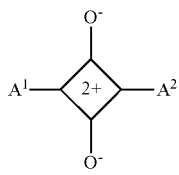
(SQ)

In Formula (SQ), $A^1$ and $A^2$ each independently represent an aryl group, a heterocyclic group, or a group represented by Formula (Ax). However, at least one of $A^1$ or $A^2$ represents a group linked to $L^1$ in Formula (1).

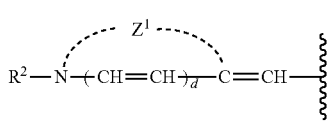
(Ax)

In Formula (Ax), $Z^1$ represents a non-metal atom atomic group forming a nitrogen-containing heterocyclic ring, $R^2$ represents an alkyl group, an alkenyl group, or an aralkyl group, d represents 0 or 1, and a wavy line represents a bonding site. With regard to details of Formula (SQ), reference can be made to the description in paragraph Nos. 0020 to 0049 of JP2011-208101A, paragraph Nos. 0043 to 0062 of JP6065169B, and paragraph Nos. 0024 to 0040 of WO2016/181987A, the contents of which are incorporated herein by reference.

As shown below, a cation in Formula (SQ) is present without being localized.

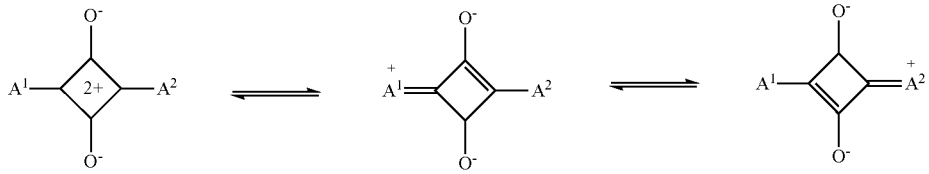

The squarylium coloring agent is preferably a compound represented by Formula (5).

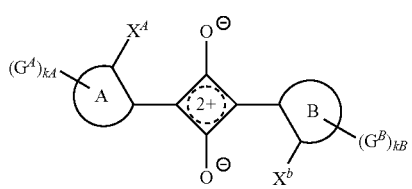
(5)

In Formula (5), a ring A and a ring B each independently represent an aromatic ring or a heteroaromatic ring, $X^A$ and $X^B$ each independently represent a substituent, $G^A$ and $G^B$ each independently represent a substituent, kA represents an integer of 0 to nA, kB represents an integer of 0 to nB, nA and nB each independently represent a maximum integer in which $G^A$ or $G^B$ can be substituted to the ring A or the ring B, $X^A$ and $G^A$ or $X^B$ and $G^B$ may be bonded to each other to form a ring, and in a case where a plurality of $G^A$'s or a plurality of $G^B$'s are present, $G^A$'s or $G^B$'s may be bonded to each other to form a ring structure. However, at least one of $X^A$, $X^B$, $G^A$, or $G^B$ represents a group linked to $L^1$ in Formula (1).

$G^A$ and $G^B$ each independently represent a substituent. Examples of the substituent include a halogen atom, a cyano group, a nitro group, an alkyl group, an alkenyl group, an alkynyl group, an aryl group, a heteroaryl group, an aralkyl group, —$OR^{10}$, —$COR^{11}$, —$COOR^{12}$, —$OCOR^{13}$, —$NR^{14}R^{15}$, —$NHCOR^{16}$, —$CONR^{17}R^{18}$, —$NHCONR^{19}R^{20}$, —$NHCOOR^{21}$, —$SR^{22}$, —$SO_2R^{23}$, —$SO_2OR^{24}$, —$NHSO_2R^{25}$, and —$SO_2NR^{26}R^{27}$. $R^{10}$ to $R^{27}$ each independently represent a hydrogen atom, an alkyl group, an alkenyl group, an alkynyl group, an aryl group, a heteroaryl group, or an aralkyl group. In a case where $R^{12}$ in —$COOR^{12}$ is a hydrogen atom (that is, a carboxy group), the hydrogen atom may be dissociated (that is, a carbonate group) or may be in a state of salt. In addition, in a case where $R^{24}$ in —$SO_2OR^{24}$ is a hydrogen atom (that is, a sulfo group), the hydrogen atom may be dissociated (that is, a sulfonate group) or may be in a state of salt.

Examples of the halogen atom include a fluorine atom, a chlorine atom, a bromine atom, and an iodine atom.

The alkyl group preferably has 1 to 20 carbon atoms, more preferably has 1 to 15 carbon atoms, and still more preferably has 1 to 8 carbon atoms. The alkyl group may be linear, branched, or cyclic, and is preferably a linear or branched alkyl group. The alkenyl group preferably has 2 to 20 carbon atoms, more preferably has 2 to 12 carbon atoms, and still more preferably has 2 to 8 carbon atoms. The alkenyl group may be linear, branched, or cyclic, and is preferably a linear or branched alkenyl group. The alkynyl group preferably has 2 to 40 carbon atoms, more preferably has 2 to 30 carbon atoms, and still more preferably has 2 to 25 carbon atoms. The alkynyl group may be linear, branched, or cyclic, and is preferably a linear or branched alkynyl group. The aryl group preferably has 6 to 30 carbon atoms, more preferably has 6 to 20 carbon atoms, and still more preferably has 6 to 12 carbon atoms. An alkyl portion in the aralkyl group is the same as the above-described alkyl group. An aryl portion in the aralkyl group is the same as the above-described aryl group. The aralkyl group preferably has 7 to 40 carbon atoms, more preferably has 7 to 30 carbon atoms, and still more preferably has 7 to 25 carbon atoms.

The heteroaryl group is preferably a monocyclic ring or a fused ring, more preferably a monocyclic ring or a fused ring composed of 2 to 8 rings, and still more preferably a monocyclic ring or a fused ring composed of 2 to 4 rings. The number of heteroatoms constituting a ring of the heteroaryl group is preferably 1 to 3. As the heteroatom constituting the ring of the heteroaryl group, a nitrogen atom, an oxygen atom, or a sulfur atom is preferable. It is preferable that the heteroaryl group is a 5-membered ring or a 6-membered ring. The number of carbon atoms constituting the ring of the heteroaryl group is preferably 3 to 30, more preferably 3 to 18, and still more preferably 3 to 12. Examples of the heteroaryl group include a pyridine ring, a piperidine ring, a furan ring group, a furfuran ring, a thiophene ring, a pyrrole ring, a quinoline ring, a morpholine ring, an indole ring, an imidazole ring, a pyrazole ring, a carbazole ring, a phenothiazine ring, a phenoxazine ring, an indoline ring, a thiazole ring, a pyrazine ring, a thiadiazine ring, a benzoquinoline ring, and a thiadiazole ring.

The alkyl group, the alkenyl group, the alkynyl group, the aralkyl group, the aryl group, and the heteroaryl group may have a substituent or may be unsubstituted. Examples of the substituent include the substituent T described later.

$X^A$ and $X^B$ each independently represent a substituent. As the substituent, a group having an active hydrogen is preferable, —OH, —SH, —COOH, —SO$_3$H, —NR$^{X1}$R$^{X2}$, —NHCOR$^{X1}$, —CONR$^{X1}$R$^{X2}$, —NHCONR$^{X1}$R$^{X2}$, —NHCOOR$^{X1}$, —NHSO$_2$R$^{X1}$, —B(OH)$_2$, or —PO(OH)$_2$ is more preferable, and —OH, —SH, or —NR$^{X1}$R$^{X2}$ is still more preferable. R$^{X1}$ and R$^{X2}$ each independently represent a hydrogen atom or a substituent. Examples of the substituent include an alkyl group, an alkenyl group, an alkynyl group, an aryl group, or a heteroaryl group. An alkyl group is preferable. The alkyl group is preferably a linear or branched alkyl group. Details of the alkyl group, alkenyl group, alkynyl group, aryl group, and heteroaryl group are synonymous with the ranges described in $G^A$ and $G^B$.

The ring A and the ring B each independently represent an aromatic ring or a heteroaromatic ring. The aromatic ring and heteroaromatic ring may be a monocyclic ring or a fused ring. Specific examples of the aromatic ring and heteroaromatic ring include a benzene ring, a naphthalene ring, a pentalene ring, an indene ring, an azulene ring, a heptalene ring, an indecene ring, a perylene ring, a pentacene ring, an acenaphthene ring, a phenanthrene ring, an anthracene ring, a naphthacene ring, a chrysene ring, a triphenylene ring, a fluorene ring, a biphenyl ring, a pyrrole ring, a furan ring, a thiophene ring, an imidazole ring, an oxazole ring, a thiazole ring, a pyridine ring, a pyrazine ring, a pyridine ring, a pyridazine ring, an indridine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring, and a phenazine ring, and a benzene ring or a naphthalene ring is preferable.

The aromatic ring and heteroaromatic ring may be unsubstituted or may have a substituent. Examples of the substituent include the substituents described in $G^A$ and $G^B$.

$X^A$ and $G^A$, or $X^B$ and $G^B$ may be bonded to each other to form a ring, and in a case where a plurality of $G^A$'s or a plurality of $G^B$'s are present, $G^A$'s or $G^B$'s may be bonded to each other to form a ring. It is preferable that the ring is a 5-membered ring or a 6-membered ring. The ring may be a monocyclic ring or a complex ring. In a case where $X^A$ and $G^A$, $X^B$ and $G^B$, $G^A$'s, or $G^B$'s are bonded to each other to form a ring, these may be directly bonded to form a ring, or may be bonded through a divalent linking group selected from the group consisting of an alkylene group, —CO—, —O—, —NH—, —BR—, and a combination thereof to form a ring. It is preferable that $X^A$ and $G^A$, $X^B$ and $G^B$, $G^A$'s, or $G^B$'s are bonded to each other through —BR— to form a ring. R represents a hydrogen atom or a substituent. Examples of the substituent include the substituents described in $G^A$ and $G^B$. An alkyl group or an aryl group is preferable.

kA represents an integer of 0 to nA, kB represents an integer of 0 to nB, nA represents the maximum integer in which $G^A$ can be substituted to the ring A, and nB represents the maximum integer in which $G^B$ can be substituted to the ring B. kA and kB are each independently preferably 0 to 4, more preferably 0 to 2, and particularly preferably 0 or 1.

Examples of one embodiment of the squarylium coloring agent include a compound represented by Formula (6). This compound has excellent heat resistance.

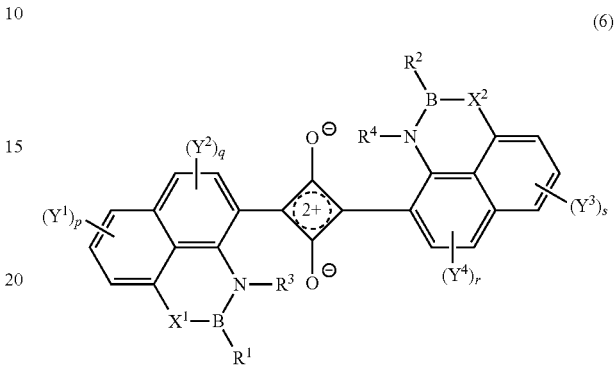

(6)

In Formula (6), $R^1$ and $R^2$ each independently represent a substituent, $R^3$ and $R^4$ each independently a hydrogen atom or an alkyl group, $X^1$ and $X^2$ each independently an oxygen atom or —N(R$^5$)—, R$^5$ represents a hydrogen atom, an alkyl group, an aryl group, or a heteroaryl group, $Y^1$ to $Y^4$ each independently represent a substituent, $Y^1$ and $Y^2$, or $Y^3$ and $Y^4$ may be bonded to each other to form a ring, in a case where a plurality of $Y^1$ to $Y^4$ are present, each $Y^1$ to $Y^4$ may be bonded to each other to form a ring, p and s each independently represent an integer of 0 to 3, and q and r each independently represent an integer of 0 to 2.

However, at least one of $Y^1$, $Y^2$, $Y^3$, or $Y^4$ represents a group linked to $L^1$ in Formula (1).

Examples of the substituent represented by $R^1$, $R^2$, and $Y^1$ to $Y^4$ include the substituents described in $G^A$ and $G^B$. $R^3$ and $R^4$ are each independently preferably a hydrogen atom, a methyl group, or an ethyl group, more preferably a hydrogen atom or a methyl group, and particularly preferably a hydrogen atom.

$X^1$ and $X^2$ each independently represent an oxygen atom (—O—) or —N(R$^5$)—. $X^1$ and $X^2$ may be the same or different from each other, but it is preferable that $X^1$ and $X^2$ are the same. R$^5$ represents a hydrogen atom, an alkyl group, an aryl group, or a heteroaryl group. R$^5$ is preferably a hydrogen atom, an alkyl group, or an aryl group. The alkyl group, aryl group, and heteroaryl group represented by R$^5$ may be an unsubstituted group or may have a substituent. Examples of the substituent include the substituents described in $G^A$ and $G^B$. The alkyl group preferably has 1 to 20 carbon atoms, more preferably has 1 to 10 carbon atoms, still more preferably has 1 to 4 carbon atoms, and particularly preferably has 1 or 2 carbon atoms. The alkyl group may be linear or branched. The number of carbon atoms in the aryl group is preferably 6 to 20 and more preferably 6 to 12. The heteroaryl group may be monocyclic or polycyclic. The number of heteroatoms constituting a ring of the heteroaryl group is preferably 1 to 3. As the heteroatom constituting the ring of the heteroaryl group, a nitrogen atom, an oxygen atom, or a sulfur atom is preferable. The number of carbon atoms constituting the ring of the heteroaryl group is preferably 3 to 30, more preferably 3 to 18, and still more preferably 3 to 12.

—Croconium Coloring Agent Structure—

As the croconium coloring agent structure, a structure derived from a compound represented by Formula (CR) is preferable.

(CR)

In Formula (CR), $A^3$ and $A^4$ each independently represent an aryl group, a heterocyclic group, or a group represented by Formula (Ax), in which at least one of $A^3$ or $A^4$ represents a group linked to $L^1$ in Formula (1).

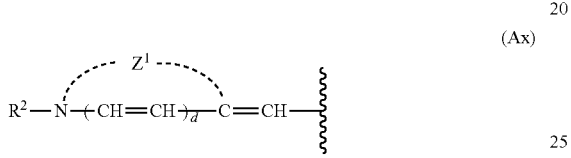

(Ax)

In Formula (Ax), $Z^1$ represents a non-metal atom atomic group forming a nitrogen-containing heterocyclic ring, $R^2$ represents an alkyl group, an alkenyl group, or an aralkyl group, d represents 0 or 1, and a wavy line represents a bonding site. With regard to details of Formula (CR), reference can be made to the compound of Eur. J. Org. Chem. 2017, pp. 3897 to 3911, the content of which is incorporated herein by reference.

As shown below, a cation in Formula (CR) is present without being localized.

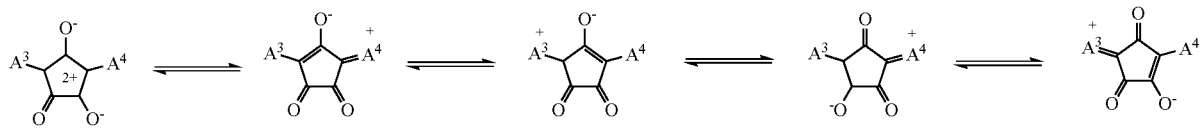

—Pyrromethene Coloring Agent Structure—

As the pyrromethene coloring agent structure, a structure derived from a compound represented by Formula (BDP) is preferable.

(BDP)

In Formula (BDP), Y represents $CR_7$ or N, $R_7$ represents a hydrogen atom or a substituent, $R_1$ to $R_6$ each independently represent a hydrogen atom or a substituent, $R_1$ and $R_3$, $R_3$ and $R_5$, $R_2$ and $R_4$, or $R_4$ and $R_6$ may be linked to each other to form a cyclic structure, $X_1$ and $X_2$ each independently represent a halogen atom, an oxygen atom, a hydroxy group, an alkoxy group, or an aryloxy group, $X_1$ and $X_2$ may be bonded to each other to form a cyclic structure, $X_1$ may be bonded to $R_5$ to form a cyclic structure, and $X_2$ may be bonded to $R_6$ to form a cyclic structure.

$R_5$ and $R_6$ are each independently preferably an aryl group or a heteroaryl group.

It is preferable that $R_1$ and $R_3$, or $R_2$ and $R_4$ are linked to each other to form a benzene ring or a naphthalene ring.

With regard to details of Formula (BDP), reference can be made to the compounds described in Chem. Soc. Rev., 2014, 43, pp. 4778 to 4823, JP2016-166284A, JP2018-123093A, and JP2019-77673A, the contents of which are incorporated herein by reference.

Specific examples of the coloring agent having a structure represented by Formula (1) include the following A-ppb-1 to A-ppb-36, A-sq-1 to A-sq-5, A-cr-1 to A-cr-5, A-bdp-1 to A-bdp-8, A-ryl-1, A-ryl-2, A-id-1, and A-id-2, but it is needless to say that the present disclosure is not limited to these coloring agents.

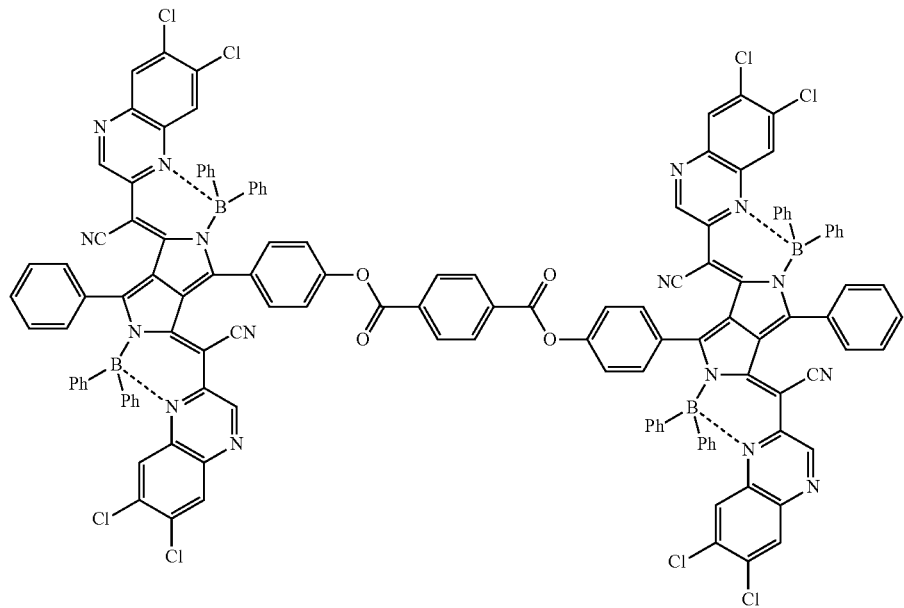
A-ppb-1
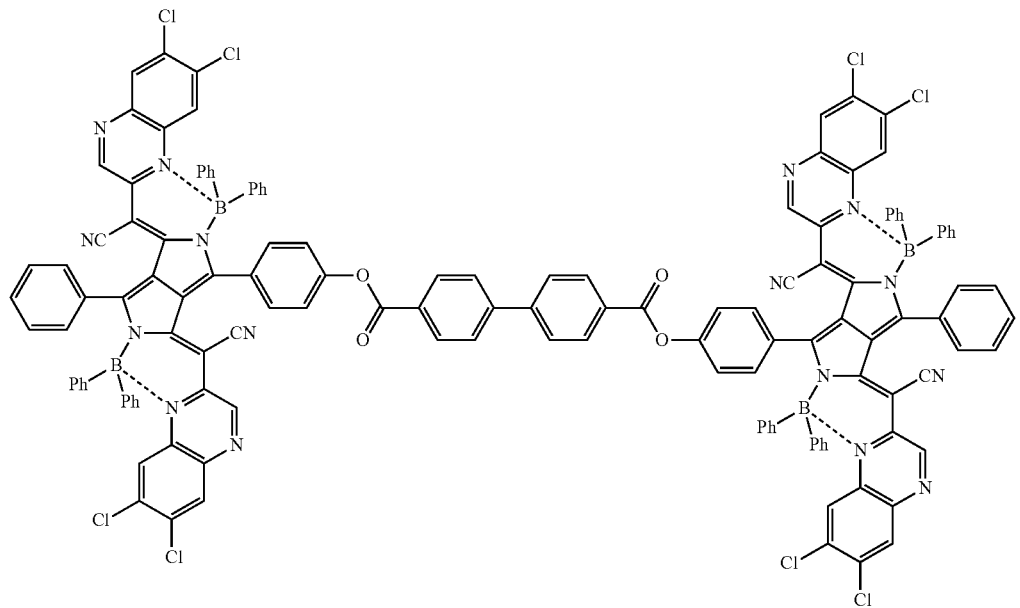
A-ppb-2

-continued
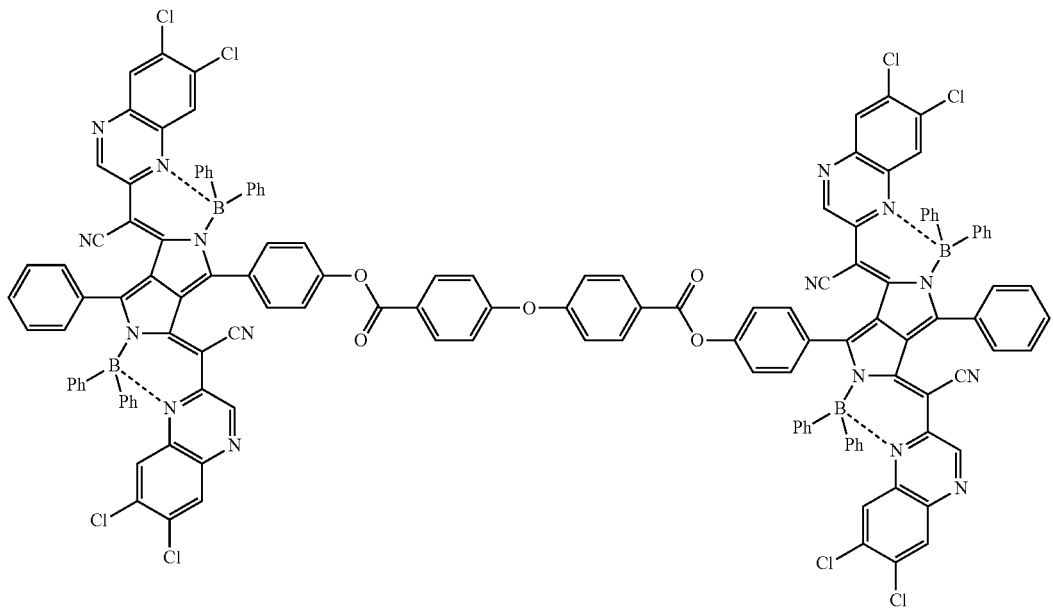
A-ppb-3
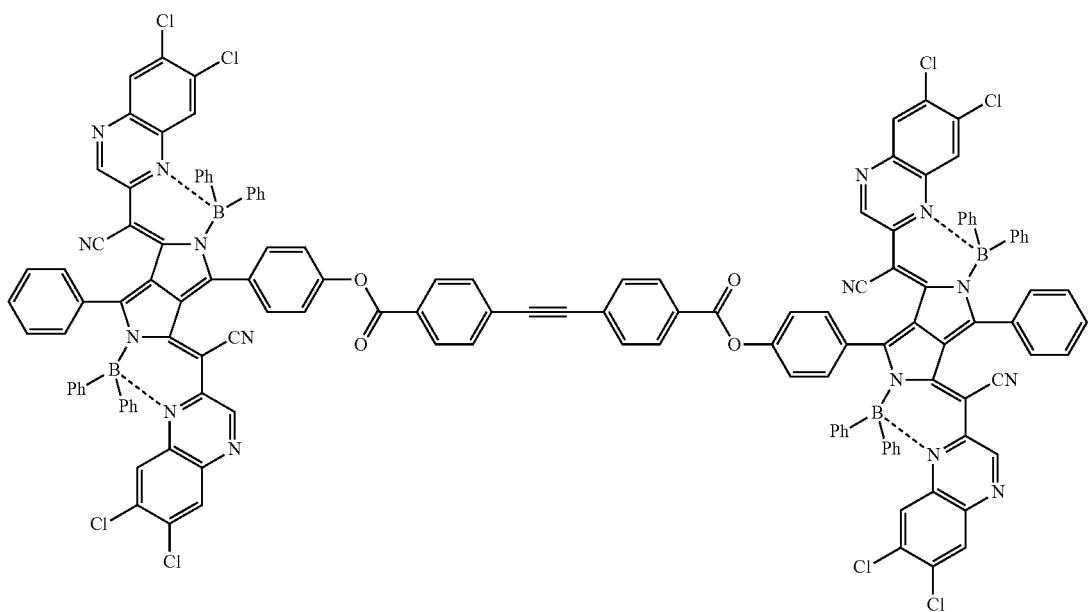
A-ppb-4

-continued
A-ppb-5
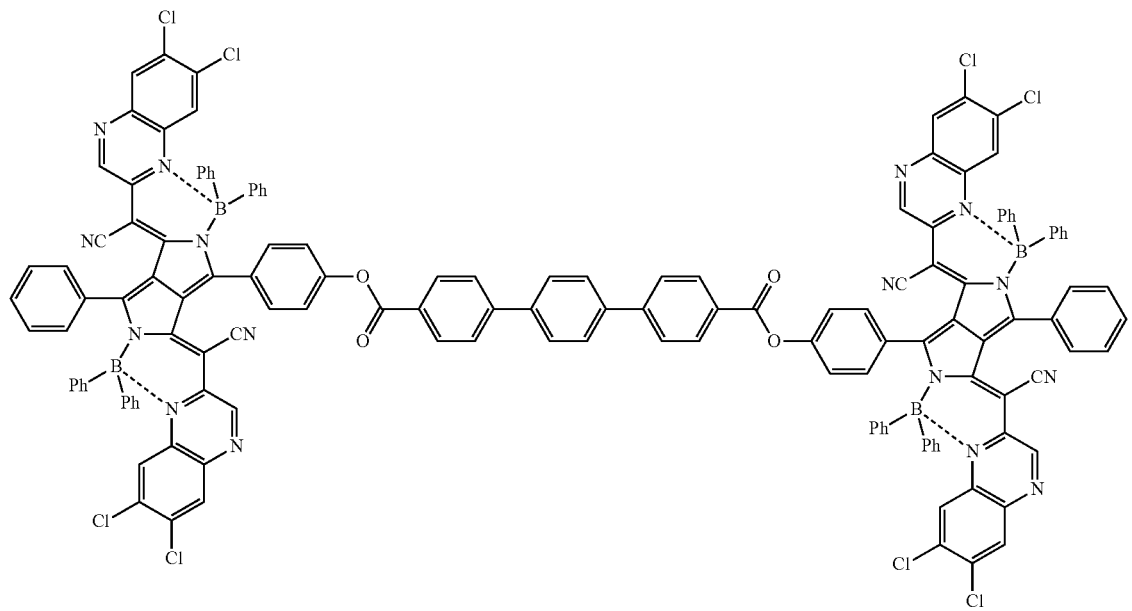
A-ppb-6
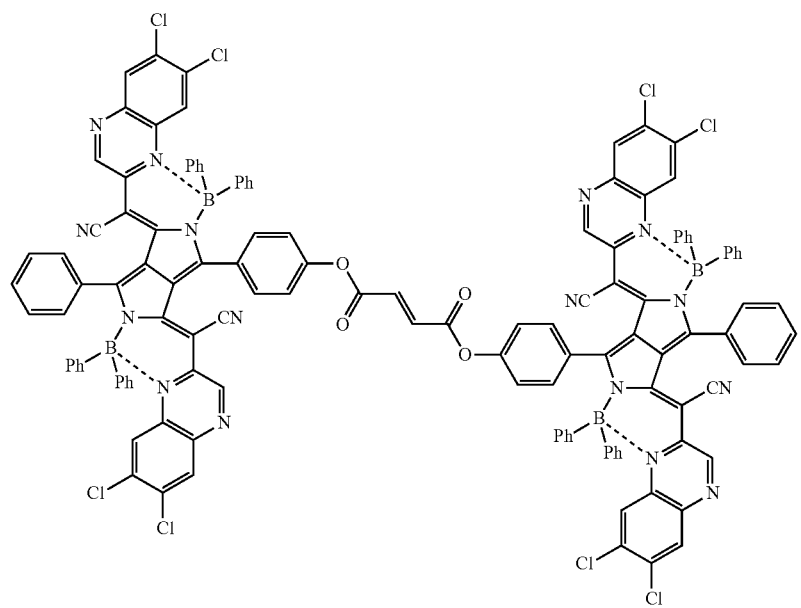

A-ppb-7
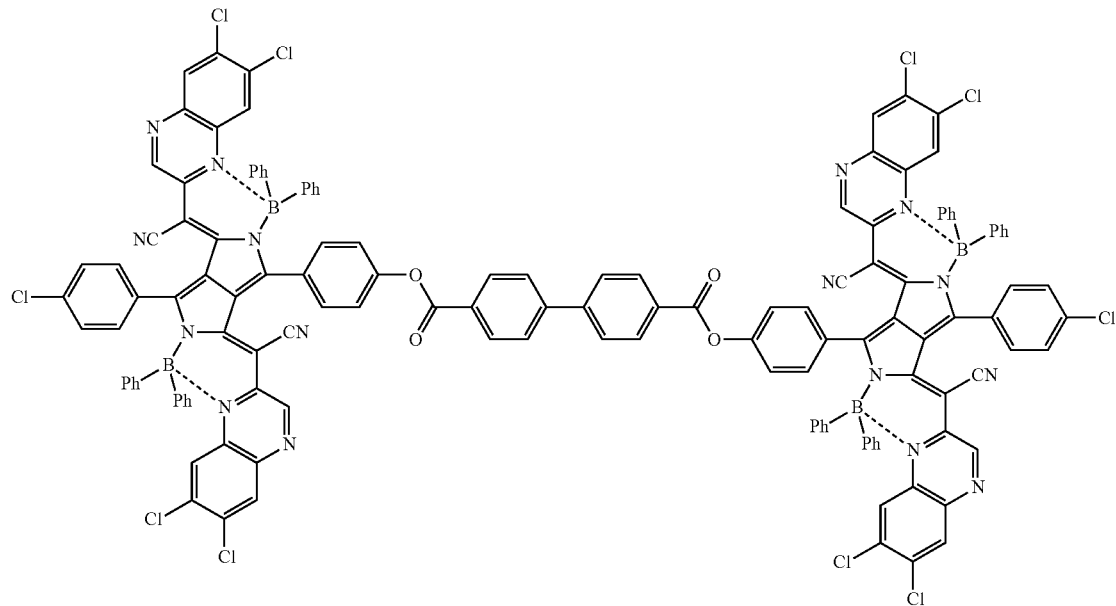
A-ppb-8
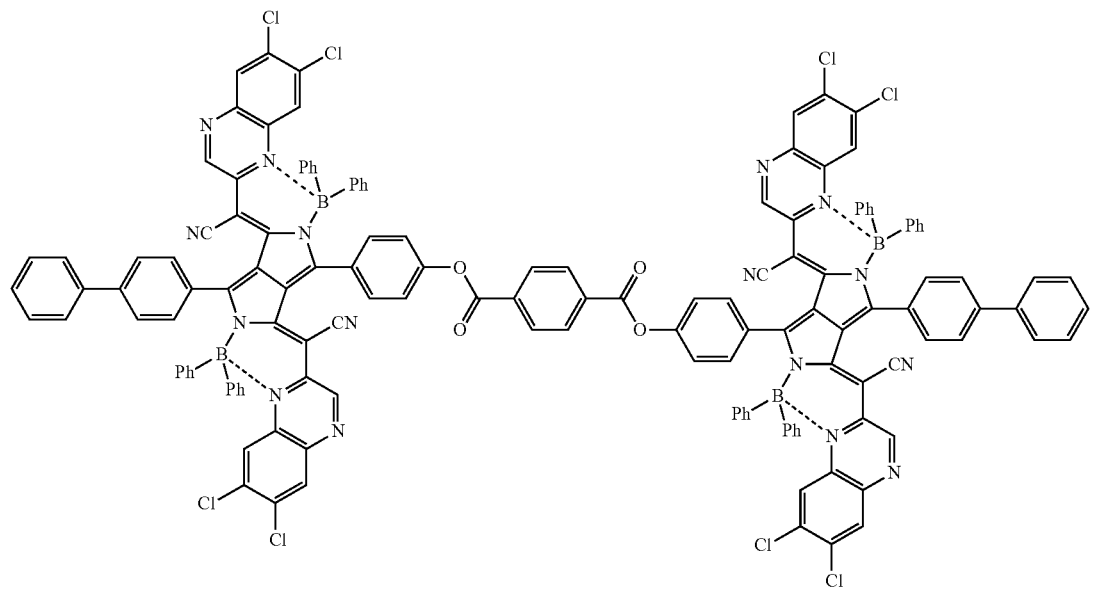

-continued
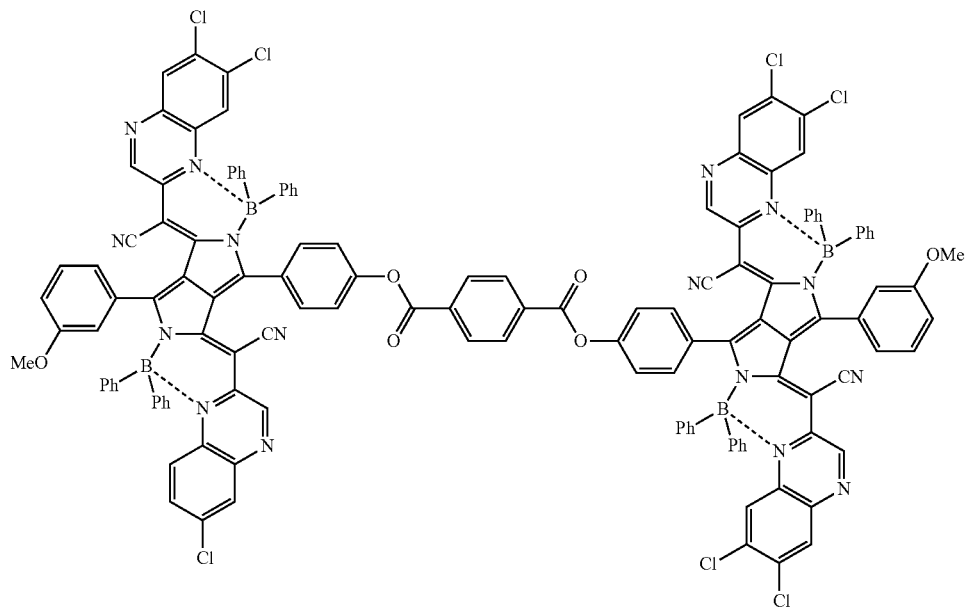
A-ppb-9
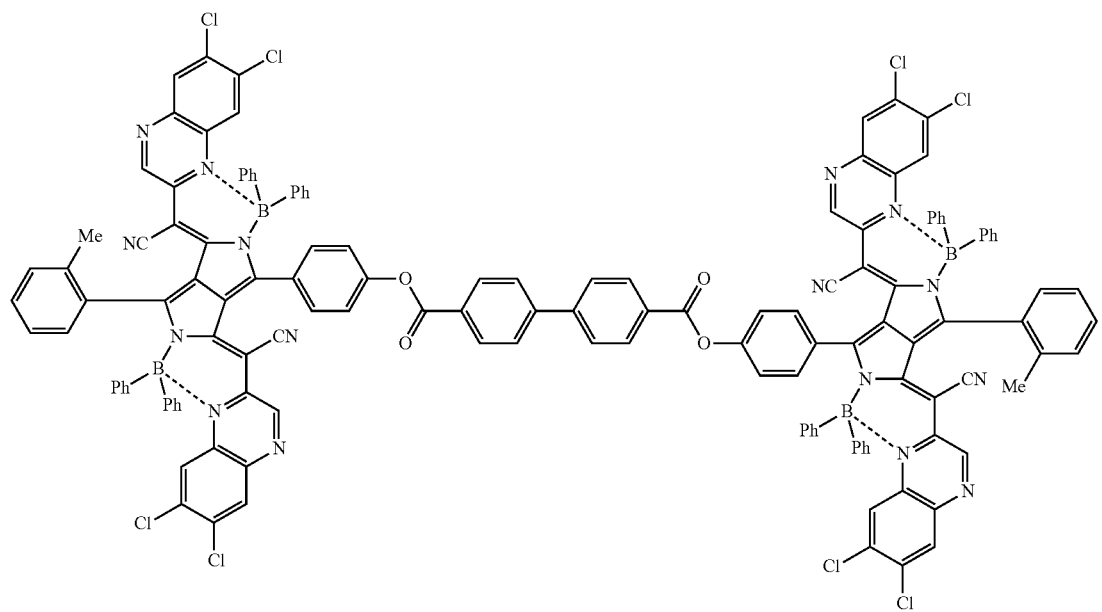
A-ppb-10

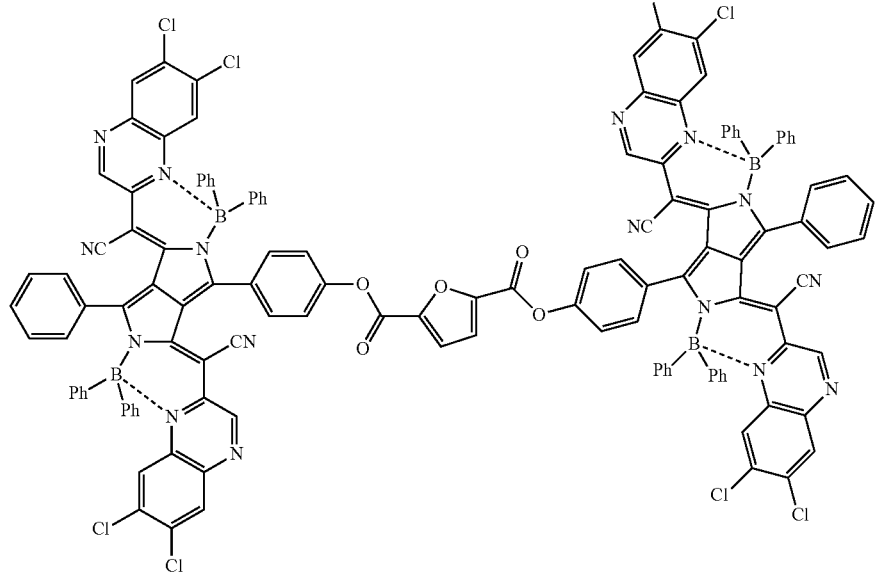
A-ppb-11
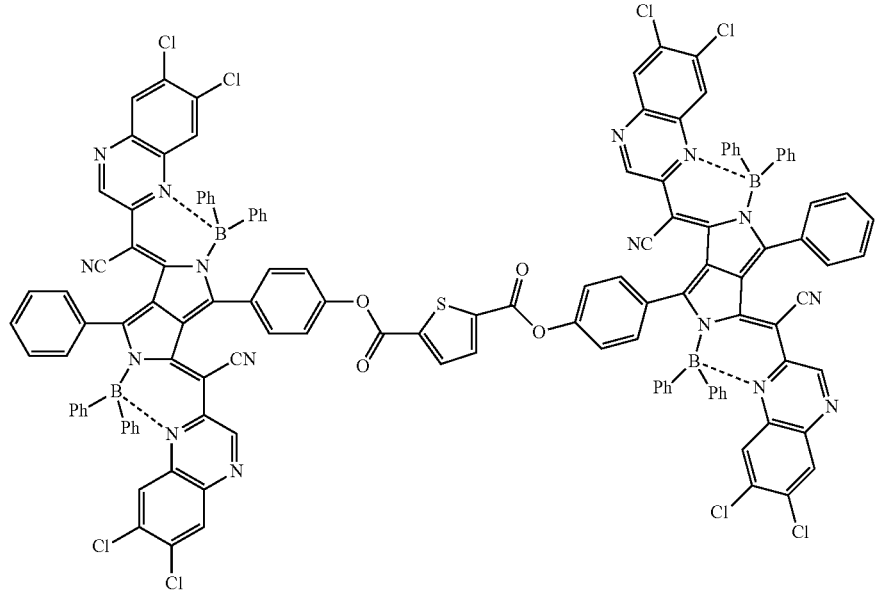
A-ppb-12

-continued
A-ppb-13
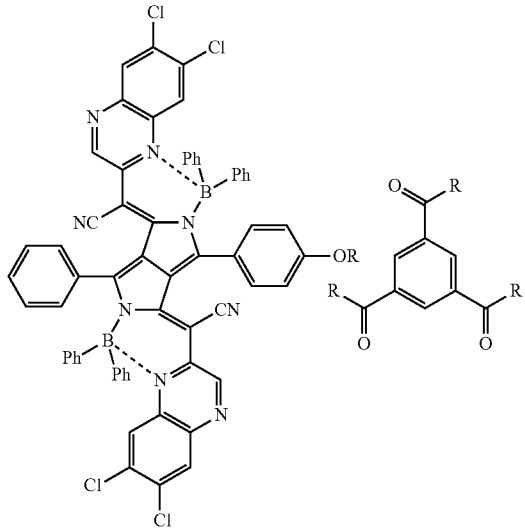
A-ppb-14
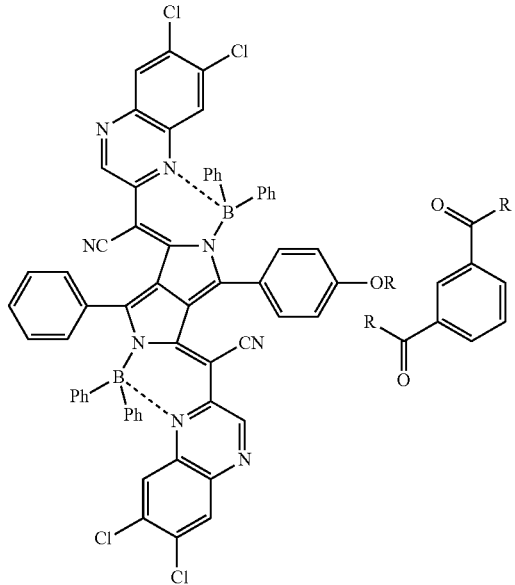
A-ppb-15
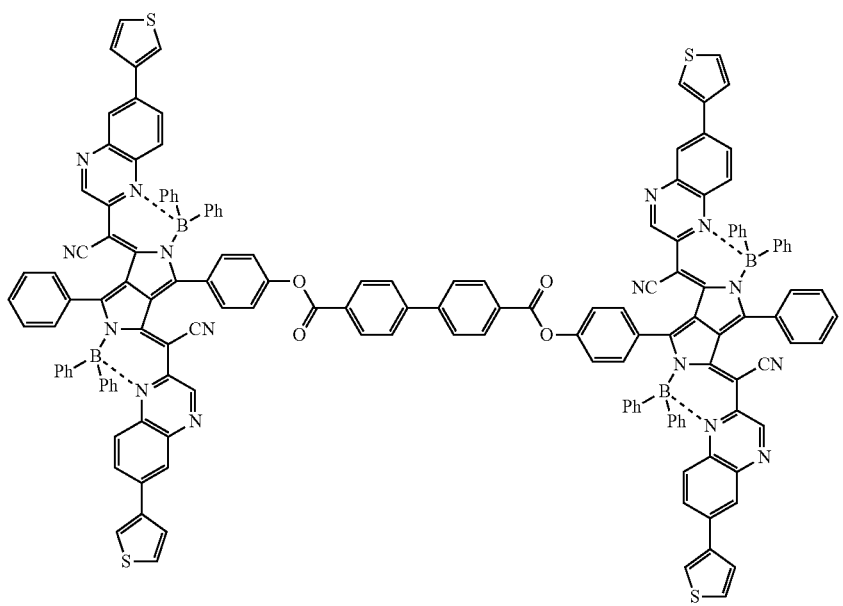

-continued
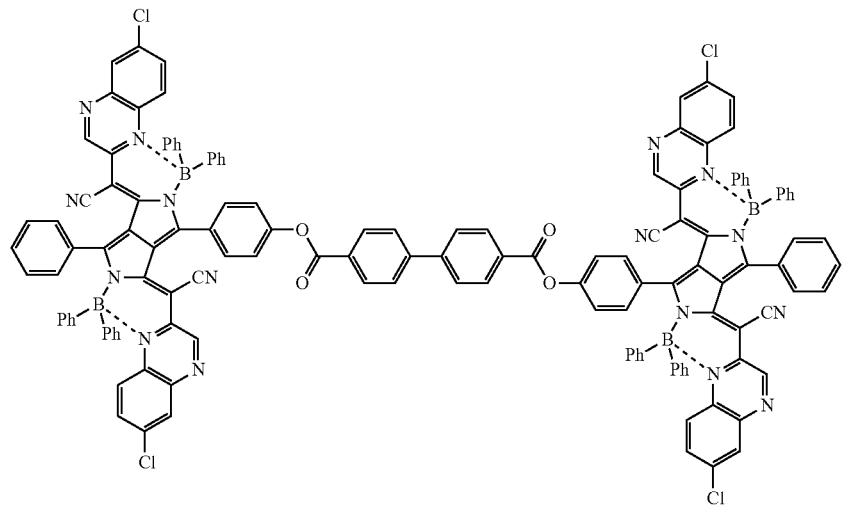
A-ppb-16
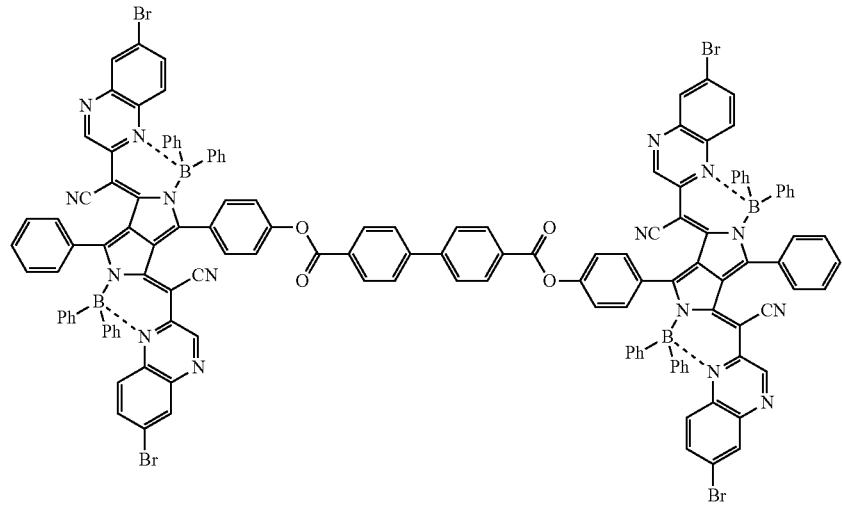
A-ppb-17
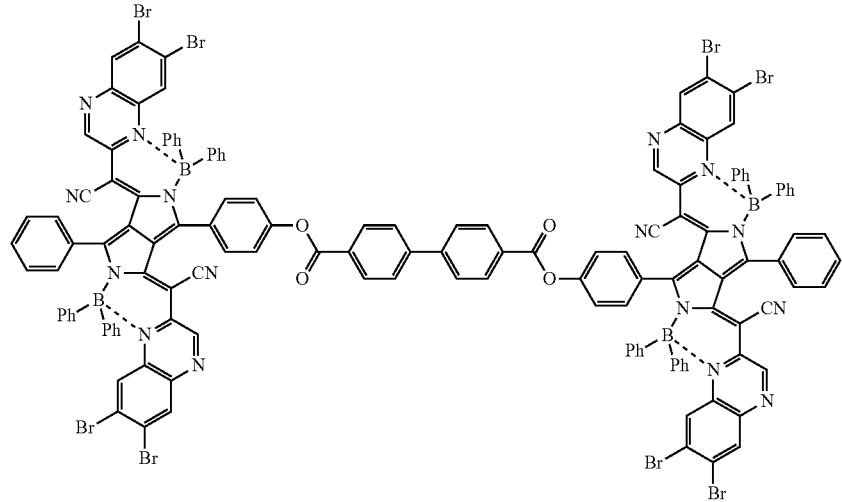
A-ppb-18

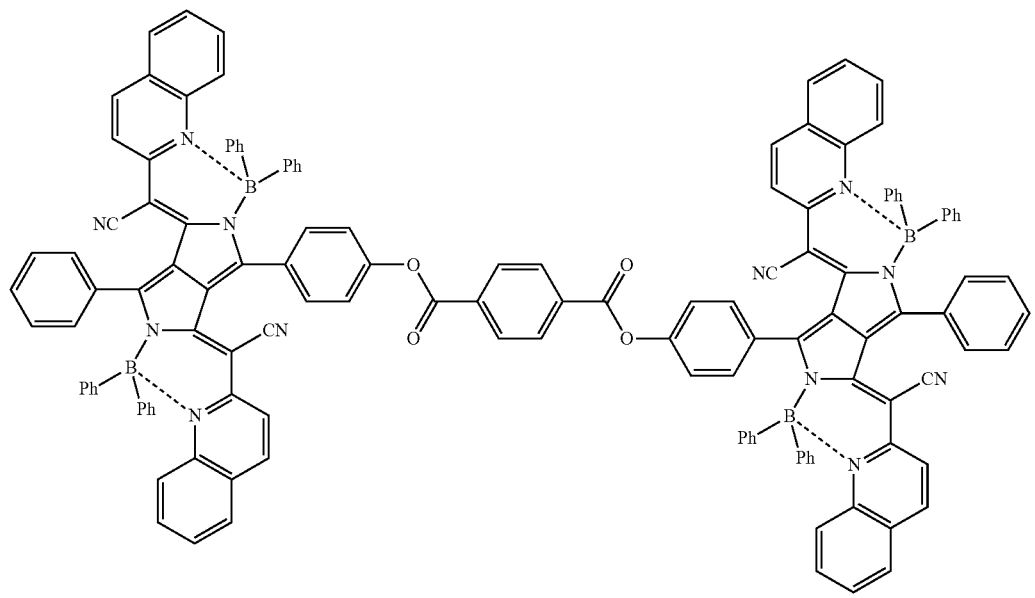
A-ppb-19
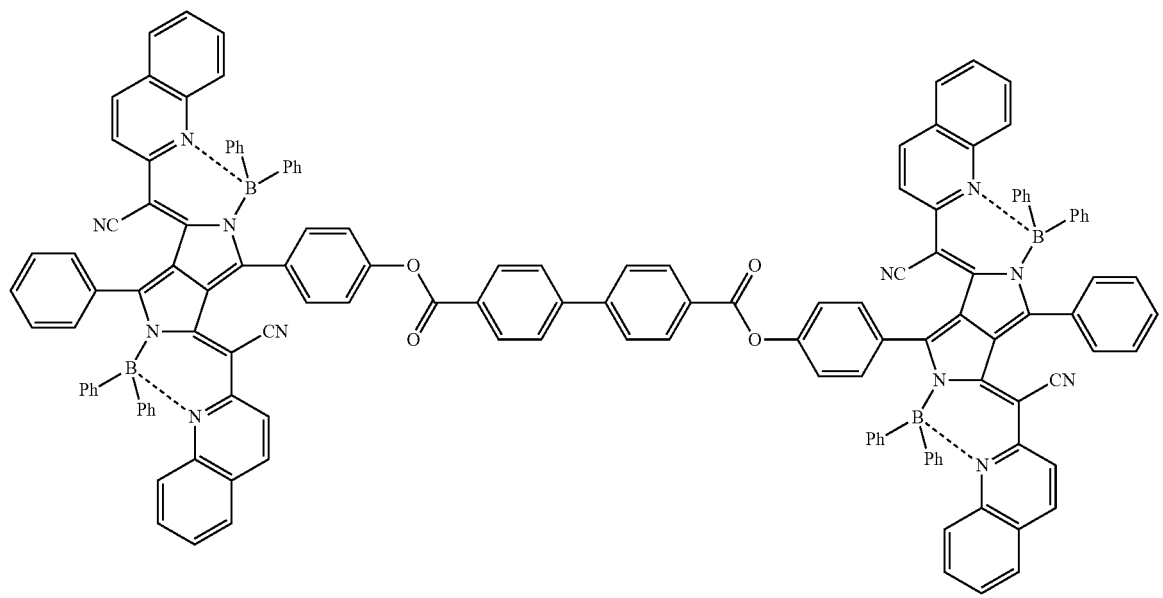
A-ppb-20

-continued
A-ppb-21
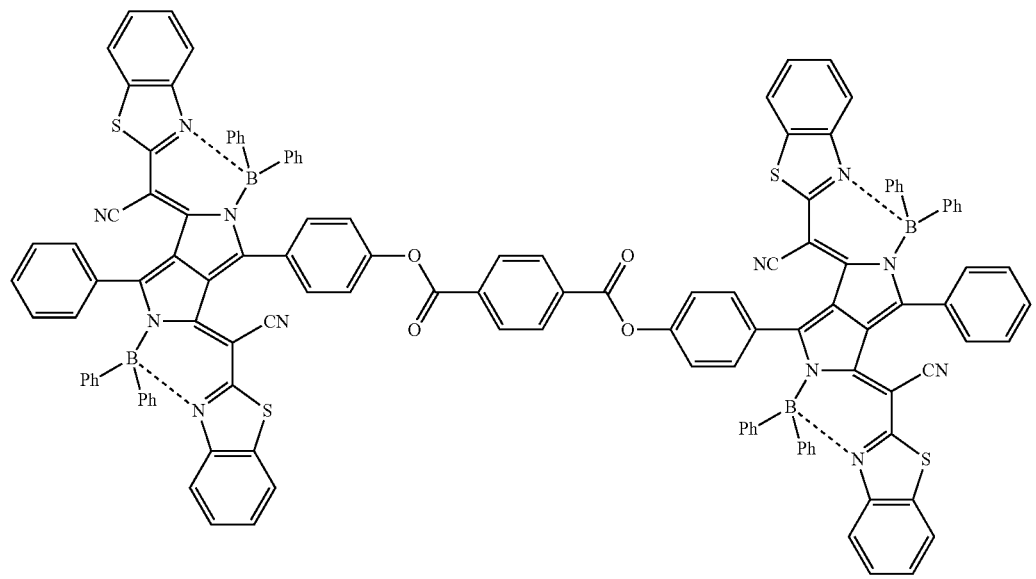
A-ppb-22
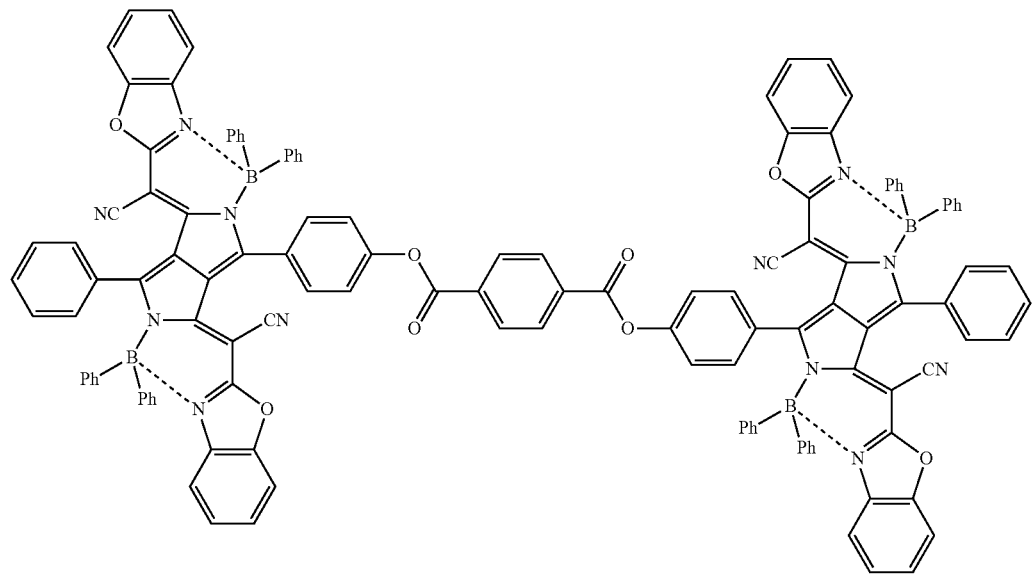

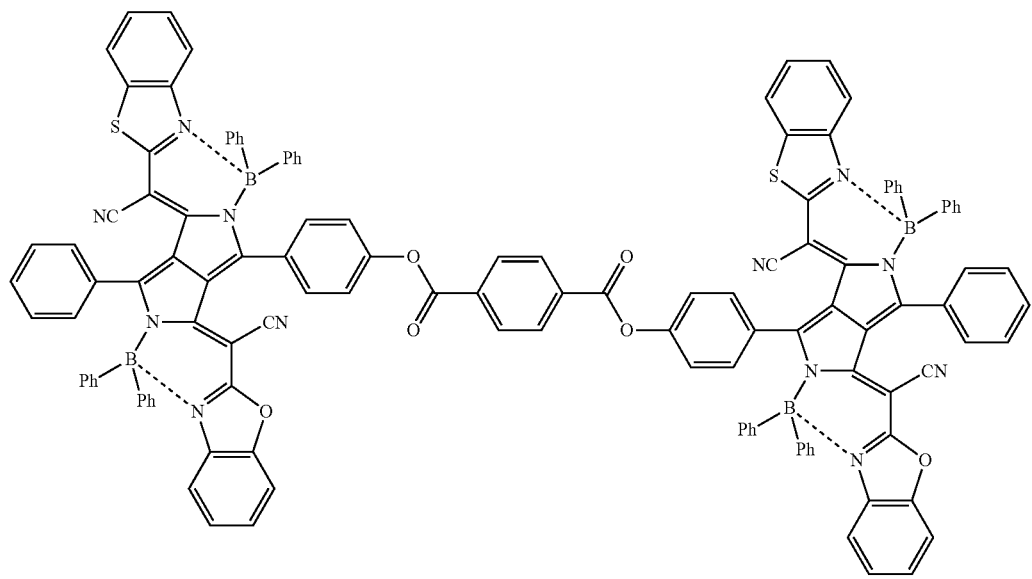
A-ppb-23
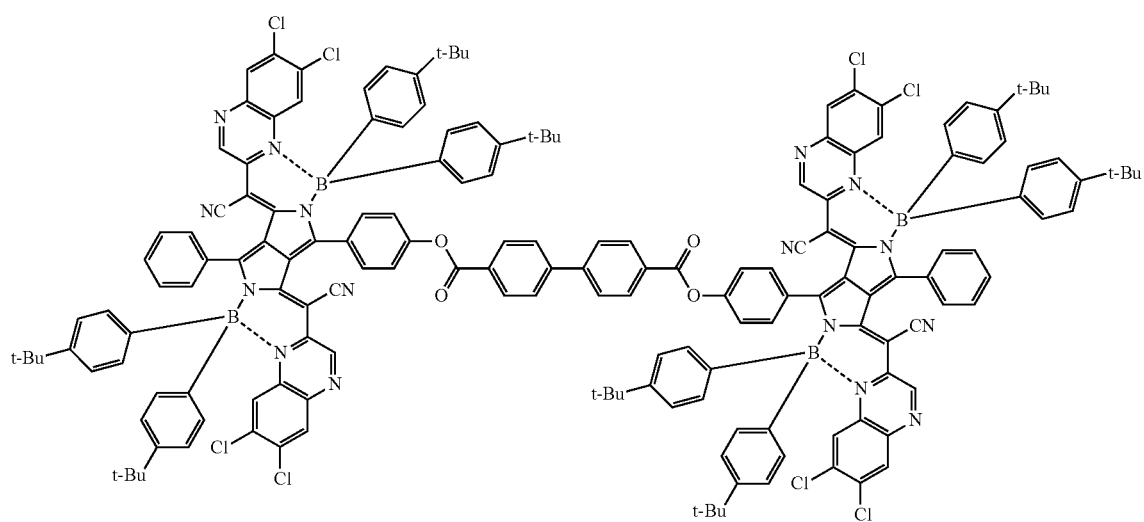
A-ppb-24

-continued
A-ppb-25
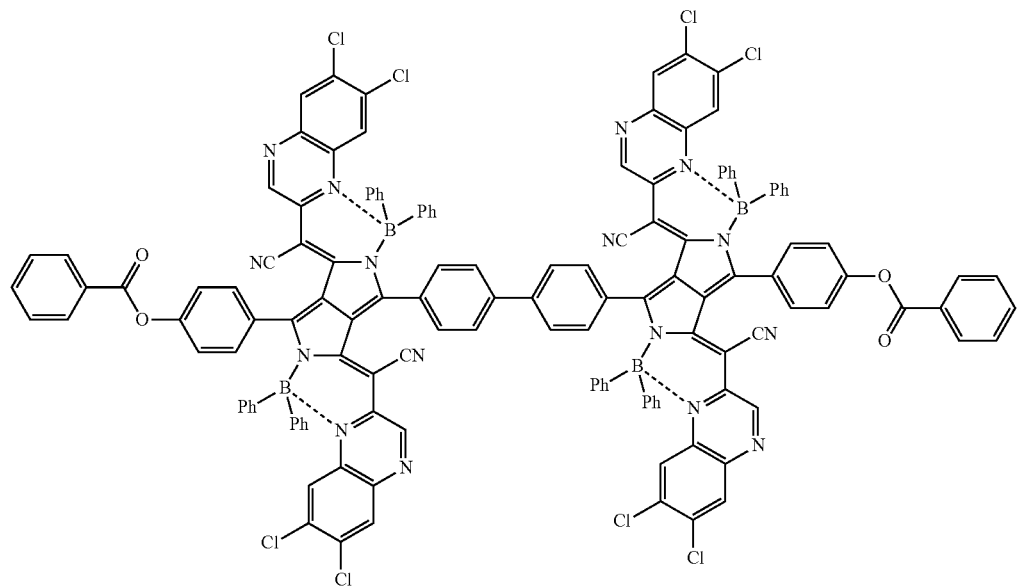
A-ppb-26
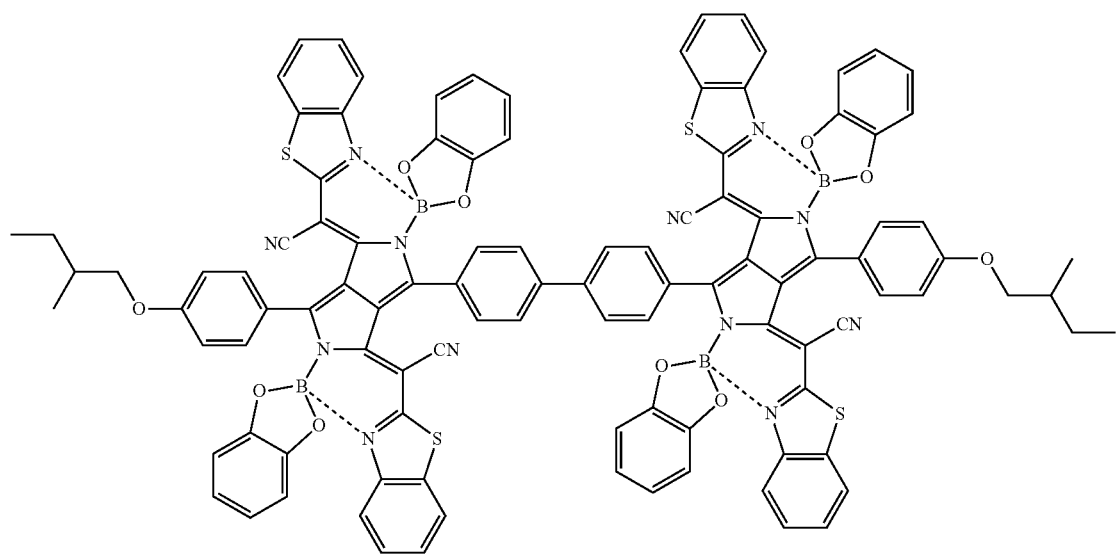

A-ppb-27
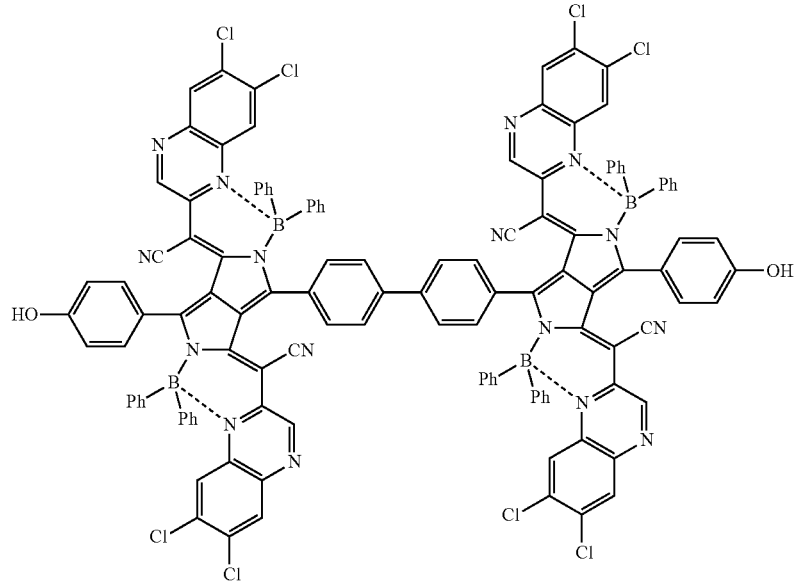
A-ppb-28
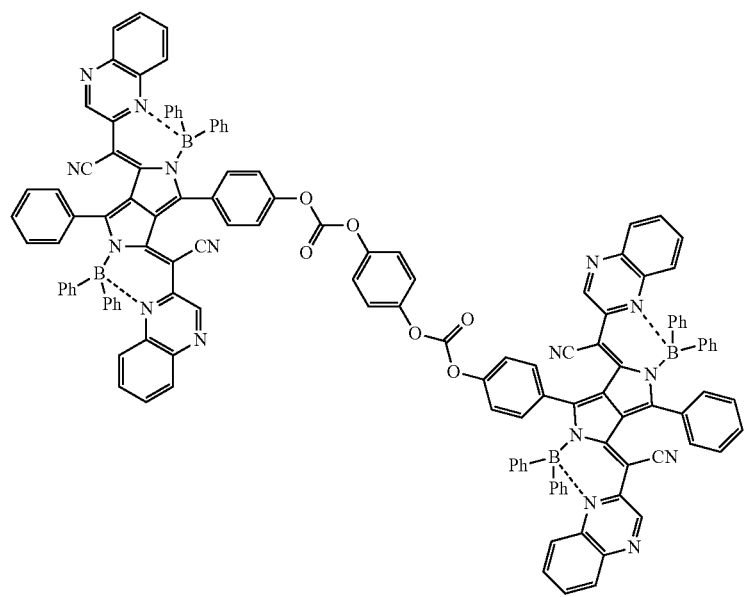

-continued
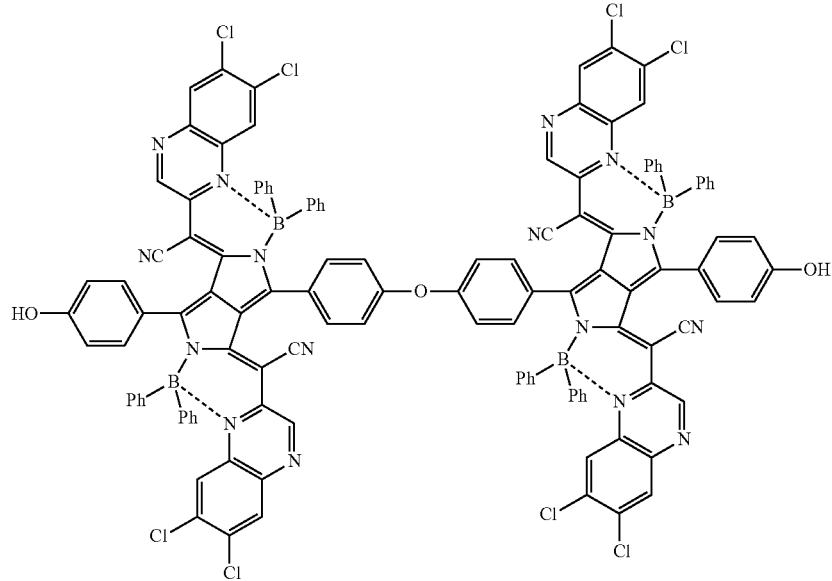
A-ppb-29
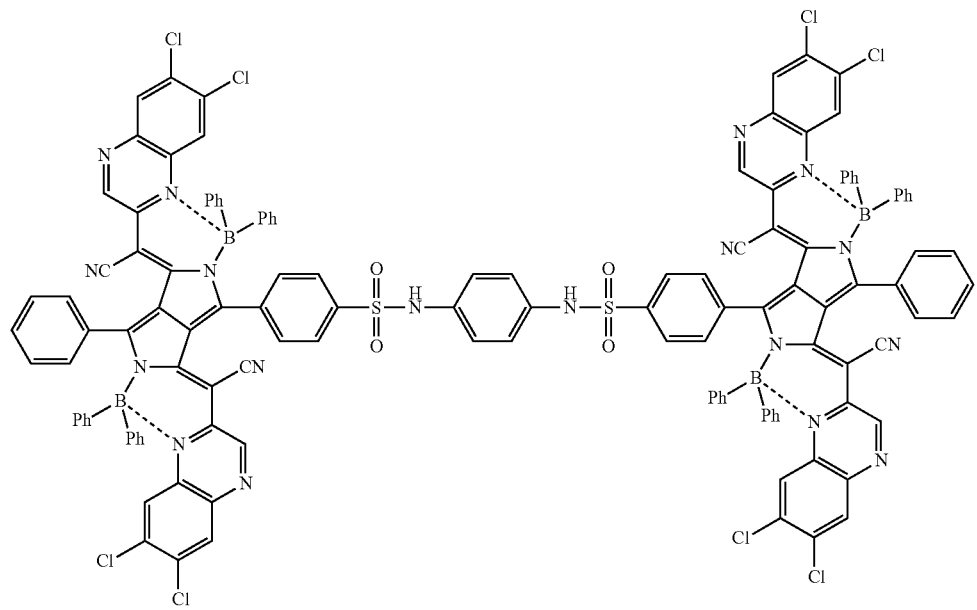
A-ppb-30

A-ppb-31
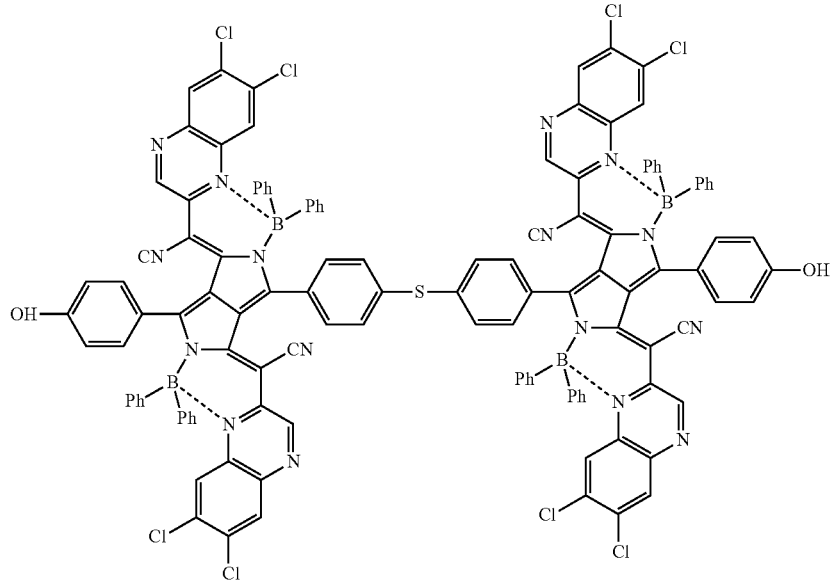
A-ppb-32
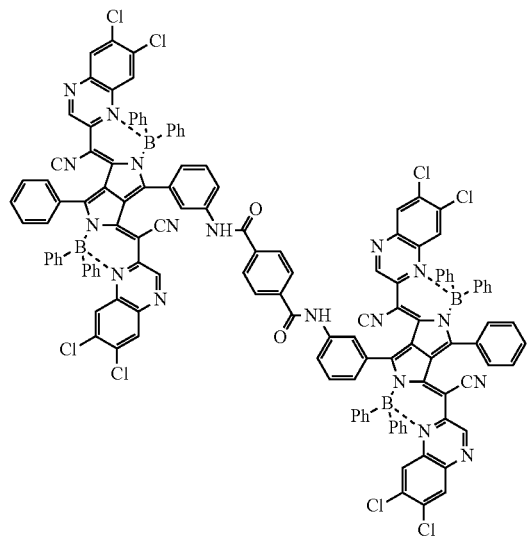

A-ppb-33
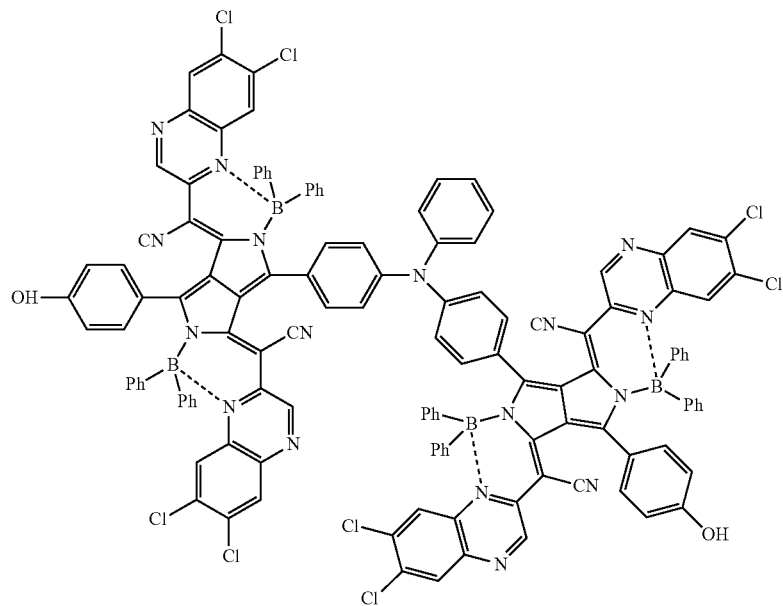
A-ppb-34
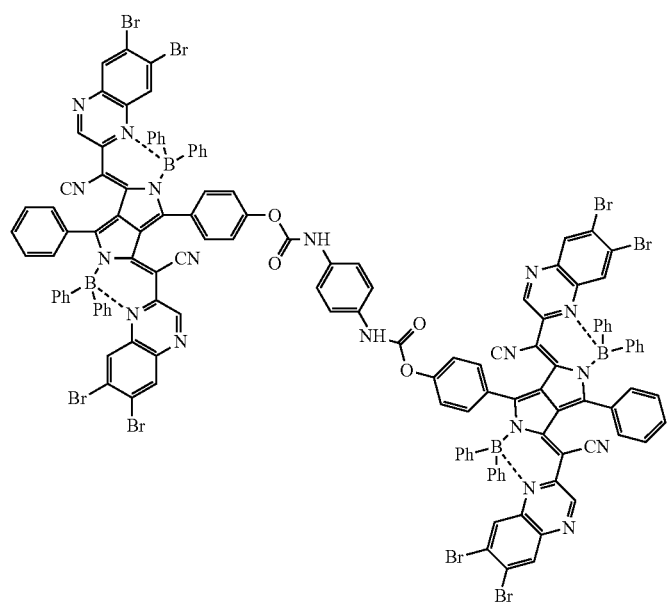

-continued
A-ppb-35
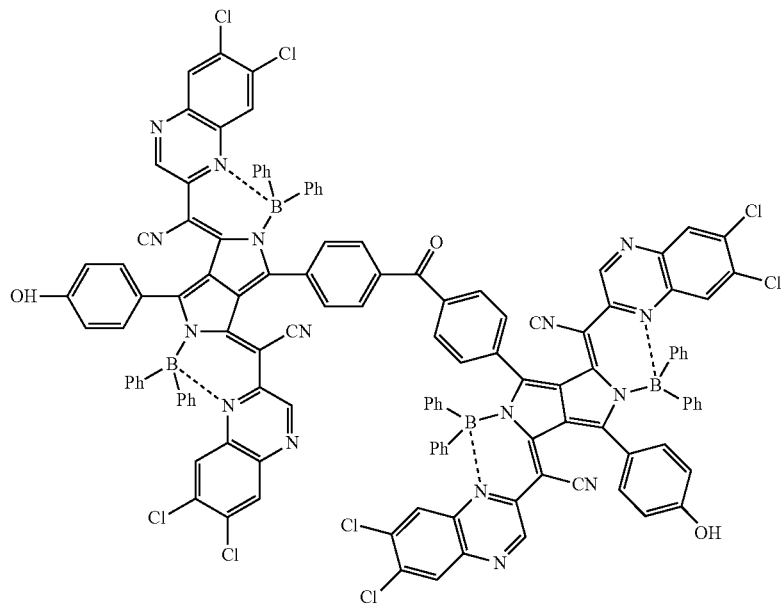
A-ppb-36
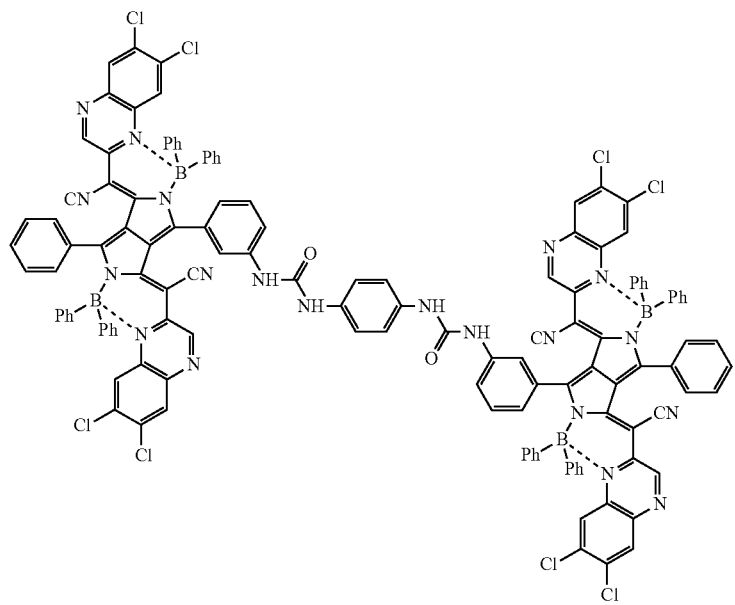
A-sq-1
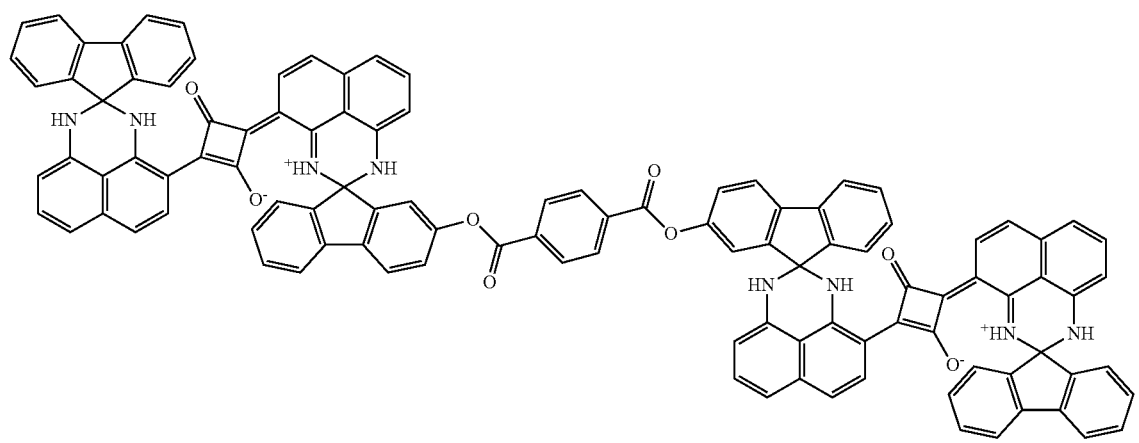

-continued
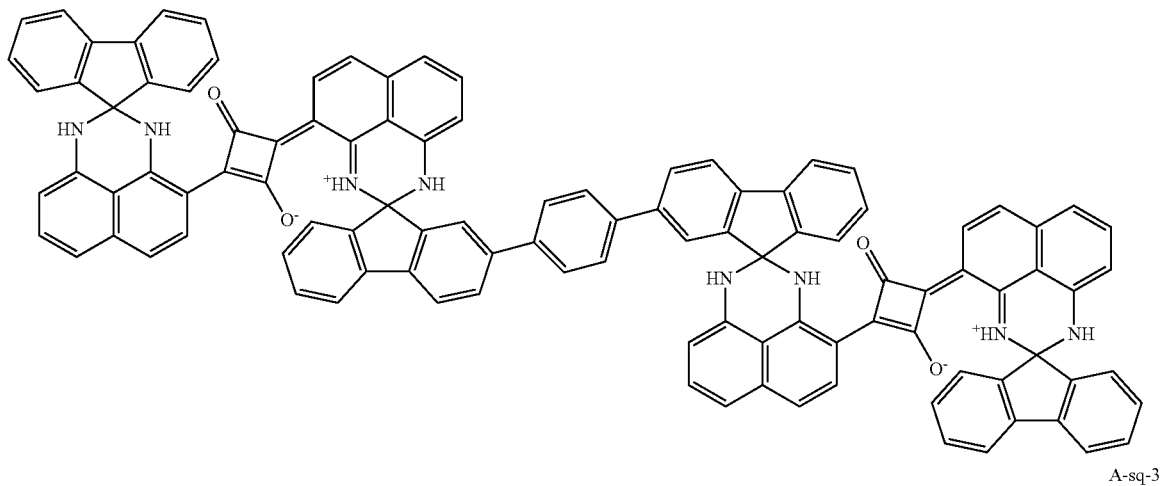
A-sq-2
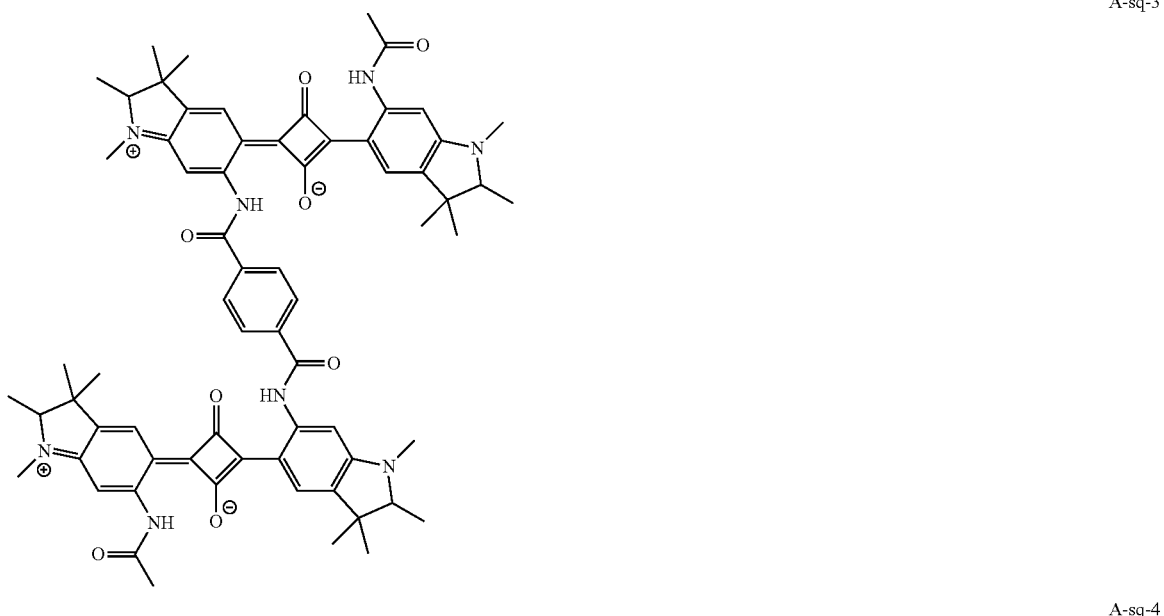
A-sq-3
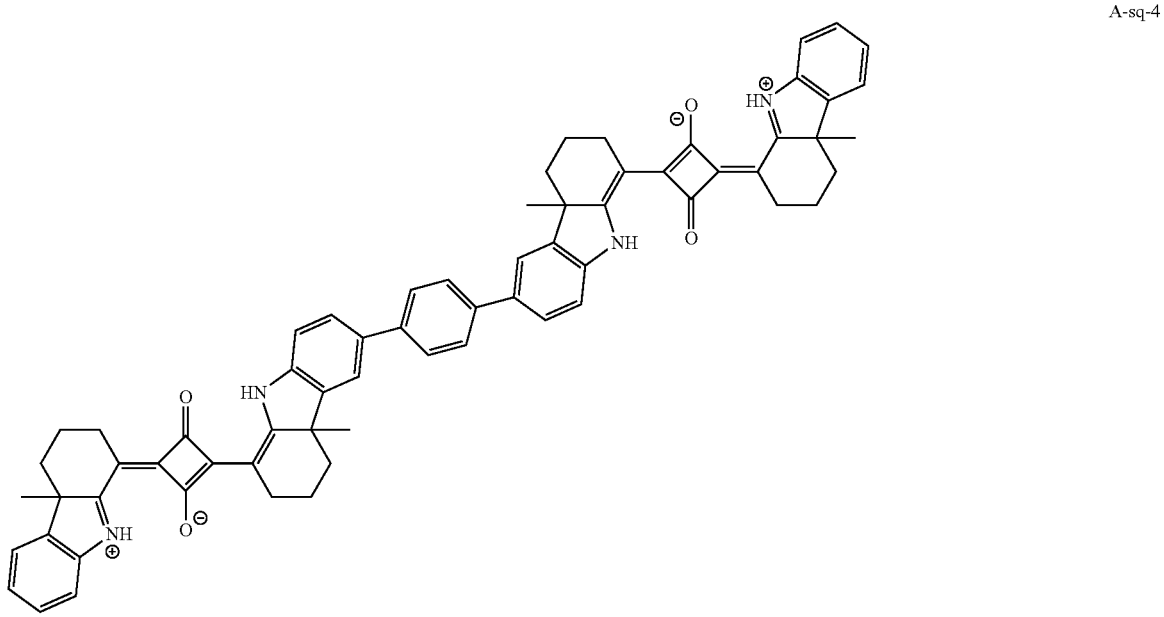
A-sq-4

A-sq-5
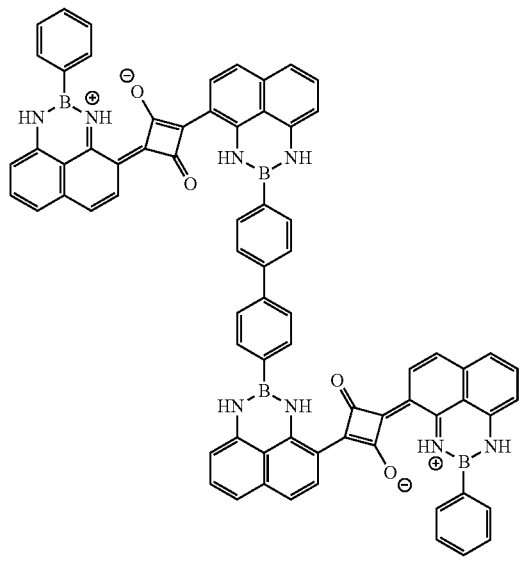
A-cr-1
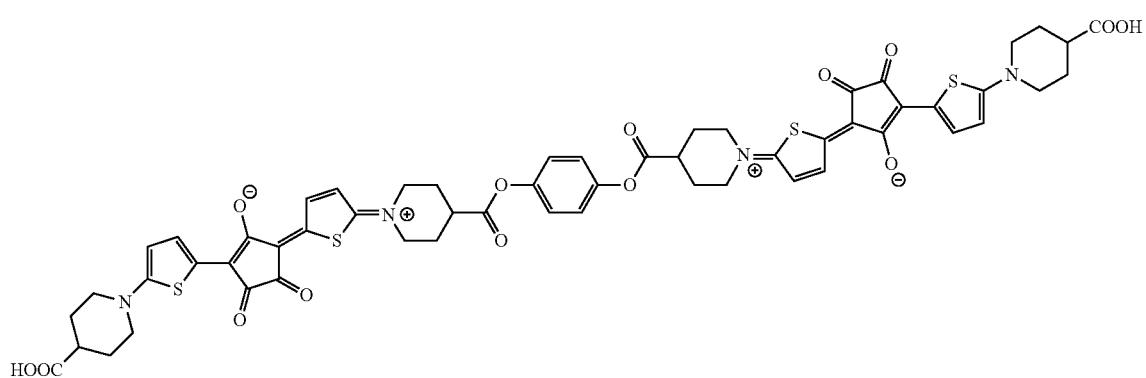
A-cr-2
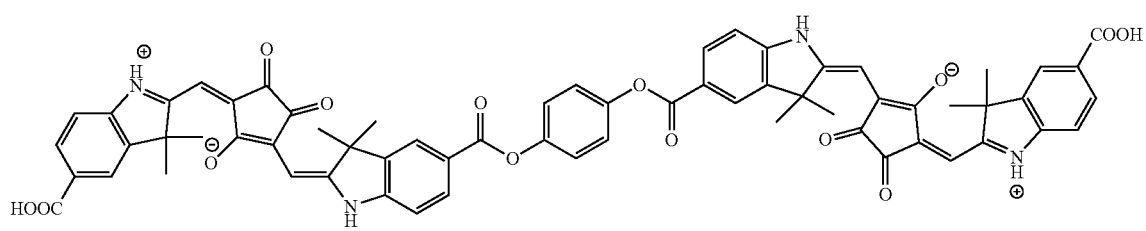
A-cr-3
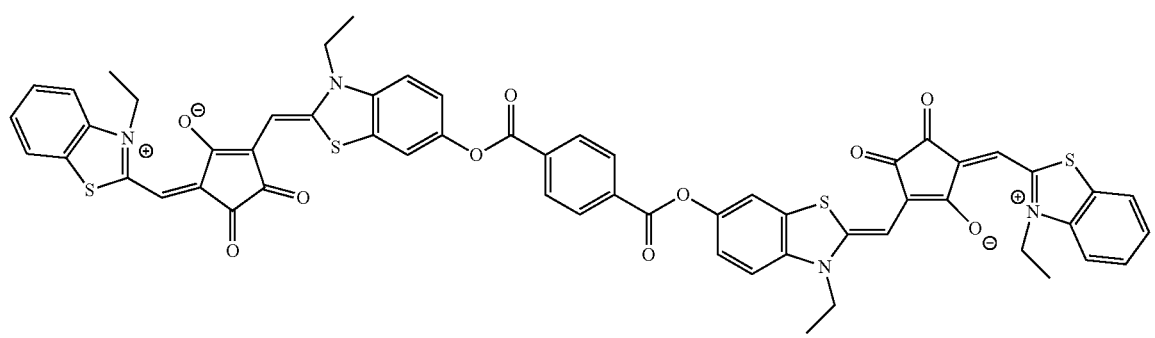

-continued
A-cr-4
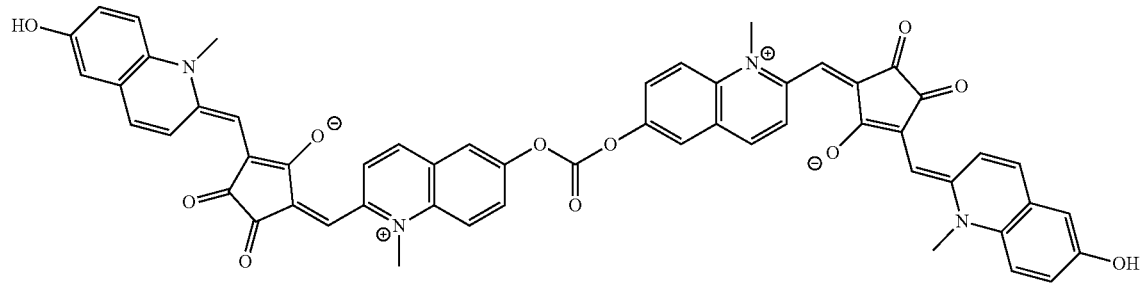
A-cr-5
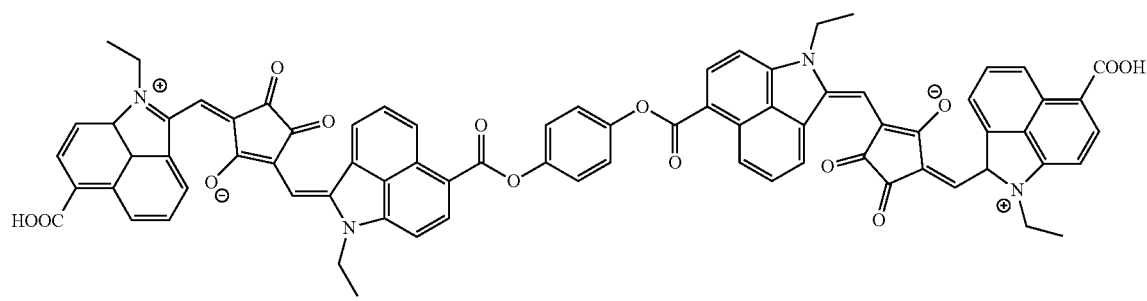
A-bdp-1
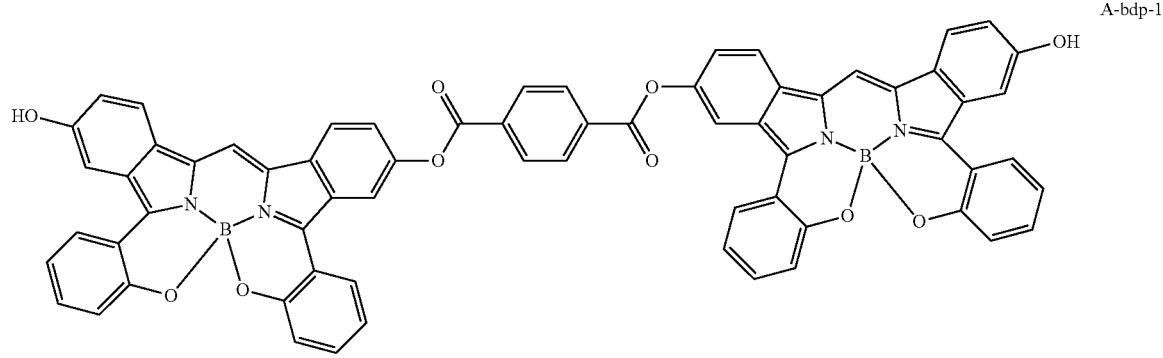
A-bdp-2
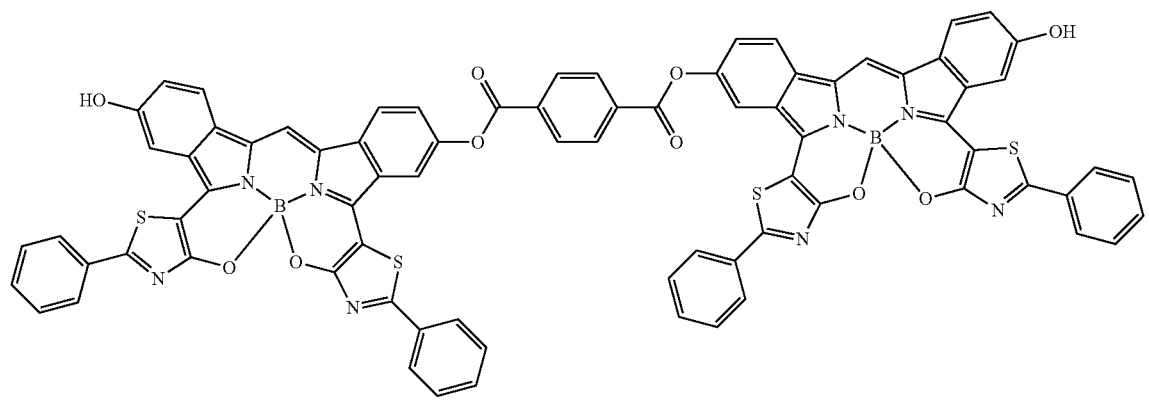

-continued
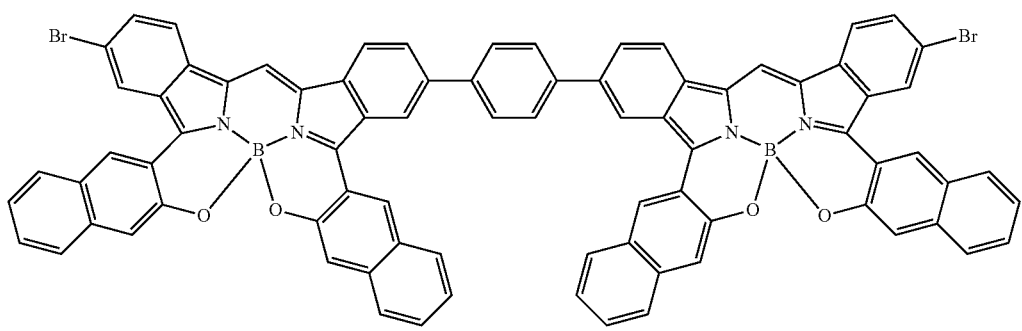
A-bdp-3
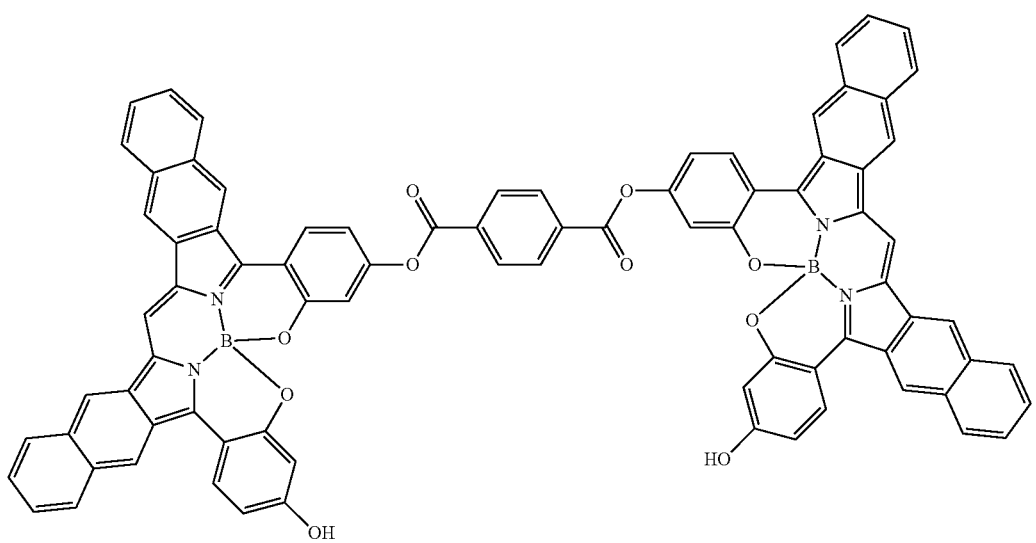
A-bdp-4
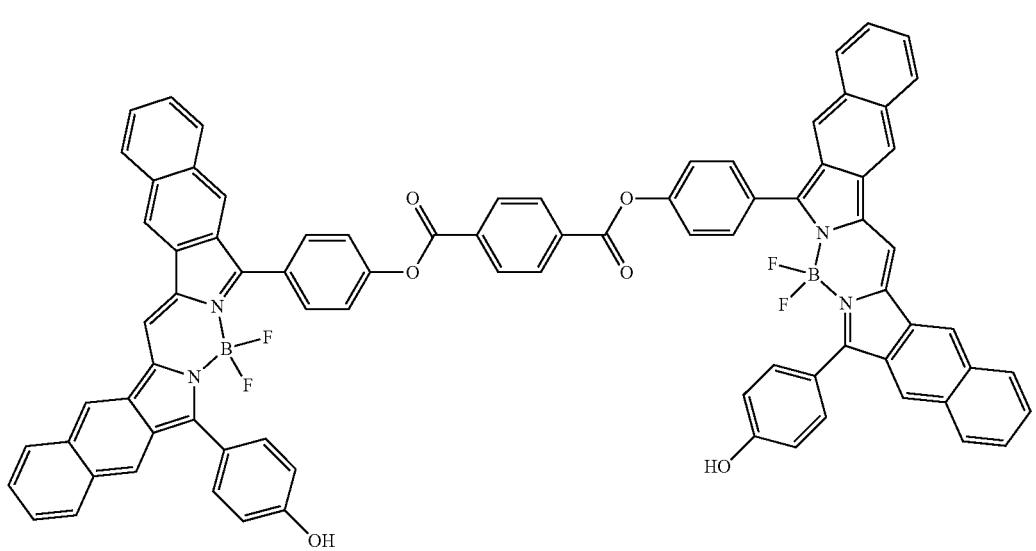
A-bdp-5

-continued
A-bdp-6
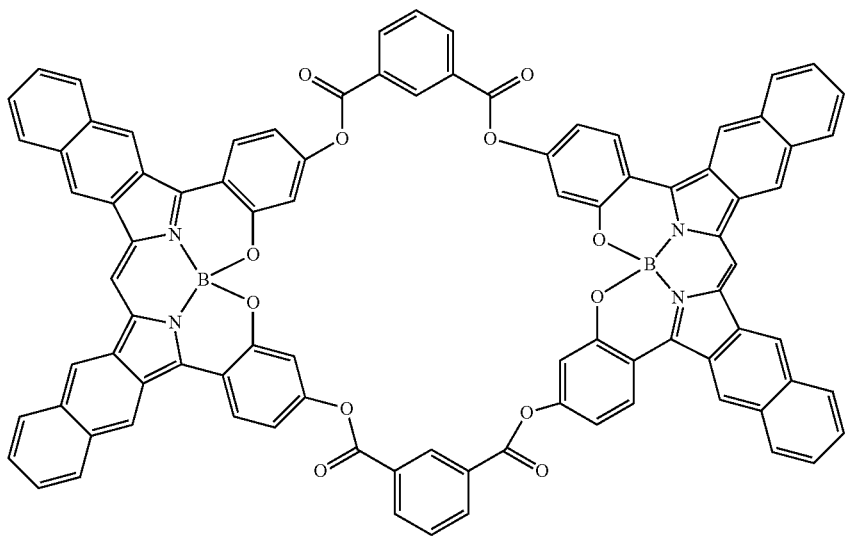
A-bdp-7
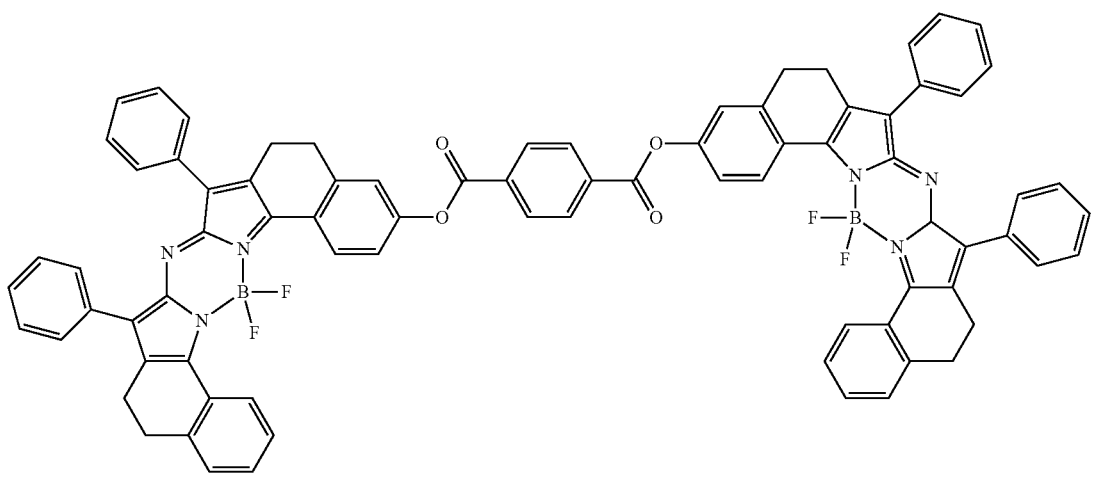
A-bdp-8
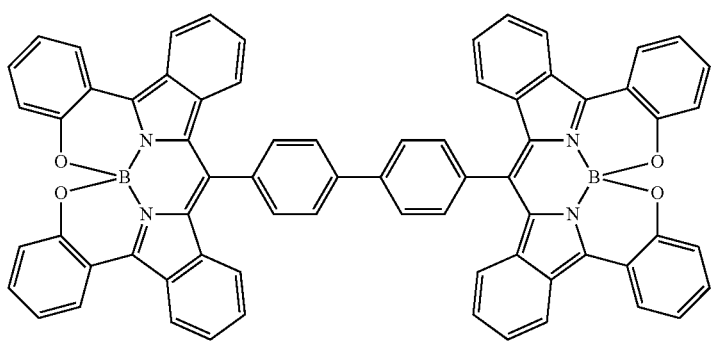

-continued
A-ryl-1
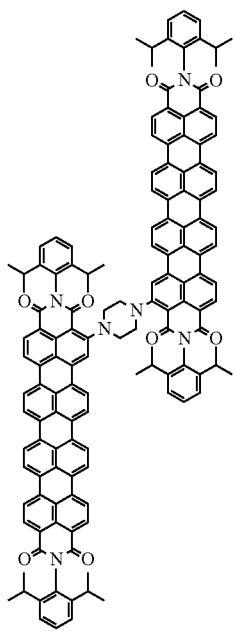
A-ryl-1
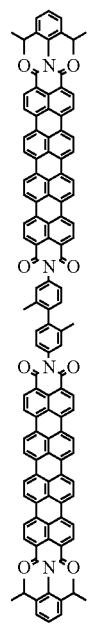
A-id-1
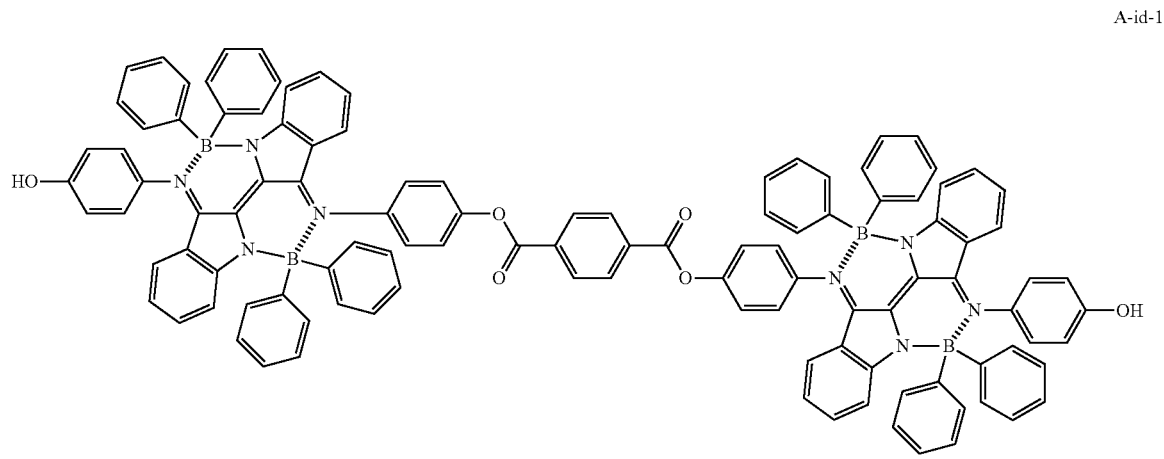
A-id-2
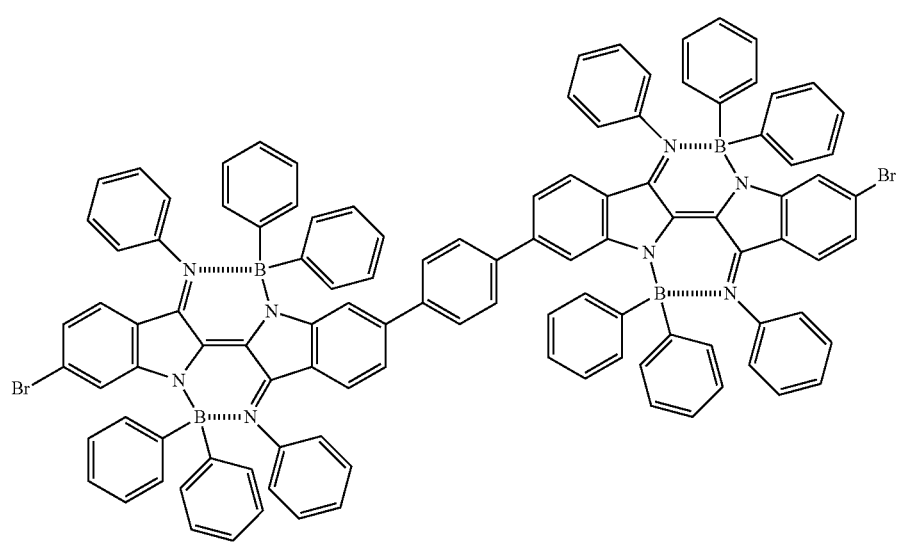

From the viewpoint of spectral characteristics, heat resistance, and light resistance, the coloring agent having a structure represented by Formula (1) is preferably at least one compound selected from the group consisting of a pyrrolopyrrole compound, a rylene compound, an oxonol compound, a squarylium compound, a croconium compound, a vanadium phthalocyanine compound, a naphthalocyanine compound, an indigo compound, and a pyrromethene compound, more preferably at least one compound selected from the group consisting of a pyrrolopyrrole compound, a squarylium compound, a croconium compound, and a pyrromethene compound, and still more preferably a pyrrolopyrrole compound or a squarylium compound.

[Molecular Weight]

The molecular weight of the coloring agent having a structure represented by the structure of Formula (1) is preferably less than 4,000, more preferably less than 3,000, and still more preferably less than 2,500.

[Volume Average Particle Diameter]

The volume average particle diameter of the coloring agent having a structure represented by the structure of Formula (1) is preferably 1 nm to 500 nm, more preferably 1 nm to 300 nm, and still more preferably 1 nm to 200 nm.

In the composition according to the embodiment of the present disclosure, by including the coloring agent of the specific structure having a volume average particle diameter of 1 nm to 500 nm, that is, by using the specific coloring agent in a fine particle dispersed state, there is a merit that durability of the coloring agent is improved. In a case where the volume average particle diameter is 1 nm or more, surface energy of the coloring agent particles is small, so that it is difficult to aggregate. Therefore, the coloring agent particles can be easily dispersed and the dispersed state can be easily maintained, which is preferable. In addition, in a case where the volume average particle diameter of the coloring agent particles is 200 nm or less, the influence of scattering of the coloring agent particles is reduced, so that the absorption spectrum is sharper, which is preferable.

From the above-described viewpoints, the volume average particle diameter of the coloring agent having a structure represented by the structure of Formula (1) is more preferably 10 nm to 200 nm and still more preferably 10 nm to 100 nm.

In the present disclosure, the volume average particle diameter of particles refers to a particle diameter of the fine particles themselves, and in a case where an additive such as a dispersant is attached to the fine particles, the volume average particle diameter thereof refers to a particle diameter to which the additive is attached.

The volume average particle diameter of particles can be measured using a Nanotrac UPA particle size analyzer (UPA-EX150, trade name, manufactured by Nikkiso Co., Ltd.) as a measuring device. The measurement can be carried out by placing 3 mL of particle dispersion in a measurement cell and following a predetermined measuring method.

As parameters to be input in the measurement, the viscosity of composition containing the coloring agent is used for a viscosity, and the density of the infrared absorbing coloring agent or the pigment as a specific colored coloring agent is used for a density of the dispersed particles.

[Maximal Absorption Wavelength]

The maximal absorption wavelength of the coloring agent having a structure represented by Formula (1) is preferably in a wavelength range of 650 nm or more, more preferably in a wavelength range of 700 nm to 1,100 nm, and still more preferably in a wavelength range of 760 nm to 950 nm.

The above-described maximal absorption wavelength is measured using Cary 5000 UV-Vis-NIR spectrophotometer (manufactured by Agilent Technologies, Inc.).

[Half-Width]

In a wavelength-absorbance curve obtained in the above-described measurement of the maximal absorption wavelength, the half-width of the wavelength peak at the maximal absorption wavelength is preferably 2,000 $cm^{-1}$ or less, more preferably 1,400 $cm^{-1}$ or less, and still more preferably 1,350 $cm^{-1}$ or less.

The lower limit of the above-described half-width is not particularly limited, but is preferably 500 $cm^{-1}$ or more.

The above-described half-width is measured using Cary 5000 UV-Vis-NIR spectrophotometer (manufactured by Agilent Technologies, Inc.), and the wavelength is converted into a wave number to calculate the half-width.

[Molar Absorption Coefficient]

The molar absorption coefficient of the coloring agent having a structure represented by Formula (1) at the maximal absorption wavelength is preferably $1.0 \times 10^5$ L/(mol·cm) or more and more preferably $1.5 \times 10^5$ L/(mol·cm) or more.

The above-described molar absorption coefficient is measured using Cary 5000 UV-Vis-NIR spectrophotometer (manufactured by Agilent Technologies, Inc.).

[Content]

In the composition according to the embodiment of the present disclosure, the content of the coloring agent having a structure represented by Formula (1) is preferably 10 mass % to 70 mass %, more preferably 15 mass % to 60 mass %, and still more preferably 20 mass % to 50 mass % with respect to the total solid content of the composition. The composition according to the embodiment of the present disclosure may include a combination of two or more kinds of the coloring agents having a structure represented by Formula (1). In a case where two or more kinds of the coloring agents having a structure represented by Formula (1) are included, the total amount thereof is preferably within the above-described range.

A method for producing the coloring agent having a structure represented by Formula (1) is not particularly limited, and the coloring agent having a structure represented by Formula (1) can be appropriately produced with reference to a known production method.

For example, in a case where n in the coloring agent having a structure represented by Formula (1) is 2 (that is, in a case of a dimer coloring agent), examples of a method for synthesizing the coloring agent having a structure represented by Formula (1) include the following method (1) or method (2), but from the viewpoint of ease of synthesis, a synthesis method of method (1) is preferable.

Method (1): one nucleophilic site is introduced into the coloring agent structure represented by Formula (1), and reacted with a polyfunctional electrophile.

Examples of the above-described nucleophilic site include OH, NHR (R represents a hydrogen atom or an alkyl group), and SH.

Examples of the polyfunctional electrophile include a polyfunctional carboxylic acid, a polyfunctional carboxylic acid chloride, a polyfunctional carboxylic acid anhydride, a polyfunctional sulfonic acid chloride, a polyfunctional isocyanate, and a polyfunctional alkyl halide (particularly, p-xylylene halide and the like).

From the viewpoint of suppressing decomposition of the coloring agent during a dimerization reaction, a highly reactive polyfunctional electrophobic reactant is preferable, and a polyfunctional carboxylic acid chloride, a polyfunctional sulfonic acid chloride, or a polyfunctional isocyanate is more preferable.

Specific examples of the method (1) include a method of introducing one OH as a nucleophilic site into the pyrrolo-pyrrole coloring agent structure and performing a reaction with a bifunctional carboxylic acid chloride as shown in the scheme below. In the following scheme, Et represents an ethyl group and Ph represents a phenyl group.

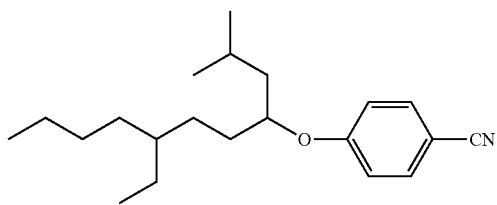

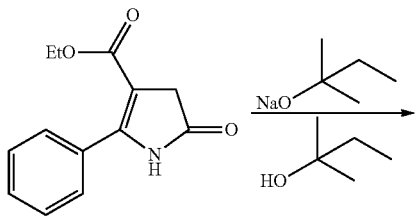

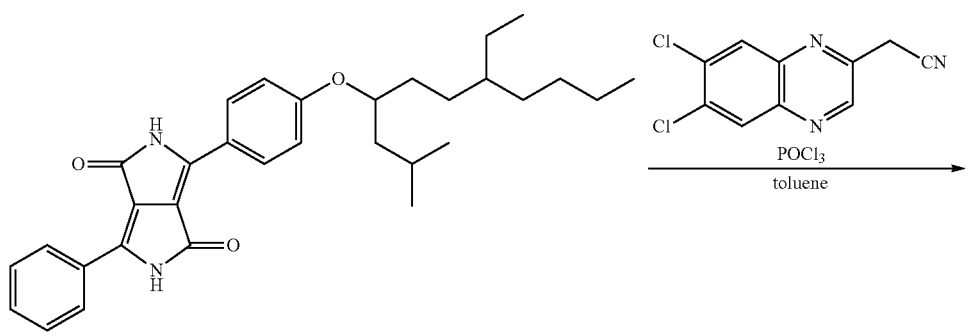

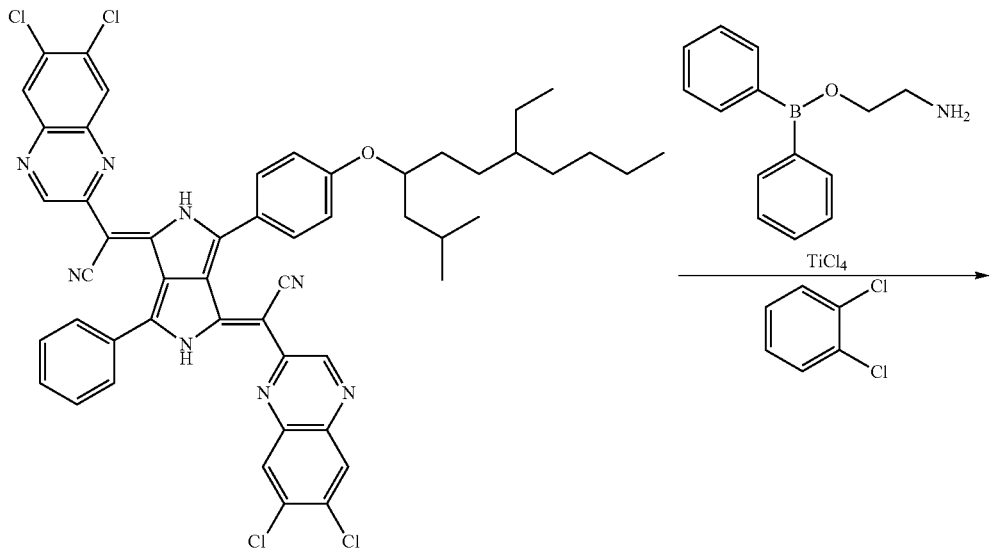

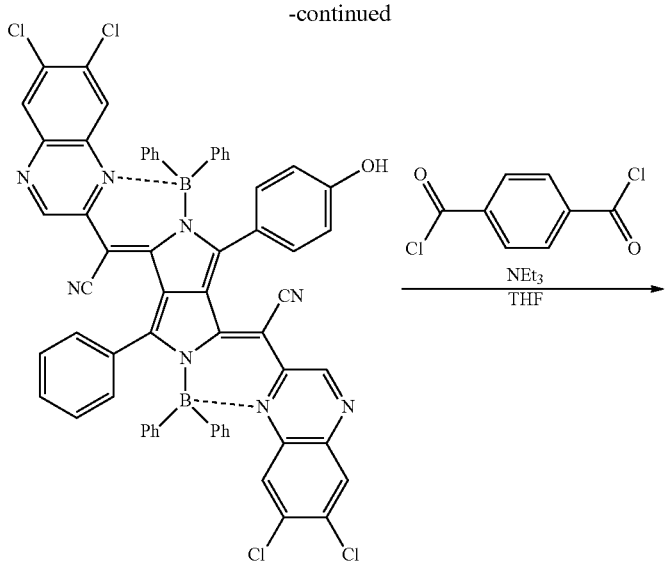

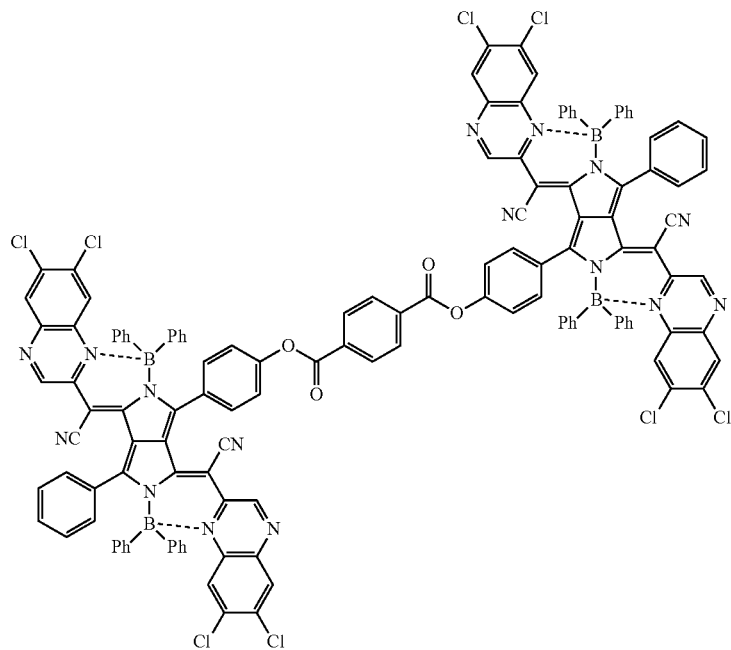

In addition, examples thereof include a method of introducing one OH into the squarylium coloring agent structure and performing a condensation reaction with a bifunctional carboxylic acid as shown in the scheme below.

In the scheme, EDC HCl represents 1-ethyl-3-(3-dimethylaminopropyl) carbodiimide hydrochloride, DMAP represents N,N-dimethyl-4-aminopyridine, and DMAc represents dimethylacetamide.

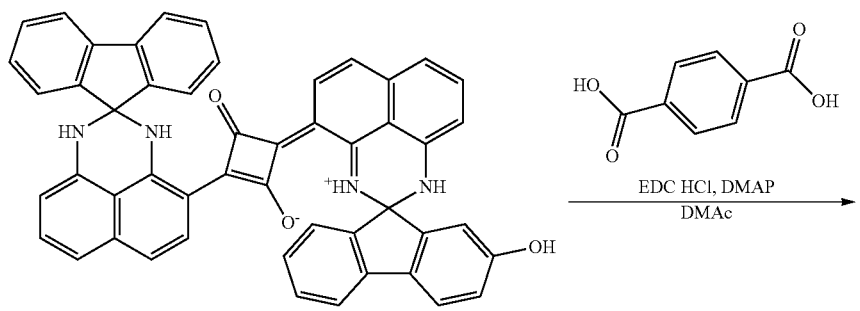

-continued

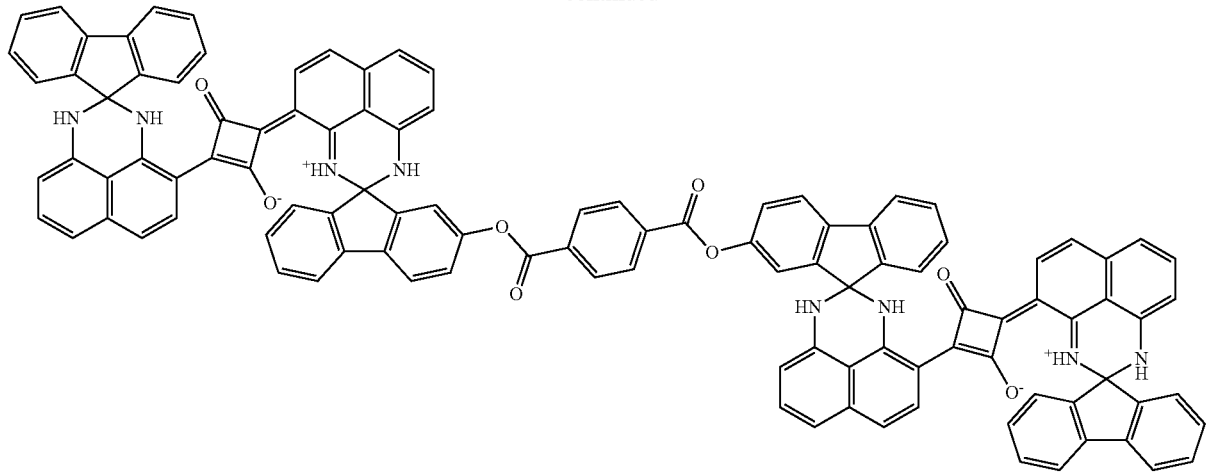

Method (2): one electrophile site is introduced into the coloring agent structure represented by Formula (1), and reacted with a polyfunctional nucleophile.

Examples of the electrophile site include carboxylic acid, carboxylic acid chloride, carboxylic acid anhydride, sulfonic acid chloride, isocyanate, and alkyl halide.

Examples of the polyfunctional nucleophilic site include a polyfunctional alcohol, a polyfunctional secondary or primary amine, and a polyfunctional thiol.

As a specific example of the method (2), as shown in the scheme below, one carboxylic acid (COOH) is introduced into the pyrrolopyrrole coloring agent structure and reacted with p-hydroquinone ($HOC_6H_4OH$; $C_6H_4$ represents a 1,4-phenylene group).

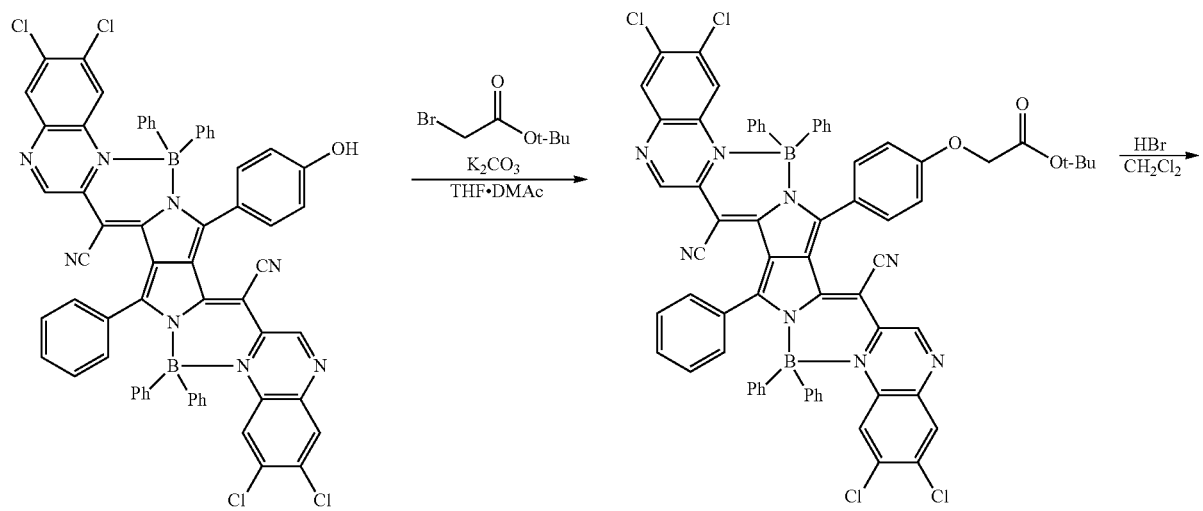

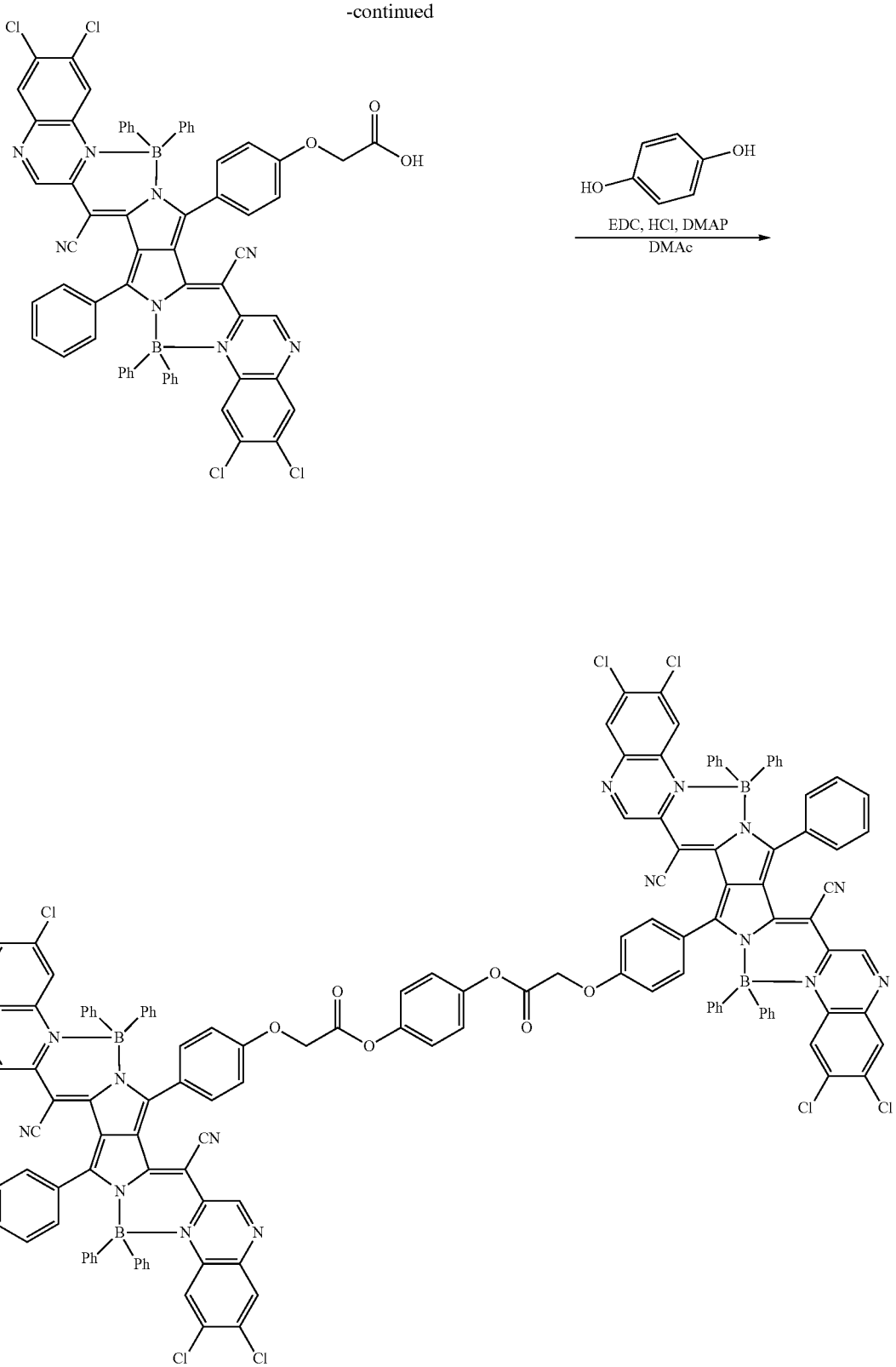

In addition, examples of other synthesis methods include a method in which, as shown in the scheme below, a croconium coloring agent having two carboxylic acids (COOH) is reacted with p-hydroquinone (HOC$_6$H$_4$OH; C$_6$H$_4$ represents a 1,4-phenylene group) under the reaction conditions described in Chem. Sci. 2017, 8. pp. 2710 to 2716, and the reaction product is purified by silica gel column chromatography.

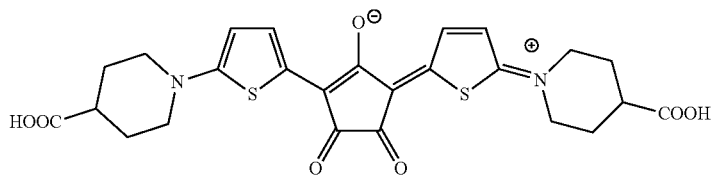
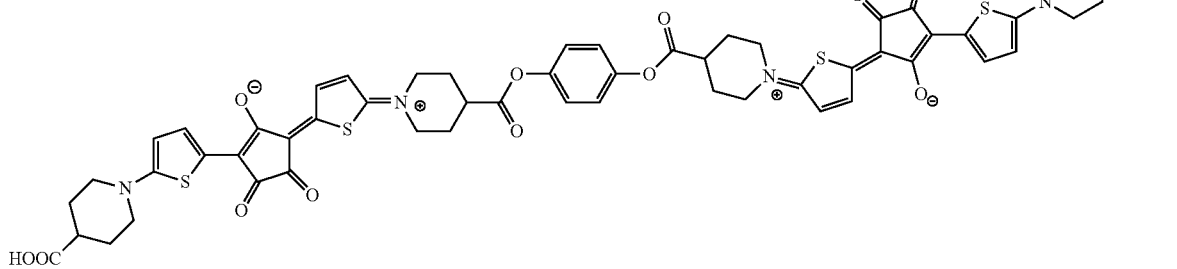

A-cr-1

In addition, a method for adjusting a crystal form of the coloring agent having a structure represented by Formula (1) will be described. Examples of the method for adjusting the crystal form include a method of contacting an organic solvent such as N,N-dimethylformamide, dimethyl sulfoxide, dimethylacetamide, N-methylpyrrolidone, tetrahydrofuran, and 1,4-dioxane with the coloring agent having a structure represented by Formula (1). In this case, heating or cooling may be performed to adjust the particle diameter of the coloring agent having a structure represented by Formula (1), or another solvent may be added before filtering.

<Other Components>

The composition according to the embodiment of the present disclosure is preferably a composition from which a film can be obtained, and is preferably a curable composition from which a cured film can be finally obtained by curing.

In addition, for example, the composition according to the embodiment of the present disclosure is preferably a composition capable of forming a pattern of a cured film by pattern exposure. That is, the composition according to the embodiment of the present disclosure is preferably a negative type composition.

In a case where the composition according to the embodiment of the present disclosure is a negative type composition, for example, an aspect of including a polymerization initiator, a polymerizable compound, and an alkali-soluble resin is preferable.

In addition, in a case where the composition according to the embodiment of the present disclosure is a positive type composition, examples thereof include an aspect of including a photoacid generator, a polymer which has a constitutional unit having a group in which an acid group is protected by an acid-decomposable group, and a polymer which has a constitutional unit having a crosslinkable group.

Hereinafter, each component included in the aspect in which the composition according to the embodiment of the present disclosure is a negative type composition will be described.

Examples of each component included in the aspect in which the composition according to the embodiment of the present disclosure is a positive type composition include each component described in WO2014/003111A, and the preferred aspect thereof is also the same.

<Resin>

From the viewpoint of film-forming property, the composition according to the embodiment of the present disclosure preferably includes a resin.

In addition, examples of the resin include a binder polymer and a dispersant.

As the resin, from the viewpoint of film-forming property and dispersibility, it is preferable to include a binder polymer.

Specific examples of the binder polymer include an acrylic resin, an ene-thiol resin, a polycarbonate resin, a polyether resin, a polyarylate resin, a polysulfone resin, a polyethersulfone resin, a polyphenylene resin, a polyarylene ether phosphine oxide resin, a polyimide resin, a polyamidoimide resin, a polyolefin resin, a cyclic olefin resin, a polyester resin, a styrene resin, a siloxane resin, and a urethane resin. Among these, it is preferable to include an acrylic resin.

These resins may be used singly or as a mixture of two or more kinds thereof.

From the viewpoint of improving heat resistance, as the cyclic olefin resin, a norbornene resin can be preferably used.

Examples of a commercially available product of the norbornene resin include ARTON series (for example, ARTON F4520) manufactured by JSR Corporation. Examples of a commercially available product of the polyimide resin include Neoprim (registered trademark) series (for example, C3450) manufactured by MITSUBISHI GAS CHEMICAL COMPANY, INC.

In addition, as the binder polymer, resins described in Examples of WO2016/088645A, resins described in JP2017-57265A, resins described in JP2017-32685A, resins described in JP2017-075248A, and resins described in JP2017-66240A can also be used, the contents of which are incorporated herein by reference.

In addition, as the binder polymer, a resin having a fluorene skeleton can also be preferably used. With regard to the resin having a fluorene skeleton, reference can be made to the description in US2017/0102610A, the content of which is incorporated herein by reference.

The weight-average molecular weight (Mw) of the binder polymer is preferably 2,000 to 2,000,000. The upper limit is more preferably 1,000,000 or less and still more preferably 500,000 or less. The lower limit is more preferably 3,000 or more and still more preferably 5,000 or more.

The content of the binder polymer is preferably 10 mass % to 80 mass % and more preferably 15 mass % to 60 mass % with respect to the total solid content of the composition. The above-described composition may include one resin or two or more kinds of resins. In a case where two or more kinds thereof are included, the total amount thereof is preferably within the above-described range.

—Dispersant—

Examples of the dispersant include polymer dispersants [for example, a resin having an amine group (polyamide amine or a salt thereof), an oligoimine-based resin, polycarboxylic acid or a salt thereof, high molecular weight unsaturated acid ester, modified polyurethane, modified polyester, modified poly(meth)acrylate, a (meth)acrylic copolymer, and a naphthalene sulfonic acid formalin condensate].

The polymer dispersant can be further classified into a linear polymer, a terminal-modified polymer, a graft polymer, and a block polymer according to the structure thereof.

In addition, suitable examples of the polymer dispersant also include a resin having an acid value of 60 mgKOH/g or more (more preferably, an acid value of 60 mgKOH/g to 300 mgKOH/g).

Examples of the terminal-modified polymer include polymers having a phosphoric acid group in the terminal, described in JP1991-112992A (JP-H3-112992A) and JP2003-533455B, polymers having a sulfonic acid group in the terminal, described in JP2002-273191A, and polymers having a partial skeleton of an organic coloring agent or a heterocyclic ring, described in JP1997-77994A (JP-H9-77994A). In addition, polymers in which two or more anchor sites (acid group, basic group, partial skeleton of an organic coloring agent, heterocyclic ring, or the like) on the pigment surface are introduced at the terminal of the polymer, described in JP2007-277514A, also have excellent dispersion stability, which is preferable.

Examples of the graft polymer include reaction products of poly(lower alkyleneimine) and polyester, described in JP1979-37082A (JP-S54-37082A), JP1996-507960B (JP-H8-507960B), JP2009-258668A, and the like, reaction products of polyallylamine and polyester, described in JP1997-169821A (JP-H9-169821A), copolymers of macromonomer and nitrogen atom monomer, described in JP1998-339949A (JP-H10-339949A), JP2004-37986A, and the like, graft polymers having a partial skeleton of an organic coloring agent or a heterocyclic ring, described in JP2003-238837A, JP2008-9426A, JP2008-81732A, and the like, and copolymers of macromonomer and acid group-containing monomer, described in JP2010-106268A.

As the macromonomer used in a case of producing the graft polymer by radical polymerization, a known macromonomer can be used, and examples thereof include Macromonomer AA-6 (polymethtyl methacrylate having a methacryloyl group as a terminal group), AS-6 (polystyrene having a methacryloyl group as a terminal group), AN-6S (copolymer of styrene and acrylonitrile, in which a terminal group is a methacryloyl group), and AB-6 (butyl polyacrylic acid having a methacryloyl group as a terminal group) manufactured by TOAGOSEI CO., LTD., Placcel FM5 (additional product of 2-hydroxyethyl methacrylate with 5 molar equivalent of ε-caprolactone) and FA10L (additional product of 2-hydroxyethyl acrylate with 10 molar equivalent of ε-caprolactone) manufactured by Daicel Corporation, and polyester-based macromonomer described in JP1990-272009A (JP-H2-272009A). Among these, a polyester-based macromonomer having excellent flexibility and solvent resistance is particularly preferable from the viewpoint of dispersibility of the pigment dispersion, dispersion stability, and developability of the composition using the pigment dispersion, and a polyester-based macromonomer represented by the polyester-based macromonomer described in JP1990-272009A (JP-H2-272009A) is most preferable.

As the block polymer, block polymers described in JP2003-49110A, JP2009-52010A, and the like are preferable.

The resin (dispersant) is also available as a commercially available product, and specific examples thereof include "Disperbyk-101 (polyamide amine phosphate), 107 (carboxylic acid ester), 110 and 111 (copolymer including an acid group), 130 (polyamide), 161, 162, 163, 164, 165, 166, and 170 (polymer copolymer)" and "BYK-P104, P105 (high molecular weight unsaturated polycarboxylic acid)" manufactured by BYK Chemie; "EFKA4047, 4050 to 4165 (polyurethane-based), EFKA4330 to 4340 (block copolymer), 4400 to 4402 (modified polyacrylate), 5010 (polyesteramide), 5765 (high molecular weight polycarboxylic acid salt), 6220 (fatty polyester), 6745 (phthalocyanine derivative), and 6750 (azo pigment derivative)" manufactured by EFKA; "AJISPER PB821, PB822, PB880, and PB881" manufactured by Ajinomoto Fine-Techno Co., Inc.; "Flowlen TG-710 (urethane oligomer)" and "Polyflow No. 50E and No. 300 (acrylic copolymer)" manufactured by KYOEISHA CHEMICAL Co., LTD.; "DISPARLON KS-860, 873SN, 874, #2150 (aliphatic polyvalent carboxylic acid), #7004 (polyether ester), DA-703-50, DA-705, and DA-725" manufactured by Kusumoto Chemicals, Ltd.; "DEMOL (registered trademark) RN, N (naphthalene sulfonic acid formalin polycondensate), MS, C, SN-B (aromatic sulfonic acid formalin polycondensate)", "HOMOGENOL L-18 (high molecular weight polycarboxylic acid)", "EMULGEN 920, 930, 935, 985 (polyoxyethylene nonylphenyl ether)", and "ACETAMIN 86 (stearylamine acetate)" manufactured by Kao Corporation; "Solsperse 5000 (phthalocyanine derivative), 22000 (azo pigment derivative), 13240 (polyesteramine), 3000, 17000, 27000 (polymer having a functional part at the terminal part), 24000, 28000, 32000, and 38500 (graft polymer)" manufactured by Lubrizol Corporation; "NIKKOL T106 (polyoxyethylene sorbitan monoolate) and MYS-IEX (polyoxyethylene monostearate)" manufactured by Nikko Chemicals Co., Ltd.; "Hinoact T-8000E" manufactured by Kawaken Fine Chemicals Co., Ltd.; "Organosiloxane Polymer KP341" manufactured by Shin-Etsu Chemical Co., Ltd.; "EFKA-46, EFKA-47, EFKA-47EA, EFKA Polymer 100, EFKA Polymer 400, EFKA Polymer 401, and EFKA Polymer 450" manufactured by MORISHITA&CO., LTD; "DISPERSE AID 6, DISPERSE AID 8, DISPERSE AID 15, and DISPERSE AID 9100" manufactured by SAN NOPCO LIMITED; "ADK Pluronic L31, F38, L42, L44, L61, L64, F68, L72, P95, F77, P84, F87, P94, L101, P103, F108, L121, and P-123" manufactured by ADEKA Corporation; and "IONET S-20" manufactured by SANYO CHEMICAL, LTD.

These resins may be used singly or in combination of two or more thereof. In addition, an alkali-soluble resin described later can also be used as the dispersant. Examples of the alkali-soluble resin include a (meth)acrylic acid copolymer, an itaconic acid copolymer, a crotonic acid copolymer, a maleic acid copolymer, a partially esterified maleic acid copolymer, an acidic cellulose derivative having a carboxylic acid group in the side chain, and a resin obtained by modifying a polymer having a hydroxy group with an acid anhydride, and a (meth)acrylic acid copolymer is particularly preferable. In addition, N-substituted maleimide monomer copolymers described in JP1998-300922A (JP-H10-300922A), ether dimer copolymers described in JP2004-300204A, or alkali-soluble resin containing a polymerizable group, described in JP1995-319161A (JP-H7-319161A), are also preferable.

Among these, as the above-described resin, from the viewpoint of dispersibility, it is preferable to include a resin having a polyester chain, and it is more preferable to include a resin having a polycaprolactone chain. In addition, from the viewpoint of dispersibility, transparency, and defect suppression of film due to foreign matters, the above-described resin (preferably acrylic resin) preferably has a constitutional unit having an ethylenically unsaturated group.

The above-described ethylenically unsaturated group is not particularly limited, but is preferably a (meth)acryloyl group.

In addition, in a case where the above-described resin has an ethylenically unsaturated group, particularly a (meth) acryloyl group in the side chain, the above-described resin preferably has a divalent linking group having an alicyclic ring structure between the main chain and the ethylenically unsaturated group.

In a case of including the compound having a partial structure represented by Formula (1), and a pigment, a dye, or a pigment derivative other than the compound having a partial structure represented by Formula (1), the content of the dispersant is preferably 1 part by mass to 100 parts by mass, more preferably 5 parts by mass to 90 parts by mass, and still more preferably 10 parts by mass to 80 parts by mass with respect to 100 parts by mass of the total content including the compound having a partial structure represented by Formula (1), and a pigment, a dye, or a pigment derivative other than the compound having a partial structure represented by Formula (1).

—Alkali-Soluble Resin—

The composition according to the embodiment of the present disclosure preferably includes an alkali-soluble resin.

From the viewpoint of developability, it is preferable that the composition according to the embodiment of the present disclosure includes an alkali-soluble resin as the binder polymer.

The alkali-soluble resin can be appropriately selected from alkali-soluble resins which are a linear organic high molecular weight polymer and have at least one group promoting alkali solubility in a molecule (preferably a molecule having an acrylic copolymer or a styrene-based copolymer as the main chain). From the viewpoint of heat resistance, a polyhydroxystyrene-based resin, a polysiloxane-based resin, an acrylic resin, an acrylamide-based resin, or an acrylic/acrylamide copolymer resin is preferable, and from the viewpoint of developability control, an acrylic resin, an acrylamide-based resin, or an acrylic/acrylamide copolymer resin is preferable.

Examples of the group promoting alkali solubility (hereinafter, also referred to as an acid group) include a carboxy group, a phosphoric acid group, a sulfonic acid group, and a phenolic hydroxy group, and a group which is soluble in an organic solvent and can be developed with a weak alkali aqueous solution is preferable and (meth)acrylic acid is particularly preferable. Among these acid groups, one kind may be used alone, or two or more kinds may be used in combination. As the alkali-soluble resin, reference can be made to the description in paragraphs 0558 to 0571 of JP2012-208494A (paragraphs 0685 to 0700 of the corresponding US2012/0235099A), the contents of which are incorporated herein by reference.

As the alkali-soluble resin, a resin having a constitutional unit represented by Formula (ED) is also preferable.

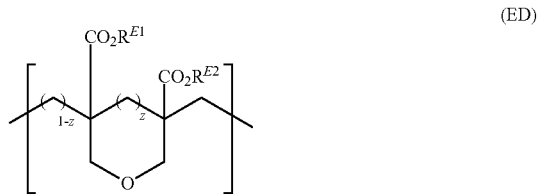

(ED)

In Formula (ED), $R^{E1}$ and $R^{E2}$ each independently represent a hydrogen atom or a hydrocarbon group having 1 to 25 carbon atoms, which may have a substituent, and z represents 0 or 1.

The hydrocarbon group having 1 to 25 carbon atoms, represented by $R^{E1}$ and $R^{E2}$, is not particularly limited, and examples thereof include linear or branched alkyl groups such as a methyl group, an ethyl group, an n-propyl group, an isopropyl group, an n-butyl group, an isobutyl group, a t-butyl group, a t-amyl group, a stearyl group, a lauryl group, and a 2-ethylhexyl group; aryl groups such as a phenyl group; alicyclic groups such as a cyclohexyl group, a t-butylcyclohexyl group, a dicyclopentadienyl group, a tricyclodecanyl group, an isobornyl group, an adamantyl group, and a 2-methyl-2-adamantyl group; alkyl groups substituted with an alkoxy group such as a 1-methoxyethyl group and a 1-ethoxyethyl group; and alkyl groups substituted with an aryl group such as a benzyl group. Among these, from the viewpoint of heat resistance, a primary or secondary hydrocarbon group such as a methyl group, an ethyl group, a cyclohexyl group, and a benzyl group, which is difficult to be eliminated by an acid or heat, is particularly preferable.

$R^{E1}$ and $R^{E2}$ may be substituents of the same type or different substituents.

Examples of the compound forming the constitutional unit represented by Formula (ED) include dimethyl-2,2'-[oxybis(methylene)]bis-2-propenoate, diethyl-2,2'-[oxybis(methylene)]bis-2-propenoate, di(n-propyl)-2,2'-[oxybis(methylene)]bis-2-propenoate, di(n-butyl)-2,2'-[oxybis(methylene)]bis-2-propenoate, di(t-butyl)-2,2'-[oxybis(methylene)]bis-2-propenoate, and di(isobutyl)-2,2'-[oxybis(methylene)]bis-2-propenoate. Among these, dimethyl-2,2'-[oxybis(methylene)]bis-2-propenoate is particularly preferable.

The above-described alkali-soluble resin may have a constitutional unit other than the constitutional unit represented by Formula (ED).

For example, as a monomer forming the above-described constitutional unit, from the viewpoint of ease of handling such as solubility in a solvent, it is also preferable to include, as a copolymerization component, an aryl (meth)acrylate, an alkyl (meth)acrylate, or a polyethyleneoxy (meth)acrylate, which imparts oil solubility, and an aryl (meth)acrylate or an alkyl (meth)acrylate is more preferable.

In addition, from the viewpoint of alkali developability, it is preferable to include, as a copolymerization component, a monomer having a carboxy group such as a (meth)acrylic acid containing an acidic group and an itaconic acid, a monomer having a phenolic hydroxy group such as N-hydroxyphenylmaleimide, or a monomer having a carboxylic acid anhydride group such as maleic acid anhydride and itaconic acid anhydride, and a (meth)acrylic acid is more preferable.

Preferred examples of the above-described alkali-soluble resin include a resin having the constitutional unit represented by Formula (ED), a constitutional unit formed from benzyl methacrylate, and a constitutional unit formed from at least one monomer selected from the group consisting of methyl methacrylate and methacrylic acid.

With regard to the resin having the constitutional unit represented by Formula (ED), reference can be made to the description in paragraphs 0079 to 0099 of JP2012-198408A, the contents of which are incorporated herein by reference.

The weight-average molecular weight (Mw) of the alkali-soluble resin is preferably 2,000 to 50,000. The lower limit is more preferably 5,000 or more and still more preferably 7,000 or more. The upper limit is more preferably 45,000 or less and still more preferably 43,000 or less.

The acid value of the alkali-soluble resin is preferably 30 mgKOH/g to 200 mgKOH/g. The lower limit is more preferably 50 mgKOH/g or more and still more preferably 70 mgKOH/g or more. The upper limit is more preferably 150 mgKOH/g or less and still more preferably 120 mgKOH/g or less.

The acid value in the present disclosure is measured according to the following method.

The acid value represents a mass of potassium hydroxide required to neutralize acidic components per 1 g of solid content. A measurement sample is dissolved in a mixed solvent of tetrahydrofuran/water=9/1 (mass ratio), and the obtained solution s subjected to neutralization titration with a 0.1 mol/L sodium hydroxide aqueous solution at 25° C. using a potentiometric titrator (trade name: AT-510, manufactured by KYOTO ELECTRONICS MANUFACTURING CO., LTD.). An inflection point of a titration pH curve is set as a titration end point, and the acid value is calculated from the following equation.

$$A = 56.11 \times Vs \times 0.1 \times f/w$$

A: acid value (mgKOH/g)

Vs: amount (mL) of the 0.1 mol/L sodium hydroxide aqueous solution used for the titration f: titer of the 0.1 mol/L sodium hydroxide aqueous solution w: mass (g) of the measurement sample (expressed in terms of solid contents)

<Curable Compound>

From the viewpoint of heat resistance and light resistance, the composition according to the embodiment of the present disclosure includes a curable compound.

As the curable compound which can be used in the present disclosure, a polymerizable compound is preferable, an ethylenically unsaturated compound is more preferable, and a compound having a terminal ethylenically unsaturated group is particularly preferable.

As such as a group of compounds, a known compound can be used without particular limitation.

These compounds have chemical forms such as a monomer, a pre-polymer, that is, a dimer, a trimer, an oligomer, a mixture of these, and a copolymer thereof. Examples of the monomer and a copolymer thereof include unsaturated carboxylic acids (such as acrylic acid, methacrylic acid, itaconic acid, crotonic acid, isocrotonic acid, and maleic acid), and esters and amides thereof, and an ester of an unsaturated carboxylic acid and an aliphatic polyhydric alcohol compound and amides of an unsaturated carboxylic acid and an aliphatic polyvalent amine compound are preferably used. In addition, addition reaction products of unsaturated carboxylic acid ester or amides having a nucleophilic substituent such as a hydroxy group, an amino group, and a mercapto group, and monofunctional or polyfunctional isocyanates or epoxies; dehydration-condensation reaction products with monofunctional or polyfunctional carboxylic acids; and the like are also suitably used. Further, addition reaction products of unsaturated carboxylic acid ester or amides having an electrophilic substituent such as an isocyanate group and an epoxy group, and monofunctional or polyfunctional alcohols, amines, or thiols; and substitution reaction products of unsaturated carboxylic acid esters or amides having a dissociable substituent such as a halogen group and a tosyloxy group, and monofunctional or polyfunctional alcohols, amines, or thiols are also suitable. In addition, as additional examples, compound groups obtained by replacing the above-described unsaturated carboxylic acids with unsaturated phosphonic acids, styrenes, vinyl ethers, or the like can also be used.

Specific examples of a monomer of the ester of the aliphatic polyhydric alcohol compound and the unsaturated carboxylic acid include, as acrylic acid esters, ethylene glycol diacrylate, triethylene glycol diacrylate, 1,3-butanediol diacrylate, tetramethylene glycol diacrylate, propylene glycol diacrylate, neopentyl glycol diacrylate, trimethylolpropane triacrylate, trimethylolpropane tri(acryloyloxypropyl)ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol hexaacrylate, sorbitol triacrylate, sorbitol tetraacrylate, sorbitol pentaacrylate, sorbitol hexaacrylate, tri(acryloyloxyethyl) isocyanurate, polyester acrylate oligomer, and isocyanuric acid EO-modified triacrylate.

Specific examples thereof include, as methacrylic acid esters, tetramethylene glycol dimethacrylate, triethylene glycol dimethacrylate, neopentyl glycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, sorbitol trimethacrylate, sorbitol tetramethacrylate, bis[p-(3-methacryloxy-2-hydroxypropoxy)phenyl]dimethylmethane, and bis-[p-(methacryloxyethoxy)phenyl] dimethylmethane.

In addition, urethane-based addition polymerizable compounds produced using an addition reaction between an isocyanate group and a hydroxy group are also suitable, and specific examples thereof include vinyl urethane compounds having two or more polymerizable vinyl groups in one molecule obtained by adding vinyl monomers having a hydroxy group represented by General Formula (I) to a polyisocyanate compound having two or more isocyanate groups in one molecule which is described in JP1973-41708B (JP-S48-41708B).

$$CH_2=C(R)COOCH_2CH(R')OH \qquad (I)$$

(however, R and R' represent H or $CH_3$)

In addition, urethane acrylates described in JP1976-37193A (JP-S51-37193A), JP1990-32293B (JP-H2-32293B), or JP1990-16765B (JP-H2-16765B), or urethane compounds having an ethylene oxide skeleton, described in JP1983-49860B (JP-S58-49860B), JP1981-17654B (JP-S56-17654B), JP1987-39417B (JP-S62-39417B), or JP1987-39418B (JP-S62-39418B), are also suitable. Further, by using addition polymerizable compounds having an amino structure or a sulfide structure in the molecule, described in JP1988-277653A (JP-S63-277653A), JP1988-260909A (JP-S63-260909A), or JP1989-105238A (JP-H1-105238A), a composition having very high photosensitive speed can be obtained.

In addition, examples of the curable compound include compounds described in paragraphs 0178 to 0190 of JP2007-277514A.

In addition, as the curable compound, epoxy compounds described in JP2015-187211A may be used.

The content of the curable compound in the composition is preferably 1 mass % to 90 mass %, more preferably 5 mass % to 80 mass %, and still more preferably 10 mass % to 70 mass % with respect to the total solid content of the composition. In a case where the content of the curable compound is within the above-described range, curing properties of the composition are excellent.

In particular, in a case where the composition according to the embodiment of the present disclosure is used for forming a colored pattern of a color filter, the above-described range of content is preferably 5 mass % to 50 mass %, more preferably 7 mass % to 40 mass %, and still more preferably 10 mass % to 35 mass %.

<Polymerization Initiator>

The composition according to the embodiment of the present disclosure preferably further includes a polymerization initiator, and more preferably further includes a photopolymerization initiator.

In addition, in the composition according to the embodiment of the present disclosure, it is particularly preferable that the above-described curable compound includes a polymerizable compound, and the composition according to the embodiment of the present disclosure further includes a photopolymerization initiator.

The photopolymerization initiator is not particularly limited as long as it has an ability to initiate the polymerization of the polymerizable compound, and can be appropriately selected from known photopolymerization initiators. For example, a compound having photosensitivity to light in a range from an ultraviolet range to a visible range is preferable. In addition, the photopolymerization initiator may be a compound which produces an active radical by causing some action with a photoexcited sensitizer. The photopolymerization initiator is preferably a photoradical polymerization initiator.

Examples of the photopolymerization initiator include a halogenated hydrocarbon derivative (for example, a compound having a triazine skeleton or a compound having an oxadiazole skeleton), an acylphosphine compound, a hexaarylbiimidazole, an oxime compound, an organic peroxide, a thio compound, a ketone compound, an aromatic onium salt, an α-hydroxyketone compound, and an α-aminoketone compound. From the viewpoint of exposure sensitivity, as the photopolymerization initiator, a trihalomethyltriazine compound, a benzyldimethylketal compound, an α-hydroxyketone compound, an α-aminoketone compound, an acylphosphine compound, a phosphine oxide compound, a metallocene compound, an oxime compound, a triarylimidazole dimer, an onium compound, a benzothiazole compound, a benzophenone compound, an acetophenone compound, a cyclopentadiene-benzene-iron complex, a halomethyl oxadiazole compound, or a 3-aryl-substituted coumarin compound is preferable, a compound selected from an oxime compound, an α-hydroxyketone compound, an α-aminoketone compound, or an acylphosphine compound is more preferable, and an oxime compound is still more preferable. With regard to the photopolymerization initiator, reference can be made to the description in paragraphs 0065 to 0111 of JP2014-130173A and paragraphs 0274 to 0306 of JP2013-29760A, and the contents of which are incorporated herein by reference.

Examples of a commercially available product of the α-hydroxyketone compound include IRGACURE-184, DAROCUR-1173, IRGACURE-500, IRGACURE-2959, and IRGACURE-127 (all manufactured by BASF). Examples of a commercially available product of the α-aminoketone compound include IRGACURE-907, IRGACURE-369, IRGACURE-379, and IRGACURE-379EG (all manufactured by BASF). Examples of a commercially available product of the acylphosphine compound include IRGACURE-819 and DAROCUR-TPO (both manufactured by BASF).

Examples of the oxime compound include the compounds described in JP2001-233842A, the compounds described in JP2000-80068A, the compounds described in JP2006-342166A, the compounds described in J. C. S. Perkin II (1979, pp. 1653 to 1660), the compounds described in J. C. S. Perkin II (1979, pp. 156 to 162), the compounds described in Journal of Photopolymer Science and Technology (1995, pp. 202 to 232), the compounds described in JP2000-66385A, the compounds described in JP2000-80068A, the compounds described in JP2004-534797A, the compounds described in JP2006-342166A, the compounds described in JP2017-19766A, the compounds described in JP6065596B, the compounds described in WO2015/152153A, and the compounds described in WO2017/051680A. Specific examples of the oxime compound include 3-benzoyloxyiminobutane-2-one, 3-acetoxyiminobutane-2-one, 3-propionyloxyiminobutane-2-one, 2-acetoxyiminopentane-3-one, 2-acetoxyimino-1-phenylpropane-1-one, 2-benzoyloxyimino-1-phenylpropane-1-one, 3-(4-toluene sulfonyloxy) iminobutane-2-one, and 2-ethoxycarbonyloxyimino-1-phenylpropane-1-one. As a commercially available product of the oxime compound, IRGACURE-OXE01, IRGACURE-OXE02, IRGACURE-OXE03, and IRGACURE-OXE04 (all manufactured by BASF) are also suitably used. In addition, examples of the commercially available product include TRONLY TR-PBG-304, TRONLY TR-PBG-309, and TRONLY TR-PBG-305 (manufactured by CHANGZHOU TRONLY NEW ELECTRONIC MATERIALS CO., LTD.), ADEKA ARKLS NCI-930 and ADEKA OPTOMER N-1919 (both manufactured by ADEKA Corporation, a photopolymerization initiator 2 described in JP2012-14052A).

In addition, as oxime compounds other than the above-described oxime compounds, the compounds described in JP2009-519904A in which oxime is linked to N of a carbazole ring, the compounds described in U.S. Pat. No. 7,626,957B in which a hetero-substituent is introduced into a benzophenone site, the compounds described in JP2010-15025A in which a nitro group is introduced into a coloring agent site, the compounds described in US2009-292039A, the ketoxime compounds described in WO2009/131189A, the compounds described in U.S. Pat. No. 7,556,910B, which contains a triazine skeleton and an oxime skeleton in the same molecule, the compound described in JP2009-221114A, which has an absorption maximum at 405 nm and has good sensitivity to a light source of g-rays, and the like may be used.

In the present disclosure, an oxime compound having a fluorene ring can also be used as the photopolymerization initiator. Specific examples of the oxime compound having a fluorene ring include the compounds described in JP2014-137466A. The contents of the publications are incorporated herein by reference.

In the present disclosure, an oxime compound having a benzofuran skeleton can also be used as the photopolymerization initiator. Specific examples thereof include compounds OE-01 to OE-75 described in WO2015/036910A.

In the present disclosure, as the photopolymerization initiator, an oxime compound having a skeleton in which at least one benzene ring of a carbazole ring is a naphthalene ring can also be used. Specific examples of such an oxime compound include the compounds described in WO2013/083505A.

In the present disclosure, an oxime compound having a fluorine atom can also be used as the photopolymerization initiator. Specific examples of the oxime compound having a fluorine atom include the compounds described in JP2010-262028A, the compounds 24, and 36 to 40 described in JP2014-500852A, and the compound (C-3) described in JP2013-164471A. The contents of the publications are incorporated herein by reference.

In the present disclosure, an oxime compound having a nitro group can be used as the photopolymerization initiator. The oxime compound having a nitro group is also preferably used in the form of a dimer. Specific examples of the oxime compound having a nitro group include the compounds described in paragraphs 0031 to 0047 of JP2013-114249A and paragraphs 0008 to 0012 and 0070 to 0079 of JP2014-137466A, the compounds described in paragraphs 0007 to 0025 of JP4223071B, and ADEKA ARKLS NCI-831 (manufactured by ADEKA Corporation).

Specific examples of the oxime compound which are preferably used in the present disclosure are shown below, but the present disclosure is not limited thereto.

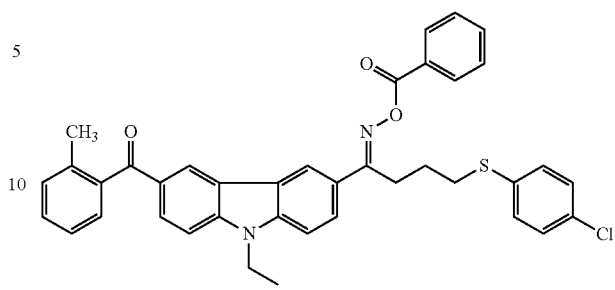

(C-1)

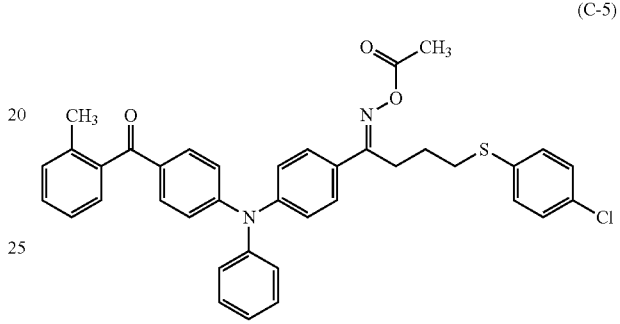

(C-2)

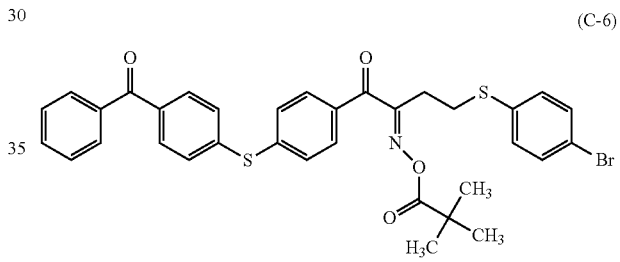

(C-3)

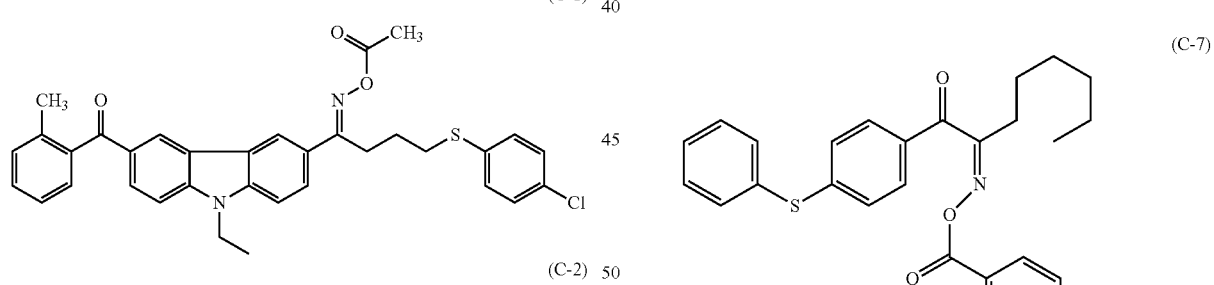

(C-4)

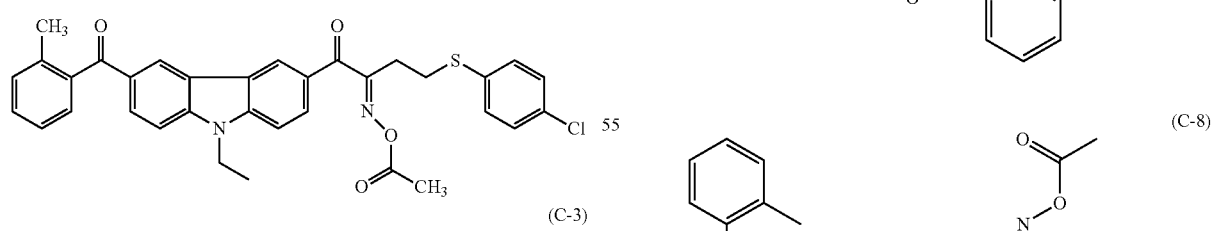

(C-5)

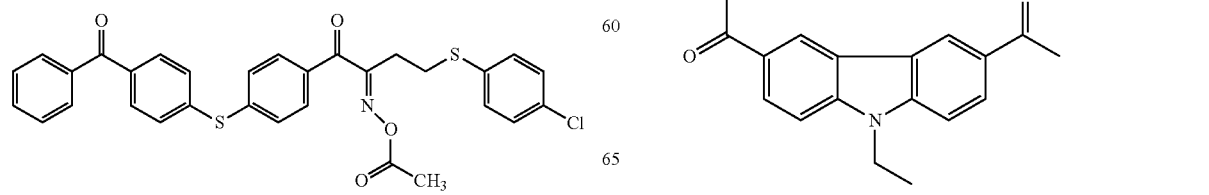

(C-6)

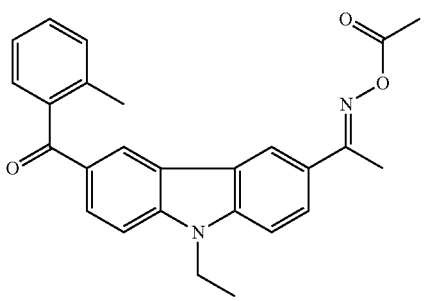

(C-7)

(C-8)

(C-9)

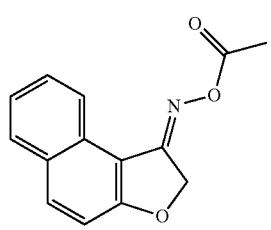

(C-10)

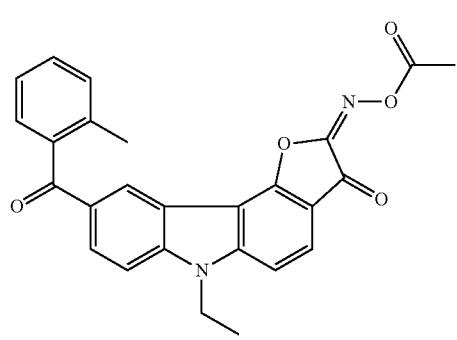

(C-11)

(C-12)

(C-13)

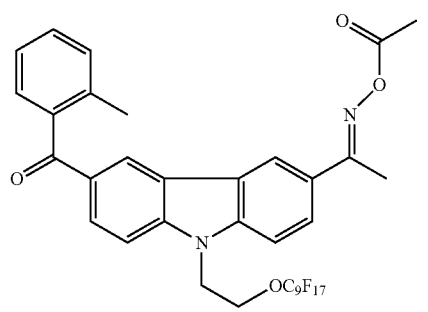

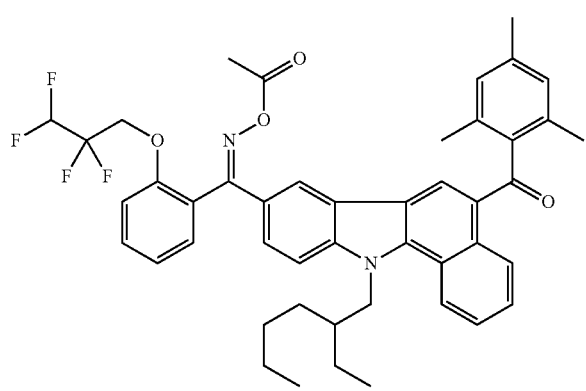

(C-14)

The oxime compound is preferably a compound having a maximal absorption wavelength in a wavelength region of 350 nm to 500 nm and more preferably a compound having a maximal absorption wavelength in a wavelength region of 360 nm to 480 nm. The oxime compound is preferably a compound having a high absorbance at wavelengths of 365 nm and 405 nm.

From the viewpoint of sensitivity, the molar absorption coefficient of the oxime compound at wavelengths of 365 nm or 405 nm is preferably 1,000 to 300,000, more preferably 2,000 to 300,000, and particularly preferably 5,000 to 200,000. The molar absorption coefficient of a compound can be measured using a known method. For example, the molar absorption coefficient is preferably measured by an ultraviolet-visible spectrophotometer (Cary-5 spectrophotometer, manufactured by Varian) using an ethyl acetate solvent at a concentration of 0.01 g/L.

In the present disclosure, as the photopolymerization initiator, a bifunctional or tri- or higher functional photopolymerization initiator may be used. Specific examples of such a photopolymerization initiator include the dimers of the oxime compounds described in JP2010-527339A, JP2011-524436A, WO2015/004565A, paragraphs 0412 to 0417 of JP2016-532675A, and paragraphs 0039 to 0055 of WO2017/033680A, the compound (E) and the compound (G) described in JP2013-522445A, and Cmpd 1 to 7 described in WO2016/034963A.

The polymerization initiator may be used singly or in combination of two or more kinds thereof.

The content of the polymerization initiator in the composition is preferably 0.1 mass % to 50 mass %, more preferably 0.5 mass % to 30 mass %, and particularly preferably 1 mass % to 20 mass % with respect to the total solid content of the above-described composition. In this range, good sensitivity and pattern formability can be obtained.

<Chromatic Colorant>

The composition according to the embodiment of the present disclosure can contain a chromatic colorant. In the present disclosure, "chromatic colorant" denotes a colorant other than a white colorant and a black colorant. It is preferable that the chromatic colorant is a colorant having an absorption in a wavelength range of 400 nm or more and less than 650 nm.

In the present disclosure, the chromatic colorant and the black colorant are also referred to as a visible colorant.

Examples of the chromatic colorant include red colorants, green colorants, blue colorants, yellow colorants, violet colorants, and orange colorants. The chromatic colorant may be a pigment or a dye. The pigment and the dye may be used in combination. In addition, the pigment may be either an inorganic pigment or an organic pigment. In addition, as the pigment, a material in which a part of an inorganic pigment or an organic-inorganic pigment is replaced with an organic chromophore can also be used. By substituting an inorganic pigment or an organic-inorganic pigment with an organic chromophore, hue design can be easily performed.

The average primary particle diameter of the pigment is preferably 1 nm to 200 nm. The lower limit is more preferably 5 nm or more and still more preferably 10 nm or more. The upper limit is more preferably 180 nm or less, still more preferably 150 nm or less, and particularly preferably 100 nm or less. In a case where the average primary particle diameter of the pigment is within the above-described range, dispersion stability of the pigment in the composition is good. In the present disclosure, the primary particle diameter of the pigment can be determined from a captured image obtained by observing primary particles of the pigment using a transmission electron microscope. Specifically, a projected area of the primary particles of the pigment is determined, and the corresponding equivalent circle diameter is calculated as the primary particle diameter of the pigment. In addition, the average primary particle diameter in the present disclosure is the arithmetic average value of the primary particle diameters with respect to 400 primary particles of the pigment. In addition, the primary particle of the pigment refers to a particle which is independent without aggregation.

It is preferable that the chromatic colorant includes a pigment. The content of the pigment in the chromatic colorant is preferably 50 mass % or more, more preferably 70 mass % or more, still more preferably 80 mass % or more, and particularly preferably 90 mass % or more. Examples of the pigment include the following pigments:

Color Index (C. I.) Pigment Yellow 1, 2, 3, 4, 5, 6, 10, 11, 12, 13, 14, 15, 16, 17, 18, 20, 24, 31, 32, 34, 35, 35:1, 36, 36:1, 37, 37:1, 40, 42, 43, 53, 55, 60, 61, 62, 63, 65, 73, 74, 77, 81, 83, 86, 93, 94, 95, 97, 98, 100, 101, 104, 106, 108, 109, 110, 113, 114, 115, 116, 117, 118, 119, 120, 123, 125, 126, 127, 128, 129, 137, 138, 139, 147, 148, 150, 151, 152, 153, 154, 155, 156, 161, 162, 164, 166, 167, 168, 169, 170, 171, 172, 173, 174, 175, 176, 177, 179, 180, 181, 182, 185, 187, 188, 193, 194, 199, 213, 214, 215, 228 (directly connected quinophthalone dimer described in WO2013/098836A), 231, 232 (methine-based), 233 (quinoline-based), and the like (all of which are yellow pigments);

C. I. Pigment Orange 2, 5, 13, 16, 17:1, 31, 34, 36, 38, 43, 46, 48, 49, 51, 52, 55, 59, 60, 61, 62, 64, 71, and 73 (all of which are orange pigments);

C. I. Pigment Red 1, 2, 3, 4, 5, 6, 7, 9, 10, 14, 17, 22, 23, 31, 38, 41, 48:1, 48:2, 48:3, 48:4, 49, 49:1, 49:2, 52:1, 52:2, 53:1, 57:1, 60:1, 63:1, 66, 67, 81:1, 81:2, 81:3, 83, 88, 90, 105, 112, 119, 122, 123, 144, 146, 149, 150, 155, 166, 168, 169, 170, 171, 172, 175, 176, 177, 178, 179, 184, 185, 187, 188, 190, 200, 202, 206, 207, 208, 209, 210, 216, 220, 224, 226, 242, 246, 254, 255, 264, 270, 272, 279, 294 (xanthene-based, Organo Ultramarine, Bluish Red), 295 (monoazo-based), 296 (diazo-based), and the like (all of which are red pigments);

C. I. Pigment Green 7, 10, 36, 37, 58, 59, 62, and 63 (all of which are green pigments);

C. I. Pigment Violet 1, 19, 23, 27, 32, 37, 42, 60 (triarylmethane-based), 61 (xanthene-based), and the like (all of which are violet pigments); and C. I. Pigment Blue 1, 2, 15, 15:1, 15:2, 15:3, 15:4, 15:6, 16, 22, 29, 60, 64, 66, 79, 80, 87 (monoazo-based), 88 (methine-based), and the like (all of which are blue pigments).

In addition, a halogenated zinc phthalocyanine pigment having an average number of halogen atoms in one molecule of 10 to 14, an average number of bromine atoms in one molecule of 8 to 12, and an average number of chlorine atoms in one molecule of 2 to 5 can also be used as the green pigment. Specific examples thereof include the compounds described in WO2015/118720A. In addition, as the green pigment, compounds described in CN2010-6909027A, phthalocyanine compounds described in WO2012/102395A, which have a phosphoric acid ester as a ligand, or the like can also be used.

In addition, as the green colorant, green colorants described in JP2019-8014A or JP2018-180023A may be used.

In addition, an aluminum phthalocyanine compound having a phosphorus atom can also be used as the blue pigment. Specific examples thereof include the compounds described in paragraphs 0022 to 0030 of JP2012-247591A and paragraph 0047 of JP2011-157478A.

In addition, as the yellow pigment, quinophthalone pigments described in JP2018-203798A, JP2018-62578A, JP6432077B, JP6432076B, JP2018-155881A, JP2018-111757A, JP2018-40835A, JP2017-197640A, JP2016-145282A, JP2014-85565A, JP2014-21139A, JP2013-209614A, JP2013-209435A, JP2013-181015A, JP2013-61622A, JP2013-54339A, JP2013-32486A, JP2012-226110A, JP2008-74987A, JP2008-81565A, JP2008-74986A, JP2008-74985A, JP2008-50420A, JP2008-31281A, or JP1973-32765B (JP-S48-32765B) can also be suitably used. In addition, pigments described in JP6443711B can also be used.

In addition, as the yellow pigment, the quinophthalone compounds described in paragraphs 0011 to 0034 of JP2013-54339A, the quinophthalone compounds described in paragraphs 0013 to 0058 of JP2014-26228A, yellow pigments described in JP2019-8014A, or the like can be used.

In addition, as the yellow pigment, compounds described in JP2018-062644A can also be used. These compounds can also be used as a pigment derivative.

Further, as described in JP2018-155881A, C. I. Pigment Yellow 129 may be added for the purpose of improving weather fastness.

As the red pigment, diketopyrrolopyrrole compounds described in JP2017-201384A, in which the structure has at least one substituted bromine atom, diketopyrrolopyrrole compounds described in paragraphs 0016 to 0022 of JP6248838B, diketopyrrolopyrrole compounds described in WO2012/102399A, diketopyrrolopyrrole compounds described in WO2012/117965A, naphtholazo compounds described in JP2012-229344, and the like can also be used. In addition, as the red pigment, a compound having a structure that an aromatic ring group in which a group bonded with an oxygen atom, a sulfur atom, or a nitrogen atom is introduced to an aromatic ring is bonded to a diketopyrrolopyrrole skeleton can be used.

In the present disclosure, a dye can also be used as the colorant. The dye is not particularly limited and a known dye can be used. Examples thereof include a pyrazoleazo-based dye, an anilinoazo-based dye, a triarylmethane-based dye, an anthraquinone-based dye, an anthrapyridone-based dye, a benzylidene-based dye, an oxonol-based dye, a pyrazolotri-azoleazo-based dye, a pyridoneazo-based dye, a cyanine-based dye, a phenothiazine-based dye, a pyrrolopyrazolea-zomethine-based dye, a xanthene-based dye, a phthalocyanine-based dye, a benzopyran-based dye, an indigo-based dye, and a pyrromethene-based dye. In addition, thiazole compounds described in JP2012-158649A, azo compounds described in JP2011-184493A, or azo compounds described in JP2011-145540A can also be preferably used. In addition, as yellow dyes, the quinophthalone compounds described in paragraphs 0011 to 0034 of JP2013-054339A, or the quinophthalone compounds described in paragraphs 0013 to 0058 of JP2014-026228A can be used.

In a case where the composition according to the embodiment of the present disclosure contains a chromatic colorant, the content of the chromatic colorant is preferably 1 mass % to 50 mass % with respect to the total solid content of the composition. In a case where the composition according to the embodiment of the present disclosure includes two or more kinds of chromatic colorants, it is preferable that the total amount of the two or more kinds of chromatic colorants is within the above-described range.

<Colorant which Allows Transmission of Near-Infrared Rays and Shields Visible Light>

The composition according to the embodiment of the present disclosure can contain a colorant which allows transmission of near-infrared rays (light having a wavelength in a near infrared range) and shields visible light (light having a wavelength in a visible region) (hereinafter, also referred to as a colorant which shields visible light). A composition including the colorant which shields visible light is preferably used as a composition for forming a near-infrared transmitting filter.

In the present disclosure, it is preferable that the colorant which shields visible light is a colorant which absorbs light in a wavelength region of violet to red. In addition, in the present disclosure, the colorant which shields visible light is preferably a colorant which shields light in a wavelength region of 450 nm to 650 nm. In addition, the colorant which shields visible light is preferably a colorant which transmits light having a wavelength of 900 nm to 1,300 nm. In the present disclosure, it is preferable that the colorant which shields visible light satisfies at least one of the following requirement (A) or (B).

(A): colorant which shields visible light contains two or more chromatic colorants, and a combination of the two or more chromatic colorants forms black.

(B): colorant which shields visible light contains an organic black colorant.

Examples of the chromatic colorant include the above-described chromatic colorants. Examples of the organic black colorant include a bisbenzofuranone compound, an azomethine compound, a perylene compound, and an azo compound. Among these, a bisbenzofuranone compound or a perylene compound is preferable. Examples of the bisbenzofuranone compound include the compounds described in JP2010-534726A, JP2012-515233A, JP2012-515234A, and the like, and the bisbenzofuranone compound is available, for example, as "Irgaphor Black" manufactured by BASF. Examples of the perylene compound include compounds described in paragraphs 0016 to 0020 of JP2017-226821A, and C. I. Pigment Black 31 and 32. Examples of the azomethine compound include the compounds described in JP1989-170601A (JP-H01-170601A) and JP1990-034664A (JP-H02-034664A), and the azomethine compound is available, for example, "CHROMOFINE BLACK A1103" manufactured by Dainichiseika Color & Chemicals Mfg. Co., Ltd.

In a case where a combination of two or more chromatic colorants forms black, examples of the combination of the chromatic colorants include the following aspects.

(1) aspect in which the colorant which shields visible light contains a yellow colorant, a blue colorant, a violet colorant, and a red colorant (2) aspect in which the colorant which shields visible light contains a yellow colorant, a blue colorant, and a red colorant (3) aspect in which the colorant which shields visible light contains a yellow colorant, a violet colorant, and a red colorant (4) aspect in which the colorant which shields visible light contains a yellow colorant and a violet colorant (5) aspect in which the colorant which shields visible light contains a green colorant, a blue colorant, a violet colorant, and a red colorant (6) aspect in which the colorant which shields visible light contains a violet colorant and an orange colorant (7) aspect in which the colorant which shields visible light contains a green colorant, a violet colorant, and a red colorant (8) aspect in which the colorant which shields visible light contains a green colorant and a red colorant The ratio (mass ratio) of each colorant is preferably as follows, for example.

| No. | Yellow colorant | Green colorant | Blue colorant | Violet colorant | Red colorant | Orange colorant |
|---|---|---|---|---|---|---|
| 1 | 0.1 to 0.4 | | 0.1 to 0.6 | 0.01 to 0.3 | 0.1 to 0.6 | |
| 2 | 0.1 to 0.4 | | 0.1 to 0.6 | | 0.2 to 0.7 | |
| 3 | 0.1 to 0.6 | | | 0.1 to 0.6 | 0.1 to 0.6 | |
| 4 | 0.2 to 0.8 | | | 0.2 to 0.8 | | |
| 5 | | 0.1 to 0.4 | 0.1 to 0.4 | 0.1 to 0.4 | 0.1 to 0.4 | |
| 6 | | | | 0.2 to 0.6 | | 0.4 to 0.8 |
| 7 | | 0.1 to 0.5 | | 0.2 to 0.7 | 0.1 to 0.4 | |
| 8 | | 0.5 to 0.8 | | | 0.2 to 0.5 | |

In No. 1, the yellow colorant is more preferably 0.1 to 0.3, the blue colorant is more preferably 0.1 to 0.5, the violet colorant is more preferably 0.01 to 0.2, and the red colorant is more preferably 0.1 to 0.5. In No. 2, the yellow colorant is more preferably 0.1 to 0.3, the blue colorant is more preferably 0.1 to 0.5, and the red colorant is more preferably 0.1 to 0.5.

The composition may include only one kind of the visible colorant, or may include two or more kinds thereof.

The content of the visible colorant is preferably 0.1 mass % to 70 mass %, more preferably 0.5 mass % to 60 mass %, and still more preferably 1 mass % to 50 mass % with respect to the total mass of the composition.

<Pigment Derivative>

The composition can contain a pigment derivative. Examples of the pigment derivative include a compound in which at least one group selected from the group consisting of an acid group, a basic group, and a hydrogen bonding group is bonded to a coloring agent skeleton.

Examples of the acid group include a sulfo group, a carboxy group, a phosphoric acid group, a boronic acid group, a sulfonimide group, a sulfonamide group, salts of these group, and a desalted structure of these salts. Examples of an atom or atomic group constituting the salts include alkali metal ions (Li$^+$, Na$^+$, K$^+$, and the like), alkaline earth metal ions (Ca$^{2+}$, Mg$^{2+}$, and the like), an ammonium ion, an imidazolium ion, a pyridinium ion, and a phosphonium ion. In addition, examples of the desalted structure of the salt include groups in which an atom or an atomic group forming the salt has been eliminated from the above-described salt. For example, a desalted structure of a salt of a carboxy group is a carboxylate group (—COO—).

Examples of the basic group include an amino group, a pyridinyl group, salts of these groups, and a desalted structure of these salts. Examples of an atom or atomic group constituting the salts include a hydroxide ion, a halogen ion, a carboxylate ion, a sulfonate ion, and a phenoxide ion. In addition, examples of the desalted structure of the salt include groups in which an atom or an atomic group forming the salt has been eliminated from the above-described salt.

The hydrogen bonding group refers to a group which interacts with each other through a hydrogen atom. Specific examples of the hydrogen bonding group include an amide group, a hydroxy group, —NHCONHR, —NHCOOR, and —OCONHR. R is preferably an alkyl group or an aryl group.

Examples of the pigment derivative include a compound represented by Formula (B1).

P$\text{-}(\text{-L-(X)}_n)_m$          (B1)

In Formula (B1), P represents a coloring agent skeleton, L represents a single bond or a linking group, X represents an acid group, a basic group, or a hydrogen bonding group, m represents an integer of 1 or more, n represents an integer of 1 or more, in a case where m represents 2 or more, a plurality of L's and a plurality of X's may be different from each other, and in a case where n represents 2 or more, a plurality of X's may be different from each other.

The above-described coloring agent skeleton represented by P is preferably at least one selected from a squarylium coloring agent skeleton, a croconium coloring agent skeleton, a pyrrolopyrrole coloring agent skeleton, a diketopyrrolopyrrole coloring agent skeleton, a quinacridone coloring agent skeleton, an anthraquinone coloring agent skeleton, a dianthraquinone coloring agent skeleton, a benzoisoindole coloring agent skeleton, a thiazine indigo coloring agent skeleton, an azo coloring agent skeleton, a quinophthalone coloring agent skeleton, a phthalocyanine coloring agent skeleton, a naphthalocyanine coloring agent skeleton, a dioxazine coloring agent skeleton, a perylene coloring agent skeleton, a perinone coloring agent skeleton, a benzimidazolone coloring agent skeleton, a benzothiazole coloring agent skeleton, a benzimidazole coloring agent skeleton, or a benzoxazole coloring agent skeleton, still more preferably at least one selected from a squarylium coloring agent skeleton, a pyrrolopyrrole coloring agent skeleton, a diketopyrrolopyrrole coloring agent skeleton, a quinacridone coloring agent skeleton, or a benzimidazolone coloring agent skeleton, and particularly preferably a squarylium coloring agent skeleton or a pyrrolopyrrole coloring agent skeleton.

The linking group represented by L is preferably a group composed of 1 to 100 carbon atoms, 0 to 10 nitrogen atoms, 0 to 50 oxygen atoms, 1 to 200 hydrogen atoms, and 0 to 20 sulfur atoms, and may be unsubstituted or may further have a substituent. Examples of the substituent include the substituent T described later.

Examples of the acid group, basic group, and hydrogen bonding group represented by X include the above-described groups.

In a case where a pigment-type compound is used as the near-infrared absorbing coloring agent, the pigment derivative is also preferably a compound having a maximal absorption wavelength in a wavelength range of 700 nm to 1,200 nm, preferably a compound having a maximal absorption wavelength in a wavelength range of 700 nm to 1,100 nm, and preferably a compound having a maximal absorption wavelength in a wavelength range of 700 nm to 1,000 nm. In a pigment derivative having a maximal absorption wavelength in the above-described wavelength range, a spread of π plane can be easily brought close to the near-infrared absorbing coloring agent, adsorptivity of the near-infrared absorbing coloring agent is improved, and more excellent dispersion stability can be easily obtained. In addition, the pigment derivative is also preferably a compound including an aromatic ring, and more preferably a compound including a structure in which two or more aromatic rings are condensed. In addition, the pigment derivative is also preferably a compound having a π-conjugated plane, and more preferably a compound having a π-conjugated plane having the same structure as the π-conjugated plane included in the near-infrared absorbing coloring agent. In addition, the number of π electrons included in the π-conjugated plane of the pigment derivative is preferably 8 to 100. The upper limit is preferably 90 or less and more preferably 80 or less. The lower limit is preferably 10 or more and more preferably 12 or more. In addition, it is also preferable that the pigment derivative is a compound having a π-conjugated plane including a partial structure represented by Formula (SQ-a).

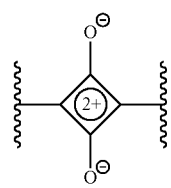

(SQ-a)

In Formula (SQ-a), a wavy line portion represents a bonding position with other structures.

The pigment derivative is also preferably a compound represented by Formula (Syn1).

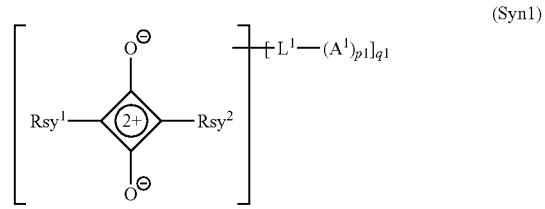

(Syn1)

In Formula (Syn1), Rsy$^1$ and Rsy$^2$ each independently represent an organic group; L represents a single bond or a p1+1-valent group; A$^1$ represents a group selected from a sulfo group, a carboxy group, a phosphoric acid group, a boronic acid group, a sulfonimide group, a sulfonamide group, an amino group, a pyridinyl group, salts of these groups, and a desalted structure of these; and p1 and q1 each independently represent an integer of 1 or more. In a case where p1 is 2 or more, a plurality of A$^1$'s may be the same or different from each other. In a case where q1 is 2 or more, a plurality of L$^1$'s and A$^1$'s may be respectively the same or different from each other.

Examples of the organic group represented by Rsy$^1$ and Rsy$^2$ in Formula (Syn1) include an aryl group, a heteroaryl group, and a group represented by Formula (R1).

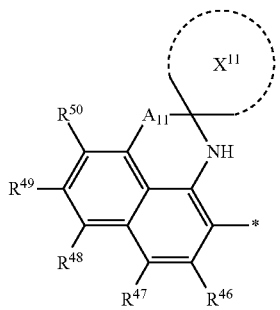

(R1)

In Formula (R1), $X^{11}$ represents a ring structure, $A^{11}$ represents O or $NR^{51}$, $R^{46}$ to $R^{51}$ each independently represent a hydrogen atom or a substituent, $R^{47}$ and $R^{48}$ may be bonded to each other to form a ring, and * represents a bonding site.

Examples of the p1+1-valent group represented by $L^1$ in Formula (Syn1) include a hydrocarbon group, a heterocyclic group, —O—, —S—, —CO—, —COO—, —OCO—, —SO$_2$—, —NR$^L$—, —NR$^L$CO—, —CONR$^L$—, —NR$^L$SO$_2$—, —SO$_2$NR$^L$—, and a group formed by a combination of two or more of these groups. $R^L$ represents a hydrogen atom, an alkyl group, or an aryl group. The hydrocarbon group may be an aliphatic hydrocarbon group or an aromatic hydrocarbon group. Examples of the hydrocarbon group include an alkylene group, an arylene group, and a group obtained by removing one or more hydrogen atoms from these groups. The number of carbon atoms in the alkylene group preferably is 1 to 30, more preferably 1 to 15, and still more preferably 1 to 10. The alkylene group may be linear, branched, or cyclic. In addition, the cyclic alkylene group may be monocyclic or polycyclic. The number of carbon atoms in the arylene group is preferably 6 to 18, more preferably 6 to 14, and still more preferably 6 to 10. The heterocyclic group is preferably a monocyclic ring or a fused ring having 2 to 4 rings. The number of heteroatoms constituting a ring of the heterocyclic group is preferably 1 to 3. The heteroatom constituting the ring of the heterocyclic group is preferably a nitrogen atom, an oxygen atom, or a sulfur atom. The number of carbon atoms constituting the ring of the heterocyclic group is preferably 3 to 30, more preferably 3 to 18, and more preferably 3 to 12. The hydrocarbon group and heterocyclic group may have a substituent. Examples of the substituent include groups listed in the substituent T described later. The number of carbon atoms in the alkyl group represented by $R^L$ is preferably 1 to 20, more preferably 1 to 15, and still more preferably 1 to 8. The alkyl group may be any of linear, branched, and cyclic forms, and is preferably linear or branched and more preferably linear. The alkyl group represented by $R^L$ may further have a substituent. Examples of the substituent include the substituent T described later. The number of carbon atoms in the aryl group represented by $R^L$ is preferably 6 to 30, more preferably 6 to 20, and still more preferably 6 to 12. The aryl group represented by $R^L$ may further have a substituent. Examples of the substituent include the substituent T described later.

—Substituent T—

Examples of the substituent T include a halogen atom, a cyano group, a nitro group, an alkyl group, an alkenyl group, an alkynyl group, an aryl group, a heteroaryl group, —ORt$^1$, —CORt$^1$, —COORt$^1$, —OCORt$^1$, —NRt$^1$Rt$^2$, —NHCORt$^1$, —CONRt$^1$Rt$^2$, —NHCONRt$^1$Rt$^2$, —NHCOORt$^1$, —SRt$^1$, —SO$_2$Rt$^1$, —SO$_2$ORt$^1$, —NHSO$_2$Rt$^1$, and —SO$_2$NRt$^1$Rt$^2$. Rt$^1$ and Rt$^2$ each independently represent a hydrogen atom, an alkyl group, an alkenyl group, an alkynyl group, an aryl group, or a heteroaryl group. Rt$^1$ and Rt$^2$ may be bonded to each other to form a ring.

Specific examples of the pigment derivative include compounds having the following structures. In addition, examples thereof include compounds described in JP1981-118462A (JP-S56-118462A), JP1988-264674A (JP-S63-264674A), JP1989-217077A (JP-H1-217077A), JP1991-9961A (JP-H3-9961A), JP1991-26767A (JP-H3-26767A), JP1991-153780A (JP-H3-153780A), JP1991-45662A (JP-H3-45662A), JP1992-285669A (JP-H4-285669A), JP1994-145546A (JP-H6-145546A), JP1994-212088A (JP-H6-212088A), JP1994-240158A (JP-H6-240158A), JP1998-30063A (JP-H10-30063A), JP1998-195326A (JP-H10-195326A), paragraphs 0086 to 0098 of WO2011/024896A, and paragraphs 0063 to 0094 of WO2012/102399A.

Further, as the pigment derivative, compounds described in JP2015-172732A (metal salt of a quinophthalone compound having a sulfo group), JP2014-199308A, JP2014-85562A, JP2014-35351A, or JP2008-81565A can also be used, the contents of which are incorporated herein by reference.

Ph represents a phenyl group.

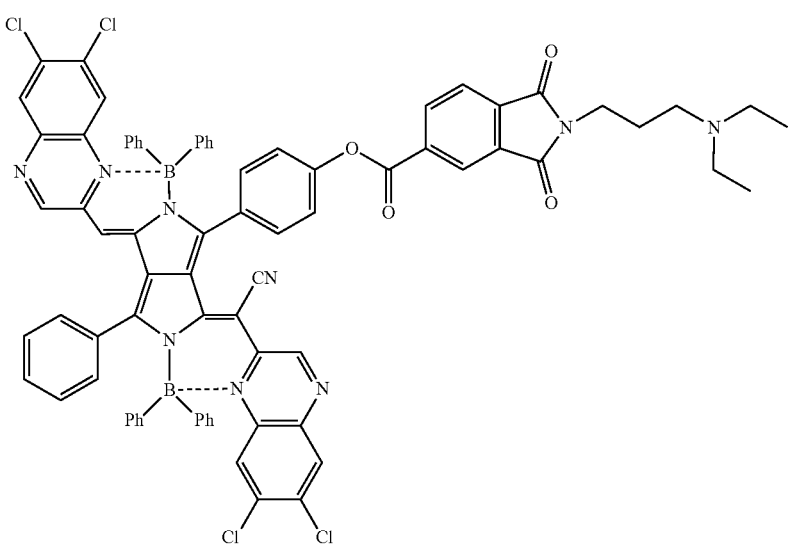

B-1

-continued
| | |
|---|---|
| B-2 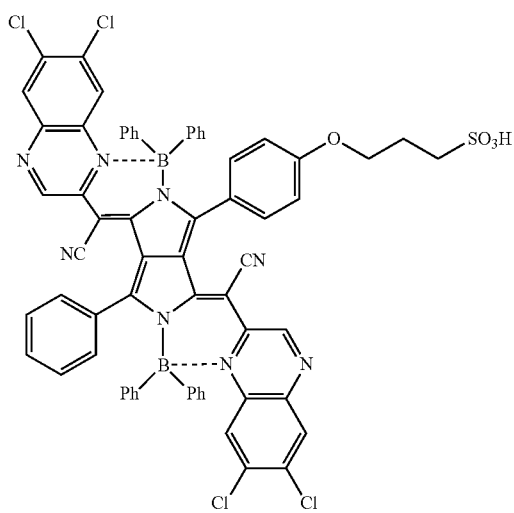 | B-3 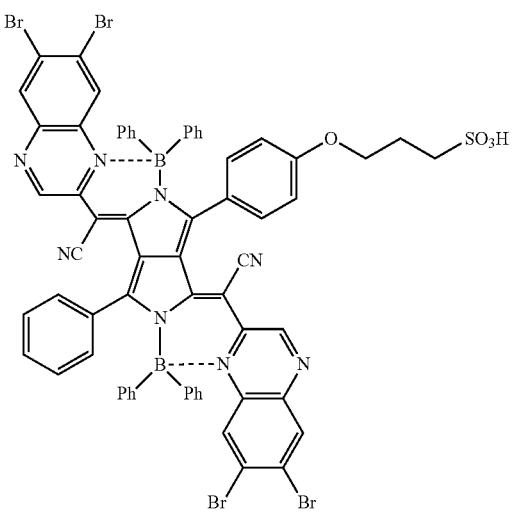 |
| B-4 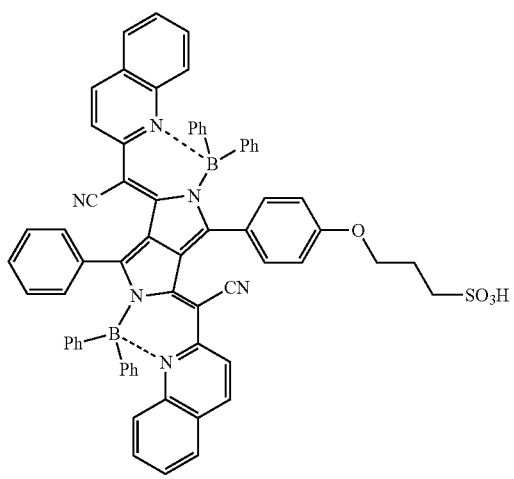 | B-5 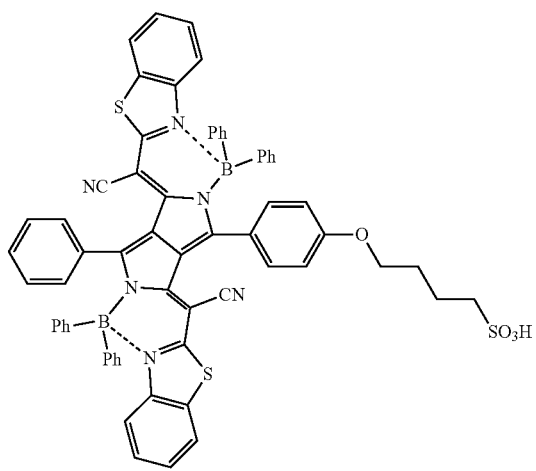 |
| B-6 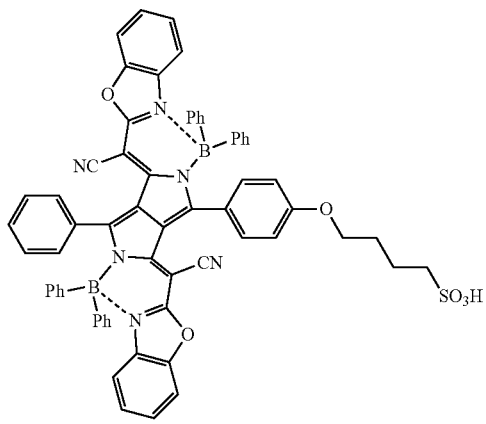 | B-7 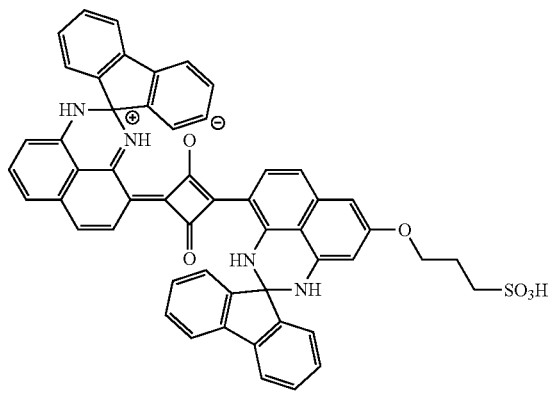 |

-continued
B-8
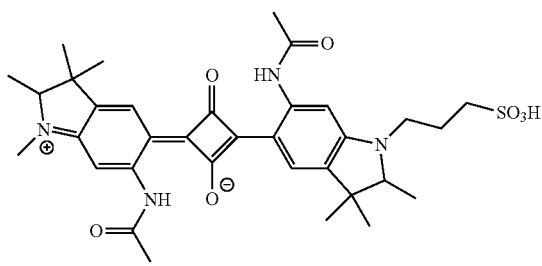
B-9
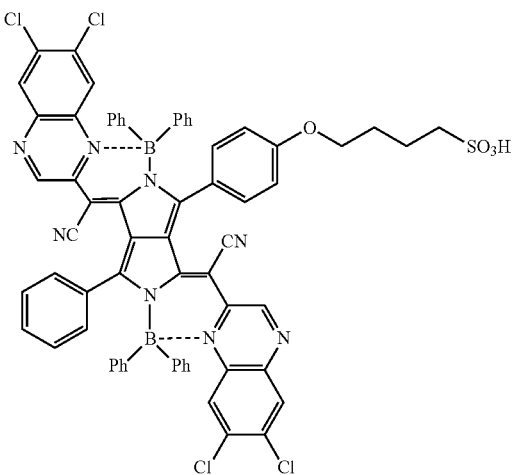
B-10
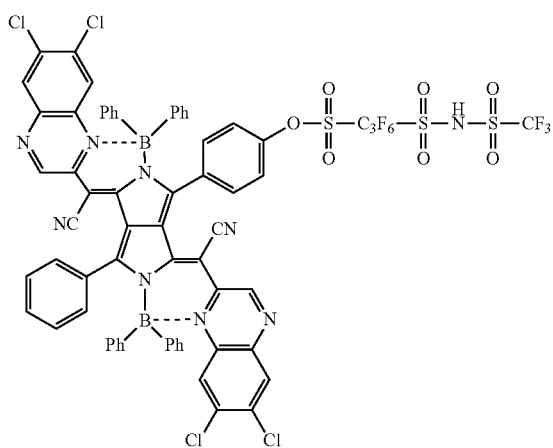
B-11
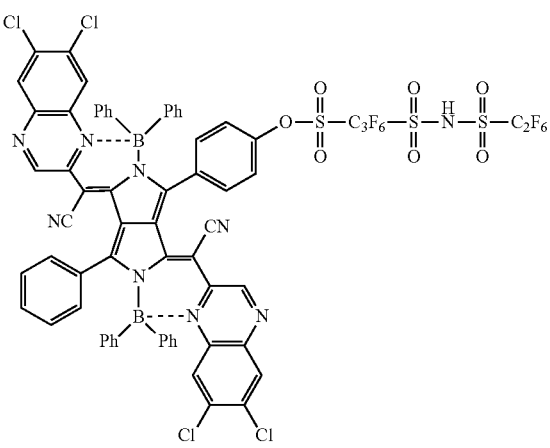
B-12
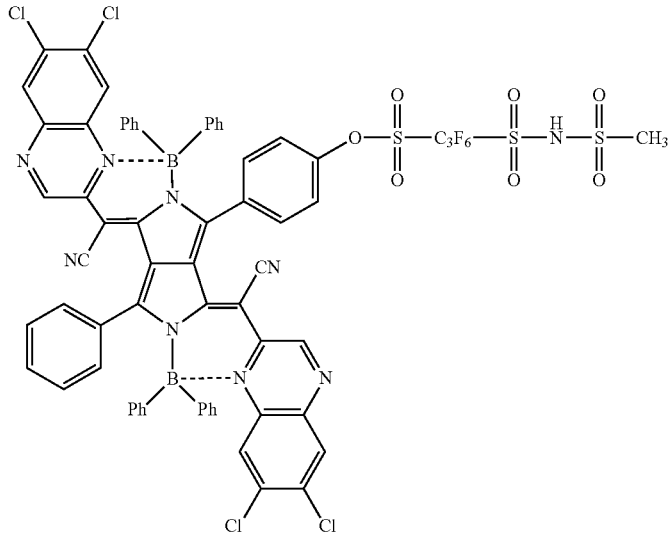

B-13
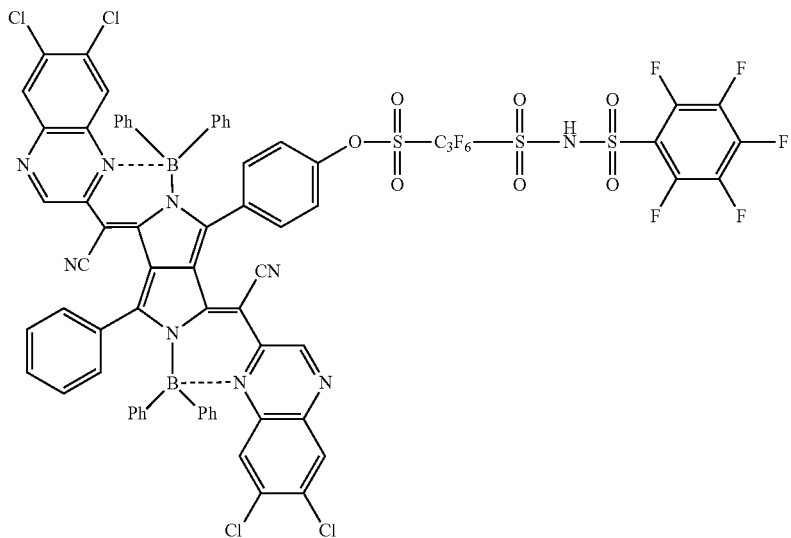
B-14
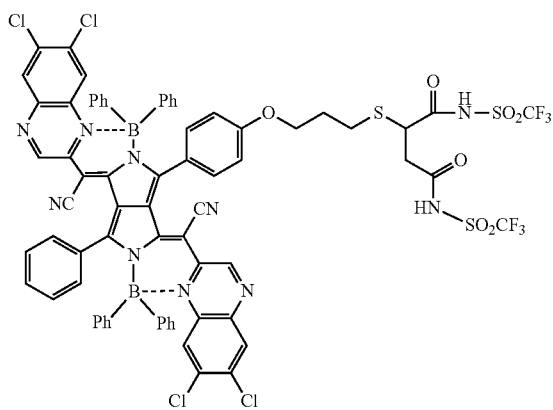
B-15
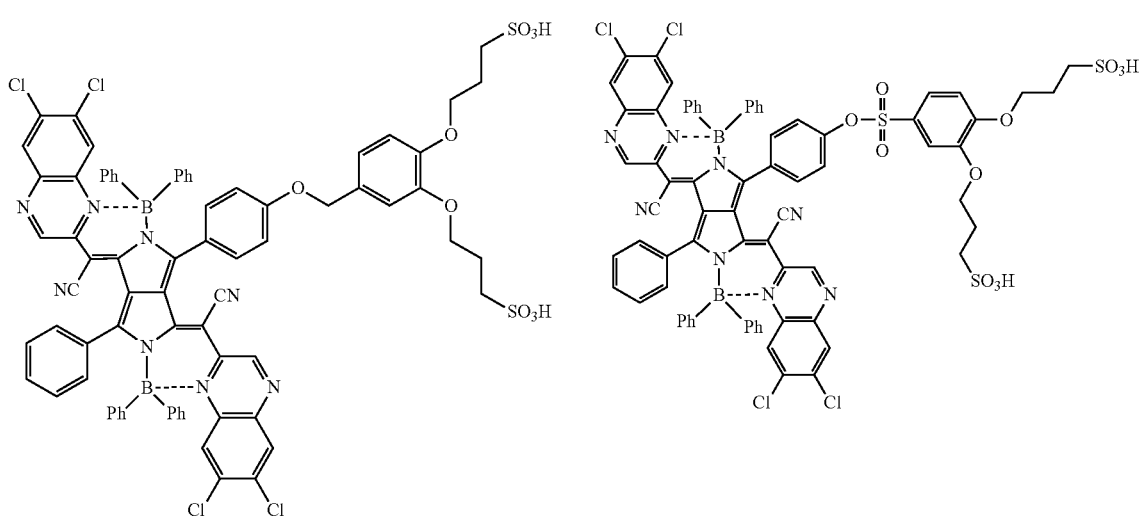
B-16
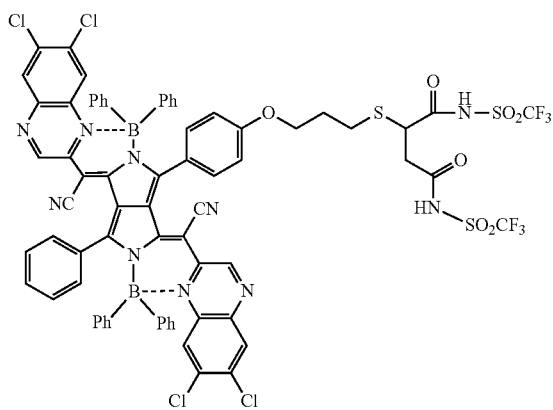
B-17
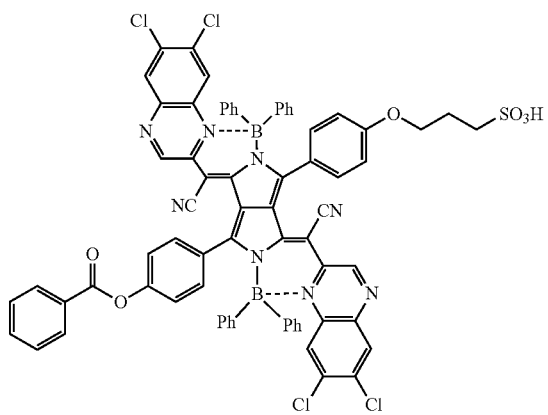

-continued
B-18
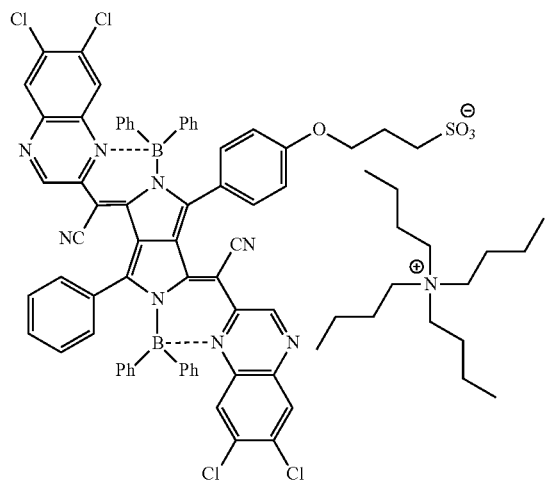
B-19
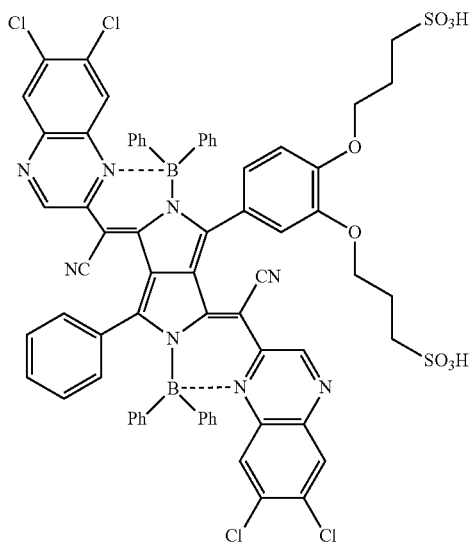
B-20
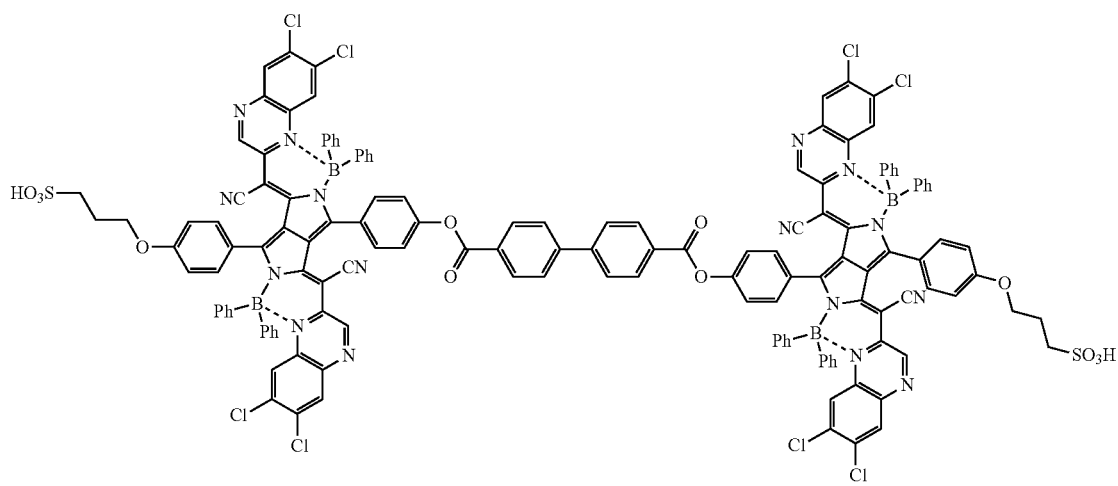
B-21
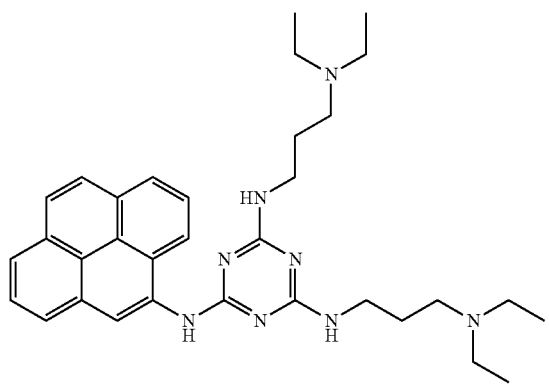
B-22
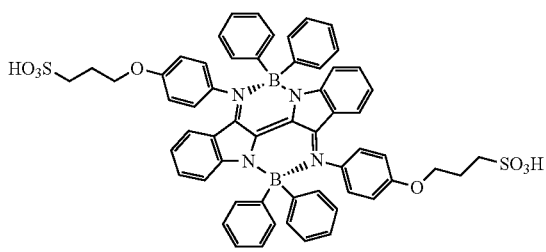

B-23
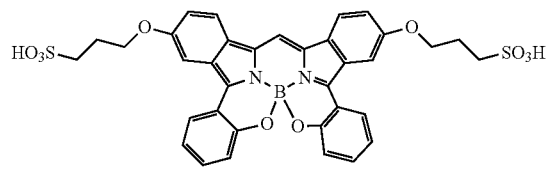
B-24
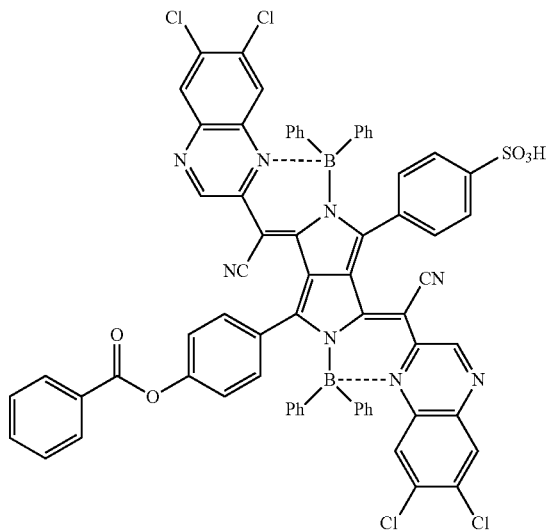
B-25
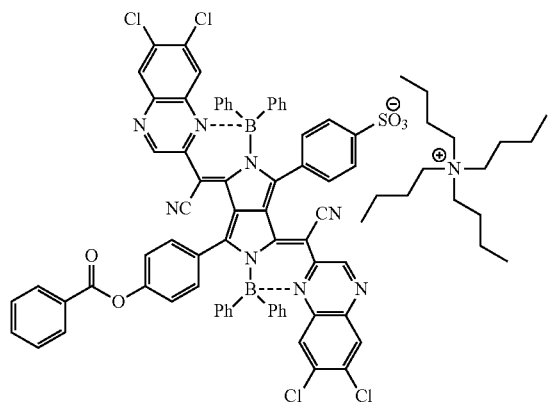
B-26
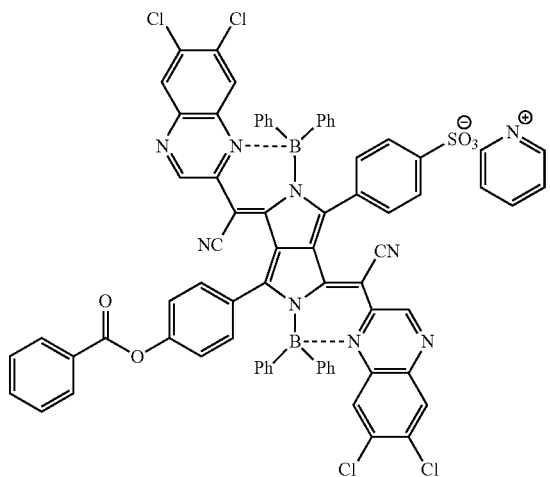
B-27
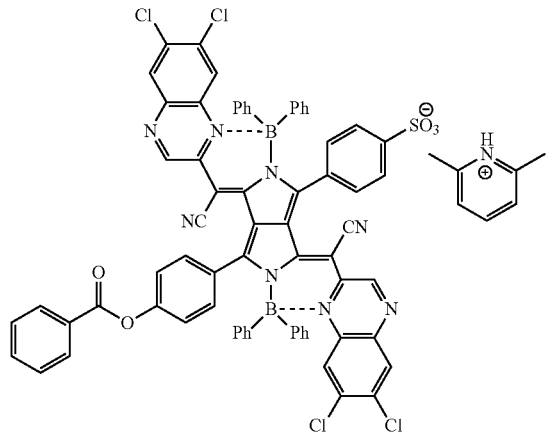
B-28
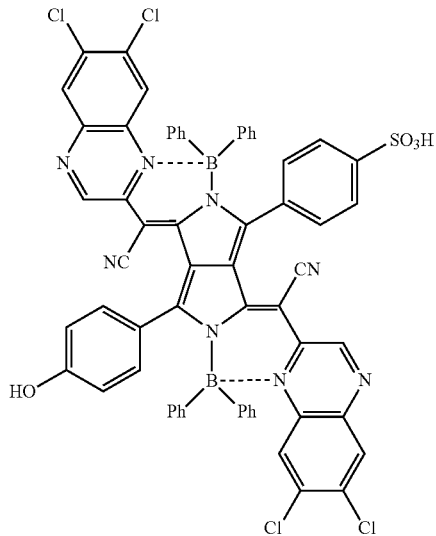

-continued
B-29
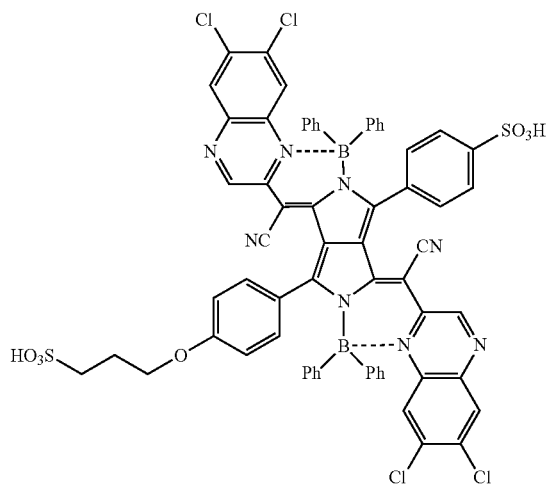
B-30
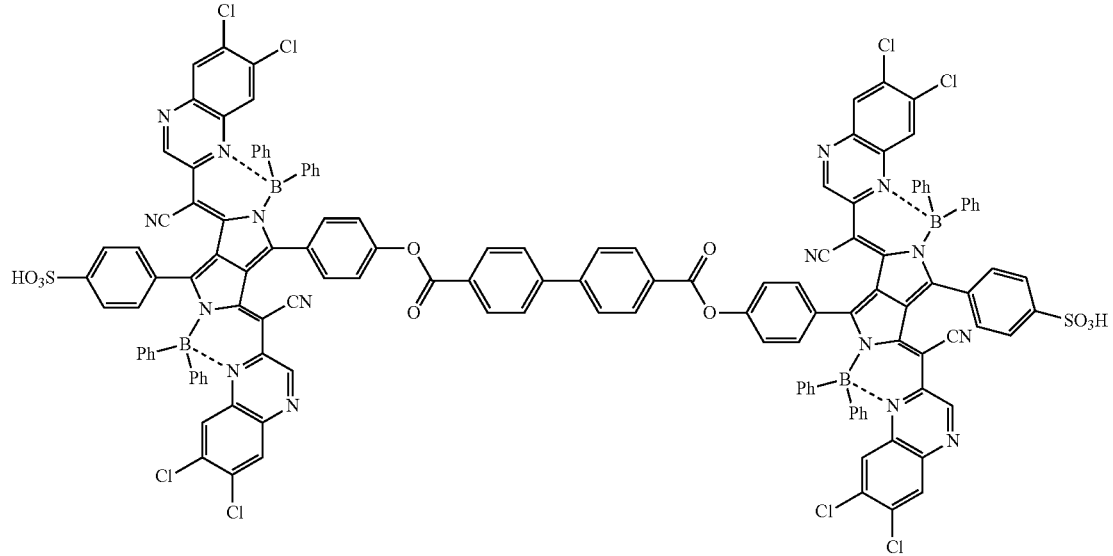
B-31
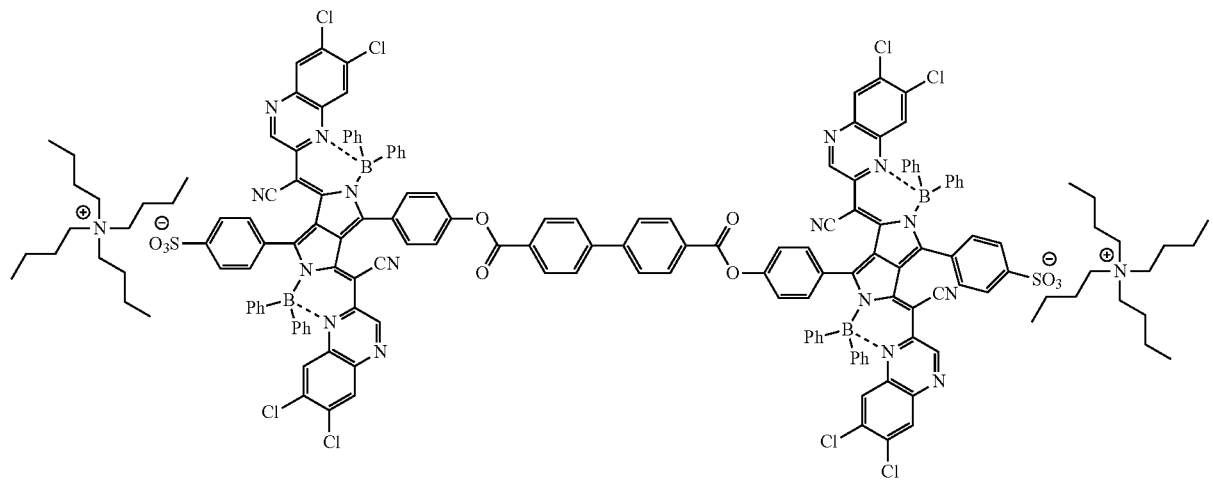

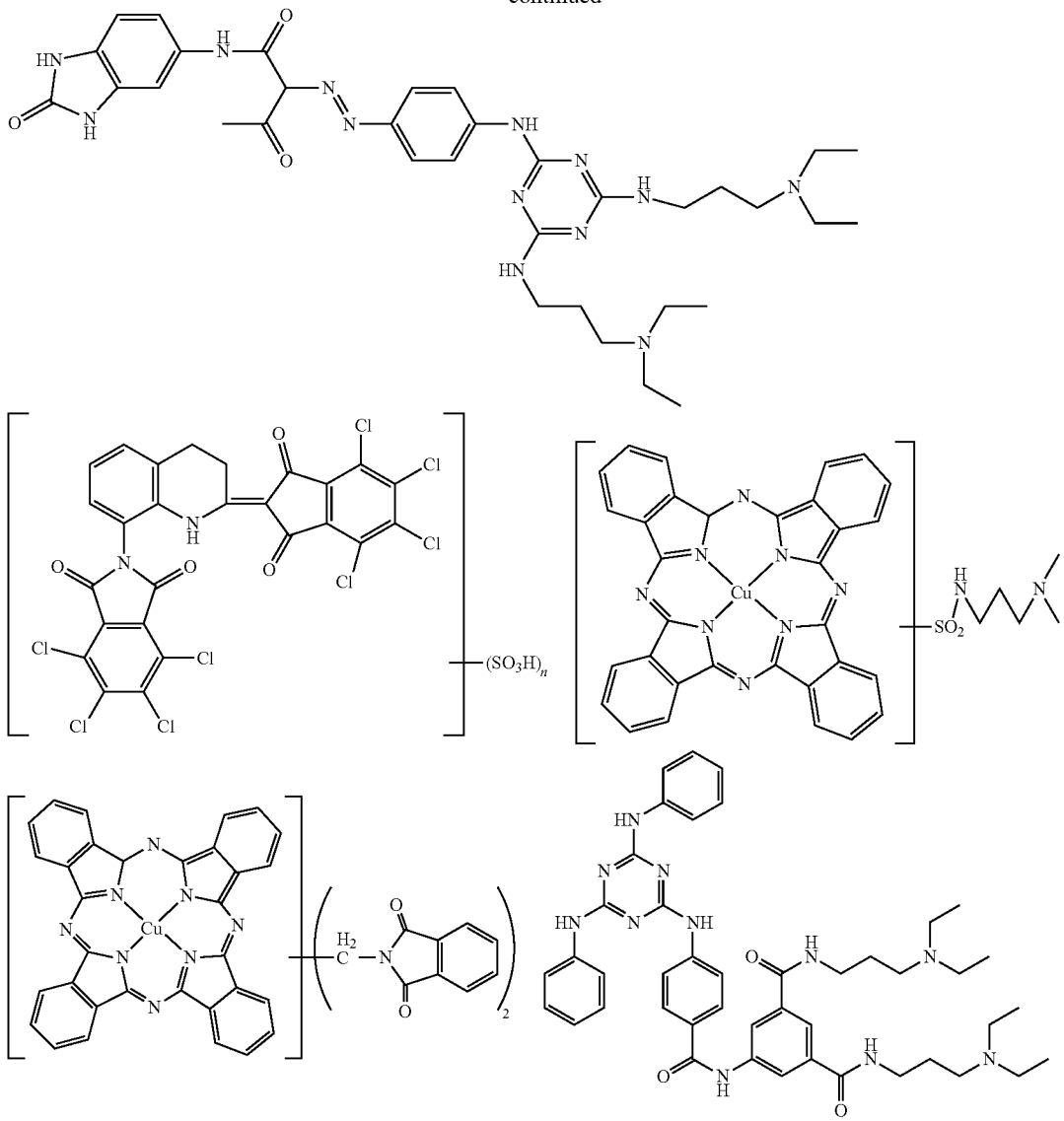

In a case where the composition contains a pigment derivative, the content of the pigment derivative is preferably 1 part by mass to 30 parts by mass and still more preferably 3 parts by mass to 20 parts by mass with respect to 100 parts by mass of the pigment among the compound having a structure represented by Formula (1) and the above-described colorant. The pigment derivative may be used singly or in combination of two or more kinds thereof.

<Polymerization Inhibitor>

From the viewpoint of storage stability, the composition according to the embodiment of the present disclosure preferably includes a polymerization inhibitor.

The polymerization inhibitor is not particularly limited, and a known polymerization inhibitor can be used.

Examples of the polymerization inhibitor include hydroquinone, p-methoxyphenol, di-t-butyl-p-cresol, pyrogallol, t-butyl catechol, benzoquinone, 4,4'-thiobis(3-methyl-6-t-butylphenol), 2,2'-methylenebis(4-methyl-6-t-butylphenol), an N-nitrosophenylhydroxylamine salt (an ammonium salt, a cerous salt, or the like), and 2,2,6,6-tetramethylpiperidin-1-oxyl. The polymerization inhibitor may also function as an antioxidant.

The polymerization inhibitor may be used singly or in combination of two or more kinds thereof.

From the viewpoint of storage stability, the content of the polymerization inhibitor is preferably 0.1 ppm to 1,000 ppm, more preferably 1 ppm to 500 ppm, and particularly preferably 1 ppm to 100 ppm with respect to the total solid content of the composition.

<Solvent>

The composition according to the embodiment of the present disclosure may contain a solvent.

Examples of the solvent include esters such as ethyl acetate, n-butyl acetate, isobutyl acetate, amyl formate, isoamyl acetate, isobutyl acetate, butyl propionate, isopropyl butyrate, ethyl butyrate, butyl butyrate, alkyl esters, methyl lactate, ethyl lactate, methyl oxyacetate, ethyl oxyacetate, butyl oxyacetate, methyl methoxyacetate, ethyl methoxyacetate, butyl methoxyacetate, methyl ethoxyacetate, ethyl ethoxyacetate, alkyl esters of 3-oxypropionate such as methyl 3-oxypropionate and ethyl 3-oxypropionate (for example, methyl 3-methoxypropionate, ethyl 3-methoxypropionate, methyl 3-ethoxypropionate, and ethyl 3-ethoxypropionate), alkyl esters of 2-oxypropionate such as methyl 2-oxypropionate, ethyl 2-oxypropionate, and propyl 2-oxypropionate (for example, methyl 2-methoxypropionate, ethyl 2-methoxypropionate, propyl 2-methoxypropionate, methyl 2-ethoxypropionate, ethyl 2-ethoxypropionate, methyl 2-oxy-2-methylpropionate, 2-ethyl 2-oxy-2-methylpropionate, methyl 2-methoxy-2-methylpropionate, and ethyl 2-ethoxy-2-methylpropionate), methyl pyruvate, ethyl pyruvate, propyl pyruvate, methyl acetoacetate, ethyl acetoacetate, methyl 2-oxobutate, and ethyl 2-oxobutate;

ethers such as diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol methyl ether acetate, propylene glycol ethyl ether acetate, propylene glycol propyl ether acetate; ketones such as methyl ethyl ketone, cyclohexanone, 2-heptanone, and 3-heptanone; and aromatic hydrocarbons such as toluene and xylene. In this case, it may be preferable that the content of aromatic hydrocarbons (such as benzene, toluene, xylene, and ethylbenzene) as the organic solvent is low (for example, 50 parts per million (ppm) by mass or less, 10 ppm by mass or less, or 1 ppm by mass or less with respect to the total mass of the organic solvent) in consideration of environmental aspects and the like.

Among these, methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, propylene glycol methyl ether acetate, or the like is suitable.

The solvent may be used alone or in combination of two or more thereof.

In the present disclosure, an organic solvent having a low metal content is preferably used. For example, the metal content in the organic solvent is preferably 10 mass parts per billion (ppb) or less. Optionally, an organic solvent having a metal content at a mass parts per trillion (ppt) level may be used. For example, such an organic solvent is available from Toyo Gosei Co., Ltd. (The Chemical Daily, Nov. 13, 2015).

Examples of a method for removing impurities such as a metal from the organic solvent include distillation (such as molecular distillation and thin-film distillation) and filtration using a filter. The filter pore size of the filter used for the filtration is preferably 10 µm or less, more preferably 5 µm or less, and still more preferably 3 µm or less. As a material of the filter, polytetrafluoroethylene, polyethylene, or nylon is preferable.

The organic solvent may include an isomer (a compound having the same number of atoms and a different structure). In addition, only one kind of isomers may be included, or a plurality of isomers may be included.

The organic solvent preferably has the content of peroxides of 0.8 mmol/L or less, and more preferably, the organic solvent does not substantially include peroxides.

The total solid content of the composition according to the embodiment of the present disclosure varies depending on the coating method and the presence or absence of the solvent, but is preferably 1 mass % to 100 mass %, for example. The lower limit is more preferably 10 mass % or more.

<Sensitizer>

The composition according to the embodiment of the present disclosure may contain a sensitizer in order to improve generation efficiency of polymerization initiation species such as radicals and cations of the polymerization initiator and lengthening the photosensitive wavelength. It is preferable that the sensitizer which can be used in the present disclosure sensitizes the above-described photopolymerization initiator using an electron migration mechanism or an energy-transfer mechanism.

Examples of the sensitizer include a sensitizer which belongs to compounds listed below and has an absorption wavelength in a wavelength region of 300 nm to 450 nm.

Examples of a preferred sensitizer include a sensitizer which belongs to the following compounds and has an absorption wavelength in a wavelength region of 330 nm to 450 nm.

Examples thereof include polynuclear aromatic compounds (for example, phenanthrene, anthracene, pyrene, perylene, triphenylene, and 9,10-dialkoxyanthracene), xanthenes (for example, fluoressein, eosin, erythrosin, Rhodamine B, and rose bengal), thioxanthons (isopropylthioxanthone, diethylthioxanthone, and chlorothioxanthone), cyanines (for example, thiacarbocyanine and oxacarbocyanine), merocyanines (for example, merocyanine and carbomerocyanine), phthalocyanines, thiazines (for example, thionine, methylene blue, and toluidine blue), acridines (for example, acridine orange, chloroflavin, and acriflavin), anthraquinones (for example, anthraquinone), squaryliums (for example, squarylium), acridine orange, coumarins (for example, 7-diethylamino-4-methylcoumarin), ketocoumarins, phenothiazines, phenazines, styrylbenzenes, azo compounds, diphenylmethane, triphenylmethane, distyrylbenzenes, carbazoles, porphyrin, spiro compounds, quinacridone, indigo, styryl, pyrylium compounds, pyrromethene compounds, pyrazorotriazole compounds, benzothiazole compounds, barbituric acid derivatives, thiobarbituric acid derivatives, aromatic ketone compounds such as acetophenone, benzophenone, and Michler's ketone, and heterocyclic compounds such as N-aryloxazolidinone. Further, examples thereof include compounds described in EP568993B, U.S. Pat. Nos. 4,508,811A, 5,227,227A, JP2001-125255A, JP1999-271969A (JP-H11-271969A), and the like.

The sensitizer may be used alone or in combination of two or more kinds thereof. From the viewpoint of light absorption efficiency to a deep portion and initial decomposition efficiency, the content of the sensitizer in the composition according to the embodiment of the present disclosure is preferably 0.1 mass % to 20 mass % and more preferably 0.5 mass % to 15 mass % with respect to the total solid content of the composition.

<Co-Sensitizer>

The composition according to the embodiment of the present disclosure may contain a co-sensitizer. The co-sensitizer has a function of further improving sensitivity of the sensitizing coloring agent or the initiator to radioactive ray, or of suppressing inhibition of polymerization of the polymerizable compound due to oxygen.

In addition, examples of the co-sensitizer include compounds described in paragraphs 0233 to 0241 of JP2007-277514A.

From the viewpoint of improving curing rate by balancing polymerization growth rate and chain transfer, the content of these co-sensitizers is preferably in a range of 0.1 mass % to 30 mass %, more preferably in a range of 0.5 mass % to 25 mass %, and still more preferably in a range of 1 mass % to 20 mass % with respect to the mass of the total solid content of the composition.

<Other Components>

Optionally, the composition according to the embodiment of the present disclosure can contain various additives such as a fluorine-based organic compound, a thermal polymerization inhibitor, a photopolymerization initiator, other fillers, a polymer compound other than the alkali-soluble resin and the dispersant, a surfactant, and adhesion promoter, an antioxidant, an ultraviolet absorber, and an anti-aggregation agent.

Examples of other components include compounds described in paragraphs 0238 to 0249 of JP2007-277514A.

<Preparation of Composition>

The composition according to the embodiment of the present disclosure can be prepared by mixing each of the above-described components. In addition, it is preferable that the composition is filtered through a filter, for example, in order to remove foreign matters or to reduce defects.

As the filter, any filters that have been used in the related art for filtration use and the like may be used without particular limitation. Examples of the filter include filters formed of a fluororesin such as polytetrafluoroethylene (PTFE), a polyamide-based resin such as nylon (for example, nylon-6 and nylon-6,6), or a polyolefin resin (including a polyolefin resin having a high-density or an ultrahigh molecular weight) such as polyethylene and polypropylene (PP). Among these materials, polypropylene (including a high-density polypropylene) or nylon is preferable.

The pore size of the filter is preferably 0.01 µm to 7.0 µm, more preferably 0.01 µm to 3.0 µm, and still more preferably 0.05 µm to 0.5 µm. Within this range, it is possible to reliably remove fine foreign matters which hinder the preparation of uniform and smooth composition in the subsequent step. In addition, it is also preferable to use a fibrous filter medium, examples of the filter medium include polypropylene fiber, nylon fiber, and glass fiber, and specifically, filter cartridges of SBP type series (SBP008 and the like), TPR type series (TPR002, TPR005, and the like), or SHPX type series (SHPX003 and the like), all manufactured by Roki Techno Co., Ltd, can be used.

In a case of using a filter, different filters may be combined. In this case, the filtration with a first filter may be performed once or may be performed twice or more times.

In addition, first filters having different pore sizes within the above-described range may be combined. Here, the pore size of the filter can refer to a nominal value of a manufacturer of the filter. As a commercially available filter, for example, various filters provided by Nihon Pall Corporation (DFA4201NXEY and the like), Advantec Toyo Kaisha., Ltd., Nihon Entegris G.K., Kitz Microfilter Corporation, or the like can be selected.

<Use of Composition>

Since the composition according to the embodiment of the present disclosure can be liquid, for example, a film can be easily manufactured by applying the composition according to the embodiment of the present disclosure to a base material or the like, and drying the composition according to the embodiment of the present disclosure.

In a case where the film is formed by coating, from the viewpoint of application property, the viscosity of the composition according to the embodiment of the present disclosure at 25° C. is preferably 1 mPa·s to 100 mPa·s. The lower limit is more preferably 2 mPa·s or more and still more preferably 3 mPa·s or more. The upper limit is more preferably 50 mPa·s or less, still more preferably 30 mPa·s or less, and particularly preferably 15 mPa·s or less.

The viscosity in the present disclosure is measured using a viscometer (trade name: VISCOMETER TV-22) manufactured by Toki Sangyo Co., Ltd. at 25° C.

The use of the composition according to the embodiment of the present disclosure is not particularly limited. For example, the composition according to the embodiment of the present disclosure can be preferably used to form an infrared cut filter or the like. For example, the composition according to the embodiment of the present disclosure can be preferably used for an infrared cut filter on a light-receiving side of a solid-state imaging element (for example, for an infrared cut filter for a wafer level lens), an infrared cut filter on a back surface side (opposite to the light-receiving side) of the solid-state imaging element, and the like. In particular, the composition according to the embodiment of the present disclosure can be preferably used as an infrared cut filter on a light-receiving side of a solid-state imaging element. In addition, by further adding the colorant which shields visible light to the composition according to the embodiment of the present disclosure, it is possible to form an infrared transmitting filter capable of transmitting infrared rays of a specific wavelength or higher. For example, it is also possible to form an infrared transmitting filter capable of transmitting infrared rays having a wavelength of 850 nm or more by shielding light from a wavelength of 400 nm to 850 nm.

In addition, the composition according to the embodiment of the present disclosure is preferably stored in a storage container.

As the storage container, for the purpose of preventing impurities from being infiltrated into raw materials and the composition, a multilayer bottle in which a container interior wall having a six-layer structure is formed of six kinds of resins or a bottle in which a container interior wall having a seven-layer structure is formed of six kinds of resins is preferably used. Examples of these containers include containers described in JP2015-123351A.

<Film>

A film according to the embodiment of the present disclosure is a film which consists of the composition according to the embodiment of the present disclosure or is obtained by curing the composition. In addition, in a case where the composition includes a solvent, the film may be dried. The film according to the embodiment of the present disclosure can be preferably used as an infrared cut filter. In addition, the film according to the embodiment of the present disclosure can also be used as a heat ray shielding filter or an infrared transmitting filter. The film according to the embodiment of the present disclosure may be used by being laminated on a support, or may be used by being peeled off from a support. The film according to the embodiment of the present disclosure may be a film having a pattern or a film (flat film) not having a pattern.

In the "drying" in the present disclosure, it is sufficient to remove at least a part of the solvent and it is not necessary to completely remove the solvent, and the amount of the solvent removed can be set as desired.

In addition, the above-described curing may be performed as long as the hardness of the film is improved, but curing by polymerization is preferable.

The thickness of the film according to the embodiment of the present disclosure can be appropriately adjusted according to the purpose. The thickness of the film is preferably 20 µm or less, more preferably 10 µm or less, and still more preferably 5 µm or less. The lower limit of the thickness of the film is preferably 0.1 µm or more, more preferably 0.2 µm or more, and still more preferably 0.3 µm or more.

The film according to the embodiment of the present disclosure preferably has a maximal absorption wavelength in a wavelength range of 650 nm to 1,500 nm, more preferably has a maximal absorption wavelength in a wavelength range of 680 nm to 1,300 nm, and still more preferably has a maximal absorption wavelength in a wavelength range of 700 nm to 850 nm.

In a case where the film according to the embodiment of the present disclosure is used as an infrared cut filter, the film according to the embodiment of the present disclosure preferably satisfies at least one condition of the following (1) to (4), and still more preferably satisfies all the conditions of (1) to (4).

(1) transmittance at a wavelength of 400 nm is preferably 70% or more, more preferably 80% or more, still more preferably 85% or more, and particularly preferably 90% or more.

(2) transmittance at a wavelength of 500 nm is preferably 70% or more, more preferably 80% or more, still more preferably 90% or more, and particularly preferably 95% or more.

(3) transmittance at a wavelength of 600 nm is preferably 70% or more, more preferably 80% or more, still more preferably 90% or more, and particularly preferably 95% or more.

(4) transmittance at a wavelength of 650 nm is preferably 70% or more, more preferably 80% or more, still more preferably 90% or more, and particularly preferably 95% or more.

The film according to the embodiment of the present disclosure can be used in combination with a color filter including a chromatic colorant. The color filter can be manufactured using a coloring composition including a chromatic colorant. Examples of the chromatic colorant include the chromatic colorants described in the section of the composition according to the embodiment of the present disclosure. The coloring composition can further contain a resin, a polymerizable compound, a polymerization initiator, a surfactant, a solvent, a polymerization inhibitor, an ultraviolet absorber, and the like. Examples of the details thereof include the above-described materials, and these can be used.

In a case where the film according to the embodiment of the present disclosure and the color filter are used in combination, it is preferable that the color filter is disposed on an optical path of the film according to the embodiment of the present disclosure. For example, the film according to the embodiment of the present disclosure and the color filter can be laminated to be used as a laminate. In the laminate, the film according to the embodiment of the present disclosure and the color filter may be or may not be adjacent to each other in a thickness direction. In a case where the film according to the embodiment of the present disclosure is not adjacent to the color filter in the thickness direction, the film according to the embodiment of the present disclosure may be formed on another support other than a support on which the color filter is formed, or another member (for example, a microlens or a planarizing layer) constituting a solid-state imaging element may be interposed between the film according to the embodiment of the present disclosure and the color filter.

In the present disclosure, an infrared cut filter refers to a filter which allows transmission of light (visible light) in the visible range and shields at least a part of light (infrared rays) in the near-infrared range. The infrared cut filter may be a filter which allows transmission of light in the entire wavelength range of the visible range, or may be a filter which allows transmission of light in a specific wavelength range of the visible range and shields light in another specific wavelength range of the visible range. In addition, in the present disclosure, a color filter refers to a filter which allows transmission of light in a specific wavelength range of the visible range and shields light in another specific wavelength range of the visible range. In addition, in the present disclosure, an infrared transmitting filter refers to a filter which shields visible light and allows transmission of at least a part of near-infrared rays.

The film according to the embodiment of the present disclosure can be used in various devices including a solid-state imaging element such as a charge coupled device (CCD) or a complementary metal-oxide semiconductor (CMOS), an infrared sensor, or an image display device.

<Method for Manufacturing Film>

Next, a method for manufacturing the film according to the embodiment of the present disclosure will be described. The film according to the embodiment of the present disclosure can be manufactured through a step of applying the composition according to the embodiment of the present disclosure.

In the method for manufacturing the film according to the embodiment of the present disclosure, it is preferable that the composition is applied to a support. Examples of the support include a substrate formed of a material such as silicon, non-alkali glass, soda glass, PYREX (registered trademark) glass, or quartz glass. For example, an organic film or an inorganic film may be formed on the substrate. Examples of a material of the organic film include the resins described above. In addition, as the support, a substrate formed of the above-described resin can also be used. In addition, a charge coupled device (CCD), a complementary metal-oxide semiconductor (CMOS), a transparent conductive film, or the like may be formed on the support. In addition, a black matrix which separates pixels from each other may be formed on the support. In addition, optionally, an undercoat layer may be provided on the support to improve adhesiveness with a layer above the support, to prevent diffusion of materials, or to planarize the surface of the support such as a substrate. In addition, in a case where a glass substrate is used as the support, it is preferable that an inorganic film is formed on the glass substrate or the glass substrate may be dealkalized to be used. According to this aspect, it is easy to manufacture a film in which the generation of foreign matters is further suppressed.

As a method of applying the composition, a known method can be used. Examples thereof include a dropping method (drop casting); a slit coating method; a spray method; a roll coating method; a spin coating method (spin coating); a cast coating method; a slit and spin method; a pre-wet method (for example, a method described in JP2009-145395A), various printing methods such as an ink jet (for example, on-demand type, piezo type, thermal type), a discharge printing such as nozzle jet, a flexo printing, a screen printing, a gravure printing, a reverse offset printing, and a metal mask printing a transfer method using molds and the like; and a nanoimprinting method. A method for applying the ink jet is not particularly limited, and examples thereof include a method described in "Extension of Use of Ink Jet—Infinite Possibilities in Patent—" (February, 2005, S. B. Research Co., Ltd.) (particularly, pp. 115 to 133) and methods described in JP2003-262716A, JP2003-185831A, JP2003-261827A, JP2012-126830A, and JP2006-169325A.

A composition layer formed by applying the composition may be dried (pre-baked). In a case where a pattern is formed through a low-temperature process, pre-baking is not necessarily performed. In a case of performing the pre-baking, the pre-baking temperature is preferably 150° C. or lower, more preferably 120° C. or lower, and still more preferably 110° C. or lower. The lower limit is, for example, preferably 50° C. or higher and more preferably 80° C. or higher. By setting the pre-baking temperature to be 150° C. or lower, the characteristics can be effectively maintained, for example, even in a case where a photoelectric conversion film of an image sensor is formed of an organic material.

The pre-baking time is preferably 10 seconds to 3,000 seconds, more preferably 40 seconds to 2,500 seconds, and still more preferably 80 seconds to 220 seconds. Drying can be performed using a hot plate, an oven, or the like.

The method of manufacturing the film according to the embodiment of the present disclosure may further include a step of forming a pattern. Examples of a pattern forming method include a pattern forming method using a photolithography method or a pattern forming method using a dry etching method.

That is, the present disclosure includes a pattern forming method including a step of forming a composition layer on a support using the composition according to the embodiment of the present disclosure and a step of forming a pattern on the composition layer by a photolithography method or a dry etching method.

In a case where the film according to the embodiment of the present disclosure is used as a flat film, the step of forming a pattern is not necessarily performed. Hereinafter, the step of forming a pattern will be described in detail.

—Case where Pattern is Formed Using Photolithography Method—

It is preferable that the pattern forming method using a photolithography method includes: a step (exposing step) of exposing the composition layer, which is formed by applying the composition according to the embodiment of the present disclosure, in a patterned manner; and a step (developing step) of forming a pattern by removing a non-exposed portion of the composition layer by development. Optionally, the pattern forming method may further include a step (post-baking step) of baking the developed pattern. Hereinafter, the respective steps will be described.

<<Exposing Step>>

In the exposing step, the composition layer is exposed in a patterned manner. For example, the composition layer can be exposed in a pattern shape using an exposure device such as a stepper through a mask having a predetermined mask pattern. Thus, the exposed portion can be cured. As radiation (light) used during the exposure, ultraviolet rays such as g-rays or i-rays are preferable, and i-rays are more preferable. For example, the irradiation amount (exposure amount) is preferably 0.03 J/cm$^2$ to 2.5 J/cm$^2$, more preferably 0.05 J/cm$^2$ to 1.0 J/cm$^2$, and particularly preferably 0.08 J/cm$^2$ to 0.5 J/cm$^2$. The oxygen concentration during the exposure can be appropriately selected, and the exposure may also be performed, for example, in a low-oxygen atmosphere having an oxygen concentration of 19% by volume or less (for example, 15% by volume, 5% by volume, and substantially oxygen-free) or in a high-oxygen atmosphere having an oxygen concentration of more than 21% by volume (for example, 22% by volume, 30% by volume, and 50% by volume), in addition to an atmospheric air. In addition, the exposure illuminance can be appropriately set, and can be preferably selected from a range of 1,000 W/m$^2$ to 100,000 W/m$^2$ (for example, 5,000 W/m$^2$, 15,000 W/m$^2$, or 35,000 W/m$^2$). Appropriate conditions of each of the oxygen concentration and the exposure illuminance may be combined, and for example, a combination of the oxygen concentration of 10% by volume and the illuminance of 10,000 W/m$^2$, a combination of the oxygen concentration of 35% by volume and the illuminance of 20,000 W/m$^2$, or the like is available.

<<Developing Step>>

Next, a pattern is formed by removing a non-exposed portion of the exposed composition layer by development. The non-exposed portion of the composition layer can be removed by development using a developer. As a result, a non-exposed portion of the composition layer in the exposing step is eluted into the developer, and only the photocured portion remains on the support. As the developer, an alkali developer which does not cause damages to a solid-state imaging element, a circuit, or the like of a base is desired. The temperature of the developer is preferably, for example, 20° C. to 30° C. The development time is preferably 20 seconds to 180 seconds. In addition, in order to improve residue removing properties, a step of removing the developer by shaking off per 60 seconds and supplying a fresh developer may be repeated multiple times.

Examples of the alkali agent used in the developer include organic alkaline compounds such as ammonia water, ethylamine, diethylamine, dimethylethanolamine, diglycol amine, diethanolamine, hydroxyamine, ethylenediamine, tetramethylammonium hydroxide, tetraethylammonium hydroxide, tetrapropylammonium hydroxide, tetrabutylammonium hydroxide, benzyltrimethylammonium hydroxide, dimethylbis(2-hydroxyethyl)ammonium hydroxide, choline, pyrrole, piperidine, and 1,8-diazabicyclo[5.4.0]-7-undecene, and inorganic alkaline compounds such as sodium hydroxide, potassium hydroxide, sodium carbonate, sodium hydrogen carbonate, sodium silicate, and sodium metasilicate. As the developer, an aqueous alkaline solution obtained by diluting these alkali agents with pure water is preferably used. The concentration of the alkali agent in the aqueous alkaline solution is preferably 0.001 mass % to 10 mass % and more preferably 0.01 mass % to 1 mass %. In addition, a surfactant may be used as the developer. Examples of the surfactant include the surfactants described in the above composition, and the surfactant is preferably a nonionic surfactant. From the viewpoint of transportation, storage, and the like, the developer may be first produced as a concentrated liquid and then diluted to a concentration required upon the use. The dilution ratio is not particularly limited, and can be set to, for example, a range of 1.5 times to 100 times. In addition, in a case where a developer consisting of such an aqueous alkaline solution is used, it is preferable to perform washing (rinsing) with pure water after development.

After the development, the film can also be dried and then heat-treated (post-baking). Post-baking is a heating treatment which is performed after development to completely cure the film. In a case where post-baking is performed, for example, the post-baking temperature is preferably 100° C. to 240° C. From the viewpoint of curing the film, the post-baking temperature is more preferably 200° C. to 230° C. In addition, in a case where an organic electroluminescence (organic EL) element is used as a light-emitting light source, or in a case where a photoelectric conversion film of an image sensor is formed of an organic material, the post-baking temperature is preferably 150° C. or lower, more preferably 120° C. or lower, still more preferably 100° C. or lower, and particularly preferably 90° C. or lower. The lower limit is, for example, 50° C. or higher. The post-baking can be performed continuously or batchwise by using a heating unit such as a hot plate, a convection oven (hot-air circulation dryer), and a high-frequency heater so that the film after development satisfies the conditions. In addition, in a case of forming a pattern by a low-temperature process, the post-baking may not be performed, or a step of re-exposure (post-exposing step) may be added.

—Case where Pattern is Formed Using Dry Etching Method—

The formation of a pattern using a dry etching method can be performed using a method including: applying the composition to a support or the like to form a composition layer; curing the formed composition layer to form a cured composition layer; forming a patterned photoresist layer on the cured composition layer; and dry-etching the cured composition layer with etching gas by using the patterned photoresist layer as a mask. It is preferable that pre-baking treatment is further performed in order to form the photoresist layer. In particular, as the forming process of the photoresist, it is desirable that a heat treatment after exposure and a heating treatment after development (post-baking treatment) are performed. The details of the pattern formation by the dry etching method can be found in paragraphs 0010 to 0067 of JP2013-64993A, the content of which is incorporated herein by reference.

<Optical Filter and Laminate>

The optical filter according to an embodiment of the present disclosure includes the film according to the embodiment of the present disclosure.

The optical filter according to the embodiment of the present disclosure can be preferably used as an infrared cut filter or an infrared transmitting filter, and more preferably used as an infrared cut filter.

In addition, a preferred aspect of the optical filter according to the embodiment of the present disclosure is also an aspect of including the film according to the embodiment of the present disclosure and a pixel selected from the group consisting of red, green, blue, magenta, yellow, cyan, black, and colorless.

In addition, the laminate according to an embodiment of the present disclosure is a laminate including the film according to the embodiment of the present disclosure and a color filter including a chromatic colorant.

The infrared cut filter according to an embodiment of the present disclosure includes the film according to the embodiment of the present disclosure.

The infrared cut filter according to the embodiment of the present disclosure may be a filter which cuts only infrared rays having a wavelength of a part of the infrared range, or a filter which cuts the entire infrared range. Examples of the filter which cuts only infrared rays having a wavelength of a part of the infrared range include a near-infrared cut filter. Examples of the near-infrared rays include infrared rays having a wavelength of 750 nm to 2,500 nm.

In addition, the infrared cut filter according to the embodiment of the present disclosure is preferably a filter which cuts infrared rays in a wavelength range of 750 nm to 1,000 nm, more preferably a filter which cuts infrared rays in a wavelength range of 750 nm to 1,200 nm, and still more preferably a filter which cuts infrared rays in a wavelength range of 750 nm to 1,500 nm.

The infrared cut filter according to the embodiment of the present disclosure may further include a layer containing copper, a dielectric multi-layer film, an ultraviolet absorbing layer, a substrate (for example, a glass substrate), or the like, in addition to the above-described film.

In a case where the infrared cut filter according to the embodiment of the present disclosure further includes at least a layer containing copper or a dielectric multi-layer film, it is easy to obtain an infrared cut filter having a wide viewing angle and excellent infrared shielding properties. In addition, in a case where the infrared cut filter according to the embodiment of the present disclosure further includes an ultraviolet absorbing layer, an infrared cut filter having excellent ultraviolet shielding properties can be obtained. The details of the ultraviolet absorbing layer can be found in the description of an absorbing layer described in paragraphs 0040 to 0070 and 0119 to 0145 of WO2015/099060A, the content of which is incorporated herein by reference. The details of the dielectric multi-layer film can be found in paragraphs 0255 to 0259 of JP2014-41318A, the content of which is incorporated herein by reference.

As the layer containing copper, a glass base material (copper-containing glass base material) formed of glass containing copper, or a layer (copper complex-containing layer) containing a copper complex may also be used. Examples of the copper-containing glass base material include a phosphate glass including copper and a fluorophosphate glass including copper. Examples of a commercially available product of the copper-containing glass include NF-50 (manufactured by AGC Techno Glass Co., Ltd.), BG-60 and BG-61 (both of which are manufactured by Schott AG), and CD5000 (manufactured by Hoya Corporation).

The infrared cut filter according to the embodiment of the present disclosure can be used in various devices including a solid-state imaging element such as a charge coupled device (CCD) or a complementary metal-oxide semiconductor (CMOS), an infrared sensor, or an image display device.

It is also preferable that the infrared cut filter according to the embodiment of the present disclosure has a pixel (pattern) of the film obtained using the composition according to the embodiment of the present disclosure, and at least one pixel (pattern) selected from the group consisting of red, green, blue, magenta, yellow, cyan, black, and colorless.

A method for manufacturing the optical filter according to the embodiment of the present disclosure is not particularly limited, but a method including a step of applying the composition according to the embodiment of the present disclosure on a support to form a composition layer, a step of exposing the composition layer in a patterned manner, and a step of removing a non-exposed portion by development to form a pattern is preferable.

In addition, as the method for manufacturing the optical filter according to the embodiment of the present disclosure, a method including a step of applying the composition according to the embodiment of the present disclosure on a support to form a composition layer, curing the composition to form a layer, a step of forming a photoresist layer on the layer, a step of obtaining a resist pattern by patterning the photoresist layer by exposure and development, and a step of dry-etching the layer using the resist pattern as an etching mask is also preferable.

As each step in the method for manufacturing the optical filter according to embodiment of the present disclosure, the each step in the method for manufacturing the film according to the embodiment of the present disclosure can be referred to.

<Solid-State Imaging Element>

The solid-state imaging element according to an embodiment of the present disclosure includes the film according to the embodiment of the present disclosure. The configuration of the solid-state imaging element is not particularly limited as long as it includes the film according to the embodiment of the present disclosure and functions as a solid-state imaging element. For example, the following configuration can be adopted.

The solid-state imaging element includes a plurality of photodiodes and transfer electrodes on the support, the photodiodes constituting a light receiving area of the solid-state imaging element, and the transfer electrode consisting of polysilicon or the like. In the solid-state imaging element, a light-shielding film consisting of tungsten or the like which has openings through only light receiving sections of the photodiodes is provided on the photodiodes and the transfer electrodes, a device protective film consisting of silicon nitride or the like is formed on the light-shielding film so as to cover the entire surface of the light-shielding film and the light receiving sections of the photodiodes, and the film according to the embodiment of the present disclosure is formed on the device protective film. Further, the solid-state imaging element may also be configured, for example, such that it has a light collecting unit (for example, a microlens, which is the same hereinafter) on the device protective film under the film according to the embodiment of the present disclosure (a side closer to the support), or has a light collecting unit on the film according to the embodiment of the present disclosure. In addition, the color filter used in the solid-state imaging element may have a structure in which a film which forms each pixel is embedded in a space which is partitioned in, for example, a lattice form by a partition wall. In this case, it is preferable that the partition wall has a lower refractive index than each pixel. Examples of an imaging apparatus having such a structure include devices described in JP2012-227478A and JP2014-179577A.

<Image Display Device>

The image display device according to an embodiment of the present disclosure includes the film according to the embodiment of the present disclosure. Examples of the image display device include a liquid crystal display device or an organic electroluminescence (organic EL) display device. The definition and details of the image display device can be found in, for example, "Electronic Display Device (written by Akio Sasaki, Kogyo Chosakai Publishing Co., Ltd., published in 1990)" or "Display Device (written by Sumiaki Ibuki, Sangyo Tosho Co., Ltd., published in 1989). In addition, the liquid crystal display device is described in, for example, "Liquid Crystal Display Technology for Next Generation (edited by Tatsuo Uchida, Kogyo Chosakai Publishing Co., Ltd., published in 1994)". The liquid crystal display device to which the present disclosure can be applied is not particularly limited, and can be applied to, for example, liquid crystal display devices employing various systems described in the "Liquid Crystal Display Technology for Next Generation". The image display device may be an image display device having a white organic EL element. It is preferable that the white organic EL element has a tandem structure. The tandem structure of the organic EL element is described in, for example, JP2003-45676A, or pp. 326 to 328 of "Forefront of Organic EL Technology Development—Know-How Collection of High Brightness, High Precision, and Long Life" (Technical Information Institute, 2008). It is preferable that a spectrum of white light emitted from the organic EL element has high maximum emission peaks in a blue range (430 nm to 485 nm), a green range (530 nm to 580 nm), and a yellow range (580 nm to 620 nm). It is more preferable that the spectrum has a maximum emission peak in a red range (650 nm to 700 nm) in addition to the above-described emission peaks.

<Infrared Sensor>

The infrared sensor according to an embodiment of the present disclosure includes the film according to the embodiment of the present disclosure. The configuration of the infrared sensor is not particularly limited as long as it functions as an infrared sensor. Hereinafter, the embodiment of the infrared sensor according to the present disclosure will be described using the drawing.

In FIG. 1, reference numeral 110 represents a solid-state imaging element. In an imaging region provided on the solid-state imaging element 110, infrared cut filters 111 and infrared transmitting filters 114 are provided. In addition, color filters 112 are laminated on the infrared cut filters 111. Microlenses 115 are disposed on an incidence ray hv side of the color filters 112 and the infrared transmitting filters 114. A planarizing layer 116 is formed so as to cover the microlenses 115.

The infrared cut filter 111 can be formed of the composition according to the embodiment of the present disclosure. Spectral characteristics of the infrared cut filters 111 can be selected according to a luminescence wavelength of an infrared light emitting diode (infrared LED) to be used.

The color filter 112 is not particularly limited as long as pixels which allow transmission of light having a specific wavelength in a visible range and absorbs the light are formed therein, and known color filters in the related art for forming a pixel can be used. For example, pixels of red (R), green (G), and blue (B) are formed in the color filters. For example, the details of the color filters can be found in paragraphs 0214 to 0263 of JP2014-43556A, the content of which is incorporated herein by reference.

Characteristics of the infrared transmitting filters 114 can be selected according to the luminescence wavelength of the infrared LED to be used. For example, in a case where the luminescence wavelength of the infrared LED is 850 nm, the infrared transmitting filter 114 preferably has 30% or less of a maximum value of the light transmittance in the film thickness direction in a wavelength range of 400 nm to 650 nm, more preferably has 20% or less thereof, still more preferably has 10% or less thereof, and particularly preferably has 0.10% or less thereof. It is preferable that the transmittance satisfies the above-described conditions in the entire range of the wavelength range of 400 nm to 650 nm.

In addition, the infrared transmitting filter 114 preferably has 70% or more of a minimum value of the light transmittance in the film thickness direction in a wavelength range of 800 nm or more (preferably 800 nm to 1,300 nm), more preferably 80% or more thereof, and still more preferably 90% or more thereof. The above-described transmittance preferably satisfies the above-described conditions in a part of the wavelength range of 800 nm or more, and more preferably satisfies the above-described conditions at a wavelength corresponding to the luminescence wavelength of the infrared LED.

The film thickness of the infrared transmitting filter 114 is preferably 100 μm or less, more preferably 15 μm or less, still more preferably 5 μm or less, and particularly preferably 1 μm or less. The lower limit value is preferably 0.1 μm. In a case where the film thickness is within the above-described range, a film satisfying the above-described spectral characteristics can be obtained.

A method for measuring the spectral characteristics, film thickness, and the like of the infrared transmitting filter 114 is as follows.

The film thickness is measured by using a stylus type surface shape measuring device (DEKTAK150 manufactured by ULVAC, Inc.) on a dried substrate having the film.

The spectral characteristics of the film are values obtained by measuring the transmittance in a wavelength range of 300 nm to 1,300 nm using an ultraviolet-visible-near infrared spectrophotometer (U-4100 manufactured by Hitachi High-Tech Corporation).

In addition, for example, in a case where the luminescence wavelength of the infrared LED is 940 nm, the infrared transmitting filter 114 preferably has 20% or less of a maximum value of the light transmittance in the film thickness direction in a wavelength range of 450 nm to 650 nm, and it is preferable that the light transmittance in the film thickness direction at a wavelength of 835 nm is 20% or less and the minimum value of the light transmittance in the film thickness direction in a wavelength of 1,000 nm to 1,300 nm is 70% or more.

In the infrared sensor shown in FIG. 1, an infrared cut filter (other infrared cut filters) other than the infrared cut filter 111 may be further disposed on the planarizing layer 116. Examples of the other infrared cut filters include an infrared cut filter including at least a layer containing copper or a dielectric multi-layer film. The details of the examples are as described above. In addition, as the other infrared cut filters, a dual band pass filter may be used.

In addition, the absorption wavelengths of the infrared transmitting filter and infrared cut filter used in the present disclosure are appropriately used in combination according to a light source and the like to be used.

(Camera Module)

The camera module according to an embodiment of the present disclosure includes a solid-state imaging element and the infrared cut filter according to the embodiment of the present disclosure.

In addition, it is preferable that the camera module according to the embodiment of the present disclosure further includes a lens and a circuit for processing an image obtained from the above-described solid-state imaging element.

The solid-state imaging element used in the camera module according to the embodiment of the present disclosure may be the above-described solid-state imaging element according to the embodiment of the present disclosure, or a known solid-state imaging element.

In addition, as the lens and the circuit for processing an image obtained from the above-described solid-state imaging element used in the camera module according to the embodiment of the present disclosure, known ones can be used.

Examples of the camera module include camera modules described in JP2016-6476A or JP2014-197190A, the contents of which are incorporated herein by reference.

The film according to the embodiment of the present disclosure can be used as a heat shield material or a heat storage material. In addition, the composition according to the embodiment of the present disclosure can also be used for paints, inkjet inks, security inks, and the like.

EXAMPLES

Hereinafter, the present disclosure will be described in detail with reference to examples, but the present disclosure is not limited thereto.

In the examples, "%" and "parts" respectively indicate "mass %" and "parts by mass" unless otherwise specified. In a polymer compound, the molecular weight indicates the weight-average molecular weight (Mw) and the proportion of constitutional units indicates mole percentage unless otherwise specified.

The weight-average molecular weight (Mw) is a value in terms of polystyrene obtained by performing measurement using a gel permeation chromatography (GPC) method.

<X-Ray Diffraction Pattern Method by CuKα Ray>

The X-ray diffraction pattern by CuKα ray was measured in a diffraction angle (2θ) in a range of 3° to 35° according to Japanese Industrial Standard JIS K0131 (general rule of X-ray diffraction analysis).

Measurement conditions were as follows.

X-ray diffractometer: RINT2100 manufactured by Rigaku Corporation
Sampling width: 0.02°
Scan speed: 2.0°/min
Divergence slit: 1°
Divergence vertical restriction slit: 10 mm
Scattering slit: 2°
Light-receiving slit: 0.3 mm
Vacuum tube: Cu
Tube voltage: 40 kV
Tube current: 40 mA (A-ppb-1) was synthesized according to the following scheme. In the following structural formulae, Et represents an ethyl group and Ph represents a phenyl group.

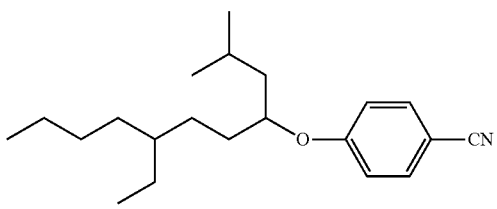

Compound b

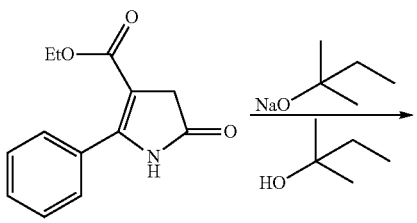

Compound a

-continued
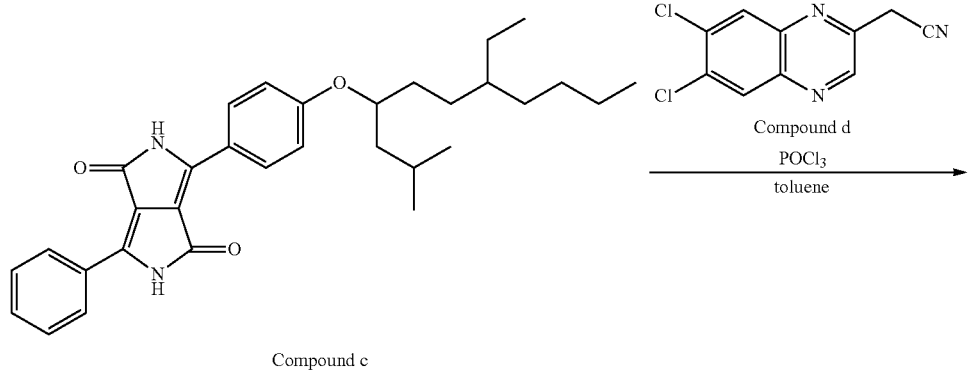
Compound c
Compound d
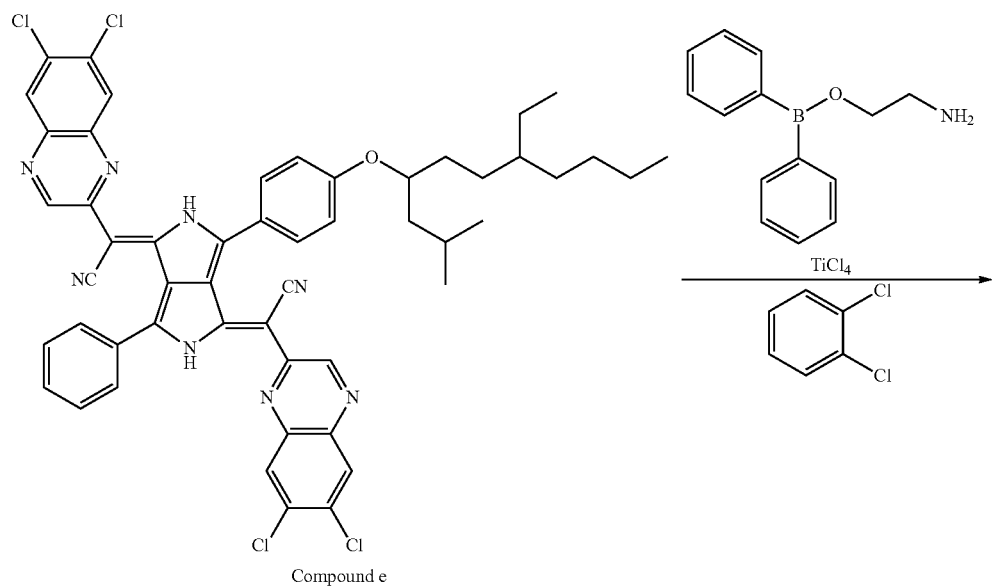
Compound e
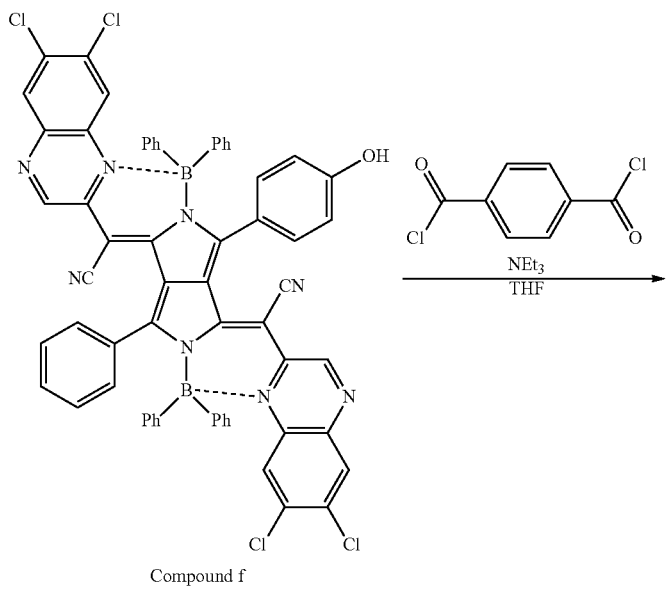
Compound f

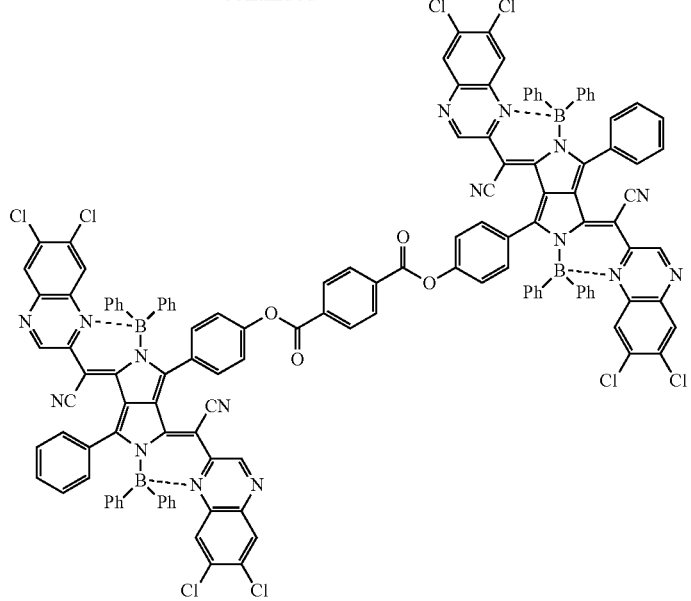

A-ppb-1

<<Synthesis of Compound a>>

A compound a was synthesized according to the method described in Tetrahedron 62 (2006), pp. 6018 to 6028.

<<Synthesis of Compound b>>

Using 7-ethyl-2-methyl-4-undecanol (manufactured by Tokyo Chemical Industry Co., Ltd.) as a raw material, a compound b was synthesized according to the method described in paragraph 0072 of JP6353060B.

<<Synthesis of Compound c>>

14.9 parts by mass of the compound b, 50 parts by mass of t-amyl alcohol, and 14.3 parts by mass of sodium t-pentoxide (manufactured by Tokyo Chemical Industry Co., Ltd.) were charged into a flask, 10 parts by mass of the compound a was added dropwise thereto over 1 hour at an external temperature of 120° C., and the mixture was stirred for 4 hours. After the reaction, the reaction solution was allowed to cool until the internal temperature reached 60° C., 100 parts by mass of methanol, 100 parts by mass of water, and 8 parts by mass of acetic acid were added thereto, and the precipitated crystals were filtered off and washed with 140 parts by mass of methanol. 100 parts by mass of methanol was added to the obtained crystals, the mixture was heated under reflux for 30 minutes and allowed to cool to 30° C., and the crystals were filtered off. The obtained crystals were blast-dried at 50° C. to obtain 10 parts by mass of a compound c.

<<Synthesis of Compound d>>

A compound d was synthesized according to the method described in paragraph 0072 of JP6353060B.

<<Synthesis of Compound e>>

7 parts by mass of the compound c and 7.5 parts by mass of the compound d were stirred in 140 parts by mass of toluene, 12 parts by mass of phosphorus oxychloride was added dropwise thereto, and the mixture was heated under reflux for 3.5 hours. After completion of the reaction, the reaction solution was cooled to an internal temperature of 25° C., and 210 parts by mass of methanol was added dropwise thereto over 60 minutes while maintaining the internal temperature of 30° C. or lower. After completion of the dropwise addition, the mixture was stirred at room temperature for 30 minutes. The precipitated crystals were filtered off and washed with 140 parts by mass of methanol. 100 parts by mass of methanol was added to the obtained crystals, the mixture was heated under reflux for 30 minutes and allowed to cool to 30° C., and the crystals were filtered off. The obtained crystals were blast-dried at 50° C. to obtain 6 parts by mass of a compound e.

<<Synthesis of Compound f>>

17 parts by mass of 2-aminoethyl ester diphenylboric acid was stirred in 120 parts by mass of 1,2-dichlorobenzene, 18 parts by mass of titanium tetrachloride was added dropwise thereto over 10 minutes at an external temperature of 40° C., and the mixture was stirred for 30 minutes. 6 parts by mass of the compound e was added thereto, the external temperature was raised to 125° C., and the mixture was heated for 60 minutes. The reaction solution was cooled to an internal temperature of 30° C., and 120 parts by mass of methanol was added dropwise thereto while maintaining the internal temperature of 30° C. or lower. After the dropwise addition, the mixture was stirred for 30 minutes, and the crystals were filtered off and washed with 60 parts by mass of methanol. 100 parts by mass of methanol was added to the obtained crystals, the mixture was heated under reflux for 30 minutes and allowed to cool to 30° C., and the crystals were filtered off. The obtained crystals were blast-dried at 50° C. to obtain 6 parts by mass of a compound f.

<Synthesis of A-ppb-1>

5 parts by mass of the compound f was stirred in 200 parts by mass of tetrahydrofuran, and 1.4 parts by mass of triethylamine was added dropwise thereto. 0.47 parts by mass of terephthaloyl chloride was added dropwise thereto over 30 minutes at room temperature, and the mixture was stirred for 30 minutes. An external temperature was raised to 75° C., and the mixture was heated under reflux for 2 hours. The reaction solution was allowed to cool until an internal temperature reached 30° C., and the crystals were filtered off and washed with 100 parts by mass of tetrahydrofuran. 200 parts by mass of methanol was added to the obtained crystals, the mixture was heated under reflux for 1 hour and allowed to cool to 30° C., and the crystals were filtered off. The obtained crystals were blast-dried at 50° C. to obtain 4 parts by mass of A-ppb-1. As a result of mass spectrometry by MALDI TOF-MASS (time-of-flight mass spectrometry) and $^1$H-NMR measurement, the compound was identified as a coloring agent [A-ppb-1].

MALDI TOF-MASS: Calc. for [M+H]$^+$: 2271.4, found: 2271.5

$^1$H-NMR (CDCl$_3$): δ 6.33 (d, 4H), 6.40 (d, 4H), 7.00 (d, 4H), 7.10 (t, 4H), 7.16 to 7.44 (m, 42H), 7.80 (s, 2H), 7.82 (s, 2H), 8.22 (s, 2H), 8.30 (s, 2H), 8.49 (s, 4H), 9.00 (s, 2H), 9.05 (s, 2H)

λmax: 882 nm (CHCl$_3$)

<Synthesis of A-ppb-2>

A compound A-ppb-2 was synthesized in the same manner as in the compound A-ppb-1, except that, in the synthesis of the compound A-ppb-1, terephthaloyl chloride was changed to 4,4'-diphenyldicarbonyl chloride. Details of the identification data are shown below.

MALDI TOF-MASS: Calc. for [M+H]$^+$: 2347.4, found: 2347.4

$^1$H-NMR (CDCl$_3$): δ 6.33 (d, 4H), 6.40 (d, 4H), 7.00 (d, 4H), 7.10 (t, 4H), 7.16 to 7.44 (m, 42H), 7.80 (s, 2H), 7.82 (s, 2H), 7.90 (d, 4H), 8.22 (s, 2H), 8.30 (s, 2H), 8.44 (d, 4H), 9.00 (s, 2H), 9.05 (s, 2H)

λmax: 882 nm (CHCl$_3$)

in a case where the X-ray diffraction pattern by CuKα ray was measured, the compound had peaks at Bragg angles 2θ=5.7° and 6.4°.

<Synthesis of A-ppb-3>

A compound A-ppb-3 was synthesized in the same manner as in the compound A-ppb-1, except that, in the synthesis of the compound A-ppb-1, terephthaloyl chloride was changed to 4,4'-oxybis(benzoyl chloride). Details of the identification data are shown below.

MALDI TOF-MASS: Calc. for [M+H]$^+$: 2363.4, found: 2363.4

$^1$H-NMR (CDCl$_3$): δ 6.33 (d, 4H), 6.37 (d, 4H), 6.97 (d, 4H), 7.09 (t, 4H), 7.16 to 7.44 (m, 46H), 7.80 (s, 2H), 7.81 (s, 2H), 8.22 (s, 2H), 8.29 (s, 2H), 8.36 (d, 4H), 8.99 (s, 2H), 9.04 (s, 2H)

λmax: 882 nm (CHCl$_3$)

in a case where the X-ray diffraction pattern by CuKα ray was measured, the compound had peaks at Bragg angles 2θ=7.7° and 9.6°.

<Synthesis of A-ppb-4>

A compound A-ppb-4 was synthesized in the same manner as in the compound A-ppb-1, except that, in the synthesis of the compound A-ppb-1, terephthaloyl chloride was changed to the following bifunctional acid chloride 1.

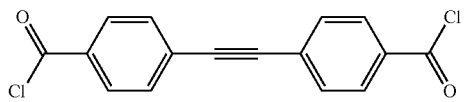

Bifunctional acid chloride 1

Details of the identification data are shown below.

MALDI TOF-MASS: Calc. for [M+H]$^+$: 2371.4, found: 2371.5

$^1$H-NMR (CDCl$_3$): δ 6.33 (d, 4H), 6.37 (d, 4H), 6.97 (d, 4H), 7.09 (t, 4H), 7.16 to 7.44 (m, 42H), 7.77 (d, 4H), 7.80 (s, 2H), 7.81 (s, 2H), 8.22 (s, 2H), 8.29 (s, 2H), 8.33 (d, 4H), 8.99 (s, 2H), 9.04 (s, 2H)

λmax: 882 nm (CHCl$_3$)

in a case where the X-ray diffraction pattern by CuKα ray was measured, the compound had a peak at Bragg angles 2θ=6.3°.

<Synthesis of A-ppb-5>

A compound A-ppb-5 was synthesized in the same manner as in the compound A-ppb-1, except that, in the synthesis of the compound A-ppb-1, terephthaloyl chloride was changed to the following bifunctional acid chloride 2.

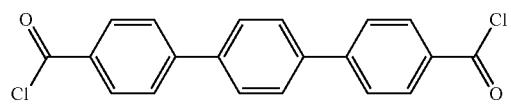

Bifunctional acid chloride 2

Details of the identification data are shown below.

MALDI TOF-MASS: Calc. for [M+H]$^+$: 2415.4, found: 2415.5

$^1$H-NMR (CDCl$_3$): δ 6.33 (d, 4H), 6.38 (d, 4H), 7.00 (d, 4H), 7.09 (t, 4H), 7.16 to 7.42 (m, 42H), 7.78 to 7.82 (m, 8H), 7.88 (d, 4H), 8.22 (s, 2H), 8.30 (s, 2H), 8.42 (d, 4H), 9.00 (s, 2H), 9.05 (s, 2H)

<Synthesis of A-ppb-6>

A compound A-ppb-6 was synthesized in the same manner as in the compound A-ppb-1, except that, in the synthesis of the compound A-ppb-1, terephthaloyl chloride was changed to fumaryl chloride.

Details of the identification data are shown below.

MALDI TOF-MASS: Calc. for [M+H]$^+$: 2221.4, found: 2221.5

$^1$H-NMR (CDCl$_3$): δ 6.33 (d, 4H), 6.38 (d, 4H), 6.94 (d, 4H), 7.09 (t, 4H), 7.16 to 7.44 (m, 44H), 7.80 (s, 2H), 7.82 (s, 2H), 8.22 (s, 2H), 8.27 (s, 2H), 9.00 (s, 2H), 9.04 (s, 2H)

λmax: 882 nm (CHCl$_3$)

in a case where the X-ray diffraction pattern by CuKα ray was measured, the compound had peaks at Bragg angles 2θ=10.0°, 11.5°, and 13.3°.

<Synthesis of A-ppb-7>

A compound A-ppb-7 was synthesized in the same manner as in the compound A-ppb-1, except that, in the synthesis of the compound A-ppb-1, the compound a was changed to the following compound a2.

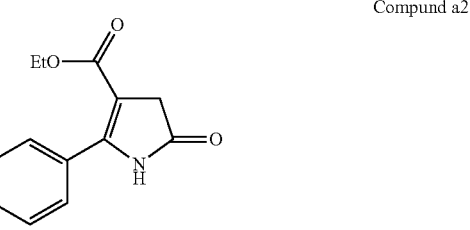

Compund a2

Details of the identification data are shown below.

MALDI TOF-MASS: Calc. for [M+H]$^+$: 2415.4, found: 2415.3

$^1$H-NMR (CDCl3): δ 6.25 (d, 4H), 6.38 (d, 4H), 7.00 (d, 4H), 7.05 (d, 4H), 7.18 to 7.42 (m, 40H), 7.82 (s, 2H), 7.83 (s, 2H), 7.90 (d, 4H), 8.26 (s, 2H), 8.30 (s, 2H), 8.44 (d, 4H), 9.03 (s, 2H), 9.04 (s, 2H)

λmax: 882 nm (CHCl$_3$)

<Synthesis of A-ppb-11>

A compound A-ppb-11 was synthesized in the same manner as in the compound A-ppb-1, except that, in the synthesis of the compound A-ppb-1, terephthaloyl chloride was changed to 2,5-furandicarbonyl dichloride.

Details of the identification data are shown below.

MALDI TOF-MASS: Calc. for [M+H]$^+$: 2261.4, found: 2261.4

$^1$H-NMR (CDCl$_3$): δ 6.33 (d, 4H), 6.38 (d, 4H), 7.00 (d, 4H), 7.09 (t, 4H), 7.16 to 7.44 (m, 42H), 7.59 (s, 2H), 7.80 (s, 2H), 7.81 (s, 2H), 8.22 (s, 2H), 8.29 (s, 2H), 8.99 (s, 2H), 9.04 (s, 2H)

λmax: 882 nm (CHCl$_3$)

<Synthesis of A-ppb-13>

A compound A-ppb-13 was synthesized in the same manner as in the compound A-ppb-1, except that, in the synthesis of the compound A-ppb-1, terephthaloyl chloride was changed to 1,3,5-benzenetricarbonyl trichloride.

Details of the identification data are shown below.

MALDI TOF-MASS: Calc. for [M+H]$^+$: 3367.5, found: 3367.4

$^1$H-NMR (CDCl$_3$): δ 6.34 (d, 6H), 6.44 (d, 6H), 7.09 (m, 12H), 7.16 to 7.46 (m, 63H), 7.80 (s, 6H), 8.22 (s, 3H), 8.33 (s, 3H), 9.00 (s, 3H), 9.09 (s, 3H), 9.49 (s, 3H)

λmax: 882 nm (CHCl$_3$)

<Synthesis of A-ppb-16 to 22>

<Synthesis of A-ppb-16>

A compound A-ppb-16 was synthesized in the same manner as in the compound A-ppb-2, except that, in the synthesis of the compound A-ppb-2, the compound d was changed to the following compound d2.

Compound d2

Details of the identification data are shown below.

MALDI TOF-MASS: Calc. for [M+H]$^+$: 2210.6, found: 2210.6

λmax: 874 nm (CHCl$_3$)

<Synthesis of A-ppb-17>

A compound A-ppb-17 was synthesized in the same manner as in the compound A-ppb-2, except that, in the synthesis of the compound A-ppb-2, the compound d was changed to the following compound d3.

Compound d3

Details of the identification data are shown below.

MALDI TOF-MASS: Calc. for [M+H]$^+$: 2387.4, found: 2387.3

λmax: 876 nm (CHCl$_3$)

<Synthesis of A-ppb-18>

A compound A-ppb-18 was synthesized in the same manner as in the compound A-ppb-2, except that, in the synthesis of the compound A-ppb-2, the compound d was changed to the following compound d4.

Compound d4

Details of the identification data are shown below.

MALDI TOF-MASS: Calc. for [M+H]$^+$: 2699.0, found: 2699.0

λmax: 887 nm (CHCl$_3$)

<Synthesis of A-ppb-19>

A compound A-ppb-19 was synthesized in the same manner as in the compound A-ppb-1, except that, in the synthesis of the compound A-ppb-1, the compound d was changed to the following compound d5.

Compound d5

Details of the identification data are shown below.

MALDI TOF-MASS: Calc. for [M+H]$^+$: 1995.7, found: 1995.6

λmax: 814 nm (CHCl$_3$)

<Synthesis of A-ppb-21>

A compound A-ppb-21 was synthesized in the same manner as in the compound A-ppb-2, except that, in the synthesis of the compound A-ppb-1, the compound d was changed to the following compound d6.

Compound d6

Details of the identification data are shown below.

MALDI TOF-MASS: Calc. for [M+H]$^+$: 2019.6, found: 2019.5

λmax: 780 nm (CHCl$_3$)

<Synthesis of A-ppb-22>

A compound A-ppb-22 was synthesized in the same manner as in the compound A-ppb-2, except that, in the synthesis of the compound A-ppb-1, the compound d was changed to the following compound d7.

Compound d7

Details of the identification data are shown below.

MALDI TOF-MASS: Calc. for [M+H]$^+$: 1955.6, found: 1955.5

λmax: 740 nm (CHCl$_3$)

<Preparation of Curable Composition>

Raw materials shown in Tables 1 to 4 shown below were mixed, and the obtained mixture was filtered using a nylon filter (manufactured by Nihon Pall Corporation) having a pore size of 0.45 μm to prepare a curable composition.

As a dispersion liquid, a dispersion liquid prepared as follows was used.

A coloring agent, a derivative, a dispersant, and a solvent A described in the column of Dispersion liquid of Tables 1 to 4 were mixed with each other in part by mass shown in the column of Dispersion liquid of Tables 1 to 4, 230 parts by mass of zirconia beads having a diameter of 0.3 mm was further added thereto, the mixture was dispersed using a paint shaker for 5 hours, and the beads were separated by filtration, thereby preparing a dispersion liquid.

TABLE 1

| | Dispersion liquid | | | | | | | | | | Curable composition | |
|---|---|---|---|---|---|---|---|---|---|---|---|---|
| | Coloring agent | | Derivative | | Dispersant | | Solvent A | | Resin | | | |
| | Compound | Part by mass | Compound | Part by mass | Type | Part by mass | Type | Part by mass | Type | Part by mass | Type | Part by mass |
| Example 1 | A-ppb-1 | 2.6 | — | — | C1 | 1.8 | Solvent 1 | 39.0 | Resin 1 | 5.5 | Curable compound 1 | 6.4 |
| Example 2 | A-ppb-1 | 2.6 | B-1 | 0.39 | C1 | 1.8 | Solvent 1 | 39.0 | Resin 2 | 5.5 | Curable compound 1 | 6.4 |
| Example 3 | A-ppb-1 | 2.6 | B-2 | 0.39 | C2 | 1.8 | Solvent 1 | 39.0 | Resin 3 | 5.5 | Curable compound 1 | 6.4 |
| Example 4 | A-ppb-2 | 2.6 | B-2 | 0.39 | C2 | 1.8 | Solvent 1 | 39.0 | Resin 3 | 5.5 | Curable compound 1 | 6.4 |
| Example 5 | A-ppb-3 | 2.6 | B-2 | 0.39 | C2 | 1.8 | Solvent 1 | 39.0 | Resin 3 | 5.5 | Curable compound 1 | 6.4 |
| Example 6 | A-ppb-4 | 2.6 | B-2 | 0.39 | C2 | 1.8 | Solvent 1 | 39.0 | Resin 3 | 5.5 | Curable compound 1 | 6.4 |
| Example 7 | A-ppb-5 | 2.6 | B-2 | 0.39 | C2 | 1.8 | Solvent 1 | 39.0 | Resin 3 | 5.5 | Curable compound 1 | 6.4 |
| Example 8 | A-ppb-6 | 2.6 | B-2 | 0.39 | C2 | 1.8 | Solvent 1 | 39.0 | Resin 3 | 5.5 | Curable compound 1 | 6.4 |
| Example 9 | A-ppb-7 | 2.6 | B-2 | 0.39 | C2 | 1.8 | Solvent 1 | 39.0 | Resin 3 | 5.5 | Curable compound 1 | 6.4 |
| Example 10 | A-ppb-11 | 2.6 | B-2 | 0.39 | C2 | 1.8 | Solvent 1 | 39.0 | Resin 3 | 5.5 | Curable compound 1 | 6.4 |
| Example 11 | A-ppb-13 | 2.6 | B-2 | 0.39 | C2 | 1.8 | Solvent 1 | 39.0 | Resin 3 | 5.5 | Curable compound 1 | 6.4 |
| Example 12 | A-ppb-16 | 2.6 | B-2 | 0.39 | C2 | 1.8 | Solvent 1 | 39.0 | Resin 3 | 5.5 | Curable compound 1 | 6.4 |
| Example 13 | A-ppb-17 | 2.6 | B-3 | 0.39 | C2 | 1.8 | Solvent 1 | 39.0 | Resin 3 | 5.5 | Curable compound 1 | 6.4 |
| Example 14 | A-ppb-18 | 2.6 | B-3 | 0.39 | C2 | 1.8 | Solvent 1 | 39.0 | Resin 3 | 5.5 | Curable compound 1 | 6.4 |
| Example 15 | A-ppb-19 | 2.6 | B-4 | 0.39 | C2 | 1.8 | Solvent 1 | 39.0 | Resin 3 | 5.5 | Curable compound 1 | 6.4 |
| Example 16 | A-ppb-21 | 2.6 | B-5 | 0.39 | C2 | 1.8 | Solvent 1 | 39.0 | Resin 3 | 5.5 | Curable compound 1 | 6.4 |
| Example 17 | A-ppb-22 | 2.6 | B-6 | 0.39 | C2 | 1.8 | Solvent 1 | 39.0 | Resin 3 | 5.5 | Curable compound 1 | 6.4 |
| Example 18 | A-sq-1 | 2.6 | — | — | C3 | 1.8 | Solvent 1 | 39.0 | Resin 3 | 5.5 | Curable compound 1 | 6.4 |
| Example 19 | A-sq-1 | 2.6 | B-7 | 0.39 | C3 | 1.8 | Solvent 1 | 39.0 | Resin 3 | 5.5 | Curable compound 1 | 6.4 |
| Example 20 | A-sq-3 | 2.6 | B-8 | 0.39 | C2 | 1.8 | Solvent 1 | 39.0 | Resin 3 | 5.5 | Curable compound 1 | 6.4 |
| Comparative example 1 | Comparative compound 1 | 2.6 | B-2 | 0.39 | C2 | 1.8 | Solvent 1 | 39.0 | Resin 3 | 5.5 | Curable compound 1 | 6.4 |
| Comparative example 2 | Comparative compound 2 | 2.6 | — | — | C2 | 1.8 | Solvent 1 | 39.0 | Resin 3 | 5.5 | Curable compound 1 | 6.4 |
| Comparative example 3 | Comparative compound 3 | 2.6 | — | — | C3 | 1.8 | Solvent 1 | 39.0 | Resin 3 | 5.5 | Curable compound 1 | 6.4 |

| | Photopolymerization initiator | | Ultraviolet absorber | | Surfactant | | Polymerization inhibitor | | Solvent B | |
|---|---|---|---|---|---|---|---|---|---|---|
| | Type | Part by mass | Type | Part by mass | Type | Part by mass | Type | Part by mass | Type | Part by mass |
| Example 1 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 2 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 3 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 4 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 5 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 6 | Photopolymerization initiator 1 | 1 | Ultraviolet absorber 1 | 0.5 | Surfactant 1 | 0.04 | Polymerization inhibitor 1 | 0.006 | Solvent 1 | 42.8 |

TABLE 1-continued

| | | | | | | | | | | | |
|---|---|---|---|---|---|---|---|---|---|---|---|
| Example 7 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 8 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 9 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 10 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 11 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 12 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 13 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 14 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 15 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 16 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 17 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 18 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 19 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 20 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Comparative example 1 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Comparative example 2 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Comparative example 3 | Photopolymerization initiator 1 | 1 | Ultraviolet absorber 1 | 0.5 | Surfactant 1 | 0.04 | Polymerization inhibitor 1 | 0.006 | Solvent 1 | 43.2 |

TABLE 2

| | Dispersion liquid | | | | | | | | | Curable composition | |
|---|---|---|---|---|---|---|---|---|---|---|---|
| | Coloring agent | | Derivative | | Dispersant | | Solvent A | | Resin | | |
| | Compound | Part by mass | Compound | Part by mass | Type | Part by mass | Type | Part by mass | Type | Part by mass | Type | Part by mass |
| Example 21 | A-ppb-2 | 2.6 | B-2 | 0.26 | C2 | 1.8 | Solvent 1 | 39.0 | Resin 3 | 5.5 | Curable compound 1 | 6.4 |
| Example 22 | A-ppb-2 | 2.6 | B-2 | 0.6 | C2 | 2.5 | Solvent 1 | 39.0 | Resin 3 | 5.5 | Curable compound 1 | 6.4 |
| Example 23 | A-ppb-2 | 1.5 | B-2 | 0.3 | C2 | 1 | Solvent 1 | 39.0 | Resin 3 | 5.5 | Curable compound 1 | 6.4 |
| Example 24 | A-ppb-2 | 2.6 | B-2 | 0.39 | C2 | 1.8 | Solvent 1 | 39.0 | Resin 3 | 5.5 | Curable compound 2 Curable compound 3 | 4.8 1.6 |
| Example 25 | A-ppb-2 | 2.6 | B-2 | 0.39 | C2 | 1.8 | Solvent 1 | 39.0 | Resin 3 | 5.5 | Curable compound 2 Curable compound 3 | 4.8 1.6 |
| Example 26 | A-ppb-2 | 2.6 | B-2 | 0.39 | C2 | 1.8 | Solvent 1 | 39.0 | Resin 3 | 5.5 | Curable compound 2 Curable compound 3 | 4.8 1.6 |
| Example 27 | A-ppb-2 | 2.6 | B-2 | 0.39 | C2 | 1.8 | Solvent 1 | 39.0 | Resin 3 | 5.5 | Curable compound 6 | 6.4 |
| Example 28 | A-ppb-2 | 2.6 | B-2 | 0.39 | C2 | 1.8 | Solvent 1 | 39.0 | Resin 3 | 5.5 | Curable compound 2 Curable compound 3 | 4.8 1.6 |
| Example 29 | A-ppb-2 | 2.6 | B-2 | 0.39 | C2 | 1.8 | Solvent 1 | 39.0 | Resin 3 | 5.5 | Curable compound 2 Curable compound 3 | 4.8 1.6 |
| Example 30 | A-ppb-2 | 2.6 | B-2 | 0.39 | C2 | 1.8 | Solvent 1 | 39.0 | Resin 3 | 5.5 | Curable compound 2 Curable compound 3 | 4.8 1.6 |

TABLE 2-continued

| Example 31 | A-ppb-2 | 2.6 | B-2 | 0.39 | C2 | 1.8 | Solvent 1 | 39.0 | Resin 3 | 5.5 | Curable compound 4 | 6.4 |
|---|---|---|---|---|---|---|---|---|---|---|---|---|
| Example 32 | A-ppb-2 | 2.6 | B-2 | 0.39 | C2 | 1.8 | Solvent 1 | 39.0 | Resin 3 | 5.5 | Curable compound 2 | 4.8 |
|  |  |  |  |  |  |  |  |  |  |  | Curable compound 5 | 1.6 |
| Example 33 | A-ppb-2 | 2.6 | B-2 | 0.39 | C2 | 1.8 | Solvent 1 | 39.0 | Resin 4 | 5.5 | Curable compound 2 | 4.8 |
|  |  |  |  |  |  |  |  |  |  |  | Curable compound 3 | 1.6 |
| Example 34 | A-ppb-2 | 2.6 | B-2 | 0.39 | C4 | 1.8 | Solvent 1 | 39.0 | Resin 3 | 5.5 | Curable compound 1 | 6.4 |
| Example 35 | A-ppb-2 | 2.6 | B-1 | 0.39 | C5 | 1.8 | Solvent 1 | 39.0 | Resin 3 | 5.5 | Curable compound 1 | 6.4 |
| Example 36 | A-ppb-2 | 2.6 | B-1 | 0.39 | C6 | 1.8 | Solvent 1 | 39.0 | Resin 3 | 5.5 | Curable compound 1 | 6.4 |
| Example 37 | A-ppb-2 | 2.6 | B-1 | 0.39 | C7 | 1.8 | Solvent 1 | 39.0 | Resin 3 | 5.5 | Curable compound 1 | 6.4 |
| Example 38 | A-ppb-2 | 2.6 | B-2 | 0.39 | C2 | 1.8 | Solvent 1 | 39.0 | Resin 3 | 5.5 | Curable compound 1 | 6.4 |
| Example 39 | A-ppb-2 | 2.6 | B-2 | 0.39 | C4 | 1.8 | Solvent 1 | 39.0 | Resin 3 | 5.5 | Curable compound 1 | 6.4 |
| Example 40 | A-ppb-2 | 2.6 | B-2 | 0.39 | C2 | 1.8 | Solvent 1 | 39.0 | Resin 3 | 5.5 | Curable compound 1 | 6.4 |

|  | Photopolymerization initiator | | Ultraviolet absorber | | Surfactant | | Polymerization inhibitor | | Solvent B | |
|---|---|---|---|---|---|---|---|---|---|---|
|  | Type | Part by mass | Type | Part by mass | Type | Part by mass | Type | Part by mass | Type | Part by mass |
| Example 21 | Photopolymerization initiator 1 | 1 | Ultraviolet absorber 1 | 0.5 | Surfactant 1 | 0.04 | Polymerization inhibitor 1 | 0.006 | Solvent 1 | 42.9 |
| Example 22 | Photopolymerization initiator 1 | 1 | Ultraviolet absorber 1 | 0.5 | Surfactant 1 | 0.04 | Polymerization inhibitor 1 | 0.006 | Solvent 1 | 41.9 |
| Example 23 | Photopolymerization initiator 1 | 1 | Ultraviolet absorber 1 | 0.5 | Surfactant 1 | 0.04 | Polymerization inhibitor 1 | 0.006 | Solvent 1 | 44.8 |
| Example 24 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 25 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 26 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 27 | Photopolymerization initiator 5 | 1 | Ultraviolet absorber 1 | 0.5 | Surfactant 1 | 0.04 | Polymerization inhibitor 1 | 0.006 | Solvent 1 | 43.2 |
| Example 28 | Photopolymerization initiator 1 | 0.5 | Ultraviolet absorber 1 | 0.5 | Surfactant 1 | 0.04 | Polymerization inhibitor 2 | 0.006 | Solvent 1 | 43.2 |
|  | Photopolymerization initiator 3 | 0.5 |  |  |  |  |  |  |  |  |
| Example 29 | Photopolymerization initiator 3 | 1 | Ultraviolet absorber 1 | 0.5 | Surfactant 1 | 0.04 | Polymerization inhibitor 1 | 0.006 | Solvent 1 | 43.2 |
| Example 30 | Photopolymerization initiator 4 | 1 | Ultraviolet absorber 1 | 0.5 | Surfactant 2 | 0.04 | Polymerization inhibitor 1 | 0.006 | Solvent 1 | 43.2 |
| Example 31 | Photopolymerization initiator 1 | 1 | Ultraviolet absorber 2 | 0.5 | Surfactant 1 | 0.04 | Polymerization inhibitor 1 | 0.006 | Solvent 1 | 43.2 |
| Example 32 | Photopolymerization initiator 1 | 1 | Ultraviolet absorber 2 | 0.5 | Surfactant 3 | 0.04 | Polymerization inhibitor 1 | 0.006 | Solvent 1 | 43.2 |
| Example 33 | Photopolymerization initiator 1 | 0.5 | Ultraviolet absorber 1 | 0.5 | Surfactant 1 | 0.04 | Polymerization inhibitor 1 | 0.006 | Solvent 1 | 43.2 |
|  | Photopolymerization initiator 2 | 0.5 |  |  |  |  |  |  |  |  |
| Example 34 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 35 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 36 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 37 | Photopolymerization initiator 1 | 1 | Ultraviolet absorber 1 | 0.5 | Surfactant 1 | 0.04 | Polymerization inhibitor 1 | 0.006 | Solvent 1 | 42.8 |
| Example 38 | Photopolymerization initiator 1 | 1 | Ultraviolet absorber 1 | 0.5 | Surfactant 1 | 0.04 | Polymerization inhibitor 2 | 0.006 | Solvent 2 | 42.8 |
| Example 39 | Photopolymerization initiator 1 | 1 | Ultraviolet absorber 1 | 0.5 | Surfactant 1 | 0.04 | Polymerization inhibitor 1 | 0.006 | Solvent 3 | 42.8 |
| Example 40 | Photopolymerization initiator 1 | 1 | Ultraviolet absorber 1 | 0.5 | Surfactant 1 | 0.04 | Polymerization inhibitor 1 | 0.006 | Solvent 4 | 42.8 |

TABLE 3

| | Dispersion liquid | | | | | | | | | Curable composition | |
|---|---|---|---|---|---|---|---|---|---|---|---|
| | Coloring agent | | Derivative | | Dispersant | | Solvent A | | Resin | | | |
| | Compound | Part by mass | Compound | Part by mass | Type | Part by mass | Type | Part by mass | Type | Part by mass | Type | Part by mass |
| Example 41 | A-sq-5 | 2.6 | — | — | C3 | 1.8 | Solvent 1 | 39.0 | Resin 3 | 5.5 | Curable compound 1 | 6.4 |
| Example 42 | A-ryl-1 | 2.6 | B-21 | 0.3 | C7 | 2.5 | Solvent 1 | 39.0 | Resin 3 | 5.5 | Curable compound 1 | 6.4 |
| Example 43 | A-id-1 | 2.6 | B-22 | 0.3 | C2 | 1 | Solvent 1 | 39.0 | Resin 3 | 5.5 | Curable compound 1 | 6.4 |
| Example 44 | A-cr-1 | 2.6 | — | — | C3 | 1.8 | Solvent 1 | 39.0 | Resin 3 | 5.5 | Curable compound 1 | 6.4 |
| Example 45 | A-bdp-1 | 2.6 | B-23 | 0.39 | C2 | 1.8 | Solvent 1 | 39.0 | Resin 3 | 5.5 | Curable compound 1 | 6.4 |
| Example 46 | A-bdp-2 | 2.6 | B-23 | 0.39 | C2 | 1.8 | Solvent 1 | 39.0 | Resin 3 | 5.5 | Curable compound 1 | 6.4 |
| Example 47 | A-bdp-3 | 2.6 | B-23 | 0.39 | C2 | 1.8 | Solvent 1 | 39.0 | Resin 3 | 5.5 | Curable compound 1 | 6.4 |
| Example 48 | A-bdp-4 | 2.6 | B-23 | 0.39 | C2 | 1.8 | Solvent 1 | 39.0 | Resin 3 | 5.5 | Curable compound 1 | 6.4 |
| Example 49 | A-ppb-2 | 2.6 | B-9 | 0.39 | C2 | 1.8 | Solvent 1 | 39.0 | Resin 3 | 5.5 | Curable compound 2 Curable compound 3 | 4.8 1.6 |
| Example 50 | A-ppb-2 | 2.6 | B-10 | 0.39 | C2 | 1.8 | Solvent 1 | 39.0 | Resin 3 | 5.5 | Curable compound 2 Curable compound 3 | 4.8 1.6 |
| Example 51 | A-ppb-2 | 2.6 | B-11 | 0.39 | C2 | 1.8 | Solvent 1 | 39.0 | Resin 3 | 5.5 | Curable compound 2 Curable compound 3 | 4.8 1.6 |
| Example 52 | A-ppb-2 | 2.6 | B-12 | 0.39 | C2 | 1.8 | Solvent 1 | 39.0 | Resin 3 | 5.5 | Curable compound 2 Curable compound 3 | 4.8 1.6 |
| Example 53 | A-ppb-2 | 2.6 | B-13 | 0.39 | C2 | 1.8 | Solvent 1 | 39.0 | Resin 3 | 5.5 | Curable compound 2 Curable compound 3 | 4.8 1.6 |
| Example 54 | A-ppb-2 | 2.6 | B-14 | 0.39 | C2 | 1.8 | Solvent 1 | 39.0 | Resin 3 | 5.5 | Curable compound 2 Curable compound 3 | 4.8 1.6 |
| Example 55 | A-ppb-2 | 2.6 | B-15 | 0.39 | C2 | 1.8 | Solvent 1 | 39.0 | Resin 4 | 5.5 | Curable compound 2 Curable compound 3 | 4.8 1.6 |
| Example 56 | A-ppb-2 | 2.6 | B-16 | 0.39 | C2 | 1.8 | Solvent 1 | 39.0 | Resin 3 | 5.5 | Curable compound 2 Curable compound 3 | 4.8 1.6 |
| Example 57 | A-ppb-2 | 2.6 | B-17 | 0.39 | C2 | 1.8 | Solvent 1 | 39.0 | Resin 3 | 5.5 | Curable compound 2 Curable compound 3 | 4.8 1.6 |
| Example 58 | A-ppb-2 | 2.6 | B-18 | 0.39 | C2 | 1.8 | Solvent 1 | 39.0 | Resin 3 | 5.5 | Curable compound 2 Curable compound 3 | 4.8 1.6 |
| Example 59 | A-ppb-2 | 2.6 | B-19 | 0.39 | C2 | 1.8 | Solvent 1 | 39.0 | Resin 3 | 5.5 | Curable compound 2 Curable compound 3 | 4.8 1.6 |
| Example 60 | A-ppb-2 | 2.6 | B-20 | 0.39 | C2 | 1.8 | Solvent 1 | 39.0 | Resin 3 | 5.5 | Curable compound 2 Curable compound 3 | 4.8 1.6 |

TABLE 3-continued

| | Photopolymerization initiator | | Ultraviolet absorber | | Surfactant | | Polymerization inhibitor | | Solvent B | |
|---|---|---|---|---|---|---|---|---|---|---|
| | Type | Part by mass | Type | Part by mass | Type | Part by mass | Type | Part by mass | Type | Part by mass |
| Example 41 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 42 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 43 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 44 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 45 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 46 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 47 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 48 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 49 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 50 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 51 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 52 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 53 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 54 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 55 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 56 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 57 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 58 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 59 | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 60 | Photopolymerization initiator 1 | 1 | Ultraviolet absorber 1 | 0.5 | Surfactant 1 | 0.04 | Polymerization inhibitor 1 | 0.006 | Solvent 1 | 43.2 |

TABLE 4

| | Dispersion liquid | | | | | | | | | | Curable composition | |
|---|---|---|---|---|---|---|---|---|---|---|---|---|
| | Coloring agent | | Derivative | | Dispersant | | Solvent A | | Resin | | | |
| | Compound | Part by mass | Compound | Part by mass | Type | Part by mass | Type | Part by mass | Type | Part by mass | Type | Part by mass |
| Example 61 | A-ppb-2 | 2.6 | B-24 | 0.39 | C2 | 1.8 | Solvent 1 | 39.0 | Resin 3 | 5.5 | Curable compound 2 | 4.8 |
| | | | | | | | | | | | Curable compound 3 | 1.6 |
| Example 62 | A-ppb-2 | 2.6 | B-25 | 0.39 | C2 | 1.8 | Solvent 1 | 39.0 | Resin 3 | 5.5 | Curable compound 2 | 4.8 |
| | | | | | | | | | | | Curable compound 3 | 1.6 |
| Example 63 | A-ppb-2 | 2.6 | B-26 | 0.39 | C2 | 1.8 | Solvent 1 | 39.0 | Resin 3 | 5.5 | Curable compound 2 | 4.8 |
| | | | | | | | | | | | Curable compound 3 | 1.6 |
| Example 64 | A-ppb-2 | 2.6 | B-27 | 0.39 | C2 | 1.8 | Solvent 1 | 39.0 | Resin 3 | 5.5 | Curable compound 2 | 4.8 |
| | | | | | | | | | | | Curable compound 3 | 1.6 |
| Example 65 | A-ppb-2 | 2.6 | B-28 | 0.39 | C2 | 1.8 | Solvent 1 | 39.0 | Resin 3 | 5.5 | Curable compound 2 | 4.8 |
| | | | | | | | | | | | Curable compound 3 | 1.6 |
| Example 66 | A-ppb-2 | 2.6 | B-29 | 0.39 | C2 | 1.8 | Solvent 1 | 39.0 | Resin 3 | 5.5 | Curable compound 2 | 4.8 |
| | | | | | | | | | | | Curable compound 3 | 1.6 |
| Example 67 | A-ppb-2 | 2.6 | B-30 | 0.39 | C2 | 1.8 | Solvent 1 | 39.0 | Resin 3 | 5.5 | Curable compound 2 | 4.8 |
| | | | | | | | | | | | Curable compound 3 | 1.6 |
| Example 68 | A-ppb-2 | 2.6 | B-31 | 0.39 | C2 | 1.8 | Solvent 1 | 39.0 | Resin 3 | 5.5 | Curable compound 2 | 4.8 |
| | | | | | | | | | | | Curable compound 3 | 1.6 |

TABLE 4-continued

| | | Photopolymerization initiator | | Ultraviolet absorber | | Surfactant | | Polymerization inhibitor | | Solvent B | |
|---|---|---|---|---|---|---|---|---|---|---|---|
| | | Type | Part by mass | Type | Part by mass | Type | Part by mass | Type | Part by mass | Type | Part by mass |
| Example 61 | | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 62 | | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 63 | | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 64 | | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 65 | | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 66 | | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 67 | | Photopolymerization initiator 1 | 1 | Ultraviolet absorber 1 | 0.5 | Surfactant 1 | 0.04 | Polymerization inhibitor 1 | 0.006 | Solvent 1 | 43.2 |
| Example 68 | | Photopolymerization initiator 1 | 1 | Ultraviolet absorber 1 | 0.5 | Surfactant 1 | 0.04 | Polymerization inhibitor 1 | 0.006 | Solvent 1 | 43.2 |

Raw materials used for each curable composition are as follows.

Derivatives B-1 to B-31 are the same compounds as B-1 to B-31 described above.

Resin 1: CYCLOMER P (ACA) 230AA (acrylic polymer having an acryloyl group and a carboxy group, manufactured by Daicel Corporation)

Resin 2: copolymer of allyl methacrylate (AMA) and methacrylic acid (MAA) (compositional ratio (mass ratio): AMA/MAA=80/20, Mw=15,000)

Resin 3: resin having the following structure (a numerical value added to a main chain represents a molar ratio; Mw=10,000, acid value=69.2 mgKOH/g)

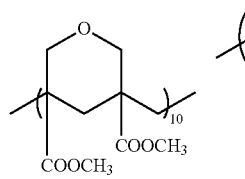 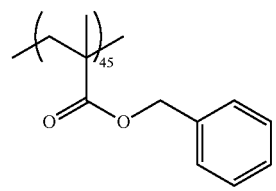

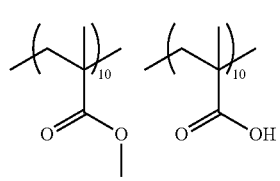

Resin 4: resin having the following structure (acid value=110 mgKOH/g, weight-average molecular weight=10,000; a numerical value added to a main chain represents a molar ratio of a repeating unit)

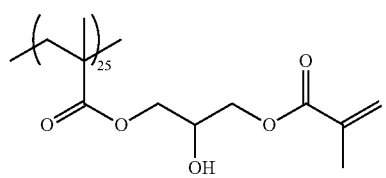

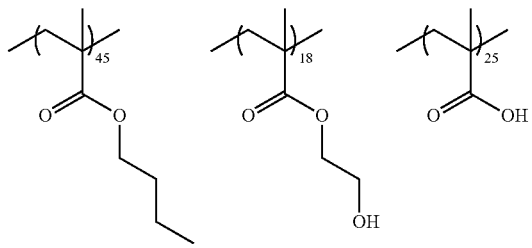

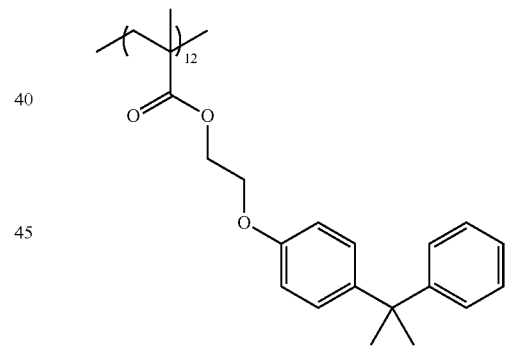

Resin 5: resin having the following structure (acid value=184 mgKOH/g, weight-average molecular weight=9,700; a numerical value added to a main chain represents a molar ratio of a repeating unit)

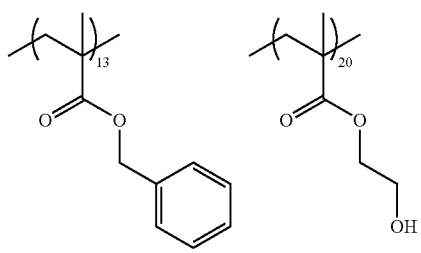

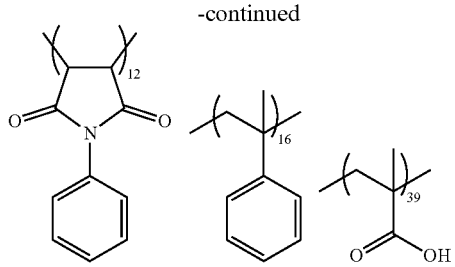

Curable compound 1: ARONIX M-350 (manufactured by TOAGOSEI CO., LTD.)

Curable compound 2: compound having the following structure (M1)

Curable compound 3: mixture of compounds having the following structures (M2) (containing 55 mol % to 63 mol % of a left compound)

Curable compound 4: compound having the following structure (M3)

Curable compound 5: mixture of compounds having the following structures (M4) (a molar ratio between a left compound and a right compound is 7:3)

Curable compound 6: DENACOL EX-611 (manufactured by Nagase ChemteX Corporation)

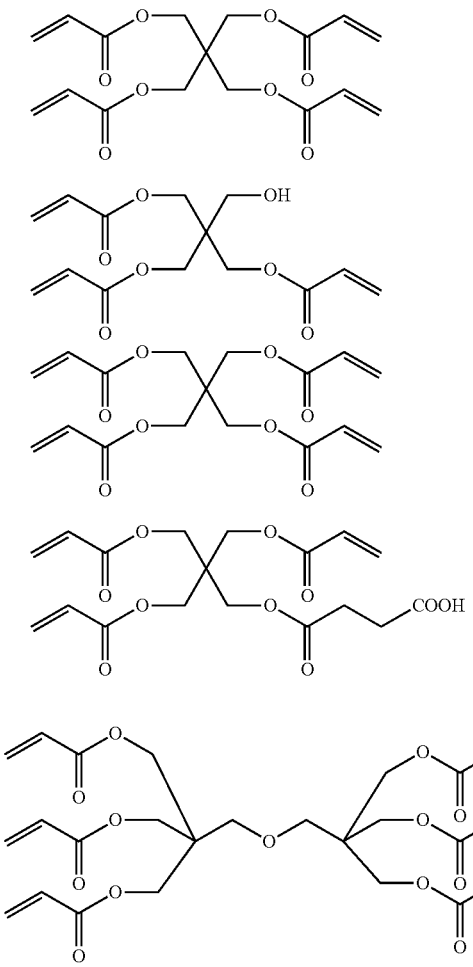

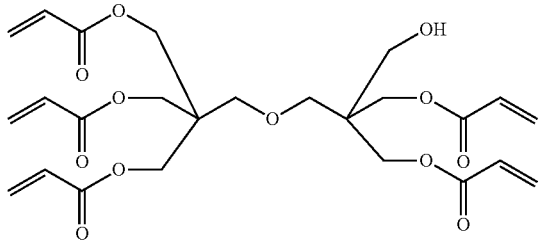

Photopolymerization initiator 1: compound having the following structure (F1)

Photopolymerization initiator 2: compound having the following structure (F2)

Photopolymerization initiator 3: compound having the following structure (F3)

Photopolymerization initiator 4: compound having the following structure (F4)

Photopolymerization initiator 5: CPI-100P (manufactured by San-Apro Ltd.)

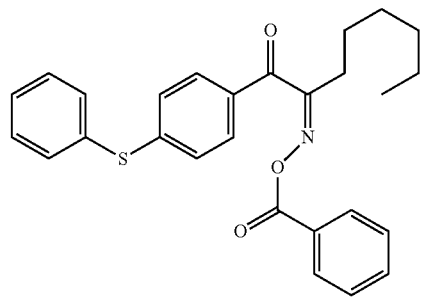

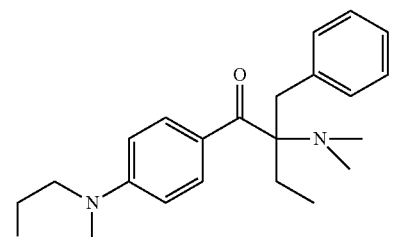

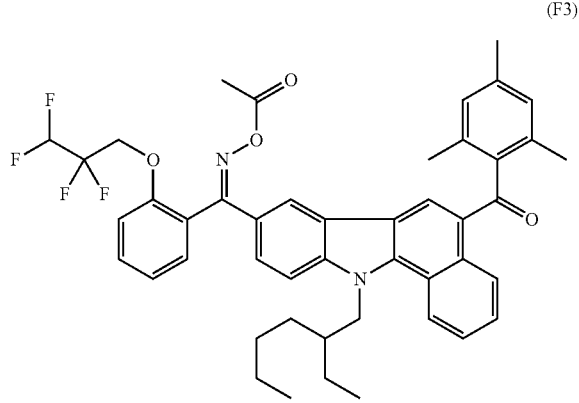

-continued

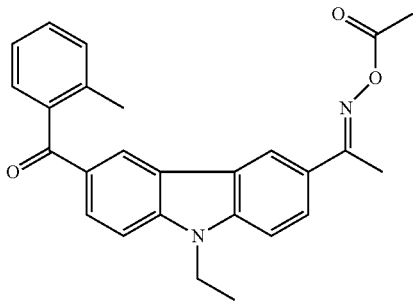
(F4)

Ultraviolet absorber 1: UV-503 (manufactured by Daito Chemical Co., Ltd.)

Ultraviolet absorber 2: compound having the following structure (UV2)

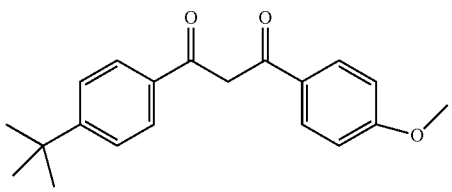
(UV2)

Surfactant 1: compound having the following structure (Mw=14,000; "%" representing the proportion of a structural repeating unit is mol %)

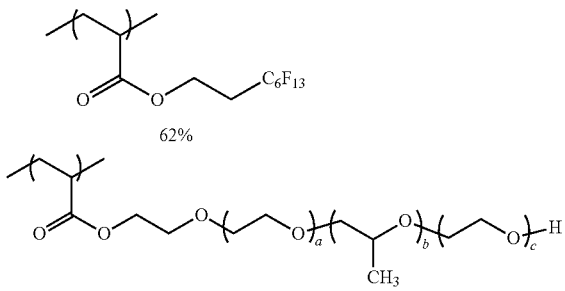

62%

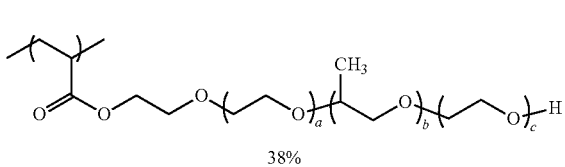

38% a + c = 14
b = 17

Surfactant 2: FTERGENT FTX-218 (manufactured by NEOS COMPANY LIMITED, fluorine-based surfactant)

Surfactant 3: KF-6001 (manufactured by Shin-Etsu Chemical Co., Ltd., silicon-based surfactant)

—Solvent—

Solvent 1: propylene glycol methyl ether acetate (PGMEA)

Solvent 2: cyclohexanone

Solvent 3: butyl acetate

Solvent 4: propylene glycol monomethyl ether

—Polymerization Inhibitor—

Polymerization inhibitor 1: p-methoxyphenol

Polymerization inhibitor: ADK STAB AO-80 (manufactured by ADEKA Corporation)

—Dispersant—

C1: resin having the following structure (a numerical value added to a main chain represents a molar ratio, and a numerical value added to a side chain represents the number of repeating units; Mw=38,000, acid value=99.1 mgKOH/g)

C2: resin having the following structure (a numerical value added to a main chain represents a molar ratio, and a numerical value added to a side chain represents the number of repeating units; Mw=21,000, acid value=36.0 mgKOH/g, amine value=47.0 mgKOH/g)

C3: block resin having the following structure (amine value=90 mgKOH/g, quaternary ammonium salt value=30 mgKOH/g, weight-average molecular weight=9800; a numerical value added to a main chain represents a molar ratio of a repeating unit)

C4: resin having the following structure (a numerical value added to a main chain represents a molar ratio, and a numerical value added to a side chain represents the number of repeating units; Mw=22,900, acid value=32.3 mgKOH/g, amine value=45.0 mgKOH/g)

C5: resin having the following structure (acid value=87.0 mgKOH/g, weight-average molecular weight=18000; a numerical value added to a main chain represents a molar ratio of a repeating unit and a numerical value added to a side chain represents the number of repeating units)

C6: resin having the following structure (acid value=85.0 mgKOH/g, weight-average molecular weight=22000; a numerical value added to a main chain represents a molar ratio of a repeating unit and a numerical value added to a side chain represents the number of repeating units)

C7: resin having the following structure (acid value=43 mgKOH/g, weight-average molecular weight=9000; a numerical value added to a main chain represents a molar ratio of a repeating unit)

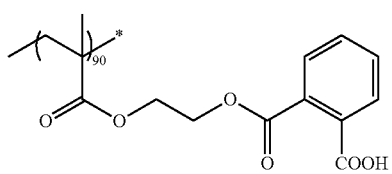
(C1)

-continued
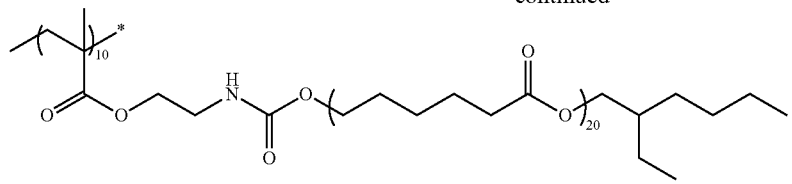
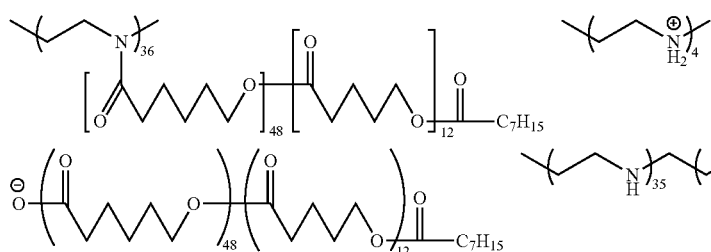
(C2)
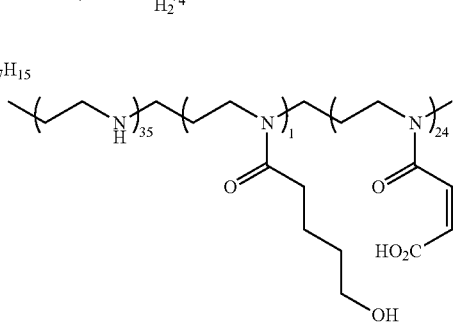
(C3)
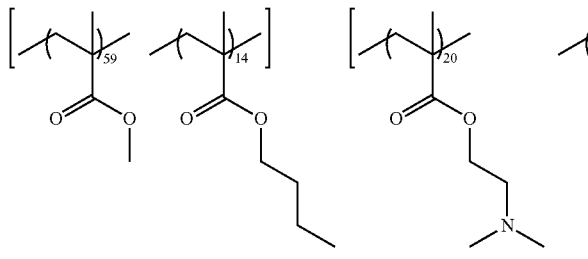
(C4)
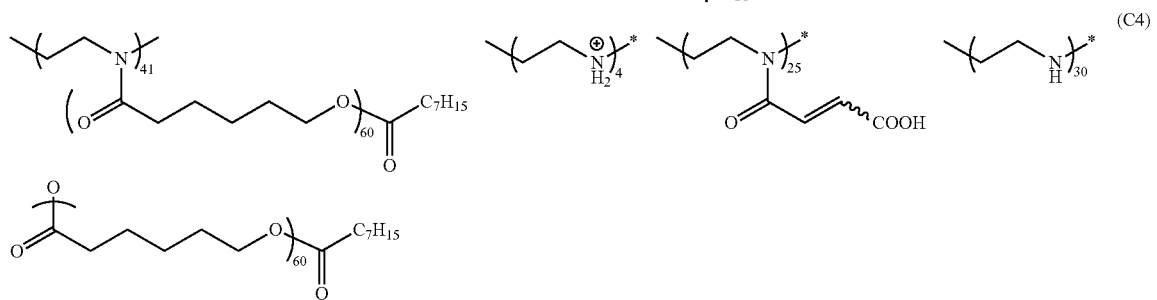
(C5)
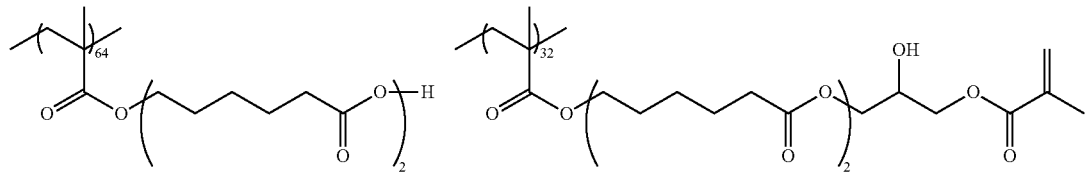
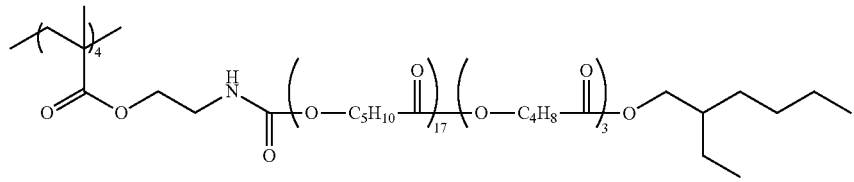
(C6)

-continued
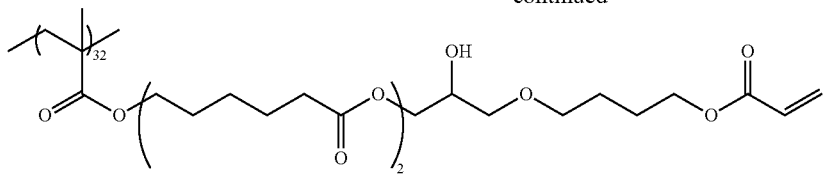
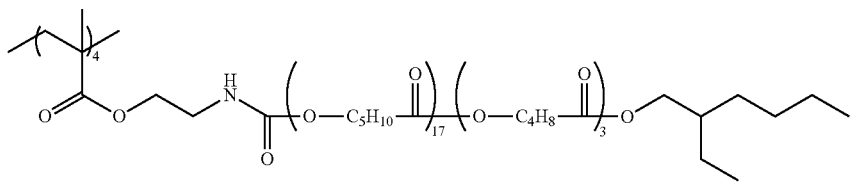
(C7)
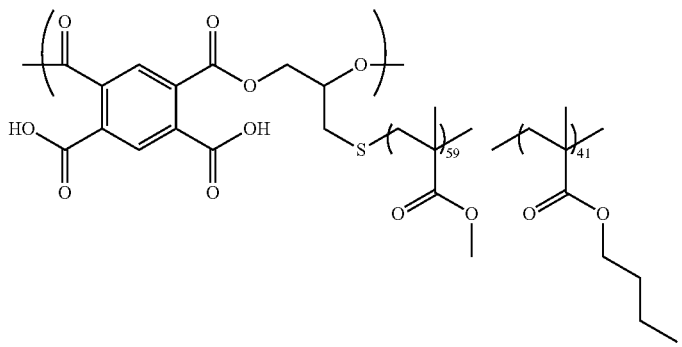
Comparative compounds A to C: coloring agents having the following structures
Comparative compound A
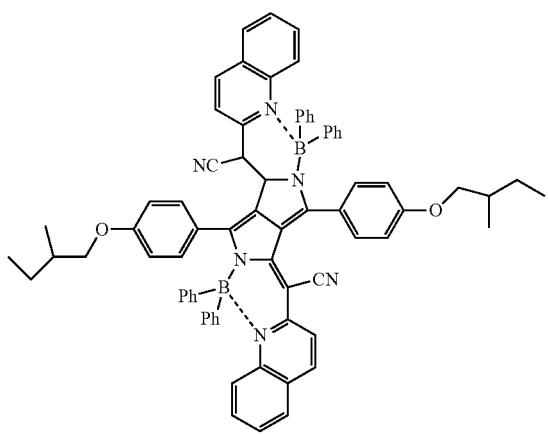
Comparative compound C
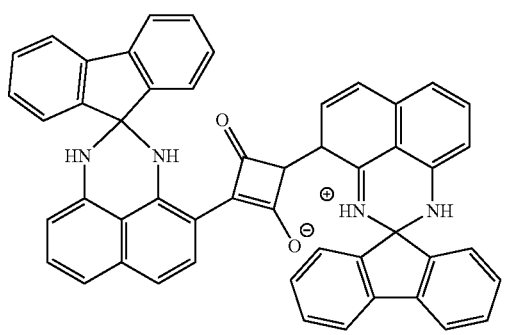

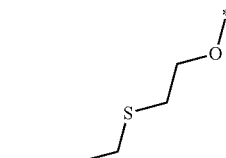

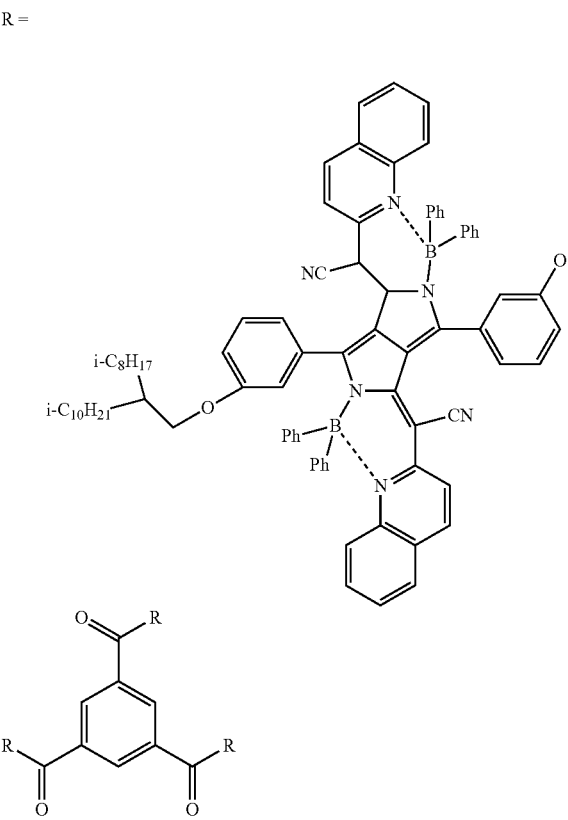

<Measurement of Solubility of Dispersion Liquids of Coloring Agents Shown in Tables 1 to 4 in PGMEA>

Under atmospheric pressure, approximately 100 mg of the dispersion liquid of the coloring agents shown in Tables 1 to 4 (value of the coloring agents shown Tables 1 to 4 precisely weighed is defined as X mg) was added to 1 L of propylene glycol methyl ether acetate at 25° C., and the mixture was stirred for 30 minutes. Next, the mixture was allowed to stand for 5 minutes and filtered, and the filtrate was dried under reduced pressure at 80° C. for 2 hours and weighed precisely (value of the filtrate precisely weighed is defined as Y mg). Solubility of the coloring agents shown in Tables 1 to 4 dissolved in propylene glycol methyl ether acetate was calculated from the following expression.

PGMEA solubility(mg/L)=X—Y

A: PGMEA solubility was less than 10 mg/L.
B: PGMEA solubility was 10 mg/L or more and less than 50 mg/L.
C: PGMEA solubility was 50 mg/L or more and 100 mg/L or less.
D: PGMEA solubility exceeded 100 mg/L.

The results are shown in Table 5 below.

TABLE 5

| Coloring agent | | |
|---|---|---|
| Type | Coloring agent structure | Solubility in PGMEA |
| A-ppb-1 | Pyrrolopyrrole coloring agent | B |
| A-ppb-2 | Pyrrolopyrrole coloring agent | A |
| A-ppb-3 | Pyrrolopyrrole coloring agent | A |
| A-ppb-4 | Pyrrolopyrrole coloring agent | C |
| A-ppb-5 | Pyrrolopyrrole coloring agent | C |
| A-ppb-6 | Pyrrolopyrrole coloring agent | B |
| A-ppb-7 | Pyrrolopyrrole coloring agent | B |
| A-ppb-11 | Pyrrolopyrrole coloring agent | B |
| A-ppb-13 | Pyrrolopyrrole coloring agent | C |
| A-ppb-16 | Pyrrolopyrrole coloring agent | A |
| A-ppb-17 | Pyrrolopyrrole coloring agent | A |
| A-ppb-18 | Pyrrolopyrrole coloring agent | A |
| A-ppb-19 | Pyrrolopyrrole coloring agent | B |
| A-ppb-21 | Pyrrolopyrrole coloring agent | A |
| A-ppb-22 | Pyrrolopyrrole coloring agent | A |
| A-sq-1 | Squarylium coloring agent | A |
| A-sq-3 | Squarylium coloring agent | A |
| A-sq-5 | Squarylium coloring agent | A |
| A-ryl-1 | Rylene coloring agent | A |
| A-id-1 | Indigo coloring agent | A |
| A-cr-1 | Croconium coloring agent | C |
| A-bdp-1 | Pyrromethene coloring agent | B |
| A-bdp-2 | Pyrromethene coloring agent | B |
| A-bdp-3 | Pyrromethene coloring agent | A |
| A-bdp-4 | Pyrromethene coloring agent | B |
| Comparative compound A | Pyrrolopyrrole coloring agent | A |
| Comparative compound B | Pyrrolopyrrole coloring agent | D |
| Comparative compound C | Squarylium coloring agent | A |

<Production of Cured Film>

Production Example 1

<<Method for Producing Cured Film Formed of Curable Composition of Composition 1>>

Each of the compositions shown in Tables 1 to 4 was applied to a glass substrate ("1737" manufactured by Corning Inc.) using a spin coater such that the thickness of a film after drying was 1.0 μm, and a heating treatment (pre-baking) was performed for 120 seconds using a hot plate at 100° C. Next, using an i-ray stepper exposure device FPA-3000 i5+(manufactured by Canon Inc.), the entire surface of the coating film was exposed at 500 mJ/cm². Next, using a developing machine (CD-2060, manufactured by FUJIFILM Electronic Materials Co., Ltd.), a puddle development was performed at 23° C. for 60 seconds, and then rinse treatment was performed with pure water and spin drying was performed. Furthermore, a heating treatment (post-baking) was performed for 300 seconds using a hot plate at 200° C., thereby obtaining a cured film.

<Evaluation of Spectral Characteristics>

Using a spectrophotometer (U-4100, manufactured by Hitachi High-Tech Corporation), the absorption spectrum of the cured film obtained above was measured in a wavelength range of 400 nm to 2,000 nm.

The maximum absorbance (Absλmax) in the wavelength of 650 nm to 2,000 nm was measured, and "average absorbance at a wavelength of 400 nm to 550 nm" in a case where the maximum absorbance was set to be 1 was evaluated according to the following standard.

As the absorbance at the wavelength of 400 nm to 550 nm is smaller in a case where this absorbance is set to be 1, since the absorption spectrum has a steep spectral shape, and both high transparency in the visible light region and high colorability in the near infrared range are achieved, it can be said that the obtained cured film has excellent spectral characteristics.

—Evaluation Standard—
  A: average absorbance at a wavelength of 400 nm to 550 nm was less than 0.05.
  B: average absorbance at a wavelength of 400 nm to 550 nm was 0.05 or more and less than 0.1.
  C: average absorbance at a wavelength of 400 nm to 550 nm was 0.1 or more and less than 0.2.
  D: average absorbance at a wavelength of 400 nm to 550 nm was 0.2 or more.

<Evaluation of Heat Resistance>

The cured film obtained above was heated at 265° C. for 300 seconds using a hot plate. Using a spectrophotometer U-4100 (manufactured by Hitachi High-Tech Corporation), the transmittance of the film before and after heating with respect to light having a wavelength of 400 to 2,000 nm was measured. In the wavelength range of 400 nm to 2,000 nm, the change in transmittance at the wavelength where the change in transmittance before and after heating was the largest was calculated from the following expression, and the change in transmittance was evaluated according to the following standard. It can be said that, as the change in transmittance is smaller, the heat resistance is more excellent.

Change in transmittance=|(Transmittance after light irradiation−Transmittance before light irradiation)|

—Evaluation Standard—
  A: change in transmittance was less than 3%.
  B: change in transmittance was 3% or more and less than 5%.
  C: change in transmittance was 5% or more and less than 10%.
  D: change in transmittance was 10% or more.

<Evaluation of Light Resistance>

The obtained cured film was set in a fading tester equipped with a super xenon lamp (200,000 lux), and was irradiated with light of 200,000 lux for 75 hours under a condition in which no ultraviolet cut filter was used. Next, using a spectrophotometer U-4100 (manufactured by Hitachi High-Tech Corporation), the transmission spectrum of the film after light irradiation was measured. In the wavelength range of 400 nm to 2,000 nm, the change in transmittance at the wavelength where the change in transmittance before and after light irradiation was the largest was calculated from the following expression, and the light resistance was evaluated according to the following standard.

Change in transmittance=|(Transmittance after light irradiation−Transmittance before light irradiation)|

—Evaluation Standard—
  A: change in transmittance was less than 3%.
  B: change in transmittance was 3% or more and less than 5%.
  C: change in transmittance was 5% or more and less than 10%.
  D: change in transmittance was 10% or more.

<Evaluation of Dispersibility>

The average particle diameter of the coloring agents in the compositions shown in Tables 1 to 4 was measured by the following method to evaluate the dispersibility. In Comparative Example 2, since the comparative compound 2 was dissolved in the solvent, the dispersibility was not evaluated.

The volume average particle diameter of the coloring agents in the compositions was measured using a Nanotrac UPA particle size analyzer (UPA-EX150, trade name, manufactured by Nikkiso Co., Ltd.), and the dispersibility was evaluated according to the following standard. It can be said that, as the volume average particle diameter of the coloring agent in the composition is smaller, the dispersibility is more excellent.

—Evaluation Standard—
  A: volume average particle diameter was 10 nm or more and 100 nm or less.
  B: volume average particle diameter was more than 100 nm and 200 nm or less.
  C: volume average particle diameter was more than 200 nm and 500 nm or less.
  D: volume average particle diameter exceeded 500 nm.

The evaluation results are summarized in Tables 6 to 9.

TABLE 6

| | Evaluation result | | | |
|---|---|---|---|---|
| | Spectral characteristics | Heat resistance | Light resistance | Dispersibility |
| Example 1 | B | B | A | C |
| Example 2 | A | B | A | B |
| Example 3 | A | B | A | A |
| Example 4 | A | A | A | A |
| Example 5 | A | A | A | A |
| Example 6 | A | A | A | A |

TABLE 6-continued

| | Evaluation result | | | |
|---|---|---|---|---|
| | Spectral characteristics | Heat resistance | Light resistance | Dispersibility |
| Example 7 | B | B | B | B |
| Example 8 | A | A | A | A |
| Example 9 | A | B | A | A |
| Example 10 | A | A | B | A |
| Example 11 | B | B | B | B |
| Example 12 | A | A | A | A |
| Example 13 | A | A | A | A |
| Example 14 | A | A | A | A |
| Example 15 | A | B | B | A |
| Example 16 | A | A | A | A |
| Example 17 | A | A | A | A |
| Example 18 | B | B | C | B |
| Example 19 | B | B | C | A |
| Example 20 | A | B | B | A |
| Comparative example 1 | C | B | C | A |
| Comparative example 2 | C | C | D | — |
| Comparative example 3 | D | C | D | C |

TABLE 7

| | Evaluation result | | | |
|---|---|---|---|---|
| | Spectral characteristics | Heat resistance | Light resistance | Dispersibility |
| Example 21 | A | A | A | B |
| Example 22 | A | A | A | A |
| Example 23 | A | A | A | A |
| Example 24 | A | A | A | A |
| Example 25 | A | A | A | A |
| Example 26 | A | A | A | A |
| Example 27 | A | A | A | A |
| Example 28 | A | A | A | A |
| Example 29 | A | A | A | A |
| Example 30 | A | A | A | A |
| Example 31 | A | A | A | A |
| Example 32 | A | A | A | A |
| Example 33 | A | A | A | A |
| Example 34 | A | A | A | A |
| Example 35 | A | A | A | A |
| Example 36 | A | A | A | A |
| Example 37 | A | A | A | A |
| Example 38 | A | A | A | A |
| Example 39 | A | A | A | A |
| Example 40 | A | A | A | A |

TABLE 8

| | Evaluation result | | | |
|---|---|---|---|---|
| | Spectral characteristics | Heat resistance | Light resistance | Dispersibility |
| Example 41 | B | B | B | B |
| Example 42 | B | A | A | C |
| Example 43 | B | B | B | B |
| Example 44 | B | C | B | C |
| Example 45 | B | B | C | B |
| Example 46 | B | B | B | B |
| Example 47 | B | B | B | B |
| Example 48 | B | B | B | B |
| Example 49 | A | A | A | A |
| Example 50 | A | A | A | A |
| Example 51 | A | A | A | A |
| Example 52 | A | A | A | A |
| Example 53 | A | A | A | A |
| Example 54 | A | A | A | A |

TABLE 8-continued

| | Evaluation result | | | |
|---|---|---|---|---|
| | Spectral characteristics | Heat resistance | Light resistance | Dispersibility |
| Example 55 | A | A | A | A |
| Example 56 | A | A | A | B |
| Example 57 | A | A | A | A |
| Example 58 | A | A | A | A |
| Example 59 | A | A | A | A |
| Example 60 | A | A | A | A |

TABLE 9

| | Evaluation result | | | |
|---|---|---|---|---|
| | Spectral characteristics | Heat resistance | Light resistance | Dispersibility |
| Example 61 | A | A | A | A |
| Example 62 | A | A | A | A |
| Example 63 | A | A | A | A |
| Example 64 | A | A | A | A |
| Example 65 | A | A | A | A |
| Example 66 | A | A | A | A |
| Example 67 | A | A | A | A |
| Example 68 | A | A | A | A |

From the results shown in Tables 6 to 9, it was found that the curable compositions of Examples 1 to 68 according to the embodiment of the present disclosure were superior in the spectral characteristics of a film to be obtained, as compared with the curable compositions of Comparative Examples 1 to 3.

In addition, it was found that the curable compositions of Examples 1 to 68 according to the embodiment of the present disclosure were also excellent in heat resistance and light resistance.

Examples 101 to 168

Using each of the compositions of Examples 1 to 68, a 2 µm square pattern (infrared cut filter) was formed by the following method. A solid-state imaging element including the obtained infrared cut filter was manufactured as follows.

Using each of the curable compositions of Examples 1 to 68, a pattern was produced by the following method.

The above-described curable composition was applied by a spin coating method so that the thickness of a film after film formation was 1.0 µm. Next, the curable composition was heated using a hot plate at 100° C. for 2 minutes. Next, using an i-ray stepper exposure device FPA-3000 i5+(manufactured by Canon Inc.), exposure was performed at 1,000 mJ/cm$^2$ through a mask having a dot pattern of 2 µm square. Next, puddle development was performed at 23° C. for 60 seconds using a 0.3 mass % of tetramethylammonium hydroxide (TMAH) aqueous solution. Next, the coating film was rinsed by spin showering and was cleaned with pure water. Next, the coating film was heated using a hot plate at 200° C. for 5 minutes. As a result, a 2 µm×2 µm pattern (infrared cut filter) was formed.

Next, a Red composition was applied to the pattern of the infrared cut filter by a spin coating method so that the thickness of a film after film formation was 1.0 µm. Next, the Red composition was heated using a hot plate at 100° C. for 2 minutes. Next, using an i-ray stepper exposure device FPA-3000 i5+ (manufactured by Canon Inc.), exposure was performed at 1,000 mJ/cm$^2$ through a mask having a dot pattern of 2 µm square. Next, puddle development was performed at 23° C. for 60 seconds using a 0.3 mass % of tetramethylammonium hydroxide (TMAH) aqueous solution. Next, the coating film was rinsed by spin showering and was cleaned with pure water. Next, the coating film was heated using a hot plate at 200° C. for 5 minutes. As a result, the Red composition was patterned on the pattern of the infrared cut filter. Likewise, a Green composition and a Blue composition were sequentially patterned to form red, green, and blue colored patterns (Bayer pattern).

The Bayer pattern refers to a pattern, as disclosed in the specification of U.S. Pat. No. 3,971,065A, in which a 2×2 array of color filter element having one Red element, two Green elements, and one Blue element is repeated. However, in this example, a 2×2 array of a filter element having one red element, one green element, one blue element, and one infrared transmitting filter element was repeated to form a Bayer pattern.

Next, a composition for forming an infrared transmitting filter (the following composition 100 or composition 101) was applied to the pattern-formed film by a spin coating method such that the thickness of a film after film formation was 2.0 µm. Next, the composition for forming an infrared transmitting filter was heated using a hot plate at 100° C. for 2 minutes. Next, using an i-ray stepper exposure device FPA-3000 i5+ (manufactured by Canon Inc.), exposure was performed with an exposure amount of 1000 mJ/cm$^2$ through a mask having a Bayer pattern of 2 µm square. Next, puddle development was performed at 23° C. for 60 seconds using a 0.3 mass % of tetramethylammonium hydroxide (TMAH) aqueous solution. Next, the coating film was rinsed by spin showering and was cleaned with pure water. Next, the coating film was heated using a hot plate at 200° C. for 5 minutes. As a result, in the Bayer pattern of the infrared cut filter, the infrared transmitting filter was patterned in a missing portion where the colored pattern was not formed. This filter was incorporated into a solid-state imaging element using a known method.

The obtained solid-state imaging element was irradiated with infrared rays by an infrared light emitting diode (infrared LED) in a low-illuminance environment (0.001 Lux) to acquire images. Next, the imaging performance of the solid-state imaging element was evaluated. In a case where any of the curable compositions obtained in Examples 1 to 68 was used, the image could be clearly recognized even in a low-illuminance environment.

The Red composition, the Green composition, the Blue composition, and the composition for forming an infrared transmitting filter used in the above-described patterning are as follows.

—Red Composition—

The following components were mixed and stirred, and the obtained mixture was filtered through a nylon filter (manufactured by Nihon Pall Corporation) having a pore size of 0.45 µm to prepare a Red composition.
  Red pigment dispersion liquid: 51.7 parts by mass
  Resin 4 (40 mass % PGMEA solution): 0.6 parts by mass
  Polymerizable compound 4: 0.6 parts by mass
  Photopolymerization initiator 1: 0.3 parts by mass
  Surfactant 1: 4.2 parts by mass
  PGMEA: 42.6 parts by mass
—Green Composition—
The following components were mixed and stirred, and the obtained mixture was filtered through a nylon filter (manufactured by Nihon Pall Corporation) having a pore size of 0.45 µm to prepare a Green composition.
  Green pigment dispersion liquid: 73.7 parts by mass
  Resin 4 (40 mass % PGMEA solution): 0.3 parts by mass
  Polymerizable compound 1: 1.2 parts by mass
  Photopolymerization initiator 1: 0.6 parts by mass
  Surfactant 1: 4.2 parts by mass
  Ultraviolet absorber (UV-503, manufactured by Daito Chemical Co., Ltd.): 0.5 parts by mass
  PGMEA: 19.5 parts by mass
—Blue Composition—
The following components were mixed and stirred, and the obtained mixture was filtered through a nylon filter (manufactured by Nihon Pall Corporation) having a pore size of 0.45 µm to prepare a Blue composition.
  Blue pigment dispersion liquid: 44.9 parts by mass
  Resin 4 (40 mass % PGMEA solution): 2.1 parts by mass
  Polymerizable compound 1: 1.5 parts by mass
  Polymerizable compound 4: 0.7 parts by mass
  Photopolymerization initiator 1: 0.8 parts by mass
  Surfactant 1: 4.2 parts by mass
  PGMEA: 45.8 parts by mass
—Composition for Forming Infrared Transmitting Filter—
Components having the following composition were mixed and stirred, and the obtained mixture was filtered through a nylon filter (manufactured by Nihon Pall Corporation) having a pore size of 0.45 µm to prepare a composition for forming an infrared transmitting filter.
<Composition 100>
  Pigment dispersion liquid 1-1: 46.5 parts by mass
  Pigment dispersion liquid 1-2: 37.1 parts by mass
  Polymerizable compound 5: 1.8 parts by mass
  Resin 4: 1.1 parts by mass
  Photopolymerization initiator 2: 0.9 parts by mass
  Surfactant 1: 4.2 parts by mass
  Polymerization inhibitor (p-methoxyphenol): 0.001 parts by mass
  Silane coupling agent: 0.6 parts by mass
  PGMEA: 7.8 parts by mass
<Composition 101>
  Pigment dispersion liquid 2-1: 1,000 parts by mass
  Polymerizable compound (dipentaerythritol hexaacrylate): 50 parts by mass
  Resin 4: 17 parts by mass
  Photopolymerization initiator (1-[4-(phenylthio)]-1,2-octanedione-2-(O-benzyloxime)): 10 parts by mass
  PGMEA: 179 parts by mass
  Alkali-soluble polymer F-1: 17 parts by mass (concentration of solid contents: 35 parts by mass)
<Synthesis Example of Alkali-Soluble Polymer F-1>

In a reaction container, 14 parts of benzyl methacrylate, 12 parts of N-phenylmaleimide, 15 parts of 2-hydroxyethyl methacrylate, 10 parts of styrene, and 20 parts of methacrylic acid were dissolved in 200 parts of propylene glycol methyl ether acetate, and 3 parts of 2,2'-azoisobutyronitrile and 5 parts of α-methylstyrene dimer were further added thereto. After purging the inside of the reaction container with nitrogen, the mixture was heated to 80° C. for 5 hours with stirring and nitrogen bubbling to obtain a solution including an alkali-soluble polymer F-1 (concentration of solid contents: 35 mass %). This polymer had a polystyrene-equivalent weight-average molecular weight of 9,700, a number-average molecular weight of 5,700, and a Mw/Mn of 1.70.

<Pigment Dispersion Liquid 2-1>

60 parts of C. I. Pigment Black 32, 20 parts of C. I. Pigment Blue 15:6, 20 parts of C. I. Pigment Yellow 139, 80 parts (concentration of solid contents: 50 mass %) of SOL-SPERSE 76500 manufactured by Lubrizol Corporation, 120 parts (concentration of solid contents: 35 mass %) of a solution including the alkali-soluble polymer F-1, and 700 parts of propylene glycol methyl ether acetate were mixed, and the mixture was dispersed for 8 hours using a paint shaker to obtain a pigment dispersion liquid 2-1.

Raw materials used in the Red composition, the Green composition, the Blue composition, and the composition for forming an infrared transmitting filter are as follows.

Red Pigment Dispersion Liquid

A mixed solution consisting of 9.6 parts by mass of C. I. Pigment Red 254, 4.3 parts by mass of C. I. Pigment Yellow 139, 6.8 parts by mass of a dispersant (Disperbyk-161, manufactured by BYK Chemie), and 79.3 parts by mass of PGMEA was mixed and dispersed using a beads mill (zirconia beads; diameter: 0.3 mm) for 3 hours to prepare a pigment dispersion liquid. Next, using a high-pressure disperser NANO-3000-10 (manufactured by Nippon BEE Chemical Co., Ltd.) equipped with a pressure reducing mechanism, the pigment dispersion liquid was further dispersed under a pressure of 2,000 kg/cm$^3$ at a flow rate of 500 g/min. This dispersion treatment was repeated 10 times, thereby obtaining a Red pigment dispersion liquid.

Green Pigment Dispersion Liquid

A mixed solution consisting of 6.4 parts by mass of C. I. Pigment Green 36, 5.3 parts by mass of C. I. Pigment Yellow 150, 5.2 parts by mass of a dispersant (Disperbyk-161, manufactured by BYK Chemie), and 83.1 parts by mass of PGMEA was mixed and dispersed using a beads mill (zirconia beads; diameter: 0.3 mm) for 3 hours to prepare a pigment dispersion liquid. Next, using a high-pressure disperser NANO-3000-10 (manufactured by Nippon BEE Chemical Co., Ltd.) equipped with a pressure reducing mechanism, the pigment dispersion liquid was further dispersed under a pressure of 2,000 kg/cm$^3$ at a flow rate of 500 g/min. This dispersion treatment was repeated 10 times. As a result, a Green pigment dispersion liquid was obtained.

Blue Pigment Dispersion Liquid

A mixed solution consisting of 9.7 parts by mass of C. I. Pigment Blue 15:6, 2.4 parts by mass of C. I. Pigment Violet 23, 5.5 parts of a dispersant (Disperbyk-161, manufactured by BYK Chemie), and 82.4 parts of PGMEA was mixed and dispersed using a beads mill (zirconia beads; diameter: 0.3 mm) for 3 hours to prepare a pigment dispersion liquid. Next, using a high-pressure disperser NANO-3000-10 (manufactured by Nippon BEE Chemical Co., Ltd.) equipped with a pressure reducing mechanism, the pigment dispersion liquid was further dispersed under a pressure of 2,000 kg/cm$^3$ at a flow rate of 500 g/min. This dispersion treatment was repeated 10 times, thereby obtaining a Blue pigment dispersion liquid.

Pigment Dispersion Liquid 1-1

A mixed solution having the composition shown below was mixed and dispersed for 3 hours using a beads mill (a high-pressure disperser with a pressure reducing mechanism, NANO-3000-10 (manufactured by Nippon BEE Chemical Co., Ltd.)) in which zirconia beads having a diameter of 0.3 mm were used. As a result, a pigment dispersion liquid 1-1 was prepared.

Mixed pigment consisting of a red pigment (C. I. Pigment Red 254) and a yellow pigment (C. I. Pigment Yellow 139): 11.8 parts by mass Resin (Disperbyk-111, manufactured by BYK Chemie): 9.1 parts by mass PGMEA: 79.1 parts by mass Pigment Dispersion Liquid 1-2

A mixed solution having the composition shown below was mixed and dispersed for 3 hours using a beads mill (a high-pressure disperser with a pressure reducing mechanism, NANO-3000-10 (manufactured by Nippon BEE Chemical Co., Ltd.)) in which zirconia beads having a diameter of 0.3 mm were used. As a result, a pigment dispersion liquid 1-2 was prepared.

Mixed pigment consisting of a blue pigment (C. I. Pigment Blue 15:6) and a violet pigment (C. I. Pigment Violet 23): 12.6 parts by mass Resin (Disperbyk-111, manufactured by BYK Chemie): 2.0 parts by mass Resin A: 3.3 parts by mass Cyclohexanone: 31.2 parts by mass PGMEA: 50.9 parts by mass Details of the abbreviations for the components used above are shown below.

Resin A: following structure (Mw=14,000, a ratio in a constitutional unit is a molar ratio)

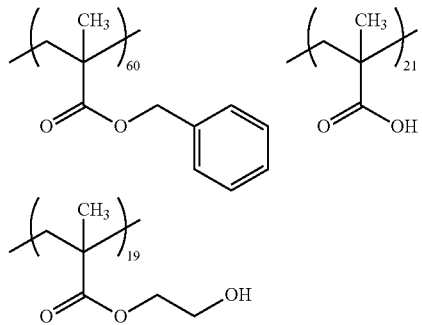

Polymerizable compound 1: KAYARAD DPHA (mixture of dipentaerythritol hexaacrylate and dipentaerythritol pentaacrylate, manufactured by Nippon Kayaku Co., Ltd.)

Polymerizable compound 4: following structure

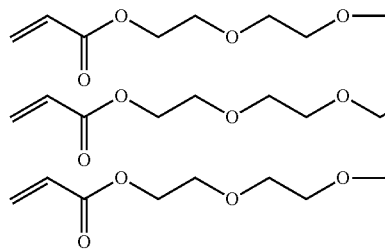

Polymerizable compound 5: following structure (mixture in which a molar ratio between a left compound and a right compound is 7:3)

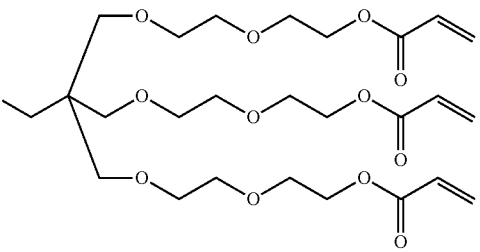

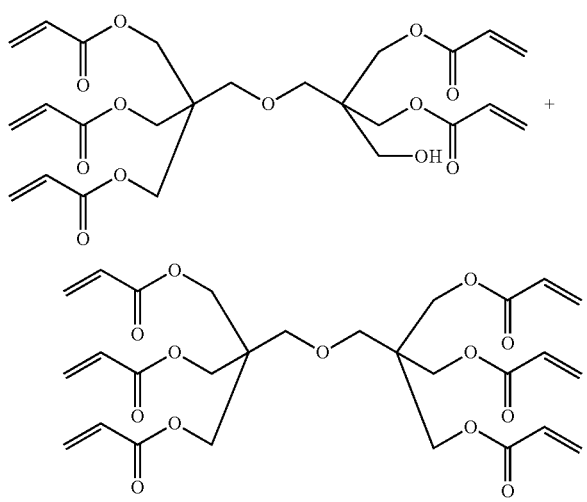

Resin 4: following structure (acid value: 70 mgKOH/g, Mw=11,000; a ratio in a constitutional unit is a molar ratio)

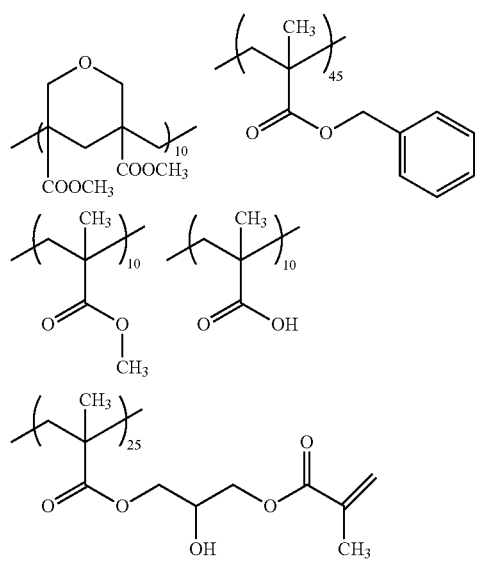

Photopolymerization initiator 1: IRGACURE-OXE01 (1-[4-(phenylthio)]-1,2-octanedione-2-(O-benzoyloxime), manufactured by BASF)

Photopolymerization initiator 2: following structure

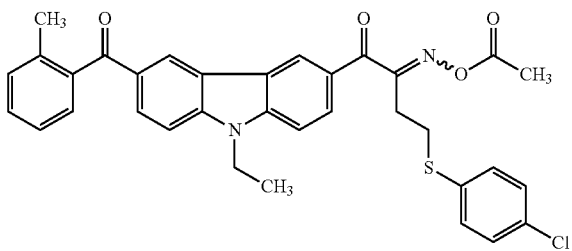 [SMILES: CCn1c2ccc(C(=O)C(CCSc3ccc(Cl)cc3)=NOC(C)=O)cc2c2cc(C(=O)c3ccccc3C)ccc21]

Surfactant 1: 1 mass % PGMEA solution of the following mixture (Mw: 14,000; in the following formula, "%" (62% and 38%) indicating the proportion of a constitutional unit is molar ratio)

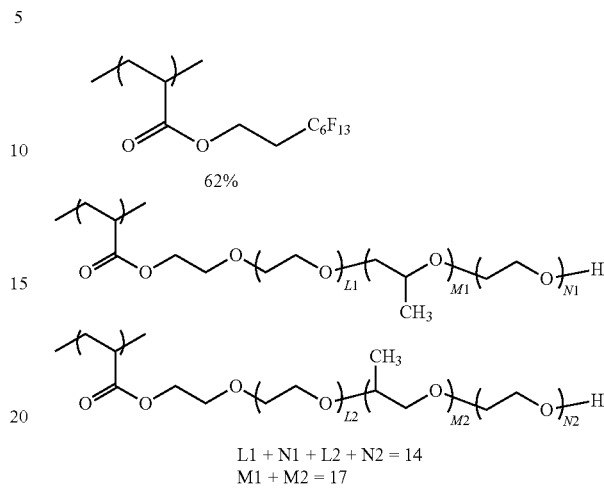

L1 + N1 + L2 + N2 = 14
M1 + M2 = 17

38%

Silane coupling agent: compound having the following structure (in the following structural formula, Et represents an ethyl group)

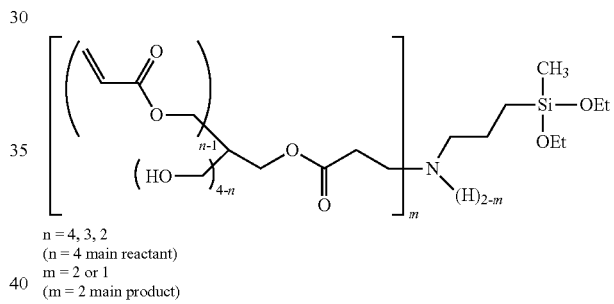

n = 4, 3, 2
(n = 4 main reactant)
m = 2 or 1
(m = 2 main product)

Example 201

The following composition was mixed and stirred, and the obtained mixture was filtered through a nylon filter (manufactured by Nihon Pall Corporation) having a pore size of 0.45 μm to prepare a composition for forming a pattern of Example 201.

Curable composition of Example 1: 22.67 parts by mass
Pigment dispersion liquid 2-1: 51.23 parts by mass In a case where the light resistance and heat resistance were evaluated in the same manner as in Example 1 using the composition for forming a pattern of Example 201, the same effects as in Example 1 were obtained. In addition, the cured film obtained using the composition for forming a pattern of Example 201 was able to shield light in the visible range and allow transmission of at least a part of light (near infrared rays) in the near infrared range.

Example 202

The following composition was mixed and stirred, and the obtained mixture was filtered through a nylon filter (manufactured by Nihon Pall Corporation) having a pore size of 0.45 μm to prepare a composition for forming a pattern of Example 202.

Curable composition of Example 1: 36.99 parts by mass
Pigment dispersion liquid 1-1: 46.5 parts by mass
Pigment dispersion liquid 1-2: 37.1 parts by mass In a case where the light resistance and heat resistance were evaluated in the same manner as in Example 1 using the composition for forming a pattern of Example 202, the same effects as in Example 1 were obtained. In addition, the cured film obtained using the composition for forming a pattern of Example 202 was able to shield light in the visible range and allow transmission of at least a part of light (near infrared rays) in the near infrared range.

Example 301

In a case where the curable compositions of Examples 1 to 68 were used and evaluated in the same manner as in Example 101, except that the substrate was changed (changed to a silicon wafer in a case of a glass substrate and changed to a glass substrate in a case of a silicon wafer), the same effects as in Examples 101 to 168 were obtained.

Example 302

In a case where the composition for forming a pattern obtained in Example 201 or Example 202 was used and evaluated in the same manner as in Example 101, except that the substrate was changed (changed to a silicon wafer in a case of a glass substrate and changed to a glass substrate in a case of a silicon wafer), the same effects as in Examples 101 were obtained.

Example 401

In a case where a composition for forming a pattern was prepared in the same manner as in Example 201, except that the curable composition of Example 1 used in Example 201 was replaced with the curable compositions of Examples 2 to 68, and the light resistance and heat resistance were evaluated in the same manner as in Example 1, the same effects as in Examples 2 to 68 were obtained. In addition, the cured film obtained using the composition for forming a pattern of Example 401 was able to shield light in the visible range and allow transmission of at least a part of light (near infrared rays) in the near infrared range.

Example 402

In a case where a composition for forming a pattern was prepared in the same manner as in Example 202, except that the curable composition of Example 1 used in Example 202 was replaced with the curable compositions of Examples 2 to 68, and the light resistance and heat resistance were evaluated in the same manner as in Example 1, the same effects as in Examples 2 to 68 were obtained. In addition, the cured film obtained using the composition for forming a pattern of Example 402 was able to shield light in the visible range and allow transmission of at least a part of light (near infrared rays) in the near infrared range.

EXPLANATION OF REFERENCES

110: solid-state imaging element
111: infrared cut filter
112: color filter
114: infrared transmitting filter
115: microlens
116: planarizing layer The disclosure of JP2019-157412 filed on Aug. 29, 2019 and the disclosure of JP2020-047017 filed on Mar. 17, 2020 are incorporated in the present specification by reference.

All documents, patent applications, and technical standards described in the present specification are incorporated herein by reference to the same extent as in a case of being specifically and individually noted that individual documents, patent applications, and technical standards are incorporated by reference.

What is claimed is:

1. A composition comprising:
a coloring agent having a structure represented by Formula (1);
an organic solvent; and
a curable compound,
wherein a solubility of the coloring agent having a structure represented by Formula (1) in propylene glycol methyl ether acetate at 25° C. is 100 mg/L or less, $$(Dye)_n\text{-}L^1 \qquad (1)$$

in Formula (1), n is 2 and $L^1$ represents a group represented by Formula (2) or Formula (3), and Dye's each independently represent a coloring agent structure having a maximal absorption wavelength in a wavelength range of 650 nm to 2,000 nm, $$*X^1\text{-}A^1\text{-}X^2\text{-}* \qquad \text{Formula (2)}$$

in Formula (2), $X^1$ and $X^2$ each independently represent a single bond, —O—, —S—, —$NR^{1A}$—, —CO—, —COO—, —OCOO—, —$SO_2NR^{1A}$—, —$CONR^{1A}$—, —$OCONR^{1A}$—, or —$NR^{1A}CONR^{1A}$— $R^{1A}$ represents a hydrogen atom, an alkyl group, or an aryl group, $A^1$ represents a single bond, an aliphatic ring structure, an aromatic ring structure, or a heterocyclic ring structure, and * represents a connection position with Dye, where in a case where $A^1$ is a single bond, both $X^1$ and $X^2$ are not single bonds, $$*\text{-}X^3\text{-}A^2\text{-}L^2\text{-}A^3\text{-}X^4\text{-}* \qquad \text{Formula (3)}$$

in Formula (3), $X^3$ and $X^4$ each independently represent a single bond, —O—, —S—, —$NR^{2A}$—, —CO—, —COO—, —OCOO—, —$SO_2NR^{2A}$—, —$CONR^{2A}$—, —$OCONR^{2A}$—, or —$NR^{2A}CONR^{2A}$—, $R^{2A}$ represents a hydrogen atom or an alkyl group, $L^2$ represents a single bond, —O—, —S—, —$NR^{2B}$—, —CO—, —COO—, —OCOO—, —$SO_2NR^{2B}$—$CONR^{2B}$—, —$OCONR^{2B}$—, —$NR^{2B}CONR^{2B}$—, an alkylene group having 1 to 6 carbon atoms, an alkenyl group, an alkynyl group, an aromatic ring structure, or a group of a combination of these groups, $R^{2B}$ represents a hydrogen atom or an alkyl group, and $A^2$ and $A^3$ each independently represent an aliphatic ring structure, an aromatic ring structure, or a heterocyclic ring structure, and the coloring agent having a structure represented by Formula (1) is at least one compound selected from the group consisting of a pyrrolopyrrole compound, a rylene compound, an oxonol compound, a squarylium compound, a croconium compound, a vanadium phthalocyanine compound, a naphthalocyanine compound, an indigo compound, and a pyrromethene compound.

2. The composition according to claim 1, wherein a molecular weight of the coloring agent having a structure represented by Formula (1) is less than 4,000.

3. The composition according to claim 1, wherein a total number of carbon atoms included in $L^1$ in Formula (1) is 1 to 18.

4. The composition according to claim 1, wherein a volume average particle diameter of the coloring agent having a structure represented by Formula (1) is 1 nm to 500 nm.

5. The composition according to claim 1, further comprising:
a pigment derivative.

6. The composition according to claim 1, wherein the curable compound includes a polymerizable compound, and
the composition further includes a photopolymerization initiator.

7. The composition according to claim 1, further comprising:
an alkali-soluble resin.

8. A film which consists of the composition according to claim 1 or is obtained by curing the composition.

9. A near-infrared cut filter comprising:
the film according to claim 8.

10. The near-infrared cut filter according to claim 9, further comprising:
a glass substrate.

11. A pattern forming method, comprising:
a step of forming a composition layer on a support using the composition according to claim 1; and
a step of forming a pattern on the composition layer by a photolithography method or a dry etching method.

12. A laminate comprising:
the film according to claim 8; and
a color filter including a chromatic colorant.

13. A solid-state imaging element comprising:
the film according to claim 8.

14. An image display device comprising:
the film according to claim 8.

15. A camera module comprising:
the film according to claim 8.

16. An infrared sensor comprising:
the film according to claim 8.

17. A pyrrolopyrrole compound represented by Formula (4-1),

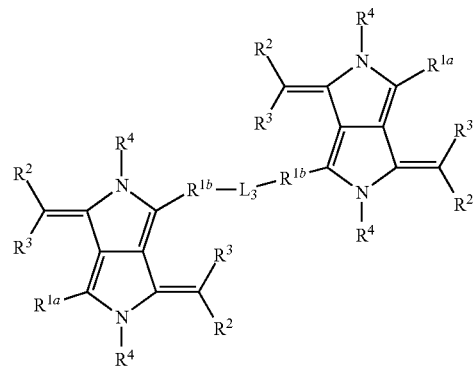

(4-1)

in Formula (4-1), $R^{1a}$ and $R^{1b}$ each independently represent an aryl group or a heteroaryl group, $R^2$ and $R^3$ each independently represent a hydrogen atom or a substituent, $R^2$ and $R^3$ may be bonded to each other to form a ring, $R^4$'s each independently represent a hydrogen atom, an alkyl group, an aryl group, a heteroaryl group, $-BR^{4A}R^{4B}$, or a metal atom, $R^4$ may be covalently or coordinately bonded to at least one selected from the group consisting of $R^{1a}$, $R^{1b}$, and $R^3$, $R^{4A}$ and $R^{4B}$ each independently represent a hydrogen atom or a substituent, and $L^3$ represents a group represented by Formula (2) or Formula (3), $$*\text{-}X^1\text{-}A^1\text{-}X^2\text{-}* \qquad \text{Formula (2)}$$

in Formula (2), $X^1$ and $X^2$ each independently represent a single bond, $-O-$, $-S-$, $-NR^{1A}-$, $-CO-$, $-COO-$, $-OCOO-$, $-SO_2NR^{1A}-$, $-CONR^{1A}-$, $-OCONR^{1A}-$, or $-NR^{1A}CONR^{1A}-$, $R^{1A}$ represents a hydrogen atom, an alkyl group, or an aryl group, $A^1$ represents a single bond, an aliphatic ring structure, an aromatic ring structure, or a heterocyclic ring structure, and * represents a connection position with Dye, where in a case where $A^1$ is a single bond, both $X^1$ and $X^2$ are not single bonds, $$*\text{-}X^3\text{-}A^2\text{-}L^2\text{-}A^3\text{-}X^4\text{-}* \qquad \text{Formula (3)}$$

in Formula (3), $X^3$ and $X^4$ each independently represent a single bond, $-O-$, $-S-$, $-NR^{2A}-$, $-CO-$, $-COO-$, $-OCOO-$, $-SO_2NR^{2A}-$, $-CONR^{2A}-$, $-OCONR^{2A}-$, or $-NR^{2A}CONR^{2A}-$, $R^{2A}$ represents a hydrogen atom or an alkyl group, $L^2$ represents a single bond, $-O-$, $-S-$, $-NR^{2B}-$, $-CO-$, $-COO-$, $-OCOO-$, $-SO_2NR^{2B}-$, $-CONR^{2B}-$, $-OCONR^{2B}-$, $-NR^{2B}CONR^{2B}-$, an alkylene group having 1 to 6 carbon atoms, an alkenyl group, an alkynyl group, an aromatic ring structure, or a group of a combination of these groups, $R^{2B}$ represents a hydrogen atom or an alkyl group, and $A^2$ and $A^3$ each independently represent an aliphatic ring structure, an aromatic ring structure, or a heterocyclic ring structure.

* * * * *